US012480126B2

(12) United States Patent
Freier et al.

(10) Patent No.: US 12,480,126 B2
(45) Date of Patent: Nov. 25, 2025

(54) MODULATION OF DYSTROPHIA MYOTONICA-PROTEIN KINASE (DMPK) EXPRESSION

(71) Applicants: Ionis Pharmaceuticals, Inc., Carlsbad, CA (US); University of Rochester, Rochester, NY (US)

(72) Inventors: Susan M. Freier, San Diego, CA (US); Charles A. Thornton, Rochester, NY (US); Thurman Wheeler, Rochester, NY (US); Seng H. Cheng, Natick, MA (US); Andrew Leger, Boston, MA (US); Bruce M. Wentworth, Northborough, MA (US)

(73) Assignees: Ionis Pharmaceuticals, Inc., Carlsbad, CA (US); University of Rochester, Rochester, NY (US)

( * ) Notice: Subject to any disclaimer, the term of this patent is extended or adjusted under 35 U.S.C. 154(b) by 0 days.

(21) Appl. No.: 17/814,120

(22) Filed: Jul. 21, 2022

(65) Prior Publication Data

US 2023/0174987 A1 Jun. 8, 2023

Related U.S. Application Data

(63) Continuation of application No. 16/722,960, filed on Dec. 20, 2019, now abandoned, which is a continuation of application No. 15/657,474, filed on Jul. 24, 2017, now abandoned, which is a continuation of application No. 14/814,174, filed on Jul. 30, 2015, now Pat. No. 9,765,338, which is a continuation of application No. 13/811,181, filed as application No. PCT/US2011/044555 on Jul. 19, 2011, now abandoned.

(60) Provisional application No. 61/478,021, filed on Apr. 21, 2011, provisional application No. 61/365,775, filed on Jul. 19, 2010, provisional application No. 61/365,762, filed on Jul. 19, 2010.

(51) Int. Cl.

| | |
|---|---|
| ***C12N 15/113*** | (2010.01) |
| ***A61P 15/00*** | (2006.01) |
| ***A61P 25/18*** | (2006.01) |
| ***A61P 35/00*** | (2006.01) |
| ***A61P 43/00*** | (2006.01) |

(52) U.S. Cl.

CPC .......... *C12N 15/1137* (2013.01); *A61P 15/00* (2018.01); *A61P 25/18* (2018.01); *A61P 35/00* (2018.01); *A61P 43/00* (2018.01); *C12N 15/113* (2013.01); *C12Y 207/11* (2013.01); *C12N 2310/11* (2013.01); *C12N 2310/315* (2013.01); *C12N 2310/3181* (2013.01); *C12N 2310/321* (2013.01); *C12N 2310/3231* (2013.01); *C12N 2310/3341* (2013.01); *C12N 2310/341* (2013.01); *C12N 2310/346* (2013.01); *C12N 2310/3525* (2013.01)

(58) Field of Classification Search

None

See application file for complete search history.

(56) References Cited

U.S. PATENT DOCUMENTS

| | | | |
|---|---|---|---|
| 3,687,808 | A | 8/1972 | Merigan et al. |
| 4,845,205 | A | 7/1989 | Huynh Dinh et al. |
| 5,130,302 | A | 7/1992 | Spielvogel et al. |
| 5,134,066 | A | 7/1992 | Rogers et al. |
| 5,175,273 | A | 12/1992 | Bischofberger et al. |
| 5,367,066 | A | 11/1994 | Urdea et al. |
| 5,432,272 | A | 7/1995 | Benner |
| 5,434,257 | A | 7/1995 | Matteucci |
| 5,457,187 | A | 10/1995 | Gmelner et al. |
| 5,459,255 | A | 10/1995 | Cook et al. |
| 5,484,908 | A | 1/1996 | Froehler et al. |
| 5,502,177 | A | 3/1996 | Matteucci et al. |
| 5,525,711 | A | 6/1996 | Hawkins et al. |
| 5,552,282 | A | 9/1996 | Caskey et al. |
| 5,552,540 | A | 9/1996 | Haralambidis |
| 5,587,469 | A | 12/1996 | Cook et al. |
| 5,594,121 | A | 1/1997 | Froehler et al. |
| 5,596,091 | A | 1/1997 | Switzer |
| 5,614,617 | A | 3/1997 | Cook et al. |
| 5,645,985 | A | 7/1997 | Froehler et al. |
| 5,646,269 | A | 7/1997 | Matteucci |
| 5,681,941 | A | 10/1997 | Cook et al. |
| 5,750,692 | A | 5/1998 | Cook et al. |
| 5,763,588 | A | 6/1998 | Matteucci et al. |

(Continued)

FOREIGN PATENT DOCUMENTS

| | | |
|---|---|---|
| WO | WO 1991/004753 | 4/1991 |
| WO | WO 1999/014226 | 3/1999 |

(Continued)

OTHER PUBLICATIONS

Albaek et al., "Bi- and Tricyclic Nucleoside Derivatives Restricted in S-Type Conformations and Obtained by RCM-Reactions" Nucleosides, Nucleotides & Nucleic Acids (2003) 22(5-8):723-725.

(Continued)

*Primary Examiner* — Brian Whiteman
(74) *Attorney, Agent, or Firm* — McNeill PLLC

(57) ABSTRACT

Provided herein are methods, compounds, and compositions for reducing expression of a DMPK mRNA and protein in an animal. Also provided herein are methods, compounds, and compositions for preferentially reducing CUGexp DMPK RNA, reducing myotonia or reducing spliceopathy in an animal. Such methods, compounds, and compositions are useful to treat, prevent, delay, or ameliorate type 1 myotonic dystrophy, or a symptom thereof.

24 Claims, No Drawings

Specification includes a Sequence Listing.

(56) References Cited

U.S. PATENT DOCUMENTS

| | | | |
|---|---|---|---|
| 5,801,154 | A | 9/1998 | Baracchini et al. |
| 5,830,653 | A | 11/1998 | Froehler et al. |
| 5,955,265 | A | 9/1999 | Brook et al. |
| 6,005,096 | A | 12/1999 | Matteucci et al. |
| 6,007,992 | A | 12/1999 | Lin et al. |
| 6,028,183 | A | 2/2000 | Lin et al. |
| 6,268,490 | B1 | 7/2001 | Imanishi et al. |
| 6,329,501 | B1 | 12/2001 | Smith |
| 6,525,191 | B1 | 2/2003 | Ramasamy |
| 6,582,908 | B2 | 6/2003 | Fodor et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 7,034,133 | B2 | 4/2006 | Wengel et al. |
| 7,053,207 | B2 | 5/2006 | Wengel |
| 7,208,174 | B2 | 4/2007 | Huwyler et al. |
| 7,374,927 | B2 | 5/2008 | Palma et al. |
| 7,399,845 | B2 | 7/2008 | Seth et al. |
| 7,427,672 | B2 | 9/2008 | Imanishi et al. |
| 7,901,882 | B2 | 3/2011 | Cao et al. |
| 7,973,019 | B1 | 7/2011 | Chatterton et al. |
| 8,158,354 | B2 | 4/2012 | Sarkar |
| RE44,779 | E | 2/2014 | Imanishi et al. |
| 9,012,421 | B2 | 4/2015 | Migawa et al. |
| 9,592,250 | B2 | 3/2017 | Woolf et al. |
| 9,765,338 | B2 | 9/2017 | Bennett et al. |
| 10,954,519 | B2 | 3/2021 | Swayze et al. |
| 2001/0053519 | A1 | 12/2001 | Fodor et al. |
| 2003/0158403 | A1 | 8/2003 | Manoharan et al. |
| 2003/0207804 | A1 | 11/2003 | Manoharan et al. |
| 2003/0228597 | A1 | 12/2003 | Cowsert et al. |
| 2004/0147023 | A1 | 7/2004 | Crooke et al. |
| 2004/0171570 | A1 | 9/2004 | Allerson et al. |
| 2004/0241651 | A1 | 12/2004 | Olek et al. |
| 2005/0019746 | A1 | 1/2005 | Seery et al. |
| 2007/0031844 | A1 | 2/2007 | Khvorova et al. |
| 2007/0031940 | A1 | 2/2007 | Van Rompaey et al. |
| 2007/0134697 | A1 | 6/2007 | Khvorova et al. |
| 2007/0243546 | A1 | 10/2007 | Cao et al. |
| 2007/0287831 | A1 | 12/2007 | Seth et al. |
| 2008/0015158 | A1 | 1/2008 | Ichiro et al. |
| 2008/0039618 | A1 | 2/2008 | Allerson et al. |
| 2008/0242629 | A1 | 10/2008 | Crooke et al. |
| 2009/0081675 | A1 | 3/2009 | Colston et al. |
| 2010/0016215 | A1 | 1/2010 | Moulton et al. |
| 2010/0047289 | A1 | 2/2010 | Fakhari et al. |
| 2010/0190837 | A1 | 7/2010 | Migawa et al. |
| 2011/0178283 | A1 | 7/2011 | Rigoutsos et al. |
| 2011/0229880 | A1 | 9/2011 | Wood et al. |
| 2013/0059902 | A1 | 3/2013 | Corey et al. |
| 2013/0225659 | A1 | 8/2013 | Bennett |
| 2015/0099791 | A1 | 4/2015 | Krieg et al. |
| 2015/0191727 | A1 | 7/2015 | Migawa et al. |
| 2019/0276832 | A1 | 9/2019 | Swayze et al. |
| 2021/0052631 | A1 | 2/2021 | Prakash et al. |
| 2023/0114429 | A1 | 4/2023 | Rigo et al. |

FOREIGN PATENT DOCUMENTS

| | | | |
|---|---|---|---|
| WO | WO 2000/058332 | | 10/2000 |
| WO | WO 2001/019161 | | 3/2001 |
| WO | WO 2002/001953 | | 1/2002 |
| WO | WO 2003/013437 | | 2/2003 |
| WO | WO 2004/028458 | | 4/2004 |
| WO | WO 2004/093783 | | 11/2004 |
| WO | WO 2004/106356 | | 12/2004 |
| WO | WO 2005/116204 | | 12/2005 |
| WO | WO 2005/121368 | | 12/2005 |
| WO | WO 2006/034348 | | 3/2006 |
| WO | WO 2007/089584 | | 8/2007 |
| WO | WO 2007/089611 | | 8/2007 |
| WO | WO 2007/121272 | | 10/2007 |
| WO | WO 2007/134181 | | 11/2007 |
| WO | WO 2008/018795 | | 2/2008 |
| WO | WO 2008/036406 | | 3/2008 |
| WO | WO 2008/049085 | | 4/2008 |
| WO | WO 2008/150729 | | 12/2008 |
| WO | WO 2008/154401 | | 12/2008 |
| WO | WO 2009/006478 | | 1/2009 |
| WO | WO 2009/099326 | | 8/2009 |
| WO | WO 2010/014592 | | 2/2010 |
| WO | WO 2010/029303 | | 3/2010 |
| WO | WO 2010/115993 | | 10/2010 |
| WO | WO 2011/097388 | | 8/2011 |
| WO | WO 2011/113889 | | 9/2011 |
| WO | WO 2013/173637 | | 11/2013 |
| WO | WO 2014/120861 | | 8/2014 |
| WO | 2023034868 | A1 | 3/2023 |
| WO | 2023034870 | A2 | 3/2023 |

OTHER PUBLICATIONS

Altmann et al., "Second Generation of Antisense Oligonucleotides: From Nuclease Resistance to Biological Efficacy in Animals" Chimia (1996) 50:168-176.

Altmann et al., "Second-generation antisense oligonucleotides: structure-activity relationships and the design of improved signal-transduction inhibitors" Biochem. Soc. Trans. (1996) 24:630-637.

Altmann et al., "Second Generation Antisense Oligonucleotides—Inhibition of PKC-a and c-RAF Kinase Expression by Chimeric Oligonucleotides Incorporating 6'-Subsituted Carbocyclic Nucleosides and 2'-O-Ethylene Glycol Substituted Ribonucleosides" Nucleosides & Nucleotides (1997) 16(7-9):917-926.

Aronin et al., "Expanded CAG repeats in the crosshairs" Nature Biotechnology (2009) 27(5): 451-452.

Ascoli et al., "Identification of a novel nuclear domain" J. Cell Biol. (1991) 112(5):785-795.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.

Ballantyne et al., "Locked nucleic acids in PCR primers increase sensitivity and performance" Genomics (2008) 91: 301-305.

Braasch et al., "Locked nucleic acid (LNA): fine-tuning the recognition of DNA and RNA" Chem. Biol. (2001) 8:1-7.

Branch et al., "A good antisense molecule is hard to find, " TIBS (1998) 23:45-50.

Brook et al., "Molecular basis of myotonic dystrophy: Expansion of a trinucleotide (CTG) repeat at the 3' end of a transcript encoding a protein kinase family member" Cell (1992) 68(4):799-808.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Cho et al., "Myotonic dystrophy: Emerging mechanisms for DM1 and DM2" Biochemica et Biophysica Acta (2007) 1772: 195-204.

Cleary et al., "The contribution of cis-elements to disease-associated repeat instability: clinical and experimental evidence" Cytogenet. Genome Res. (2003) 100:25-55.

Clemson et al., "An Architectural Role for a Nuclear Noncoding RNA: NEAT1 RNA Is Essential for the Structure of Paraspeckles" Mol. Cell (2009) 33:717-726.

Conte et al., "Conformational properties and thermodynamics of the RNA duplex r(CGCAAAUUUGCG)2: comparison with the DNA analogue d(CGCAAATTTGCG)2" Nucleic Acids Res. (1997) 25(13):2627-2634.

Cooper, "RNA and Disease" Cell (2009) 136:777-793.

Costa, "Non-coding RNAs and new opportunities for the private secotr" Drug Discovery today (2009) 14:446-452.

Cremer et al., "Chromosome Territories, Interchromatin Domain Compartment, and Nuclear Matrix: An Integrated View of the Functional Nuclear Architecture" Crit. Rev. Eukaroytic Gene Expr. (2000) 10:179-212.

Crooke et al., "Basic Principles of Antisense Therapeutics" Antisense Research and Application (1998) Chapter 1:1-50.

(56) References Cited

OTHER PUBLICATIONS

Davis et al., "Expansion of a CUG trinucleotide repeat in the 3* untranslated region of myotonic dystrophy protein kinase transcripts results in nuclear retention of transcripts" PNAS (1997) 94:7388-7393.
De Die-Smulders et al., "Age and causes of death in adult-onset myotonic dystrophy." *Brain* (1998) 121:1557-1563.
Denegri et al., "Human Chromosomes 9, 12, and 15 Contain the Nucleation Sites of Stress-Induced Nuclear Bodies" Mol. Biol. Cell (2002) 13:2069-2079.
Dong et al., "Implication of snoRNA U50 in human breast cancer" Journal of Genetics and Genomics (2009) 36(8): 447-454.
Doucas et al., "The PML nuclear compartment and cancer" Biochem. Biophys. Acta (1996) 1288(3):M25-M29.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Agnew Chem. Int. Ed. Engl. (1991) 30:613-629.
Fakan et al., "Ultrastructural Distribution of Nuclear Ribonucleoproteins as Visualized by Immunocytochemistry on Thin Sections" J. Cell Biol. (1984) 98:358-363.
Flanagan et al., "A cytosine analog that confers enhanced potency to antisense oligonucleotides" PNAS (1999) 96:3513-3518.
Fox et al., "P54nrb Forms a Heterodimer with PSP1 That Localizes to Paraspeckles in an RNA-dependent Manner" Mol. Biol. Cell (2005) 16:5304-5315.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Fu et al., "Factor required for mammalian spliceosome assembly is localized to discrete regions in the nucleus" Nature (1990) 343:437-441.
Galderisi et al., "" Biochem. Biophys. Res. Commun. (1996) 221(3):750-754.
Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.
Guo et al., "Inhibition of metastasis-associated lung adenocarcinoma transcript 1 in CaSki human cervical cancer cells suppresses cell proliferation and invasion" Acta Biochimica et Biophysica Sinica (2010) 42(3): 224-229.
Guttman et al., "Chromatin signature reveals over a thousand highly conserved large non-coding RNAs in mammals" Nature (2009) 458:223-227.
Hu et al., "Allele-specific silencing of mutant huntingtin and ataxin-3 genes by targeting expanded CAG repeats in mRNAs" Nature Biotechnology (2009) 27(5): 478-484.
Hu et al., "Allele-selective inhibition of mutant huntingtin by peptide nucleic acid-peptide conjugates, locked nucleic acid, and small interfering RNA" Annals of the New York Academy of Sciences (2009) 1175: 24-31.
Huang, "Review: Perinucleolar Structures" J. Struct. Biol. (2000) 129:233-240.
Ideue et al., "Efficient oligonucleotide-mediated degradation of nuclear noncoding RNAs in mammalian cultured cells" RNA (2009) 15(8): 1578-1587.
Ionis Pharmaceuticals, Inc. Press Release, Recently Published Preclinical Data Show Significant and Sustained Reduction of Muscle DMPK RNA with a Generation 2.5 Antisense Compound, Sep. 1, 2015, 1 Page.
Ji et al., "MALAT-1, a novel noncoding RNA, and thymosin b4 predict metastasis and survival in early-stage non-small cell lung cancer" Oncogene (2003) 22:8031-8041.
Jolly et al., "In vivo binding of active heat shock transcription factor 1 to human chromosome 9 heterochromatin during stress" J. Cell Biol. (2002) 156:775-781.
Kanadia et al., "Reversal of RNA missplicing and myotonia after muscleblind overexpression in a mouse poly(CUG) model for myotonic dystrophy" PNAS (2006) 103(31):11748-11753.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Krol et al., "Ribonuclease dicer cleaves triplet repeat hairpins into shorter repeats that silence specific targets" Molecular Cell (2007) 25:575-586.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Kurchavov et al., "A New Phosphoramidite Reagent for the Incorporation of Diazaphenoxazinone Nucleoside with Enhanced Base-Pairing Properties into Oligodeoxynucleotides" Nucleosides and Nucleotides (1997) 16)10 & 11):1837-1846.
Lavorgna et al., "In search of antisense" Trends Biochem. Sci. (2004) 29:88-94.
Lebedev at el., "Oligonucleotides containing 2-aminoadenine and 5-methylcytosine are more effective as primers for PCR amplification than their nonmodified counterparts," Genetic Analysis: Biomolecular Engineering (1996) 13:15-21.
Lee et al., "Targeted Degradation of Toxic RNA in Myotonic Dystrophy" p. 35, Abstracts of papers presented at the 2010 meeting on RNA & oligonucleotide therapeutics. Apr. 7-10. 2010.
Lehner et al., "Antisense transcripts in the human genome" Trends. Genet. (2002) 18:63-65.
Lesnik et al., "Relative Thermodynamic Stability of DNA, RNA, and DNA:RNA Hybried Duplexes: Relationship with Base Composition and Structure" Biochemistry (1995) 34:10807-10815.
Leumann, "DNA Analogues: From Supramolecular Principles to Biological Properties" Bioorg. & Med. Chem. (2002) 10:841-854.
Liang et al., "Efficient and specific knockdown of small non-coding RNAs in mammalian cells and in mice" Nucleic Acids Research (2010) 39(3): E13.
Lin et al., "Tricyclic 2'-Deoxycytidine Analogs: Synthesis and Incorporation into Oligodeoxynucleotides Which Have Enhanced Binding to Complementary RNA" J. Am. Chem. Soc. (1995) 117:3873-3874.
Lin et al., "A Cytosine Analogue Capable of Clamp-Like Binding to a Guanine in Helical Nucleic Acids" J. Am. Chem. Soc. (1998) 120:8531-8532.
Lin et al., "Failure of MBNL1-dependent post-natal splicing transitions in myotonic dystrophy" Human Mol. Genet. (2006) 15(13):2087-2097.
Liquori et al., "Myotonic Dystrophy Type 2 Caused by a CCTG Expansion in Intron 1 of ZNF9" Science (2001) 293:864-867.
Lolle, "Genome-wide non-mendelian inheritance of extra-genomic information in *Arabidopsis*" Nature (2005) 434:505-509.
Maher e tal., "Comparative hybrid arrest by tandem antisense oligodeoxyribonucleotides or oligodeoxyribonucleoside methylphosphonates in a cell-free system" Nuc. Acid. Res. (1988) 16:3341-3358.
Mankodi et al., "Expanding CUG Repeats Trigger Aberrant Splicing of CIC-1 Chloride Channel Pre-mRNA and Hyperexcitability of Skeletal Muscle in Myotonic Dystrophy" Mol. Cell. (2002) 10:35-44.
Martin, "Ein neuer Zugang zu 2'-O-Alkylribonucleosiden und Eigenschaften deren Oligonucleotide" Helv. Chim. Acta. (1995) 78:486-504.
Melone et al., "Antisense Oligonucleotides and Myotonin Gene Expression in C2 Mouse Cells" Antisense & Nucleic Acid Drug Development (1998) 8: 25-33.
Mercer et al., "Specific expression of long noncoding RNAs in the mouse brain" PNAS (2008) 105(2):716-721.
Miller et al., "Recruitment of human muscleblind proteins to (CUG)(n) expansions associated with myotonic dystrophy." EMBO J. (2000) 19:4439-4448.

(56) References Cited

OTHER PUBLICATIONS

Mouritzen et al., "ProbeLibrary: A new method for faster design and execution of quantitative real-time PCR" Nature Methods (2005) 2:313-317.
Mulders et al., "Triplet-repeat oligonucleotide-mediated reversal of RNA toxicity in myotonic dystrophy" Proceedings of the National Academy of Sciences (2009) 106: 13915-13928.
New England Biolabs 1998/99 Catalog (cover page and pp. 121 and 284).
Noronha et al., "Amplimers with 1-15 3'-terminal phosphorothioate linkages resist degradation by Vent polymersase and reduce Taq polymerase mispriming," PCR Methods & Applicatio, Cold Spring Harbor Laboratory Press (1992) 2: 131-136.
Orum et al., "Locked nucleic acids: A promising molecular family for gene-function analysis and antisense drug development" Curr. Opinion Mol. Ther. (2001) 3:239-243.
O'Rourke, "Mechanisms of RNA-mediated Disease" J. Biol. Chem. (2009) 284(12):7419-7423.
Osborne et al., "RNA-dominant diseases." Hum Mol Genet. (2006) 15:R162-9.
Pandey et al., "Identification and Characterization of Modified Antisense Oligonucleotides Targeting DMPK in Mice and Nonhuman Primates for the Treatment of Myotonic Dystrophy Type 1," J Pharmacol Exp Ther (2015) 355: 329-340.
Peng et al., "The poly(A)-limiting element enhances mRNA accumulation by increasing the efficiency of pre-mRNA 3' processing" RNA (2005) 11:958-965.
Ploner et al., "Methodological obstacles in knocking down small noncoding RNAs" RNA (2009) 15(10): 1797-1804.
Prasanth et al., "Regulating Gene Expression through RNA Nuclear Retention" Celll (2005) 123(2): 249-263.
Ranum et al., "RNA-mediated neuromuscular disorders." Annu Rev Neurosci (2006) 29:259-277.
Rassoulzadegan et al., "RNA-mediated non-mendelian inheritance of an epigenetic change in the mouse" Nature (2006) 441:469-474.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Sasaki et al., "MENε/β noncoding RNAs are essential for structural integrity of nuclear paraspeckles" PNAS (2009) 106(8):2525-2530.
Scholefield et al., "Therapeutic gene silencing strategies for polyglutamine disorders" Trends in Genetics (2010) 26(1): 29-38.
Searle et al., "On the stability of nucleic acid structures in solution: enthalpy-entropy compensations, internal rotations and reversibility" Nucleic Acids Res. (1993) 21:2051-2056.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
*Sun Pharmaceutical Industries, Ltd.* Vs. *Eli Lilly & Co* (2010) 1-16.
Sunwoo et al., "MEN e/b nuclear-retained non-coding RNAs are up-regulated upon muscle differentiation and are essential components of paraspeckles" Genome Res. (2009) 19:347-359.
Swayze et al., "The Medicinal Chemistry of Oligonucleotides" in Antisense Drug Technology, 2nd Edition, Chapter 6, pp. 143-182, Crooke ed., 2008.
Thiry, "Birth of a nucleolus: the evolution of nucleolar compartments " Trends. Cell Biol. (2005) 15:194-199.
Van Der Burg et al., "Beyond the brain: widespread pathology in Huntington's disease", Lancet Neurology (2009) 8(8): 765-774.
Viegas et al., "Regulating the regulators: How ribonucleases dictate the rules in the control of small non-coding RNAs" RNA Biol. (2008) 5:230-243.
Wahlestedt et al., "Potent and nontoxic antisense oligonucleotide containing locked nucleic acids" Proc. Natl. Acad. Sci. USA (2000) 97: 5633-5638.
Wang et al., "Synthesis and binding property of an oligonucleotide containing tetraflurophenoxazine" Tetrahedron Lett. (1998) 39:8385-8388.
Watts e tal., "Chemically modified siRNAs: tools and applications" Drug Discovery Today (2008) 13(19-20): 842-855.
Wheeler et al., "Reversal of RNA dominance by displacement of protein sequestered on triplet repeat RNA" Science (2009) 325:336-339.
Wheeler et al., "Myotonic dystrophy: RNA-mediated muscle disease." Curr Opin Neurol (2007) 20:572-576.
Wheeler et al., "Targeting Nuclear RNA for in vivo Correstoin of Myotonic Dystrophy," Nature (2012) 488:111-117.
Wilusz et al., "3' End Processing of a Long Nuclear-Retained Noncoding RNA Yields a tRNA-like Cytoplasmic RNA" Cell (2008) 135:919-932.
Woolf et al., "Specificity of antisense oligonucleotides in vivo" PNAS (1992) 89:7305-7309.
Yelin et al., "Widespread occurrence of antisense transcription in the human genome" Nat. Biotechnol. (2003) 21(4):379-386.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
European Seach Report for Application EP 16153949.9 dated May 11, 2016.
European Search Report for application EP 11740540.7 dated Aug. 19, 2014.
European Search Report for application EP 11810309.2 dated Aug. 19, 2014.
European Search Report for application EP 11810291.2 dated Feb. 4, 2014.
European Search Report for application EP 14834532.5 dated Feb. 20, 2017.
Partial Search Report for application EP 18199910.3 dated Apr. 11, 2019.
European Search Report for application EP 19191940.6 dated Jun. 26, 2020.
Partial Search Report for application EP 21187583.6 dated Mar. 21, 2022.
International Search Report for application PCT/US11/24099 dated Jun. 22, 2011.
International Search Report for application PCT/US11/44583 dated Mar. 1, 2012.
International Search Report for application PCT/US11/44555 dated Apr. 11, 2012.
International Search Report for application PCT/US14/050481 dated Feb. 2, 2015.
Bennett et al., "RNA Targeting Therapeutics: Molecular Mechanisms of Antisense Oligonucleotides as a Therapeutic Platform" Ann Rev Pharmacol Toxicol (2010) 50: 259-293.
Cenik et al., "Argonaute proteins" Current Biology (2011) 21: R446-R449.
Doucet et al., "RNA-based gene therapy for myotonic dystrophy type 1 (DM1)" Abstract 150 for the Ottawa Conference on New Directions in Biology & Disease of Skeleta (May 5-8, 2010) Ottawa, Canada.
Furling et al., "Viral vector producing antisense RNA restores myotonic dystrophy myoblast functions" Gene Ther (2003) 10: 795-802.
Furling et al., "Therapeutic RNA strategies for myotonic dystrophy with CTG repeats" Abstract for Nucleotide Repeat Expansion Disorders I: Poster Presentations (2004) Neuromuscular Disorders 14.
Gagnon et al., "RNAi Factors are Present and Active in Human Cell Nuclei" Cell Rep (2014) 6: 211-221.
Koshelev et al., "Therapeutic application for a cell culture model of myotonic dystrophy" Abstract 130 for New Directions in Biology & Disease of Skeletal Muscle (Apr. 27-30, 2008) New Orleans.
Kurreck et al., "Antisense technologies" Eur J Biochem (2003) 270: 1628-1644.

(56) References Cited

OTHER PUBLICATIONS

Langlois et al., "Cytoplasmic and Nuclear Retained DMPK mRNAs Are Targets for RNA Interference in Myotonic Dystrophy Cells" J Biol Chem (2005) 280: 16949-16954.
Langlois et al., "Hammerhead Ribozyme-Mediated Destruction of Nuclear Foci in Myotonic Dystrophy Myoblasts" Mol Ther (2003) 7: 670-680.
Langlois et al., "Ribozyme and Antisense RNA-Based Gene Therapies for Myotonic Dystrophy" Mol Ther (2003) 7: S320.
Mignon et al., "Update on IONIS-DMPKRx Program" MDF Annual Conference (Sep. 14-15, 2018) Nashville, TN.
Monia et al., "Evaluation of 2'-Modified Oligonucleotides Containing 2'-Deoxy Gaps as Antisense Inhibitors of Gene Expression" J of Biol Chem (1993) 268: 14514-14522.
Mulders et al., "Molecular therapy in myotonic dystrophy: focus on RNA gain-of-function" Human Mol Genetics (2010) 19: R90-R97.
Sato et al., "In vivo gene delivery to tumor cells by transferrin-streptavidin-DNA conjugate" FASEB J (2000) 14: 2108-2118.
Scanlon et al., "Anti-Genes: siRNA, Ribozymes and Antisense" Curr Pharma Biotech (2004) 56: 415-420.
Scherr et al., "Detection of Antisense and Ribozyme Accessible Sites on Native mRNAs: Application to NCOA3 mRNA" Mol Ther (2001) 4: 454-460.
Stein "The experimental use of antisense oligonucleotides: a guide for the perplexed" J Clin Invest (2001) 108: 641-644.
Vickers et al., "Efficient Reduction of Target RNAs by Small Interfering RNA and Rnase H-dependent Antisense Agents" J Biol Chem (2003) 278: 7108-7118.
Wheeler et al., "Myotonic Dystrophy: Therapeutic Strategies for the Future" Neurotherapeutics: J Am Soc Exp Neurotherapeutics (2008) 5: 592-600.
European Search Report for application EP 21187583.6 dated Jun. 22, 2022.
International Search Report for application PCT/US22/075768 dated Jan. 17, 2023.
GenBank Accession No. NT_011109.16, Aug. 13, 2013.
GenBank NCBI Ref. No. XM_035463770.1, Geosmithia morbida cyclin H (GMORB2_1789), partial mRNA, 2020, 2 pages.
GenBank NCBI Ref. No. XM_051814311.1, Candida margitis RAD52 (CANMA_002262), partial mRNA, 2022, 2 pages.
Henry et al., "Chemically modified oligonucleotides exhibit decreased immune stimulation in mice" J Pharmacol Exp Ther (2000) 292: 468-479.
International Search Report for PCT/US22/075772 dated Feb. 23, 2023, 13 pages.

SEQUENCE LISTING

```
Sequence total quantity: 837
SEQ ID NO: 1           moltype = DNA  length = 2877
FEATURE                Location/Qualifiers
source                 1..2877
                       mol_type = genomic DNA
                       organism = Homo sapiens
SEQUENCE: 1
aggggggctg gaccaagggg tggggagaag gggaggaggc ctcggccggc cgcagagaga  60
agtggccaga gaggcccagg ggacagccag ggacaggcag acatgcagcc agggctccag  120
ggcctggaca ggggctgcca ggccctgtga caggaggacc ccgagccccc ggcccgggga  180
ggggccatgg tgctgcctgt ccaacatgtc agccgaggtg cggctgaggc ggctccagca  240
gctggtgttg gacccgggct tcctggggct ggagcccctg ctcgaccttc tcctgggcgt  300
ccaccaggag ctgggcgcct ccgaactggc ccaggacaag tacgtggccg acttcttgca  360
gtgggcggag cccatcgtgg tgaggcttaa ggaggtccga ctgcagaggg acgacttcga  420
gattctgaag gtgatcggac gcggggcgtt cagcgaggta gcggtagtga agatgaagca  480
```

-continued

```
gacgggccag gtgtatgcca tgaagatcat gaacaagtgg gacatgctga agaggggcga  540
ggtgtcgtgc ttccgtgagg agagggacgt gttggtgaat ggggaccggc ggtggatcac  600
gcagctgcac ttcgccttcc aggatgagaa ctacctgtac ctggtcatgg agtattacgt  660
gggcggggac ctgctgacac tgctgagcaa gtttggggag cggattccgg ccgagatggc  720
gcgcttctac ctggcggaga ttgtcatggc catagactcg gtgcaccggc ttggctacgt  780
gcacagggac atcaaacccg acaacatcct gctggaccgc tgtggccaca tccgcctggc  840
cgacttcggc tcttgcctca agctgcgggc agatggaacg gtgcggtcgc tggtggctgt  900
gggcacccca gactacctgt cccccgagat cctgcaggct gtgggcggtg ggcctgggac  960
aggcagctac gggcccgagt gtgactggtg ggcgctgggt gtattcgcct atgaaatgtt  1020
ctatgggcag acgcccttct acgcggattc cacggcggag acctatggca agatcgtcca  1080
ctacaaggag cacctctctc tgccgctggt ggacgaaggg gtccctgagg aggctcgaga  1140
cttcattcag cggttgctgt gtcccccgga gacacggctg ggccggggtg gagcaggcga  1200
cttccggaca catcccttct tctttggcct cgactgggat ggtctccggg acagcgtgcc  1260
ccccttaca ccggatttcg aaggtgccac cgacacatgc aacttcgact tggtggagga  1320
cgggctcact gccatggaga cactgtcgga cattcgggaa ggtgcgccgc taggggtcca  1380
cctgcctttt gtgggctact cctactcctg catggccctc agggacagtg aggtcccagg  1440
ccccacaccc atggaactgg aggccgagca gctgcttgag ccacacgtgc aagcgcccag  1500
cctggagccc tcggtgtccc cacaggatga aacagctgaa gtggcagttc cagcggctgt  1560
ccctgcggca gaggctgagg ccgaggtgac gctgcgggag ctccaggaag ccctggagga  1620
ggaggtgctc acccggcaga gcctgagccg ggagatggag gccatccgca cggacaacca  1680
gaacttcgcc agtcaactac gcgaggcaga ggctcggaac cgggacctag aggcacacgt  1740
ccggcagttg caggagcgga tggagttgct gcaggcagag ggagccacag ctgtcacggg  1800
ggtccccagt ccccgggcca cggatccacc ttcccatcta gatggccccc cggccgtggc  1860
tgtgggccag tgcccgctgg tggggccagg ccccatgcac cgccgccacc tgctgctccc  1920
tgccagggtc cctaggcctg gcctatcgga ggcgctttcc ctgctcctgt tcgccgttgt  1980
tctgtctcgt gccgccgccc tgggctgcat tgggttggtg gcccacgccg gccaactcac  2040
cgcagtctgg cgccgcccag gagccgcccg cgctccctga accctagaac tgtcttcgac  2100
tccggggccc cgttggaaga ctgagtgccc ggggcacggc acagaagccg cgcccaccgc  2160
ctgccagttc acaaccgctc cgagcgtggg tctccgccca gctccagtcc tgtgatccgg  2220
gcccgccccc tagcggccgg ggagggaggg gccgggtccg cggccggcga acggggctcg  2280
aagggtcctt gtagccggga atgctgctgc tgctgctgct gctgctgctg ctgctgctgc  2340
tgctgctgct gctgctgctg ctggggggat cacagaccat ttctttcttt cggccaggct  2400
gaggccctga cgtggatggg caaactgcag gcctgggaag gcagcaagcc gggccgtccg  2460
tgttccatcc tccacgcacc cccacctatc gttggttcgc aaagtgcaaa gctttcttgt  2520
gcatgacgcc ctgctctggg gagcgtctgg cgcgatctct gcctgcttac tcgggaaatt  2580
tgcttttgcc aaacccgctt tttcggggat cccgcgcccc cctcctcact tgcgctgctc  2640
tcggagcccc agccggctcc gcccgcttcg gcggtttgga tatttattga cctcgtcctc  2700
cgactcgctg acaggctaca ggacccccaa caaccccaat ccacgttttg gatgcactga  2760
gaccccgaca ttcctcggta tttattgtct gtccccacct aggaccccca cccccgaccc  2820
tcgcgaataa aaggccctcc atctgcccaa aaaaaaaaaa aaaaaaaaaa aaaaaaa     2877

SEQ ID NO: 2            moltype = DNA  length = 14411
FEATURE                 Location/Qualifiers
source                  1..14411
                        mol_type = genomic DNA
                        organism = Homo sapiens
SEQUENCE: 2
ctcccagccc agcgcctccc accccttttc atagcaggaa aagccggagc ccagggaggg  60
aacggacctg cgagtcacac aactggtgac ccacaccagc ggctggagca ggaccctctt  120
ggggagaaga gcatcctgcc cgcagccagg gcccctcatc aaagtcctcg gtgtttttta  180
aattatcaga actgcccagg accacgtttc ccaggccctg cccagctggg actcctcggt  240
ccttgcctcc tagtttctca ggcctggccc tctcaaggcc caggcacccc aggccggttg  300
gaggccccga cttccactct ggagaaccgt ccaccctgga aagaagagct cagattcctc  360
ttggctctcg gagccgcagg gagtgtgtct tcccgcgcca ccctccaccc cccgaaatgt  420
ttctgtttct aatcccagcc tgggcaggaa tgtggctccc cggccagggg ccaaggagct  480
attttggggt ctcgtttgcc cagggagggc ttggctccac cactttcctc ccccagcctt  540
tgggcagcag gtcaccccctg ttcaggctct gagggtgccc cctcctggtc ctgtcctcac  600
cacccttcc ccacctcctg ggaaaaaaaa aaaaaaaaaa aaaaaaagct ggtataaagc  660
agagagcctg agggctaaat ttaactgtcc gagtcggaat ccatctctga gtcacccaag  720
aagctgccct ggcctcccgt ccccttccca ggcctcaacc cctttctccc acccagcccc  780
aacccccagc cctcaccccc tagcccccag ttctggagct tgtcgggagc aagggggtgg  840
ttgctactgg gtcactcagc ctcaattggc cctgtttcag caatgggcag gttcttcttg  900
aaattcatca cacctgtggc ttcctctgtg ctctaccttt ttattggggt gacagtgtga  960
cagctgagat tctccatgca ttccccctac tctagcactg aagggttctg aagggccctg  1020
gaaggaggga gcttgggggg ctggcttgtg aggggttaag gctgggaggc gggagggggg  1080
ctggaccaag ggtggggag aaggggagga ggcctcggcc ggccgcagag agaagtggcc  1140
agagaggccc aggggacagc cagggacagg cagacatgca gccagggctc cagggcctgg  1200
acaggggctg ccaggccctg tgacaggagg accccgagcc cccggcccgg ggaggggcca  1260
tggtgctgcc tgtccaacat gtcagccgag gtgcggctga ggcggctcca gcagctggtg  1320
ttggacccgg gcttcctggg gctggagccc ctgctcgacc ttctcctggg cgtccaccag  1380
gagctgggcg cctccgaact ggcccaggac aagtacgtgg ccgacttctt gcagtggggt  1440
gagtgcctac cctcggggct cctgcagatg gggtgggggt ggggcaggag acaggtctgg  1500
gcacagaggc ctggctgttg ggggggcagg atggcaggat gggcatgggg agatcctccc  1560
atcctggggc tcagagtgtg gacctgggcc ctggggcaac atttctctgt cctatgccac  1620
cactctggag gggcagagta aggtcagcag aggctagggt ggctgtgact cagagccatg  1680
gcttaggagt cacagcaggc taggctgcca acagcctccc atggcctctc tgcaccccgc  1740
ctcagggtca gggtcagggt catgctggga gctccctctc ctaggaccct ccccccaaaa  1800
gtgggctcta tggccctctc ccctggtttc ctgtggcctg ggcaagccca ggagggccag  1860
catggggcag ctgccagggg cgcagccgac aggcaggtgt tcggcgccag cctctccagc  1920
```

-continued

```
tgccccaaca ggtgcccagg cactgggagg gcggtgactc acgcgggccc tgtgggagaa  1980
ccagctttgc agacaggcgc caccagtgcc ccctcctctg cgatccagga gggacaactt  2040
tgggttcttc tgggtgtgtc tccttctttt gtaggttctg cacccacccc cacccccagc  2100
cccaaagtct cggttcctat gagccgtgtg ggtcagccac cattcccgcc accccgggtc  2160
cctgcgtcct ttagttctcc tggcccaggg cctccaacct tccagctgtc ccacaaaacc  2220
ccttcttgca agggctttcc agggcctggg gccagggctg gaaggaggat gcttccgctt  2280
ctgccagctg ccttgtctgc ccacctcctc cccaagccca ggactcgggc tcactggtca  2340
ctggtttctt tcattcccag caccctgccc ctctggccct catatgtctg gccctcagtg  2400
actggtgttt ggtttttggc ctgtgtgtaa caaactgtgt gtgacacttg tttcctgttt  2460
ctccgccttc ccctgcttcc tcttgtgtcc atctctttct gacccaggcc tggttccttt  2520
ccctcctcct cccatttcac agatgggaag gtggaggcca agaagggcca ggccattcag  2580
cctctggaaa aaccttctcc caacctccca cagcccctaa tgactctcct ggcctccctt  2640
tagtagagga tgaagttggg ttggcagggt aaactgagac cgggtggggt aggggtctgg  2700
cgctcccggg aggagcactc cttttgtggc ccgagctgca tctcgcggcc cctcccctgc  2760
caggcctggg gcgggggagg gggccagggt tcctgctgcc ttaaaagggc tcaatgtctt  2820
ggctctctcc tccctccccc gtcctcagcc ctggctggtt cgtccctgct ggcccactct  2880
cccggaaccc cccggaaccc ctctctttcc tccagaaccc actgtctcct ctccttccct  2940
cccctcccat acccatccct ctctccatcc tgcctccact tcttccaccc ccgggagtcc  3000
aggcctccct gtccccacag tccctgagcc acaagcctcc accccagctg gtcccccacc  3060
caggctgccc agtttaacat tcctagtcat aggaccttga cttctgagag gcctgattgt  3120
catctgtaaa taaggggtag gactaaagca ctcctcctgg aggactgaga gatgggctgg  3180
accggagcac ttgagtctgg gatatgtgac catgctacct ttgtctccct gtcctgttcc  3240
ttcccccagc cccaaatcca gggttttcca aagtgtggtt caagaaccac ctgcatctga  3300
atctagaggt actggataca accccacgtc tgggccgtta cccaggacat tctacatgag  3360
aacgtggggg tggggccctg gctgcacctg aactgtcacc tggagtcagg gtggaaggtg  3420
gaagaactgg gtcttatttc cttctcccct tgttctttag ggtctgtcct tctgcagact  3480
ccgttacccc accctaacca tcctgcacac ccttggagcc ctctgggcca atgccctgtc  3540
ccgcaaaggg cttctcaggc atctcacctc tatgggaggg catttttggc cccagaacc  3600
ttacacggtg tttatgtggg gaagcccctg ggaagcagac agtcctaggg tgaagctgag  3660
aggcagagag aaggggagac agacagaggg tggggctttc cccttgtct ccagtgccct  3720
ttctggtgac cctcggttct tttcccccac cacccccca gcggagccca tcgtggtgag  3780
gcttaaggag gtccgactgc agagggacga cttcgagatt ctgaaggtga tcggacgcgg  3840
ggcgttcagc gaggtaagcc gaaccgggcg ggagcctgac ttgactcgtg gtgggcgggg  3900
catagggtt ggggcggggc cttagaaatt gatgaatgac cgagccttag aacctagggc  3960
tgggctggag gcggggcttg ggaccaatgg gcgtggtgtg gcaggtgggg cggggccacg  4020
gctgggtgca gaagcgggtg gagttgggtc tgggcgagcc cttttgtttt cccgccgtct  4080
ccactctgtc tcactatctc gacctcaggt agcggtagtg aagatgaagc agacggcca  4140
ggtgtatgcc atgaagatca tgaacaagtg ggacatgctg aagaggggcg aggtgagggg  4200
ctgggcggac gtgggggct ttgaggatcc gcgccccgtc tccggctgca gctcctccgg  4260
gtgccctgca ggtgtcgtgc ttccgtgagg agagggacgt gttggtgaat ggggaccggc  4320
ggtggatcac gcagctgcac ttcgccttcc aggatgagaa ctacctggtg agctccgggc  4380
cggggtgact aggaagaggg acaagagccc gtgctgtcac tggacgagga ggtggggaga  4440
ggaagctcta ggattggggg tgctgcccgg aaacgtctgt gggaaagtct gtgtgcggta  4500
agagggtgtg tcaggtggat gaggggcctt ccctatctga gacggggatg gtgtccttca  4560
ctgcccgttt ctggggtgat ctgggggact cttataaaga tgtctctgtt gcggggggtc  4620
tcttacctgg aatgggatag gtcttcagga attctaacgg ggccactgcc tagggaagga  4680
gtgtctggga cctattctct gggtgttggg tggcctctgg gttctctttc ccagaacatc  4740
tcagggggag tgaatctgcc cagtgacatc ccaggaaagt ttttttgttt gtgttttttt  4800
ttgaggggcg ggggcggggg ccgcaggtgg tctctgattt ggcccggcag atctctatgg  4860
ttatctctgg gctggggctg caggtctctg cccaaggatg gggtgtctct gggaggggtt  4920
gtcccagcca tccgtgatgg atcagggcct caggggacta ccaaccaccc atgacgaacc  4980
ccttctcagt acctggtcat ggagtattac gtgggcgggg acctgctgac actgctgagc  5040
aagtttgggg agcggattcc ggccgagatg gcgcgcttct acctggcgga gattgtcatg  5100
gccatagact cggtgcaccg gcttggctac gtgcacaggt gggtgcagca tggccgaggg  5160
gatagcaagc ttgttccctg gccgggttct tggaaggtca gagcccagag aggccagggc  5220
ctggagaggg accttcttgg ttggggccca ccggggggtg cctgggagta ggggtcagaa  5280
ctgtagaagc cctacagggg cggaacccga ggaagtgggg tcccaggtgg cactgcccgg  5340
aggggcggag cctggtggga ccacagaagg gaggttcatt tatcccaccc ttctcttttc  5400
ctccgtgcag ggacatcaaa cccgacaaca tcctgctgga ccgctgtggc cacatccgcc  5460
tggccgactt cggctcttgc ctcaagctgc gggcagatgg aacggtgagc cagtgccctg  5520
gccacagagc aactggggct gctgatgagg gatggaaggc acagagtgtg ggagcgggac  5580
tggatttgga ggggaaaaga ggtggtgtga cccaggctta agtgtgcatc tgtgtggcgg  5640
agtattagac caggcagagg gaggggctaa gcatttgggg agtggttgga aggagggccc  5700
agagctggtg ggcccagagg ggtgggccca agcctcgctc tgctcctttt ggtccaggtg  5760
cggtcgctgg tggctgtggg caccccagac tacctgtccc ccgagatcct gcaggctgtg  5820
ggcggtgggc ctgggacagg cagctacggg cccgagtgtg actggtgggc gctgggtgta  5880
ttcgcctatg aaatgttcta tgggcagacg cccttctacg cggattccac ggcggagacc  5940
tatggcaaga tcgtccacta caaggtgagc acggccgcag ggagacctgg cctctcccgg  6000
taggcgctcc caggctatcg cctcctctcc ctctgagcag gagcacctct ctctgccgct  6060
ggtggacgaa ggggtccctg aggaggctcg agacttcatt cagcggttgc tgtgtccccc  6120
ggagacacgg ctgggccggg gtggagcagg cgacttccgg acacatccct tcttctttgg  6180
cctcgactgg gatggtctcc gggacagcgt gcccccccttt acaccggatt tcgaaggtgc  6240
caccgacaca tgcaacttcg acttggtgga ggacgggctc actgccatgg tgagcggggg  6300
cggggtaggt acctgtggcc cctgctcggc tgcgggaacc tccccatgct ccctccataa  6360
agttggagta aggacagtgc ctaccttctg gggtcctgaa tcactcattc cccagagcac  6420
ctgctctgtg cccatctact actgaggacc cagcagtgac ctagacttac agtccagtgg  6480
gggaacacag agcagtcttc agacagtaag gccccagagt gatcagggct gagacaatgg  6540
agtgcagggg gtgggggact cctgactcag caaggaaggt cctggagggc tttctggagt  6600
ggggagctat ctgagctgag acttggaggg atgagaagca ggagaggact cctcctccct  6660
```

-continued

```
taggccgtct ctcttcaccg tgtaacaagc tgtcatggca tgcttgctcg gctctgggtg  6720
cccttttgct gaacaatact ggggatccag cacggaccag atgagctctg gtccctgccc  6780
tcatccagtt gcagtctaga gaattagaga attatggaga gtgtggcagg tgccctgaag  6840
ggaagcaaca ggatacaaga aaaaatgatg gggccaggca cggtggctca cgcctgtaac  6900
cccagcaatt tggcaggccg aagtgggtgg attgcttgag cccaggagtt cgagaccagc  6960
ctgggcaatg tggtgagacc cccgtctcta caaaaaatgtt ttaaaaattg gttgggcgtg  7020
gtggcgcatg cctgtatact cagctactag ggtggccgac gtgggcttga gcccaggagg  7080
tcaaggctgc agtgagctgt gattgtgcca ctgcactcca gcctgggcaa cggagagaga  7140
ctctgtctca aaaataagat aaactgaaat taaaaaatag gctgggctgg ccgggcgtgg  7200
tggctcacgc ctgtaatctc agcactttgg gaggccgagg cgggtggatc acgaggtcag  7260
gagatcgaga ccatcttggc taacacggtg aaaccccatc tctcctaaaa atacaaaaaa  7320
ttagccaggc gtggtggcgg gcgcctgtag tcccagctac tcaggaggct gaggcaggag  7380
aatggcgtga acccgggagg cagagtttgc agtgagccga gatcgtgcca ctgcactcca  7440
gcctgggcga cagagcgaga ctctgtctca gaaaaaaaaa aaaaaaaaaa aaaaaatagg  7500
ctggaccgcg gccgggcgct gtggctcatg cctgtaatcc cagcactttg ggagtccaag  7560
gccggtgggt catgagatca ggagttttga gactaggctg gccaacacgg tgaaaccccg  7620
tctctactaa aaatacaaga aaattagctg ggtgtggtct cgggtgcctg taattccagt  7680
tactggggaa gctgaggcag gagaattgct tgaacctggg aggcagagtt tgcagtgagc  7740
caagatcatg ccactacact ccagtctggg tgacagagtg agactctgtc tcaaaaaaaa  7800
aaaaaaaaaa aagggttggg caaggtggtt cacgcctgta atcccagaac tttgggaggc  7860
tgaggcaggc agatcactgg aagtcaggag ttcaagacca gcctggccaa catggtgaaa  7920
ccctgtgtct actaaaaata caaaatttag ccaggcttgg tggcgtatgc ctgtaatgcc  7980
agctactcag gaggctgagg caggagaatc gcttgattga acctgggagg cagagtttgc  8040
agtgggctgg ggttgtgcca ctgcactcta ggctgggaga cagcaagact ccatctaaaa  8100
aaaaaaaaca gaactgggct gggcacagtg gcttatattt gtaatcccag cactttggga  8160
ggctgaggtt ggaggactgc ttgagcccag agtttgggac tacaacagct gaggtaggcg  8220
gatcacttga ggtcagaaga tggagaccag cctggccagc gtggcgaaac cccgtctcta  8280
ccaaaaatat aaaaaattag ccaggcgtgg tagagggcgc ctgtaatctc agctactcag  8340
gacgctgagg caggagaatc gcctgaacct gggaggcgga ggttgcagtg agctgagatt  8400
gcaccactgc actccagcct gggtaacaga gcgagactcc gtatcaaaga aaaagaaaaa  8460
agaaaaaatg ctggaggggc cactttagat aagccctgag ttggggctgg tttgggggga  8520
acatgtaagc caagatcaaa aagcagtgag gggcccgccc tgacgactgc tgctcacatc  8580
tgtgtgtctt gcgcaggaga cactgtcgga cattcgggaa ggtgcgccgc taggggtcca  8640
cctgcctttt gtgggctact cctactcctg catggccctc aggtaagcac tgccctggac  8700
ggcctccagg ggccacgagg ctgcttgagc ttcctgggtc ctgctccttg gcagccaatg  8760
gagttgcagg atcagtcttg gaaccttact gttttgggcc caaagactcc taagaggcca  8820
gagttggagg accttaaatt ttcagatcta tgtacttcaa aatgttagat tgaattttaa  8880
aacctcagag tcacagactg ggcttcccag aatcttgtaa ccattaactt ttacgtctgt  8940
agtacacaga gccacaggac ttcagaactt ggaaaatatg aagtttagac ttttacaatc  9000
agttgtaaaa gaatgcaaat tctttgaatc agccatataa caataaggcc atttaaaagt  9060
attaatttag gcgggccgcg gtggctcacg cctgtaatcc tagcactttg ggaggccaag  9120
gcaggtggat catgaggtca ggagatcgag accatcctgg ctaacacggt gaaaccccgt  9180
ctctactaaa aatacaaaaa aattagccgg gcatggtggc gggcgcttgc ggtcccagct  9240
acttgggagg cgaggcagga gaatggcatg aacccgggag gcggagcttg cagtgagccg  9300
agatcatgcc actgcactcc agcctgggcg acagagcaag actccgtctc aaaaaaaaaa  9360
aaaaaaaagt atttatttag gccgggtgtg gtggctcacg cctgtaattc cagtgctttg  9420
ggaggatgag gtgggtggat cacctgaggt caggagttcg agaccagcct gaccaacgtg  9480
gagaaacctc atctctacta aaaaacaaaa ttagccaggc gtggtggcat atacctgtaa  9540
tcccagctac tcaggaggct gaggcaggag aatcagaacc caggaggggg aggttgtggt  9600
gagctgagat cgtgccattg cattccagcc tgggcaacaa gagtgaaact tcatctcaaa  9660
aaaaaaaaaa aaaaagtact aatttacagg ctgggcatgg tggctcacgc ttggaatccc  9720
agcactttgg gaggctgaag tggacggatt gcttcagccc aggagttcaa gaccagcctg  9780
agcaacataa tgagaccctg tctctacaaa aaattgaaaa aatcgtgcca ggcatggtgg  9840
tctgtgcctg cagtcctagc tactcaggag tctgaagtag gagaatcact tgagcctgga  9900
gtttgaggct tcagtgagcc atgatagatt ccagcctagg caacaaagtg agacctggtc  9960
tcaacaaaag tattaattac acaaataatg cattgcttat cacaagtaaa ttagaaaata  10020
cagataagga aaaggaagtt gatatctcgt gagctcacca gatggcagtg gtccctggct  10080
cacacgtgta ctgacacatg tttaaatagt ggagaacagg tgttttttttg gtttgttttt  10140
ttccccttcc tcatgctact ttgtctaaga gaacagttgg ttttctagtc agcttttatt  10200
actggacaac attacacata ctatacctta tcattaatga actccagctt gattctgaac  10260
cgctgcgggg cctgaacggt gggtcaggat tgaacccatc ctctattaga acccaggcgc  10320
atgtccagga tagctaggtc ctgagccgtg ttcccacagg agggactgct gggttggagg  10380
ggacagccac ttcatacccc agggaggagc tgtcccottc ccacagctga gtggggtgtg  10440
ctgacctcaa gttgccatct tggggtccca tgcccagtct taggaccaca tctgtggagg  10500
tggccagagc caagcagtct ccccatcagg tcggcctccc tgtcctgagg ccctgagaag  10560
aggggtctgc agcggtcaca tgtcaaggga ggagatgagc tgaccctaga acatgggggt  10620
ctggacccca agtccctgca gaaggtttag aaagagcagc tcccaggggc ccaaggccag  10680
gagaggggca gggcttttcc taagcagagg aggggctatt ggcctacctg ggactctgtt  10740
ctcttcgctc tgctgctccc cttcctcaaa tcaggaggtc ttggaagcag ctgcccctac  10800
ccacaggcca gaagttctgg ttctccacca gagaatcagc attctgtctc cctccccact  10860
ccctcctcct ctccccaggg acagtgaggt cccaggcccc acacccatgg aactggaggc  10920
cgagcagctg cttgagccac acgtgcaagc gcccagcctg gagccctcgg tgtccccaca  10980
ggatgaaaca gtaagttggt ggaggggagg gggtccgtca gggacaattg ggagagaaaa  11040
ggtgagggct tcccgggtgg cgtgcactgt agagccctct agggacttcc tgaacagaag  11100
cagacagaaa ccacggagag acgaggttac ttcagacatg ggacggtctc tgtagttaca  11160
gtggggcatt aagtaagggt gtgtgtgttg ctggggatct gagaagtcga tctttgagct  11220
gagcgctggt gaaggagaaa caagccatgg aaggaaaggt gccaagtggt caggcgagag  11280
cctccagggc aaaggccttg ggcaggtggg aatcctgatt tgttcctgaa aggtagtttg  11340
gctgaatcat tcctgagaag gctggagagg ccagcaggaa acaaaaccca gcaaggcctt  11400
```

```
ttgtcgtgag ggcattaggg agctggaggg attttgagca gcagagggac ataggttgtg  11460
ttagtgtttg agcaccagcc ctctggtccc tgtgtagatt tagaggacca gactcaggga  11520
tggggctgag ggaggtaggg aagggagggg gcttggatca ttgcaggagc tatggggatt  11580
ccagaaatgt tgaggggacg gaggagtagg ggataaacaa ggattcctag cctggaacca  11640
gtgcccaagt cctgagtctt ccaggagcca caggcagcct taagcctggt ccccatacac  11700
aggctgaagt ggcagttcca gcggctgtcc ctgcggcaga ggctgaggcc gaggtgacgc  11760
tgcgggagct ccaggaagcc ctggaggagg aggtgctcac ccggcagagc ctgagccggg  11820
agatggaggc catccgcacg gacaaccaga acttcgccag gtcgggatcg gggccggggc  11880
cggggccggg atgcgggccg gtggcaaccc ttggcatccc ctctcgtccg gcccggacgg  11940
actcaccgtc cttacctccc cacagtcaac tacgcgaggc agaggctcgg aaccgggacc  12000
tagaggcaca cgtccggcag ttgcaggagc ggatggagtt gctgcaggca gagggagcca  12060
caggtgagtc cctcatgtgt ccccttcccc ggaggaccgg gaggaggtgg gccgtctgct  12120
ccgcggggcg tgtatagaca cctggaggag ggaagggacc cacgctgggg cacgccgcgc  12180
caccgccctc cttcgcccct ccacgcgccc tatgcctctt tcttctcctt ccagctgtca  12240
cgggggtccc cagtccccgg gccacggatc caccttccca tgtaagaccc ctctctttcc  12300
cctgcctcag acctgctgcc cattctgcag atcccctccc tggctcctgg tctccccgtc  12360
cagatatagg gctcacccta cgtctttgcg actttagagg gcagaagccc tttattcagc  12420
cccagatctc cctccgttca ggcctcacca gattccctcc gggatctccc tagataacct  12480
ccccaacctc gattcccctc gctgtctctc gccccaccgc tgagggctgg gctgggctcc  12540
gatcgggtca cctgtccctt ctctctccag ctagatggcc ccccggccgt ggctgtgggc  12600
cagtgcccgc tggtggggcc aggccccatg caccgccgcc acctgctgct ccctgccagg  12660
gtacgtccgg ctgcccacgc cccccttccgc cgtcgcgccc cgcgctccac ccgcccccttg  12720
ccacccgctt agctgcgcat ttgcggggct gggcccacgg caggagggcg gatcttcggg  12780
cagccaatca acacaggccg ctaggaagca gccaatgacg agttcggacg ggattcgagg  12840
cgtgcgagtg gactaacaac agctgtaggc tgttggggcg ggggcggggc gcagggaaga  12900
gtgcgggccc acctatgggc gtaggcgggg cgagtcccag gagccaatca gaggcccatg  12960
ccgggtgttg acctcgccct ctccccgcag gtccctaggc ctggcctatc ggaggcgctt  13020
tccctgctcc tgttcgccgt tgttctgtct cgtgccgccg ccctgggctg cattgggttg  13080
gtggcccacg ccggccaact caccgcagtc tggcgccgcc caggagccgc ccgcgctccc  13140
tgaaccctag aactgtcttc gactccgggg ccccgttgga agactgagtg cccggggcac  13200
ggcacagaag ccgcgcccac cgcctgccag ttcacaaccg ctccgagcgt gggtctccgc  13260
ccagctccag tcctgtgatc cgggcccgcc ccctagcggc cggggaggga ggggccgggt  13320
ccgcggccgg cgaacggggc tcgaagggtc cttgtagccg ggaatgctgc tgctgctgct  13380
gctgctgctg ctgctgctgc tgctgctgct gctgctgctg ctgctggggg gatcacagac  13440
catttctttc tttcggccag gctgaggccc tgacgtggat gggcaaactg caggcctggg  13500
aaggcagcaa gccgggccgt ccgtgttcca tcctccacgc acccccacct atcgttggtt  13560
cgcaaagtgc aaagcttttct tgtgcatgac gccctgctct ggggagcgtc tggcgcgatc  13620
tctgcctgct tactcgggaa atttgctttt gccaaacccg ctttttcggg gatcccgcgc  13680
cccctcctc acttgcgctg ctctcggagc cccagccggc tccgcccgct tcggcggttt  13740
ggatatttat tgacctcgtc ctccgactcg ctgacaggct acaggacccc caacaacccc  13800
aatccacgtt ttggatgcac tgagaccccg acattcctcg gtatttattg tctgtcccca  13860
cctaggaccc ccacccccga ccctcgcgaa taaaaggccc tccatctgcc caaagctctg  13920
gactccacag tgtccgcggt ttgcgttgtg ggccggaggc tccgcagcgg gccaatccgg  13980
aggcgtgtgg aggcggccga aggtctggga ggagctagcg ggatgcgaag cggccgaatc  14040
agggttgggg gaggaaaagc cacggggcgg ggctttggcg tccggccaat aggagggcga  14100
gcgggccacc cggaggcacc gcccccgccc agctgtggcc cagctgtgcc accgagcgtc  14160
gagaagaggg ggctgggctg gcagcgcgcg cggccatcct ccttccactg cgcctgcgca  14220
cgccacgcgc atccgctcct gggacgcaag ctcgagaaaa gttgctgcaa actttctagc  14280
ccgttccccg cccctcctcc cggccagacc cgcccccccct gcggagccgg gaattccgag  14340
gggcggagcg caggccgaga tggggaatgt gggggcctgc agaggaccct ggagacggag  14400
gcgtgcagaa g                                                        14411

SEQ ID NO: 3            moltype = DNA  length = 15000
FEATURE                 Location/Qualifiers
source                  1..15000
                        mol_type = genomic DNA
                        organism = Mus musculus
SEQUENCE: 3
cagtgtcccc actgcccaag gctggctcca tcacgtaccg ctttggctca gctggccagg  60
acacacagtt ctgcctgtgg gacctcacag aagatgtgct ctcccctcat ccgtctctgg  120
cccgtacccg caccettccg ggcacacctg gtgccaccec accagcttct ggtagttctc  180
gggccggaga gacaggtgca ggccccctgc cccgctccct gtctcgttcc aacagtctcc  240
cacacccagc tggtggtggc aaggctggtg ggcctagtgc atcgatggag cctggcatac  300
cattcagcat tggccgcttt gccacactga ccctgcagga gcggcgggac cggggagctg  360
agaaggaaca caaacgctac catagcctgg gaaacatcag ccgcggtggc agtgggggca  420
atagcagcaa tgacaagctc agtggtcctg ccccccgaag ccgattggac ccagctaagg  480
tgctgggcac ggcactgtgc cctcggatcc atgaggtgcc actgctggag cctctcgtgt  540
gcaagaagat tgctcaggaa cgcctgaccg tgctactgtt cctggaggat tgtatcatca  600
ctgcctgcca agagggcctc atctgcacct gggcccggcc aggcaaggcg gtgagtccgc  660
acctgcccaa gcgctgaggg gcaccagttc tgtccctacc ggatgccagt tatccgtcag  720
cagaaaggtc aggtatagga gacagaatgg ggggaaccac agctaacgtc tttagagcct  780
ctgctggccc atatggctca tccttagtac ttcacactca aggcagaacc tgtgtttata  840
ggaaatctga agtgtagatg gtgaaacttt attcaggtct agggatgtga ttgagctggg  900
ggcccacttc tggcctgcct cttagacact gtttctgagc cagctgctga aggcctggat  960
gggaattagc cagggtccag gcctgcactt cctcttgctg ctgtgtggtc ctggtcattg  1020
ggtctcacag atgggctgtg cagtggctgt gctcttagtt ggtgaggtgc aggcctgtca  1080
cctggtcagg cttgagcatg tggtctcagt gtctaggacc ctactctgcc ctcagtcctt  1140
cagtcccttg ctttggaagg ctagagtcca gaagccttag aacgtcaggc agttgcagag  1200
ccactgccag gctagtaggg ctgcgggagt tgactgagtt ctcacagaca cccctctgtc  1260
```

-continued

```
tccctagttc acagacgagg agaccgaggc ccaggcaggg caagcaagtt ggcccaggtc  1320
acccagcaag tcagttgtag aggtaggaca acccctgaag ctgcaagtgg accccagttt  1380
cttttctctc cactgtcgtc ccctgtatgc ccaggacacc tggggccaca ttactgtgga  1440
agtgctactc tgggtcagtg gagacggccg agctgtttgt tcctagctag gacagcagct  1500
ttaggcctgg ggggcagatc ccagctgggg cagcagctcc aaggcctttg ggtggctcct  1560
tctccgggtt ctggcagaag cccaggtgct gtctaatcca cctttctcct cttgttctcc  1620
ccagggcatc tcctcccaac caggcagctc ccccagtggc actgtggtgt gaaatgtgga  1680
tgtcccatgt tcccggcctc ctagccataa ccctccccgc tgacctcaag aatcactgta  1740
ttaacaagac taatcatgat ggaaggactg ctccaagccc cacgctgcac acatactggg  1800
ggtcccctag gttggcccag ccatggggat gtagtgtcct gtgtggcctt ggccctgtcc  1860
tccacccact gccaagtaca atgacctgtt ctctgaaaca tcagtgttaa ccatatccct  1920
gtcccagcat gtgactgttc actcctggga gagacttagc ccacagtacc cctgggtgag  1980
agggcagggc aggggccatc cccactcctg cccaaactcc accccttgct atggtctgtg  2040
attttgaaag tgttaaatta tggaagccct gagggccctc cttgttcccc tggacctctt  2100
atttatacta aagtccttgt ttgcacagtg tttctgttcc ctggggcagg gtagggtggg  2160
ggttgcagta cttggcctcc aagctgtgct ctgaccaaag gaagcccaat cttagctgtt  2220
tccccatccc tagccccgag cagagagccc tctgaaagat gagtctcgac ccccaaagtc  2280
aagaggctga gatggccttc ctactaggtc cttggagatg tttgaaactt gttttaaaca  2340
ccaggactat ccaagcatgc tctccttggg gagaggagga tgctggaatt gactgcactc  2400
cctgcctcct ctgaacatgc ctttgcagtc tgctgcccct ggcccattta tgactggcca  2460
tctagtgcca gctggaggtc atgatttcct ccccagagaa ctggccaccc tagaaagaag  2520
ctaacttgtc gcctggcttg ctgtccaggc agctccgccc tcaaccccta aaatgtttct  2580
gtctctaatc ctagcccagg caggaatgtg gctgccccgg cctgtggcca aggagctatt  2640
ttggggttct cttttgctta aggagggcct ggatccacca cttgcctccc ccaggctggg  2700
gccagcaggt caccccctggc cctggcggct gagcaaactc tctcctgatc ttccttctac  2760
ctcctgccaa aaaatggggg ggcgggtaat acagcaggca caggggctaa atttaactgt  2820
cccaaagtcg gaatccattg ctgagtcacg aagaagctgc ccctggcctt tgcccccccc  2880
actacccct cacccctgt tgcccaggca tcagcccttt cccccaaccc ctcccagctc  2940
tgagtctata gactggctct cctgggcact gacacctccc acctgtaact ccctgtgctc  3000
tctttatggg tgggtagagt caatgggggg gggcaaccct ggagtattac tctgtcccct  3060
gacattgggc tctgaagagt tttgaggggc cctggaagaa gggagttggg gtgttggctc  3120
aggaggggtt aaaaactggg aggcgggagg ggggctgggc caaggggtgg agaaaagagg  3180
aggaggcctt aagcatagaa ctggccagag agacccaagg gatagtcagg gacgggcaga  3240
catgcagcta gggttctggg gcctggacag gggcagccag gccctgtgac gggaagaccc  3300
cgagctccgg cccggggagg ggccatggtg ttgcctgccc aacatgtcag ccgaagtgcg  3360
gctgaggcag ctccagcagc tggtgctgga cccaggcttc ctgggactgg agcccctgct  3420
cgaccttctc ctgggcgtcc accaggagct gggtgcctct cacctagccc aggacaagta  3480
tgtggccgac ttcttgcagt ggggtgagta tggataggaa gcctggggtt gggtgcaagg  3540
cagaggtggg tctacagggc aagaatgggc tatggagggg caggagggcc tggaaagggc  3600
tttttgtaag ggagccaagc agagctcatg acctgacccc aagctcccct ggtgaggcac  3660
cagggtcagt gaggccacct atgactcagc cagtgcaggc tggggtgggc atagcctcct  3720
gctatctcag cacccacact aggacctggc agctttctct tttaggaccc ttggctcctc  3780
aaactggctt catagccctc cccagtttcc cagagtgtgg ggagggacag cgtggggcag  3840
ctgccagggt gtggcccata ggcaggtgtt tggcgtctgc ctccccagct gccctgacag  3900
gtgtccagga gctatgaggg cactgtgact cacagaggcc ctgggggaga accagcccgg  3960
cagacaggcg ccaccgagca ccctttctgt tccccaaatt aagaggaagg aacaacttca  4020
gcttctgagt gtgcccatcc ctagcactct gatcccgccc agcctttgtg ggccagattg  4080
gtcatccctc ctggcttctc atctgctttt gtggttctag ctcaagacct ctaattcctc  4140
tgctgactta aatgcccttc cccagaggtc ttctcaggcc tagtggacaa gcttggagcc  4200
ttatctgctc ctgcccaaca ttgagccaaa gctccagctt accccagctt ccttacaagt  4260
aacgacctgt tttgttgctc tgtgcctatt attaagggtc caggtcttga ttcttggctg  4320
tctgcccatg tgtgtgaccc tagtgcattc tcccctcctc ccccgtttca cagatggaaa  4380
ggttgaggcc atcggttaga ctgctaagcc tgtgaaagac tttttctcct ctccagtctt  4440
tagtgtctcc ctcaaccttt cttttgaagg atggggtttg ggctggcagg gtaaactgag  4500
aactggggtg ggggcagggg gtctgaccct ctgggaagga gcagtccttt tgtggcctga  4560
gcagcatcct gtgggcccct cccctgccag gcctgggcgg gggaggggggc ctgggttccc  4620
gctgccttaa aagggctcaa cgccttggct ctctcctcct ccccaccccc cagccttggc  4680
cctagctgta tcttccccgg ctgcccactt tcccaaaccc ctttcttctc tgtgacccca  4740
tctccccgct tccccacacg tccctcctcc atccttactc cccggcctta gaacttccct  4800
aagggagatc tgacctccct ctgcccaccc cgcaccccca gtcgccagcc tcagacctag  4860
ctgctctccc ctctggctga accaccctag cacaggacct tataccctgg agctttggtt  4920
ataagaagac tctccttcac cctttggaaa ccaagaaagc ccttccaaca gtgtccagga  4980
tgctggaggg cagtgaccct cccccacttc ttcttcgtgc tggctgtgct gacacagctc  5040
cagttcgagg ttgtggcccg agacattaag tgagagcccc gggtgacctg acttagcacc  5100
ctgatcatca catgggagtg aaaggcctga tgcgccagct tctcccactg cctccctttc  5160
tgccctgcaa ccctgtggaa acaggcagtt ctgggtccca caaacatcac agaggttttg  5220
aaagcagaat cctaaagccg atttaagggg cagaaggaag gaggctataa agtcactacc  5280
cttaccgcta gtgttctgat gacccttggt tcttcttccc ccacccccgc ccagtggagc  5340
ccattgcagc aaggcttaag gaggtccgac tgcagaggga tgattttgag attttgaagg  5400
tgatcgggcg tggggcgttc agcgaggtga gtcttcagtg gcctgggaat ggaactttac  5460
ttgatgtggg tggggcataa cagctggggc agagccttaa aaattgatga atgagcttga  5520
atttaaggct ggaggggtgg gggcggagct tgtggtcagt gggcggtgtg cacgtgaggg  5580
cggggctaag gttgggtgga gataagggtg gagtcctgtc tgggtgagcc ttgctggttt  5640
tccctgccac ctcttgctgt catctcggtt ccgtatttag gtagcggtgg tgaagatgaa  5700
acagacgggc caagtgtatg ccatgaagat tatgaataag tgggacatgc tgaagagagg  5760
cgaggtgagg gccagggatt agggcagcgc cctcatctct ccaactcacc tcctgtagct  5820
tctctcctac ctcacaggtg tcgtgcttcc gggaagaaag ggatgtatta gtgaaagggg  5880
accggcgctg gatcacacag ctgcactttg ccttccagga tgagaactac ctggtaagct  5940
ccgggttcag gtgactagga aagagtgaca gttacatcgc cccaagtcaa gaaggctgga  6000
```

-continued

```
gaagggagaa gctgctgtag atcggggggg tgggggtggg ggggacacac acaggggatg  6060
ggggacgggg gtaggattgt gtctcaagta taggagagac cttccttgag acaggagtga  6120
tatctggttt ggcctttgga tggggcgctc tctcactgtg cgggggtcct ctgtgcttgg  6180
gaacggggtg tctttgggag tcttgggggc taccaaaccc ctgtgacaca cccgctccca  6240
gtacctggtc atggaatact acgtgggcgg ggacctgcta acgctgctga gcaagtttgg  6300
ggagcggatc cccgccgaga tggctcgctt ctacctggcc gagattgtca tggccataga  6360
ctccgtgcac cggctgggct acgtgcacag gtgggcgtgg cggggccctt ggagggttag  6420
cagaatttgt gtgggaagga agggtacctg aaggtcagat cccattgggg acagaatcgg  6480
ggtctagaat tgtagaatcc tgggtggggt ggaagtggat cgagctgacg ggccctaaga  6540
gggaaggttt tcaagaaagc acactttccc tcttctctct atgcacaggg acatcaaacc  6600
agataacatt ctgctggacc gatgtgggca cattcgcctg gcagacttcg gctcctgcct  6660
caaactgcag cctgatggaa tggtaagaag agcctggcga aactctcctc attggtgaag  6720
gaccggatta gggggcgggg ctgggttgag gagcaggagg ggagcttggt ctgggatgtc  6780
ctgcgcacca tatttggaca gtcaagggaa aggttttaag cattcaggtc tgattggcac  6840
aggtgaggtc gctggtggct gtgggcaccc cggactacct gtctcctgag attctgcagg  6900
ccgttggtgg agggcctggg gcaggcagct acgggccaga gtgtgactgg tgggcactgg  6960
gcgtgttcgc ctatgagatg ttctatgggc agacccccctt ctacgcggac tccacagccg  7020
agacatatgc caagattgtg cactacaggg tgagcacaag caccatgcag gggggctgac  7080
ttagtggctt gtgctcccag actgtctttt ttaaaagata tttatttata tgtgtgtgtt  7140
ttctgtgtat gtatatctgt gcactgagta ggtgtgcgaa ggtcagaggg catgggatcc  7200
cctggaactg gagtcacaga ctattgtgtg ctgccatgct gagtgctggg aaacagaacc  7260
ttgatcactc tgcaagagca gccagtgcac tgaaacgaca gagccagctc tgcagcccag  7320
ggctaactgt tgcttttctt tctaaatagg aacacttgtc gctgccgctg gcagacacag  7380
ttgtccccga ggaagctcag gacctcattc gtgggctgct gtgtcctgct gagataaggc  7440
taggtcgagg tggggcaggt gatttccaga aacatccttt cttctttggc cttgattggg  7500
agggtctccg agacagtgta cccccctta caccagactt cgagggtgcc acggacacat  7560
gcaatttcga tgtggtggag gaccggctca ctgccatggt gagcgggggc ggggtacgta  7620
cctgcagttc ctgatccgtt gaggggactt ccctagcctc ttccataaaa ttggggtgat  7680
tggccaggtg tggtggtgca tacctttaat cgtagaactt cataggcaga ggcaggtggc  7740
tctctggtaa atcaaggcca tcttggtcta catagtgact tctaggccag tcaggagtga  7800
gatcctccct tgaaaaataa aaaagggggt gttgaccttc ctgggtccca aattattatc  7860
ctagagcact gctatgtatc cactcaggta tgaggacaca caggtgacca gtcccaaaga  7920
cagtgagtga ggcctcactc ttggcagtac taaaattgat tgtagggggc tgggctcttg  7980
acccagcctg gaaagtgctg gagggcttcc tggaggagga gactagctga gcccagaagg  8040
atgcaggaga tcctttctcg ggtgagtgct ctcagcattt taacaagctc taggccctgc  8100
agagagaagt ctggtgtggg cagagcccca atagaaagca acaagataga agagaaaatg  8160
gtggagtttg ttagtggggg cagttatgcc gtgaacatag aggggcgaag ggccatctcg  8220
gataactgct agccacaaga gccctgtctg tcttcctagg agacgctgtc agacatgcag  8280
gaagacatgc cccttggggt gcgcctgccc ttcgtgggct actcctactg ctgcatggcc  8340
ttcaggtgag cacgactgcc ccctgctggg gcctgtgtgc aggcccacca cagccactca  8400
attgaaggct cagtcttcaa accaagtatt cctaggagct gtctaagtta ggctttctgc  8460
tgctgcgatg aaccctgact aaaagcaagc tggggaggaa aaggcttatc gggcttacgt  8520
ttccacatgg gagcccatca ctgaaggaag ccaggacagg aactcacagc ggggcaggaa  8580
cgtggagctg atgcagaggc aatggagggg agctgcttac tgacttgatc cttatgtctt  8640
cctcagcctg tttccttgta gagcccagga ccaccaggcc agtgagggct ccactcacaa  8700
tgggctgagc tctcatctat gatcactagt tatgaaaatg cccgataggc ttgcctgcag  8760
cttcagtttt tgaggcactt tccttccttc cttccttcct tccttccttc cttccttcct  8820
ttctttcttt ctttctttct ttctttcttt ctttctttct ttctttcttt ctttctttct  8880
tagtctttta gagacagggt ctttctatgt agctctggct gtcttggaat tcattctgta  8940
gaccaggctg gtcttattta tttattttat gtatgtgagt ccactatcac tgtcctcaga  9000
cacaccagaa gagggcatca gatcccatta cagatggctg tgagccacca tgtggttgct  9060
gggaattgaa ctcaggacct ctggaagagc agccagtgct cctgccctgt agaggcattt  9120
tcttcatgaa ggctgtctcc tctctgatga cttgatgact ctagcttgtt gtgtcaagtg  9180
gacataagac taggaaagca gctacacatg cactttgttt atttttgttt tgctttttga  9240
gactgggtct ctccatctca tagctctggc catcctgcct ggtgacattc cagtccagtt  9300
gtataaccta agaatctgag actcagcctt gcagaatcct gctattaacg ggtctaggac  9360
actccataga atccaggatc ttagaaaaac aaacctgaag tgtgacagtt tattttaaga  9420
acacaattgg agcacataac aataatacaa cttttcagtt ttaaaaagtt ttctgtcttg  9480
tttttgagg caggagctcc ttaatatagt ctaagccgcc ctgcgagtgc tgtgattgat  9540
gggcatgtac caccatgcct agtcaataaa gcctttaaaa agcatccgtt atgctggctg  9600
tggtgccaca aacctgtaat cccagcactt agaaggtaga ggcaagatta tcagaaattc  9660
aaggccatcc tgggctatac agtaatctaa ggctagcctg gtctacaaga gactctgtct  9720
aaagaaacaa aagataaata gcacccacta ttgctaggca atataaccct ataaccccac  9780
cattgaggag gctgaggctg gagcatcact gcaaatttga ggccaggatg gtcaacaaat  9840
aagtcccaga gctggcatag aggaactctg tctcaacaat aaagagaact tatctagcat  9900
ttatgagggt aaataaaaat ttaccattgc cacaaaaaat gtaaatgaag agactgcttt  9960
taggagtgaa ctgggaagca gggaacactt agaggatgct cactcacaca ggtatccacc  10020
atcaggcatg cctcaggcct gcacagggaa ggacaacttg tttcatgatt tgcaagcagc  10080
atcccatgct ccttagagcg ggttgggccc agcccaccct ctgtggagtt atcgctcagc  10140
caggcagcaa ggcagccaag gtgctgaggc cctggcagtc tgctctcttc tctgctctga  10200
acctccttta gctttagcct aggagcctgg cctggtgccc acaggctagg gagtccctag  10260
cctcttcctc ttctcagaga caatcaggtc ccggacccca cccctatgga actagaggcc  10320
ctgcagttgc ctgtgtcaga cttgcaaggg cttgacttgc agccccccagt gtccccaccg  10380
gatcaagtgg tgagtagact gagaggtggg caaagcttcc tgggtgggtg tacctgcagt  10440
gccaactgcc aggctgttaa ttcagtagga cactgtcccc aactggccca actgcacatc  10500
ctgtagtcag gaggcacagg cagaaaaatc ccaaattcaa ggcttgctcc cgttatgtaa  10560
tgagatcctg tcttggagta aaaaacaaag aagagaacta gggatagctc agaggtagat  10620
gctctcctgg catgggggtg gggtcagaaa gcaacaccaa ccggggcctg ggagggaggg  10680
actgccaacc acctggagga gtctggggta gacttggtga acaaagttca gaggccatca  10740
```

-continued

```
ggtgggatgc tggtttctta aaagccacag ataggtgggt agcattggaa agaggagtgg  10800
ggggttgcag aaagtgacaa gacacaaact ggggaggcct aagggtaaag ccagggttgt  10860
ctgaagcact gtggagctgg gaggaacacg ctaaacttct gacttcagcc cttcagttcc  10920
cctgttgact acactgtccc cagggaccca gggatgggga gaggtggacg ggggagggaa  10980
gtacgggact gatccagctc caggtcccaa ctctgatccc caccgacagg ctgaagaggc  11040
tgacctagtg gctgtccctg cccctgtggc tgaggcagag accacggtaa cgctgcagca  11100
gctccaggaa gccctggaag aagaggttct cacccggcag agcctgagcc gcgagctgga  11160
ggccatccgg accgccaacc agaacttctc caggtcaggg tcacagtgct ggggtgaggg  11220
gagaggagag cagcaaccct cgcagtctcc tcaccgatag gtcggctcac tcccctatct  11280
ttcccagcca actacaggag gccgaggtcc gaaaccgaga cctggaggcg catgttcggc  11340
agctacagga acggatggag atgctgcagg ccccaggagc cgcaggcgag tccctcacct  11400
gcttccagcc aagggggcac tgggtggaga tggggggcat gttgggtgtg tgaaccctcg  11460
gggcagggga ggagtccagg ctggggcacc gcagccgcgc cactgccttt ctcctccatc  11520
ctccacactc catacacctc tctcttctcc ttccagccat cacgggggtc cccagtcccc  11580
gggccacgga tccaccttcc catgtaagac ccctctctcc cctccccgat ccccatctta  11640
gatatgctac ccacagccct tctcccgtcc acgtttaggg tccattctcc ttgggggttc  11700
cagaagaaag ctgcccttca ctcatccatt cagcatgcac tatctaccag ctctccctcg  11760
tttcaggctt ctcgccaaat cctccccaag ggaactccct atactcccgt tctggcctcg  11820
actagattcc cgcactgcct ctcgccctgc tgctgggctc cgatcgggtc acctgtccct  11880
tctctctcca gctagatggc cccccggccg tggctgtggg ccagtgcccg ctggtggggc  11940
caggccccat gcaccgccgt cacctgctgc tccctgccag ggtatgtccc acgtccgccc  12000
accacgggcc tctgcctagc tctgcccact gagtgtcacc actgcttgct gtgcctctgt  12060
ggagctcggc ccaccgcagg gagggggggt attcgggcgg ccaatcaaca caggctgctg  12120
ctaagtagcc aatgacgagt tccaacagga gctctttctt gcgagcagac caactttagc  12180
tgcgggctgt ggggaccaga gatgcgctca gaggcccatc tatgggtata ggctgggcgg  12240
ctcccaggag ccagtgggcc cctgtagcct agtgctaatc caaccttctc tcctgcagat  12300
ccctaggcct ggcctatccg aggcgcgttg cctgctcctg ttcgccgctg ctctggctgc  12360
tgccgccaca ctgggctgca ctgggttggt ggcctatacc ggcggtctca ccccagtctg  12420
gtgtttcccg ggagccacct tcgcccccctg aaccctaaga ctccaagcca tctttcattt  12480
aggcctccta ggaaggtcga gcgaccaggg agcgacccaa agcgtctctg tgcccatcgc  12540
gcccccccc cccccccacc gctccgctcc acacttctgt gagcctgggt ccccacccag  12600
ctccgctcct tgtgatccagg cctgccacct ggcggccggg gagggaggaa cagggctcgt  12660
gcccagcacc cctggttcct gcagagctgg tagccaccgc tgctgcagca gctgggcatt  12720
cgccgacctt gctttactca gccccgacgt ggatgggcaa actgctcagc tcatccgatt  12780
tcactttttc actctcccag ccatcagtta caagccataa gcatgagccc cctatttcca  12840
gggacatccc attcccatag tgatggatca gcaagacctc tgccagcaca cacggagtct  12900
ttggcttcgg acagcctcac tcctggggggt tgctgcaact ccttccccgt gtacacgtct  12960
gcactctaac aacggagcca cagctgcact ccccctccc ccaaagcagt gtgggtattt  13020
attgatcttg ttatctgact cactgacaga ctccgggacc cacgttttag atgcattgag  13080
actcgacatt cctcggtatt tattgtctgt ccccacctac gacctccact cccgaccctt  13140
gcgaataaaa tacttctggt ctgccctaaa tcccgcgcaa tatctctgtt gtggaaagga  13200
aaccgccccg caggccaatg gagagtccaa tagagacaac caatggcttg agtgggagct  13260
agaggggagg caaagcgcac gaatcaggtt gaagggtggg gcttaggcat ccagccagta  13320
ggagagaagc aacaagccac cagagacacc accgcccccc accctccccc ccagctgtga  13380
cccagctgtg ccactcaagt ttggaaaaaa gtagggggtt gggccagcag cgggcacacc  13440
atcttcccac tgcgcctgcg caagccacgc gcatccgctt tttggaccga cactccagaa  13500
aagttgctgc aaactttcta gcgcgattcc ccgcccctcc tcccagctag atccaccgcc  13560
tacccgcggg gccgggaatt ccgaggggcg gagcacggcg cggagatggg aagggagggg  13620
gcccttcaag ggacccggga gatgggagcg gcttcgcgcc cttaaccctc cggacggccc  13680
attaccttct ccgttgctct gatagggaaa ctgaggccct gagtcagagg cacacaaggg  13740
gggaaggcca aaagcgcggc cagagacgga gggaaaacaa agaatcctga cagcccggga  13800
ggggggcgga cacacaggga caaggacaga cccgagtgca gagctgggtc tagtctttgg  13860
gagggggcca gaagactgca aggggaccgg ggggggggggc ggcgaggagg actgggcgga  13920
ggagggggct ggggaagccc gcgggaggcg gcaaaggagg gaggaacttt ccaaagttgc  13980
caaacatggc tacctcgcct gcggagccga gcgcggggcc cgcggctcgg ggggaggcgg  14040
cggcggcgac cgaggagcag gaggaggaag cgcgccagct tctgcagact ctgcaggcag  14100
ccgaggggga ggcggcggcg gccggggcgg gagatgcggc ggcggcggcg gactctgggt  14160
ccccgagtgg cccggggtct ccccgggaga ccgtgaccga ggtgcccact ggccttcgct  14220
tctcgcccga acaggtggca tgcgtgtgcg aggcgctgct gcaggcgggc cacgccggcc  14280
gcttgagccg cttcctgggc gcgctgcccc cggccgagcg cctacgtggc agcgatccgg  14340
tgctgcgcgc gcgggcccta gtggccttcc agcggggtga atacgccgag ctctaccaac  14400
ttctcgagag ccgccctttc cccgccgccc accacgcctt cctgcaggac ctctacctgc  14460
gcgcgcgcta ccacgaggcc gagcgggccc gtggccgtgc gctgggcgct gtggacaaat  14520
accggctgcg caagaagttc cctctgccca agaccatctg ggatggcgag gagaccgtct  14580
attgcttcaa ggagcgctcg cgagcggcgc tcaaggcctg ctaccgcggc aaccgctatc  14640
ccacgcctga cgagaagcgc cgcctggcca cgctcaccgg cctctcgctt acacaggtca  14700
gcaactggtt caagaaccgg cgacagcgcg accgcactgg gaccggcggt ggagcgcctt  14760
gcaaaaggtg aggggggaac cgaccctcct tcctcggtgg ccgctggagt ctgcgcaagt  14820
gacccttcac atccctcttc ggtggcgtcg gcgagtgcat aggctgagcg tggagagacc  14880
aggcacaccc tgggttctct gggcatcact gcctcagggg cagaggttgt tccagctact  14940
tctaagctgg gaacgcagtg ccaggaatgg ggggggggc gggggcggga cgggcagtga  15000
```

```
SEQ ID NO: 4           moltype = DNA  length = 1896
FEATURE                Location/Qualifiers
source                 1..1896
                       mol_type = genomic DNA
                       organism = Mus musculus
SEQUENCE: 4
atgtcagccg aagtgcggct gaggcagctc cagcagctgg tgctggaccc aggcttcctg  60
```

-continued

```
ggactggagc ccctgctcga ccttctcctg ggcgtccacc aggagctggg tgcctctcac  120
ctagcccagg acaagtatgt ggccgacttc ttgcagtggg tggagcccat tgcagcaagg  180
cttaaggagg tccgactgca gagggatgat tttgagattt tgaaggtgat cgggcgtggg  240
gcgttcagcg aggtagcggt ggtgaagatg aaacagacgg gccaagtgta tgccatgaag  300
attatgaata agtgggacat gctgaagaga ggcgaggtgt cgtgcttccg ggaagaaagg  360
gatgtattag tgaaagggga ccggcgctgg atcacacagc tgcactttgc cttccaggat  420
gagaactacc tgtacctggt catggaatac tacgtgggcg gggacctgct aacgctgctg  480
agcaagtttg gggagcggat ccccgccgag atggctcgct tctacctggc cgagattgtc  540
atggccatag actccgtgca ccggctgggc tacgtgcaca gggacatcaa accagataac  600
attctgctgg accgatgtgg gcacattcgc ctggcagact tcggctcctg cctcaaactg  660
cagcctgatg gaatggtgag gtcgctggtg gctgtgggca ccccggacta cctgtctcct  720
gagattctgc aggccgttgg tggagggcct ggggcaggca gctacgggcc agagtgtgac  780
tggtgggcac tgggcgtgtt cgcctatgag atgttctatg ggcagacccc cttctacgcg  840
gactccacag ccgagacata tgccaagatt gtgcactaca gggaacactt gtcgctgccg  900
ctggcagaca cagttgtccc cgaggaagct caggacctca ttcgtgggct gctgtgtcct  960
gctgagataa ggctaggtcg aggtggggca ggtgatttcc agaaacatcc tttcttcttt  1020
ggccttgatt gggagggtct ccgagacagt gtaccccct ttacaccaga cttcgagggt  1080
gccacggaca catgcaattt cgatgtggtg gaggaccggc tcactgccat ggtgagcggg  1140
ggcggggaga cgctgtcaga catgcaggaa gacatgcccc ttggggtgcg cctgcccttc  1200
gtgggctact cctactgctg catggccttc agagacaatc aggtcccgga ccccacccct  1260
atggaactag aggccctgca gttgcctgtg tcagacttgc aagggcttga cttgcagccc  1320
ccagtgtccc caccggatca agtggctgaa gaggccgacc tagtggctgt ccctgcccct  1380
gtggctgagg cagagaccac ggtaacgctg cagcagctcc aggaagccct ggaagaagag  1440
gttctcaccc ggcagagcct gagccgcgag ctggaggcca tccggaccgc caaccagaac  1500
ttctccagcc aactacagga ggccgaggtc cgaaaccgag acctggaggc gcatgttcgg  1560
cagctacagg aacggatgga gatgctgcag gccccaggag ccgcagccat cacgggggtc  1620
cccagtcccc gggccacgga tccaccttcc catctagatg gcccccggc cgtggctgtg  1680
ggccagtgcc cgctggtggg gccaggcccc atgcaccgcc gtcacctgct gctccctgcc  1740
aggatcccta ggcctggcct atccgaggcg cgttgcctgc tcctgttcgc cgctgctctg  1800
gctgctgccg ccacactggg ctgcactggg ttggtggcct ataccggcgg tctcacccca  1860
gtctggtgtt tcccgggagc caccttcgcc ccctga                          1896
```

```
SEQ ID NO: 5            moltype = DNA  length = 771
FEATURE                 Location/Qualifiers
misc_feature            89
                        note = n is a, c, g, or t
misc_feature            238
                        note = n is a, c, g, or t
misc_feature            506
                        note = n is a, c, g, or t
source                  1..771
                        mol_type = genomic DNA
                        organism = Mus musculus
SEQUENCE: 5
cctgcccctg tggctgaggc agagaccacg gtaacgctgc agcagctcca ggaagccctg  60
gaagaagagg ttctcacccg gcagagctng agccgcgagc tggaggccat ccggaccgcc  120
aaccagaact tctccagcca actacaggag gccgaggtcc gaaaccgaga cctggaggcg  180
catgttcggc agctacagga acggatggag atgctgcagg ccccaggagc cgccggantc  240
cctcacctgc ttccagccaa gggggcactg ggtggagatg gggggcatgt tgggtgtgtg  300
aaccctcggg gcaggggagg agtccaggct ggggcaccgc gccgcgccac tgcctttctc  360
ctccatcctc cacactccat acacctctct cttctccttc cagccatcac gggggtccca  420
gtccccgggc cacggatcca ccttcccatc tagatggccc cccggcggtg gctgtgggcc  480
agtgcccgct ggtggggcca ggacantgtc accgccgtca cctgctgctc cctgccagga  540
ttcctaggcc tggctatccg aggcgcgttg ctgctcctgt tcgccgctgc tctggctgct  600
gcgccacact gggctgcact gggttggttg gctataccgg cggtcttcac ccagtctggt  660
gtttcccgtg agcacccttc gcccctgaaa cctaagactt caagccatct ttcatttagg  720
ccttctagga aggtcgagcg acaggggagc gacccaaagc gtctctgtgc c          771
```

```
SEQ ID NO: 6            moltype = DNA  length = 434
FEATURE                 Location/Qualifiers
source                  1..434
                        mol_type = genomic DNA
                        organism = Mus musculus
SEQUENCE: 6
gagagaccca aggggtagtc agggacgggc agacatgcag ctagggttct ggggcctgga  60
caggggcagc caggccctgt gacgggaaga ccccgagctc cggcccgggg aggggccatg  120
gtgttgcctg cccaacatgt cagccgaagt gcggctgagg cagctccagc agctggtgct  180
ggacccaggc ttcctgggac tggagcccct gctcgacctt ctcctgggcg tccaccagga  240
gctgggtgcc tctcacctag cccaggacaa gtatgtggcc gacttcttgc agtgggtgga  300
gcccattgca gcaaggctta aggaggtccg actgcagagg gatgattttg agattttgaa  360
ggtgatcggg cgtggggcgt tcagcgaggt agcggtggtg aagatgaaac acacggagtc  420
tttggcttcg gaca                                                   434
```

```
SEQ ID NO: 7            moltype = DNA  length = 2688
FEATURE                 Location/Qualifiers
source                  1..2688
                        mol_type = genomic DNA
                        organism = Mus musculus
SEQUENCE: 7
```

-continued

```
ccacgcgtcc gcccacgcgt ccggggcaga catgcagcta gggttctggg gcctggacag  60
gggcagccag gccctgtgac gggaagaccc cgagctccgg cccggggagg ggccatggtg  120
ttgcctgccc aacatgtcag ccgaagtgcg gctgaggcag ctccagcagc tggtgctgga  180
cccaggcttc ctgggactgg agcccctgct cgaccttctc ctgggcgtcc accaggagct  240
gggtgcctct cacctagccc aggacaagta tgtggccgac ttcttgcagt gggtggagcc  300
cattgcagca aggcttaagg aggtccgact gcagagggat gattttgaga ttttgaaggt  360
gatcgggcgt ggggcgttca gcgaggtagc ggtggtgaag atgaaacaga cgggccaagt  420
gtatgccatg aagattatga ataagtggga catgctgaag agaggcgagg tgtcgtgctt  480
ccgggaagaa agggatgtat tagtgaaagg ggaccggcgc tggatcacac agctgcactt  540
tgccttccag gatgagaact acctgtacct ggtcatggaa tactacgtgg gcggggacct  600
gctaacgctg ctgagcaagt ttggggagcg gatccccgcc gagatggctc gcttctacct  660
ggccgagatt gtcatggcca tagactccgt gcaccggctg ggctacgtgc acagggacat  720
caaaccagat aacattctgc tggaccgatg tgggcacatt cgcctggcag acttcggctc  780
ctgcctcaaa ctgcagcctg atggaatggt gaggtcgctg gtggctgtgg gcaccccgga  840
ctacctgtct cctgagattc tgcaggccgt tggtggaggg cctggggcag gcagctacgg  900
gccagagtgt gactggtggg cactgggcgt gttcacctat gagatgttct atgggcagac  960
cccctctac gcggactcca cagccgagac atatgccaag attgtgcact acagggaaca  1020
cttgtcgctg ccgctggcag acacagttgt ccccgaggaa gctcaggacc tcattcgtgg  1080
gctgctgtgt cctgctgaga taaggctagg tcgaggtggg gcaggtgatt tccagaaaca  1140
tcctttcttc tttggccttg attgggaggg tctccgagac agtgtacccc cctttacacc  1200
agacttcgag ggtgccacgg acacatgcaa tttcgatgtg gtggaggacc ggctcactgc  1260
catggtgagc gggggcgggg agacgctgtc agacatgcag gaagacatgc cccttggggt  1320
gcgcctgccc ttcgtgggct actcctactg ctgcatggcc ttcagagaca atcaggtccc  1380
ggaccccacc cctatggaac tagaggccct gcagttgcct gtgtcagact tgcaagggct  1440
tgacttgcag cccccagtgt ccccaccgga tcaagtggct gaagaggctg acctagtggc  1500
tgtccctgcc cctgtggctg aggcagagac cacggtaacg ctgcagcagc tccaggaagc  1560
cctggaagaa gaggttctca cccggcagag cctgagccgc gagctggagg ccatccggac  1620
cgccaaccag aacttctcca gccaactaca ggaggccgag gtccgaaacc gagacctgga  1680
ggcgcatgtt cggcagctac aggaacggat ggagatgctg caggccccag gagccgcaga  1740
tccctaggcc tggcctatcc gaggcgcgtt gcctgctcct gttcgccgct gctctggctg  1800
ctgccgccac actgggctgc actgggttgg tggcctatac cggcggtctc accccagtct  1860
ggtgtttccc gggagccacc ttcgcccccct gaaccctaag actccaagcc atctttcatt  1920
taggcctcct aggaaggtcg agcgaccagg gagcgaccca aagcgtctct gtgcccatcg  1980
cccccccccc ccccccacc gctccgctcc acacttctgt gagcctgggt ccccacccag  2040
ctccgctcct gtgatccagg cctgccacct ggcggccggg gagggaggaa cagggctcgt  2100
gcccagcacc cctggttcct gcagagctgg tagccaccgc tgctgcagca gctgggcatt  2160
cgccgacctt gctttactca gccccgacgt ggatgggcaa actgctcagc tcatccgatt  2220
tcactttttc actctcccag ccatcagtta caagccataa gcatgagccc cctatttcca  2280
gggacatccc attcccatag tgatggatca gcaagacctc tgccagcaca cacggagtct  2340
ttggcttcgg acagcctcac tcctgggggt tgctgcaact ccttccccgt gtacacgtct  2400
gcactctaac aacggagcca cagctgcact cccccctccc ccaaagcagt gtgggtattt  2460
attgatcttg ttatctgact cactgacaga ctccgggacc cacgttttag atgcattgag  2520
actcgacatt cctcggtatt tattgtctgt ccccacctac gacctccact cccgaccctt  2580
gcgaataaaa tacttctggt ctgccctaaa aaaaaaaaaa aaaaaaaaaa aaaaaaaaaa  2640
aaaaaaaaaa aaaaaaaaaa aaaaaaaaaa aaaaaaaaaa aaaaaaaa  2688

SEQ ID NO: 8            moltype = DNA  length = 2862
FEATURE                 Location/Qualifiers
source                  1..2862
                        mol_type = genomic DNA
                        organism = Mus musculus
SEQUENCE: 8
gggatagtca gggacgggca gacatgcagc tagggttctg gggcctggac aggggcagcc  60
aggccctgtg acgggaagac cccgagctcc ggcccgggga ggggccatgg tgttgcctgc  120
ccaacatgtc agccgaagtg cggctgaggc agctccagca gctggtgctg gacccaggct  180
tcctgggact ggagcccctg ctcgaccttc tcctgggcgt ccaccaggag ctgggtgcct  240
ctcacctagc ccaggacaag tatgtggccg acttcttgca gtgggtggag cccattgcag  300
caaggcttaa ggaggtccga ctgcagaggg atgattttga gattttgaag gtgatcgggc  360
gtggggcgtt cagcgaggta gcggtggtga agatgaaaca gacgggccaa gtgtatgcca  420
tgaagattac gaataagtgg gacatgctga agagaggcga ggtgtcgtgc ttccgggaag  480
aaagggatgt attagtgaaa ggggaccggc gctggatcac acagctgcac tttgccttcc  540
aggatgagaa ctacctgtac ctggtcatgg aatactacgt gggcggggac ctgctaacgc  600
tgctgagcaa gtttggggag cggatccccg ccgagatggc tcgcttctac ctggccgaga  660
ttgtcatggc catagactcc gtgcaccggc tgggctacgt gcacagggac atcaaaccag  720
ataacattct gctggaccga tgtgggcaca ttcgcctggc agacttcggc tcctgcctca  780
aactgcagcc tgatggaatg gtgaggtcgc tggtggctgt gggcaccccg gactacctgt  840
ctcctgagat tctgcaggcc gttggtggag ggcctggggc aggcagctac gggccagagt  900
gtgactggtg ggcactgggc gtgttcacct atgagatgtt ctatgggcag acccccttct  960
acgcggactc cacagccgag acatatgcca agattgtgca ctacagggaa cacttgtcgc  1020
tgccgctggc agacacagtt gtccccgagg aagctcagga cctcattcgt gggctgctgt  1080
gtcctgctga gataaggcta ggtcgaggtg gggcaggtga tttccagaaa catcctttct  1140
tctttggcct tgattgggag ggtctccgag acagtgtacc cccctttaca ccagacttcg  1200
agggtgccac ggacacatgc aatttcgatg tggtggagga ccggctcact gccatggaga  1260
cgctgtcaga catgcaggaa gacatgcccc ttggggtgcg cctgcccttc gtgggctact  1320
cctactgctg catggccttc agagacaatc aggtcccgga ccccacccct atggaactag  1380
aggccctgca gttgcctgtg tcagacttgc aagggcttga cttgcagccc ccagtgtccc  1440
caccggatca agtggctgaa gaggctgacc tagtggctgt ccctgcccct gtggctgagg  1500
cagagaccac ggtaacgctg cagcagctcc aggaagccct ggaagaagag gttctcaccc  1560
ggcagagcct gagccgcgag ctggaggcca tccggaccgc caaccagaac ttctccagcc  1620
```

-continued

```
aactacagga ggccgaggtc cgaaaccgag acctggaggc gcatgttcgg cagctacagg  1680
aacggatgga gatgctgcag gccccaggag ccgcagccat cacgggggtc cccagtcccc  1740
gggccacgga tccaccttcc catgcttctc gccaaatcct ccccaaggga actccctaga  1800
ctcccgttct ggcctcgact agattcccgc actgcctctc gccctgctgc tgggctccga  1860
tcgggtcacc tgtcccttct ctctccagct agatggcccc ccggccgtgg ctgtgggcca  1920
gtgcccgctg gtggggccag gccccatgca ccgccgtcac ctgctgctcc ctgccaggat  1980
ccctaggcct ggcctatccg aggcgcgttg cctgctcctg ttcgccgctg ctctggctgc  2040
tgccgccaca ctgggctgca ctgggttggt ggcctatacc ggcggtctca ccccagtctg  2100
gtgtttcccg ggagccacct tcgccccctg aaccctaaga ctccaagcca tctttcattt  2160
aggcctccta ggaaggtcga gcgaccaggg agcgacccaa agcgtctctg tgcccatcgc  2220
cccccccccc ccccccaccg ctccgctcca cacttctgtg agcctgggtc cccacccagc  2280
tccgctcctg tgatccaggc ctgccacctg gcggccgggg agggaggaac agggctcgtg  2340
cccagcaccc ctggttcctg cagagctggt agccaccgct gctgcagcag ctgggcattc  2400
gccgaccttg ctttactcag ccccgacgtg gatgggcaaa ctgctcagct catccgattt  2460
cactttttca ctctcccagc catcagttac aagccataag catgagcccc ctatttccag  2520
ggacatccca ttcccatagt gatggatcag caagacctct gccagcacac acggagtctt  2580
tggcttcgga cagcctcact cctgggggtt gctgcaactc cttccccgtg tacacgtctg  2640
cactctaaca acggagccac agctgcactc ccccctcccc caaagcagtg tgggtattta  2700
ttgatcttgt tatctgactc actgacagac tccgggaccc acgttttaga tgcattgaga  2760
ctcgacattc ctcggtattt attgtctgtc cccacctacg acctccactc ccgacccttg  2820
cgaataaaat acttctggtc tgccctaaaa aaaaaaaaaa aa                    2862

SEQ ID NO: 9           moltype = DNA  length = 18
FEATURE                Location/Qualifiers
misc_feature           1..18
                       note = Primer
source                 1..18
                       mol_type = other DNA
                       organism = synthetic construct
SEQUENCE: 9
agcctgagcc gggagatg                                                18

SEQ ID NO: 10          moltype = DNA  length = 21
FEATURE                Location/Qualifiers
misc_feature           1..21
                       note = Primer
source                 1..21
                       mol_type = other DNA
                       organism = synthetic construct
SEQUENCE: 10
gcgtagttga ctggcgaagt t                                            21

SEQ ID NO: 11          moltype = DNA  length = 21
FEATURE                Location/Qualifiers
misc_feature           1..21
                       note = Probe
source                 1..21
                       mol_type = other DNA
                       organism = synthetic construct
SEQUENCE: 11
aggccatccg cacggacaac c                                            21

SEQ ID NO: 12          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 12
ctggctgcat gtctgcctgt                                              20

SEQ ID NO: 13          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 13
ccaggagaag gtcgagcagg                                              20

SEQ ID NO: 14          moltype = DNA  length = 20
FEATURE                Location/Qualifiers
misc_feature           1..20
                       note = Synthetic oligonucleotide
source                 1..20
                       mol_type = other DNA
                       organism = synthetic construct
```

```
SEQUENCE: 14
tctatggcca tgacaatctc                                              20

SEQ ID NO: 15          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 15
atgtccctgt gcacgtagcc                                              20

SEQ ID NO: 16          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 16
atgtgtccgg aagtcgcctg                                              20

SEQ ID NO: 17          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 17
ctcaggctct gccgggtgag                                              20

SEQ ID NO: 18          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 18
ggcactggcc cacagccacg                                              20

SEQ ID NO: 19          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 19
cctggccgaa agaaagaaat                                              20

SEQ ID NO: 20          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 20
aaagaaatgg tctgtgatcc                                              20

SEQ ID NO: 21          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 21
aagaaagaaa tggtctgtga                                              20

SEQ ID NO: 22          moltype = DNA  length = 20
FEATURE                Location/Qualifiers
misc_feature           1..20
                       note = Synthetic oligonucleotide
source                 1..20
                       mol_type = other DNA
```

```
                        organism = synthetic construct
SEQUENCE: 22
ggccgaaaga aagaaatggt                                           20

SEQ ID NO: 23           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 23
cctcagcctg gccgaaagaa                                           20

SEQ ID NO: 24           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 24
gggcctcagc ctggccgaaa                                           20

SEQ ID NO: 25           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 25
tcagggcctc agcctggccg                                           20

SEQ ID NO: 26           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 26
ctgcagtttg cccatccacg                                           20

SEQ ID NO: 27           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 27
ggcctgcagt ttgcccatcc                                           20

SEQ ID NO: 28           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 28
ccaggcctgc agtttgccca                                           20

SEQ ID NO: 29           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 29
gccttcccag gcctgcagtt                                           20

SEQ ID NO: 30           moltype = DNA  length = 20
FEATURE                 Location/Qualifiers
misc_feature            1..20
                        note = Synthetic oligonucleotide
source                  1..20
```

```
                       mol_type = other DNA
                       organism = synthetic construct
SEQUENCE: 30
gctgccttcc caggcctgca                                              20

SEQ ID NO: 31          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 31
cttgctgcct tcccaggcct                                              20

SEQ ID NO: 32          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 32
gcccggcttg ctgccttccc                                              20

SEQ ID NO: 33          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 33
acggcccggc ttgctgcctt                                              20

SEQ ID NO: 34          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 34
cggacggccc ggcttgctgc                                              20

SEQ ID NO: 35          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 35
acacggacgg cccggcttgc                                              20

SEQ ID NO: 36          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 36
gatggaacac ggacggcccg                                              20

SEQ ID NO: 37          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 37
gaggatggaa cacggacggc                                              20

SEQ ID NO: 38          moltype = DNA  length = 20
FEATURE                Location/Qualifiers
misc_feature           1..20
                       note = Synthetic oligonucleotide
```

```
source                  1..20
                        mol_type = other DNA
                        organism = synthetic construct
SEQUENCE: 38
gtggaggatg gaacacggac                                                    20

SEQ ID NO: 39           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 39
gcgaaccaac gataggtggg                                                    20

SEQ ID NO: 40           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 40
tttgcgaacc aacgataggt                                                    20

SEQ ID NO: 41           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 41
ttgcactttg cgaaccaacg                                                    20

SEQ ID NO: 42           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 42
gctttgcact ttgcgaacca                                                    20

SEQ ID NO: 43           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 43
aaagctttgc actttgcgaa                                                    20

SEQ ID NO: 44           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 44
aagaaagctt tgcactttgc                                                    20

SEQ ID NO: 45           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 45
cacaagaaag ctttgcactt                                                    20

SEQ ID NO: 46           moltype = DNA  length = 20
FEATURE                 Location/Qualifiers
misc_feature            1..20
```

-continued

```
                         note = Synthetic oligonucleotide
source                   1..20
                         mol_type = other DNA
                         organism = synthetic construct
SEQUENCE: 46
gtcatgcaca agaaagcttt                                                20

SEQ ID NO: 47            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 47
acgctcccca gagcagggcg                                                20

SEQ ID NO: 48            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 48
gcagagatcg cgccagacgc                                                20

SEQ ID NO: 49            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 49
caggcagaga tcgcgccaga                                                20

SEQ ID NO: 50            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 50
aagcaggcag agatcgcgcc                                                20

SEQ ID NO: 51            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 51
ccgagtaagc aggcagagat                                                20

SEQ ID NO: 52            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 52
ttcccgagta agcaggcaga                                                20

SEQ ID NO: 53            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 53
gcaaatttcc cgagtaagca                                                20

SEQ ID NO: 54            moltype = DNA  length = 20
FEATURE                  Location/Qualifiers
```

```
misc_feature          1..20
                      note = Synthetic oligonucleotide
source                1..20
                      mol_type = other DNA
                      organism = synthetic construct
SEQUENCE: 54
aaagcaaatt tcccgagtaa                                              20

SEQ ID NO: 55         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 55
ttggcaaaag caaatttccc                                              20

SEQ ID NO: 56         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 56
ggtttggcaa aagcaaattt                                              20

SEQ ID NO: 57         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 57
gcgggtttgg caaaagcaaa                                              20

SEQ ID NO: 58         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 58
aaagcgggtt tggcaaaagc                                              20

SEQ ID NO: 59         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 59
cccgaaaaag cgggtttggc                                              20

SEQ ID NO: 60         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 60
atccccgaaa aagcgggttt                                              20

SEQ ID NO: 61         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 61
cgggatcccc gaaaaagcgg                                              20

SEQ ID NO: 62         moltype = DNA  length = 20
```

-continued

```
FEATURE                 Location/Qualifiers
misc_feature            1..20
                        note = Synthetic oligonucleotide
source                  1..20
                        mol_type = other DNA
                        organism = synthetic construct
SEQUENCE: 62
gcgcgggatc cccgaaaaag                                                       20

SEQ ID NO: 63           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 63
gagagcagcg caagtgagga                                                       20

SEQ ID NO: 64           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 64
tccgagagca gcgcaagtga                                                       20

SEQ ID NO: 65           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 65
ggctccgaga gcagcgcaag                                                       20

SEQ ID NO: 66           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 66
aagcgggcgg agccggctgg                                                       20

SEQ ID NO: 67           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 67
ccgaagcggg cggagccggc                                                       20

SEQ ID NO: 68           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 68
aaaccgccga agcgggcgga                                                       20

SEQ ID NO: 69           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 69
tccaaaccgc cgaagcgggc                                                       20
```

```
SEQ ID NO: 70           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 70
atatccaaac cgccgaagcg                                              20

SEQ ID NO: 71           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 71
taaatatcca aaccgccgaa                                              20

SEQ ID NO: 72           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 72
caataaatat ccaaaccgcc                                              20

SEQ ID NO: 73           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 73
cgaggtcaat aaatatccaa                                              20

SEQ ID NO: 74           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 74
ggacgaggtc aataaatatc                                              20

SEQ ID NO: 75           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 75
ggaggacgag gtcaataaat                                              20

SEQ ID NO: 76           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 76
gtcggaggac gaggtcaata                                              20

SEQ ID NO: 77           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 77
cgagtcggag gacgaggtca                                              20
```

-continued

```
SEQ ID NO: 78           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 78
tgtcagcgag tcggaggacg                                                 20

SEQ ID NO: 79           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 79
gcctgtcagc gagtcggagg                                                 20

SEQ ID NO: 80           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 80
gtagcctgtc agcgagtcgg                                                 20

SEQ ID NO: 81           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 81
cctgtagcct gtcagcgagt                                                 20

SEQ ID NO: 82           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 82
ggtcctgtag cctgtcagcg                                                 20

SEQ ID NO: 83           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 83
aaataccgag gaatgtcggg                                                 20

SEQ ID NO: 84           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 84
aataaatacc gaggaatgtc                                                 20

SEQ ID NO: 85           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 85
```

```
gacaataaat accgaggaat                                              20

SEQ ID NO: 86          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 86
cggggccccg gagtcgaaga                                              20

SEQ ID NO: 87          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 87
ccaacggggc cccggagtcg                                              20

SEQ ID NO: 88          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 88
ttccaacggg gccccggagt                                              20

SEQ ID NO: 89          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 89
gtcttccaac ggggccccgg                                              20

SEQ ID NO: 90          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 90
cagtcttcca acggggcccc                                              20

SEQ ID NO: 91          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 91
ctcagtcttc caacggggcc                                              20

SEQ ID NO: 92          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 92
gcactcagtc ttccaacggg                                              20

SEQ ID NO: 93          moltype = DNA  length = 20
FEATURE                Location/Qualifiers
misc_feature           1..20
                       note = Synthetic oligonucleotide
source                 1..20
                       mol_type = other DNA
                       organism = synthetic construct
```

```
SEQUENCE: 93
ccccgggcac tcagtcttcc                                                20

SEQ ID NO: 94          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 94
tgccccgggc actcagtctt                                                20

SEQ ID NO: 95          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 95
cgtgccccgg gcactcagtc                                                20

SEQ ID NO: 96          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 96
gtgccgtgcc ccgggcactc                                                20

SEQ ID NO: 97          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 97
tctgtgccgt gccccgggca                                                20

SEQ ID NO: 98          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 98
gcttctgtgc cgtgccccgg                                                20

SEQ ID NO: 99          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 99
gcggcttctg tgccgtgccc                                                20

SEQ ID NO: 100         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 100
gcgcggcttc tgtgccgtgc                                                20

SEQ ID NO: 101         moltype = DNA  length = 20
FEATURE                Location/Qualifiers
misc_feature           1..20
                       note = Synthetic oligonucleotide
source                 1..20
                       mol_type = other DNA
```

```
                       organism = synthetic construct
SEQUENCE: 101
gggcgcggct tctgtgccgt                                                   20

SEQ ID NO: 102         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 102
ggcggtgggc gcggcttctg                                                   20

SEQ ID NO: 103         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 103
ggcaggcggt gggcgcggct                                                   20

SEQ ID NO: 104         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 104
ctggcaggcg gtgggcgcgg                                                   20

SEQ ID NO: 105         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 105
aactggcagg cggtgggcgc                                                   20

SEQ ID NO: 106         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 106
gtgaactggc aggcggtggg                                                   20

SEQ ID NO: 107         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 107
ggttgtgaac tggcaggcgg                                                   20

SEQ ID NO: 108         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 108
gcggttgtga actggcaggc                                                   20

SEQ ID NO: 109         moltype = DNA  length = 20
FEATURE                Location/Qualifiers
misc_feature           1..20
                       note = Synthetic oligonucleotide
source                 1..20
```

-continued

```
                        mol_type = other DNA
                        organism = synthetic construct
SEQUENCE: 109
cggagcggtt gtgaactggc                                                  20

SEQ ID NO: 110          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 110
cgctcggagc ggttgtgaac                                                  20

SEQ ID NO: 111          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 111
cccacgctcg gagcggttgt                                                  20

SEQ ID NO: 112          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 112
agacccacgc tcggagcggt                                                  20

SEQ ID NO: 113          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 113
cggagaccca cgctcggagc                                                  20

SEQ ID NO: 114          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 114
gggcggagac ccacgctcgg                                                  20

SEQ ID NO: 115          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 115
gctgggcgga gacccacgct                                                  20

SEQ ID NO: 116          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 116
ggagctgggc ggagacccac                                                  20

SEQ ID NO: 117          moltype = DNA  length = 20
FEATURE                 Location/Qualifiers
misc_feature            1..20
                        note = Synthetic oligonucleotide
```

```
source                  1..20
                        mol_type = other DNA
                        organism = synthetic construct
SEQUENCE: 117
ctggagctgg gcggagaccc                                               20

SEQ ID NO: 118          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 118
ggactggagc tgggcggaga                                               20

SEQ ID NO: 119          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 119
caggactgga gctgggcgga                                               20

SEQ ID NO: 120          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 120
atcacaggac tggagctggg                                               20

SEQ ID NO: 121          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 121
gggcgggccc ggatcacagg                                               20

SEQ ID NO: 122          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 122
gggggcgggc ccggatcaca                                               20

SEQ ID NO: 123          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 123
aggcagcacc atggcccctc                                               20

SEQ ID NO: 124          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 124
ggtccaacac cagctgctgg                                               20

SEQ ID NO: 125          moltype = DNA  length = 20
FEATURE                 Location/Qualifiers
misc_feature            1..20
```

-continued

```
                        note = Synthetic oligonucleotide
source                  1..20
                        mol_type = other DNA
                        organism = synthetic construct
SEQUENCE: 125
cgatcacctt cagaatctcg                                           20

SEQ ID NO: 126          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 126
cttgttcatg atcttcatgg                                           20

SEQ ID NO: 127          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 127
ccccattcac caacacgtcc                                           20

SEQ ID NO: 128          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 128
gcgtgatcca ccgccggtcc                                           20

SEQ ID NO: 129          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 129
gtaatactcc atgaccaggt                                           20

SEQ ID NO: 130          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 130
gcagtgtcag caggtccccg                                           20

SEQ ID NO: 131          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 131
caccgagtct atggccatga                                           20

SEQ ID NO: 132          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 132
acgtagccaa gccggtgcac                                           20

SEQ ID NO: 133          moltype = DNA  length = 20
FEATURE                 Location/Qualifiers
```

-continued

```
misc_feature          1..20
                      note = Synthetic oligonucleotide
source                1..20
                      mol_type = other DNA
                      organism = synthetic construct
SEQUENCE: 133
atgtggccac agcggtccag                                              20

SEQ ID NO: 134        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 134
cttcgtccac cagcggcaga                                              20

SEQ ID NO: 135        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 135
gacccccttcg tccaccagcg                                             20

SEQ ID NO: 136        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 136
cctgctccac cccggcccag                                              20

SEQ ID NO: 137        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 137
cggaagtcgc ctgctccacc                                              20

SEQ ID NO: 138        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 138
cggagaccat cccagtcgag                                              20

SEQ ID NO: 139        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 139
tgagggccat gcaggagtag                                              20

SEQ ID NO: 140        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 140
ctccagttcc atgggtgtgg                                              20

SEQ ID NO: 141        moltype = DNA  length = 20
```

-continued

```
FEATURE                Location/Qualifiers
misc_feature           1..20
                       note = Synthetic oligonucleotide
source                 1..20
                       mol_type = other DNA
                       organism = synthetic construct
SEQUENCE: 141
gcgcttgcac gtgtggctca                                              20

SEQ ID NO: 142         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 142
gccacttcag ctgtttcatc                                              20

SEQ ID NO: 143         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 143
gcctcagcct ctgccgcagg                                              20

SEQ ID NO: 144         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 144
gcagcgtcac ctcggcctca                                              20

SEQ ID NO: 145         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 145
ggctcaggct ctgccgggtg                                              20

SEQ ID NO: 146         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 146
ttccgagcct ctgcctcgcg                                              20

SEQ ID NO: 147         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 147
ggtcccggtt ccgagcctct                                              20

SEQ ID NO: 148         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 148
atccgctcct gcaactgccg                                              20
```

-continued

```
SEQ ID NO: 149          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 149
gcaactccat ccgctcctgc                                              20

SEQ ID NO: 150          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 150
aggtggatcc gtggcccggg                                              20

SEQ ID NO: 151          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 151
cgcggcttct gtgccgtgcc                                              20

SEQ ID NO: 152          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 152
ttgctgcctt cccaggcctg                                              20

SEQ ID NO: 153          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 153
tgctcccgac aagctccaga                                              20

SEQ ID NO: 154          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 154
agaacctgcc cattgctgaa                                              20

SEQ ID NO: 155          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 155
cactgagggc cagacatatg                                              20

SEQ ID NO: 156          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 156
ctctagattc agatgcaggt                                              20
```

```
SEQ ID NO: 157          moltype = DNA  length = 15
FEATURE                 Location/Qualifiers
misc_feature            1..15
                        note = Primer
source                  1..15
                        mol_type = other DNA
                        organism = synthetic construct
SEQUENCE: 157
cgggccgtcc gtgtt                                                   15

SEQ ID NO: 158          moltype = DNA  length = 20
FEATURE                 Location/Qualifiers
misc_feature            1..20
                        note = Primer
source                  1..20
                        mol_type = other DNA
                        organism = synthetic construct
SEQUENCE: 158
ctttgcactt tgcgaaccaa                                              20

SEQ ID NO: 159          moltype = DNA  length = 21
FEATURE                 Location/Qualifiers
misc_feature            1..21
                        note = Probe
source                  1..21
                        mol_type = other DNA
                        organism = synthetic construct
SEQUENCE: 159
catcctccac gcaccccac c                                             21

SEQ ID NO: 160          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 160
gcctggcagc ccctgtccag                                              20

SEQ ID NO: 161          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 161
ggcctggcag cccctgtcca                                              20

SEQ ID NO: 162          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 162
gggcctggca gcccctgtcc                                              20

SEQ ID NO: 163          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 163
atggcccctc cccgggccgg                                              20

SEQ ID NO: 164          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 164
```

```
catggcccct ccccgggccg                                              20

SEQ ID NO: 165          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 165
ccatggcccc tccccgggcc                                              20

SEQ ID NO: 166          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 166
accatggccc ctccccgggc                                              20

SEQ ID NO: 167          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 167
caccatggcc cctccccggg                                              20

SEQ ID NO: 168          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 168
gcaccatggc ccctccccgg                                              20

SEQ ID NO: 169          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 169
agcaccatgg cccctccccg                                              20

SEQ ID NO: 170          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 170
cagcaccatg gcccctcccc                                              20

SEQ ID NO: 171          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 171
gcagcaccat ggcccctccc                                              20

SEQ ID NO: 172          moltype = DNA  length = 20
FEATURE                 Location/Qualifiers
misc_feature            1..20
                        note = Synthetic oligonucleotide
source                  1..20
                        mol_type = other DNA
                        organism = synthetic construct
```

-continued

```
SEQUENCE: 172
ggcagcacca tggcccctcc                                        20

SEQ ID NO: 173         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 173
caggcagcac catggcccct                                        20

SEQ ID NO: 174         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 174
acaggcagca ccatggcccc                                        20

SEQ ID NO: 175         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 175
ggacaggcag caccatggcc                                        20

SEQ ID NO: 176         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 176
tggacaggca gcaccatggc                                        20

SEQ ID NO: 177         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 177
ttggacaggc agcaccatgg                                        20

SEQ ID NO: 178         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 178
gttggacagg cagcaccatg                                        20

SEQ ID NO: 179         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 179
tgttggacag gcagcaccat                                        20

SEQ ID NO: 180         moltype = DNA  length = 20
FEATURE                Location/Qualifiers
misc_feature           1..20
                       note = Synthetic oligonucleotide
source                 1..20
                       mol_type = other DNA
```

```
                        organism = synthetic construct
SEQUENCE: 180
atgttggaca ggcagcacca                                              20

SEQ ID NO: 181          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 181
catgttggac aggcagcacc                                              20

SEQ ID NO: 182          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 182
acatgttgga caggcagcac                                              20

SEQ ID NO: 183          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 183
gacatgttgg acaggcagca                                              20

SEQ ID NO: 184          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 184
tgacatgttg gacaggcagc                                              20

SEQ ID NO: 185          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 185
ctgacatgtt ggacaggcag                                              20

SEQ ID NO: 186          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 186
gctgacatgt tggacaggca                                              20

SEQ ID NO: 187          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 187
ggctgacatg ttggacaggc                                              20

SEQ ID NO: 188          moltype = DNA  length = 20
FEATURE                 Location/Qualifiers
misc_feature            1..20
                        note = Synthetic oligonucleotide
source                  1..20
```

```
                        mol_type = other DNA
                        organism = synthetic construct
SEQUENCE: 188
cggctgacat gttggacagg                                            20

SEQ ID NO: 189          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 189
tcggctgaca tgttggacag                                            20

SEQ ID NO: 190          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 190
ctcggctgac atgttggaca                                            20

SEQ ID NO: 191          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 191
cctcggctga catgttggac                                            20

SEQ ID NO: 192          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 192
acctcggctg acatgttgga                                            20

SEQ ID NO: 193          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 193
cacctcggct gacatgttgg                                            20

SEQ ID NO: 194          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 194
gcacctcggc tgacatgttg                                            20

SEQ ID NO: 195          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 195
cgcacctcgg ctgacatgtt                                            20

SEQ ID NO: 196          moltype = DNA  length = 20
FEATURE                 Location/Qualifiers
misc_feature            1..20
                        note = Synthetic oligonucleotide
```

```
source                  1..20
                        mol_type = other DNA
                        organism = synthetic construct
SEQUENCE: 196
ccgcacctcg gctgacatgt                                                20

SEQ ID NO: 197          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 197
gccgcacctc ggctgacatg                                                20

SEQ ID NO: 198          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 198
agccgcacct cggctgacat                                                20

SEQ ID NO: 199          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 199
cagccgcacc tcggctgaca                                                20

SEQ ID NO: 200          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 200
tcagccgcac ctcggctgac                                                20

SEQ ID NO: 201          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 201
ctcagccgca cctcggctga                                                20

SEQ ID NO: 202          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 202
cctcagccgc acctcggctg                                                20

SEQ ID NO: 203          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 203
gcctcagccg cacctcggct                                                20

SEQ ID NO: 204          moltype = DNA  length = 20
FEATURE                 Location/Qualifiers
misc_feature            1..20
```

-continued

```
                         note = Synthetic oligonucleotide
source                   1..20
                         mol_type = other DNA
                         organism = synthetic construct
SEQUENCE: 204
ccaacaccag ctgctggagc                                          20

SEQ ID NO: 205           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 205
tccaacacca gctgctggag                                          20

SEQ ID NO: 206           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 206
gtccaacacc agctgctgga                                          20

SEQ ID NO: 207           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 207
gggtccaaca ccagctgctg                                          20

SEQ ID NO: 208           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 208
ggctccagcc ccaggaagcc                                          20

SEQ ID NO: 209           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 209
gggctccagc cccaggaagc                                          20

SEQ ID NO: 210           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 210
caggagaagg tcgagcaggg                                          20

SEQ ID NO: 211           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 211
cccaggagaa ggtcgagcag                                          20

SEQ ID NO: 212           moltype = DNA  length = 20
FEATURE                  Location/Qualifiers
```

```
misc_feature           1..20
                       note = Synthetic oligonucleotide
source                 1..20
                       mol_type = other DNA
                       organism = synthetic construct
SEQUENCE: 212
gcccaggaga aggtcgagca                                          20

SEQ ID NO: 213         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 213
cgcccaggag aaggtcgagc                                          20

SEQ ID NO: 214         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 214
acgcccagga gaaggtcgag                                          20

SEQ ID NO: 215         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 215
tcctgggcca gttcggaggc                                          20

SEQ ID NO: 216         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 216
gtcctgggcc agttcggagg                                          20

SEQ ID NO: 217         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 217
tgtcctgggc cagttcggag                                          20

SEQ ID NO: 218         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 218
ttgtcctggg ccagttcgga                                          20

SEQ ID NO: 219         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 219
cttgtcctgg gccagttcgg                                          20

SEQ ID NO: 220         moltype = DNA  length = 20
```

```
FEATURE                Location/Qualifiers
misc_feature           1..20
                       note = Synthetic oligonucleotide
source                 1..20
                       mol_type = other DNA
                       organism = synthetic construct
SEQUENCE: 220
acttgtcctg ggccagttcg                                              20

SEQ ID NO: 221         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 221
tacttgtcct gggccagttc                                              20

SEQ ID NO: 222         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 222
gtacttgtcc tgggccagtt                                              20

SEQ ID NO: 223         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 223
cgtacttgtc ctgggccagt                                              20

SEQ ID NO: 224         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 224
actgcaagaa gtcggccacg                                              20

SEQ ID NO: 225         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 225
ccactgcaag aagtcggcca                                              20

SEQ ID NO: 226         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 226
cccactgcaa gaagtcggcc                                              20

SEQ ID NO: 227         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 227
gcccactgca agaagtcggc                                              20
```

```
SEQ ID NO: 228          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 228
cgcccactgc aagaagtcgg                                              20

SEQ ID NO: 229          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 229
ccgcccactg caagaagtcg                                              20

SEQ ID NO: 230          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 230
tccgcccact gcaagaagtc                                              20

SEQ ID NO: 231          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 231
ctccgcccac tgcaagaagt                                              20

SEQ ID NO: 232          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 232
gctccgccca ctgcaagaag                                              20

SEQ ID NO: 233          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 233
ggctccgccc actgcaagaa                                              20

SEQ ID NO: 234          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 234
gggctccgcc cactgcaaga                                              20

SEQ ID NO: 235          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 235
tgggctccgc ccactgcaag                                              20
```

-continued

```
SEQ ID NO: 236          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 236
atgggctccg cccactgcaa                                              20

SEQ ID NO: 237          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 237
gatgggctcc gcccactgca                                              20

SEQ ID NO: 238          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 238
cgatgggctc cgcccactgc                                              20

SEQ ID NO: 239          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 239
acgatgggct ccgcccactg                                              20

SEQ ID NO: 240          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 240
cacgatgggc tccgcccact                                              20

SEQ ID NO: 241          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 241
ccacgatggg ctccgcccac                                              20

SEQ ID NO: 242          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 242
accacgatgg gctccgccca                                              20

SEQ ID NO: 243          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 243
```

```
caccacgatg ggctccgccc                                            20

SEQ ID NO: 244          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 244
tcaccacgat gggctccgcc                                            20

SEQ ID NO: 245          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 245
ctcaccacga tgggctccgc                                            20

SEQ ID NO: 246          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 246
cctcaccacg atgggctccg                                            20

SEQ ID NO: 247          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 247
gcctcaccac gatgggctcc                                            20

SEQ ID NO: 248          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 248
agcctcacca cgatgggctc                                            20

SEQ ID NO: 249          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 249
aagcctcacc acgatgggct                                            20

SEQ ID NO: 250          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 250
taagcctcac cacgatgggc                                            20

SEQ ID NO: 251          moltype = DNA  length = 20
FEATURE                 Location/Qualifiers
misc_feature            1..20
                        note = Synthetic oligonucleotide
source                  1..20
                        mol_type = other DNA
                        organism = synthetic construct
```

```
SEQUENCE: 251
ttaagcctca ccacgatggg                                        20

SEQ ID NO: 252          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 252
cttaagcctc accacgatgg                                        20

SEQ ID NO: 253          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 253
ccttaagcct caccacgatg                                        20

SEQ ID NO: 254          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 254
tccttaagcc tcaccacgat                                        20

SEQ ID NO: 255          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 255
ctccttaagc ctcaccacga                                        20

SEQ ID NO: 256          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 256
cctccttaag cctcaccacg                                        20

SEQ ID NO: 257          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 257
acctccttaa gcctcaccac                                        20

SEQ ID NO: 258          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 258
gacctcctta agcctcacca                                        20

SEQ ID NO: 259          moltype = DNA  length = 20
FEATURE                 Location/Qualifiers
misc_feature            1..20
                        note = Synthetic oligonucleotide
source                  1..20
                        mol_type = other DNA
```

```
                      organism = synthetic construct
SEQUENCE: 259
ggacctcctt aagcctcacc                                             20

SEQ ID NO: 260        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 260
cggacctcct taagcctcac                                             20

SEQ ID NO: 261        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 261
tcggacctcc ttaagcctca                                             20

SEQ ID NO: 262        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 262
gtcggacctc cttaagcctc                                             20

SEQ ID NO: 263        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 263
cagtcggacc tccttaagcc                                             20

SEQ ID NO: 264        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 264
gcagtcggac ctccttaagc                                             20

SEQ ID NO: 265        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 265
tgcagtcgga cctccttaag                                             20

SEQ ID NO: 266        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 266
ccttcagaat ctcgaagtcg                                             20

SEQ ID NO: 267        moltype = DNA  length = 20
FEATURE               Location/Qualifiers
misc_feature          1..20
                      note = Synthetic oligonucleotide
source                1..20
```

-continued

```
                          mol_type = other DNA
                          organism = synthetic construct
SEQUENCE: 267
accttcagaa tctcgaagtc                                                20

SEQ ID NO: 268            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 268
tcaccttcag aatctcgaag                                                20

SEQ ID NO: 269            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 269
atcaccttca gaatctcgaa                                                20

SEQ ID NO: 270            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 270
gatcaccttc agaatctcga                                                20

SEQ ID NO: 271            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 271
ccgatcacct tcagaatctc                                                20

SEQ ID NO: 272            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 272
tccgatcacc ttcagaatct                                                20

SEQ ID NO: 273            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 273
gtccgatcac cttcagaatc                                                20

SEQ ID NO: 274            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 274
cgtccgatca ccttcagaat                                                20

SEQ ID NO: 275            moltype = DNA  length = 20
FEATURE                   Location/Qualifiers
misc_feature              1..20
                          note = Synthetic oligonucleotide
```

```
source                  1..20
                        mol_type = other DNA
                        organism = synthetic construct
SEQUENCE: 275
cccgtctgct tcatcttcac                                                20

SEQ ID NO: 276          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 276
gcccgtctgc ttcatcttca                                                20

SEQ ID NO: 277          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 277
ggcccgtctg cttcatcttc                                                20

SEQ ID NO: 278          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 278
tggcccgtct gcttcatctt                                                20

SEQ ID NO: 279          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 279
ctggcccgtc tgcttcatct                                                20

SEQ ID NO: 280          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 280
cctggcccgt ctgcttcatc                                                20

SEQ ID NO: 281          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 281
acctggcccg tctgcttcat                                                20

SEQ ID NO: 282          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 282
cacctggccc gtctgcttca                                                20

SEQ ID NO: 283          moltype = DNA  length = 20
FEATURE                 Location/Qualifiers
misc_feature            1..20
```

```
                        note = Synthetic oligonucleotide
source                  1..20
                        mol_type = other DNA
                        organism = synthetic construct
SEQUENCE: 283
acacctggcc cgtctgcttc                                         20

SEQ ID NO: 284          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 284
tacacctggc ccgtctgctt                                         20

SEQ ID NO: 285          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 285
ttgttcatga tcttcatggc                                         20

SEQ ID NO: 286          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 286
acttgttcat gatcttcatg                                         20

SEQ ID NO: 287          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 287
cacttgttca tgatcttcat                                         20

SEQ ID NO: 288          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 288
ccacttgttc atgatcttca                                         20

SEQ ID NO: 289          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 289
cccacttgtt catgatcttc                                         20

SEQ ID NO: 290          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 290
tcccacttgt tcatgatctt                                         20

SEQ ID NO: 291          moltype = DNA  length = 20
FEATURE                 Location/Qualifiers
```

```
misc_feature           1..20
                       note = Synthetic oligonucleotide
source                 1..20
                       mol_type = other DNA
                       organism = synthetic construct
SEQUENCE: 291
gtcccacttg ttcatgatct                                              20

SEQ ID NO: 292         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 292
tgtcccactt gttcatgatc                                              20

SEQ ID NO: 293         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 293
atgtcccact tgttcatgat                                              20

SEQ ID NO: 294         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 294
catgtcccac ttgttcatga                                              20

SEQ ID NO: 295         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 295
gcatgtccca cttgttcatg                                              20

SEQ ID NO: 296         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 296
agcatgtccc acttgttcat                                              20

SEQ ID NO: 297         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 297
cagcatgtcc cacttgttca                                              20

SEQ ID NO: 298         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 298
tcagcatgtc ccacttgttc                                              20

SEQ ID NO: 299         moltype = DNA  length = 20
```

```
FEATURE                 Location/Qualifiers
misc_feature            1..20
                        note = Synthetic oligonucleotide
source                  1..20
                        mol_type = other DNA
                        organism = synthetic construct
SEQUENCE: 299
ttcagcatgt cccacttgtt                                              20

SEQ ID NO: 300          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 300
cttcagcatg tcccacttgt                                              20

SEQ ID NO: 301          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 301
tcttcagcat gtcccacttg                                              20

SEQ ID NO: 302          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 302
cctcttcagc atgtcccact                                              20

SEQ ID NO: 303          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 303
ccctcttcag catgtcccac                                              20

SEQ ID NO: 304          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 304
cccctcttca gcatgtccca                                              20

SEQ ID NO: 305          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 305
gcccctcttc agcatgtccc                                              20

SEQ ID NO: 306          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 306
cgcccctctt cagcatgtcc                                              20
```

```
SEQ ID NO: 307          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 307
tcgcccctct tcagcatgtc                                              20

SEQ ID NO: 308          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 308
ctcgcccctc ttcagcatgt                                              20

SEQ ID NO: 309          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 309
cctcgcccct cttcagcatg                                              20

SEQ ID NO: 310          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 310
acctcgcccc tcttcagcat                                              20

SEQ ID NO: 311          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 311
cacctcgccc ctcttcagca                                              20

SEQ ID NO: 312          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 312
acacctcgcc cctcttcagc                                              20

SEQ ID NO: 313          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 313
gacacctcgc ccctcttcag                                              20

SEQ ID NO: 314          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 314
gccaggcgga tgtggccaca                                              20
```

```
SEQ ID NO: 315          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 315
accgcaccgt tccatctgcc                                              20

SEQ ID NO: 316          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 316
gaccgcaccg ttccatctgc                                              20

SEQ ID NO: 317          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 317
acagcctgca ggatctcggg                                              20

SEQ ID NO: 318          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 318
cacagcctgc aggatctcgg                                              20

SEQ ID NO: 319          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 319
ccacagcctg caggatctcg                                              20

SEQ ID NO: 320          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 320
cccacagcct gcaggatctc                                              20

SEQ ID NO: 321          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 321
gcccacagcc tgcaggatct                                              20

SEQ ID NO: 322          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 322
```

```
cgcccacagc ctgcaggatc                                              20

SEQ ID NO: 323          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 323
ccgcccacag cctgcaggat                                              20

SEQ ID NO: 324          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 324
accgcccaca gcctgcagga                                              20

SEQ ID NO: 325          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 325
caccgcccac agcctgcagg                                              20

SEQ ID NO: 326          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 326
ccaccgccca cagcctgcag                                              20

SEQ ID NO: 327          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 327
cccaccgccc acagcctgca                                              20

SEQ ID NO: 328          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 328
gcccaccgcc cacagcctgc                                              20

SEQ ID NO: 329          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 329
ggcccaccgc ccacagcctg                                              20

SEQ ID NO: 330          moltype = DNA  length = 20
FEATURE                 Location/Qualifiers
misc_feature            1..20
                        note = Synthetic oligonucleotide
source                  1..20
                        mol_type = other DNA
                        organism = synthetic construct
```

```
SEQUENCE: 330
aggcccaccg cccacagcct                                        20

SEQ ID NO: 331          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 331
caggcccacc gcccacagcc                                        20

SEQ ID NO: 332          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 332
ccaggcccac cgcccacagc                                        20

SEQ ID NO: 333          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 333
cccaggccca ccgcccacag                                        20

SEQ ID NO: 334          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 334
tcccaggccc accgcccaca                                        20

SEQ ID NO: 335          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 335
gtcccaggcc caccgcccac                                        20

SEQ ID NO: 336          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 336
tgtcccaggc ccaccgccca                                        20

SEQ ID NO: 337          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 337
ctgtcccagg cccaccgccc                                        20

SEQ ID NO: 338          moltype = DNA  length = 20
FEATURE                 Location/Qualifiers
misc_feature            1..20
                        note = Synthetic oligonucleotide
source                  1..20
                        mol_type = other DNA
```

```
                       organism = synthetic construct
SEQUENCE: 338
cctgtcccag gcccaccgcc                                              20

SEQ ID NO: 339         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 339
gcctgtccca ggcccaccgc                                              20

SEQ ID NO: 340         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 340
tgcctgtccc aggcccaccg                                              20

SEQ ID NO: 341         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 341
ctgcctgtcc caggcccacc                                              20

SEQ ID NO: 342         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 342
gctgcctgtc ccaggcccac                                              20

SEQ ID NO: 343         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 343
agctgcctgt cccaggccca                                              20

SEQ ID NO: 344         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 344
tagctgcctg tcccaggccc                                              20

SEQ ID NO: 345         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 345
gtagctgcct gtcccaggcc                                              20

SEQ ID NO: 346         moltype = DNA  length = 20
FEATURE                Location/Qualifiers
misc_feature           1..20
                       note = Synthetic oligonucleotide
source                 1..20
```

```
                          mol_type = other DNA
                          organism = synthetic construct
SEQUENCE: 346
cgtagctgcc tgtcccaggc                                                20

SEQ ID NO: 347            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 347
ccgtagctgc ctgtcccagg                                                20

SEQ ID NO: 348            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 348
cccgtagctg cctgtcccag                                                20

SEQ ID NO: 349            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 349
gcccgtagct gcctgtccca                                                20

SEQ ID NO: 350            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 350
ggcccgtagc tgcctgtccc                                                20

SEQ ID NO: 351            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 351
tagaacattt cataggcgaa                                                20

SEQ ID NO: 352            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 352
tctccgccgt ggaatccgcg                                                20

SEQ ID NO: 353            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 353
gtctccgccg tggaatccgc                                                20

SEQ ID NO: 354            moltype = DNA  length = 20
FEATURE                   Location/Qualifiers
misc_feature              1..20
                          note = Synthetic oligonucleotide
```

```
source                  1..20
                        mol_type = other DNA
                        organism = synthetic construct
SEQUENCE: 354
ggtctccgcc gtggaatccg                                        20

SEQ ID NO: 355          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 355
aggtctccgc cgtggaatcc                                        20

SEQ ID NO: 356          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 356
taggtctccg ccgtggaatc                                        20

SEQ ID NO: 357          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 357
ttgtagtgga cgatcttgcc                                        20

SEQ ID NO: 358          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 358
cttgtagtgg acgatcttgc                                        20

SEQ ID NO: 359          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 359
ccttgtagtg gacgatcttg                                        20

SEQ ID NO: 360          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 360
tccttgtagt ggacgatctt                                        20

SEQ ID NO: 361          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 361
ctccttgtag tggacgatct                                        20

SEQ ID NO: 362          moltype = DNA  length = 20
FEATURE                 Location/Qualifiers
misc_feature            1..20
```

```
                          note = Synthetic oligonucleotide
source                    1..20
                          mol_type = other DNA
                          organism = synthetic construct
SEQUENCE: 362
gctccttgta gtggacgatc                                              20

SEQ ID NO: 363            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 363
tgctccttgt agtggacgat                                              20

SEQ ID NO: 364            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 364
gtgctccttg tagtggacga                                              20

SEQ ID NO: 365            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 365
ggtgctcctt gtagtggacg                                              20

SEQ ID NO: 366            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 366
aggtgctcct tgtagtggac                                              20

SEQ ID NO: 367            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 367
gaggtgctcc ttgtagtgga                                              20

SEQ ID NO: 368            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 368
agaggtgctc cttgtagtgg                                              20

SEQ ID NO: 369            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 369
gagaggtgct ccttgtagtg                                              20

SEQ ID NO: 370            moltype = DNA  length = 20
FEATURE                   Location/Qualifiers
```

```
misc_feature          1..20
                      note = Synthetic oligonucleotide
source                1..20
                      mol_type = other DNA
                      organism = synthetic construct
SEQUENCE: 370
agagaggtgc tccttgtagt                                                20

SEQ ID NO: 371        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 371
gagagaggtg ctccttgtag                                                20

SEQ ID NO: 372        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 372
agagagaggt gctccttgta                                                20

SEQ ID NO: 373        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 373
cagagagagg tgctccttgt                                                20

SEQ ID NO: 374        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 374
ggcagagaga ggtgctcctt                                                20

SEQ ID NO: 375        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 375
cggcagagag aggtgctcct                                                20

SEQ ID NO: 376        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 376
gcggcagaga gaggtgctcc                                                20

SEQ ID NO: 377        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 377
agcggcagag agaggtgctc                                                20

SEQ ID NO: 378        moltype = DNA  length = 20
```

```
FEATURE                Location/Qualifiers
misc_feature           1..20
                       note = Synthetic oligonucleotide
source                 1..20
                       mol_type = other DNA
                       organism = synthetic construct
SEQUENCE: 378
cagcggcaga gagaggtgct                                              20

SEQ ID NO: 379         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 379
ccagcggcag agagaggtgc                                              20

SEQ ID NO: 380         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 380
ggcccagccg tgtctccggg                                              20

SEQ ID NO: 381         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 381
cggcccagcc gtgtctccgg                                              20

SEQ ID NO: 382         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 382
ccggcccagc cgtgtctccg                                              20

SEQ ID NO: 383         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 383
cccggcccag ccgtgtctcc                                              20

SEQ ID NO: 384         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 384
ccccggccca gccgtgtctc                                              20

SEQ ID NO: 385         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 385
accccggccc agccgtgtct                                              20
```

-continued

```
SEQ ID NO: 386          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 386
caccccggcc cagccgtgtc                                              20

SEQ ID NO: 387          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 387
ccaccccggc ccagccgtgt                                              20

SEQ ID NO: 388          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 388
tccaccccgg cccagccgtg                                              20

SEQ ID NO: 389          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 389
ctccaccccg gcccagccgt                                              20

SEQ ID NO: 390          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 390
gctccacccc ggcccagccg                                              20

SEQ ID NO: 391          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 391
tgctccaccc cggcccagcc                                              20

SEQ ID NO: 392          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 392
ctgctccacc ccggcccagc                                              20

SEQ ID NO: 393          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 393
aagggatgtg tccggaagtc                                              20
```

```
SEQ ID NO: 394          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 394
gaagggatgt gtccggaagt                                              20

SEQ ID NO: 395          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 395
agaagggatg tgtccggaag                                              20

SEQ ID NO: 396          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 396
aagaagggat gtgtccggaa                                              20

SEQ ID NO: 397          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 397
gaagaaggga tgtgtccgga                                              20

SEQ ID NO: 398          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 398
agaagaaggg atgtgtccgg                                              20

SEQ ID NO: 399          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 399
aagaagaagg gatgtgtccg                                              20

SEQ ID NO: 400          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 400
aaagaagaag ggatgtgtcc                                              20

SEQ ID NO: 401          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 401
```

-continued

```
caaagaagaa gggatgtgtc                                              20

SEQ ID NO: 402          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 402
ccaaagaaga agggatgtgt                                              20

SEQ ID NO: 403          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 403
ggccaaagaa gaagggatgt                                              20

SEQ ID NO: 404          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 404
aggccaaaga agaagggatg                                              20

SEQ ID NO: 405          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 405
gaggccaaag aagaagggat                                              20

SEQ ID NO: 406          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 406
cgaggccaaa gaagaaggga                                              20

SEQ ID NO: 407          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 407
tcgaggccaa agaagaaggg                                              20

SEQ ID NO: 408          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 408
gtcgaggcca aagaagaagg                                              20

SEQ ID NO: 409          moltype = DNA  length = 20
FEATURE                 Location/Qualifiers
misc_feature            1..20
                        note = Synthetic oligonucleotide
source                  1..20
                        mol_type = other DNA
                        organism = synthetic construct
```

```
SEQUENCE: 409
agtcgaggcc aaagaagaag                                              20

SEQ ID NO: 410          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 410
cagtcgaggc caaagaagaa                                              20

SEQ ID NO: 411          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 411
ccagtcgagg ccaaagaaga                                              20

SEQ ID NO: 412          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 412
cccagtcgag gccaaagaag                                              20

SEQ ID NO: 413          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 413
tcccagtcga ggccaaagaa                                              20

SEQ ID NO: 414          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 414
atcccagtcg aggccaaaga                                              20

SEQ ID NO: 415          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 415
catcccagtc gaggccaaag                                              20

SEQ ID NO: 416          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 416
ccatcccagt cgaggccaaa                                              20

SEQ ID NO: 417          moltype = DNA  length = 20
FEATURE                 Location/Qualifiers
misc_feature            1..20
                        note = Synthetic oligonucleotide
source                  1..20
                        mol_type = other DNA
```

```
                        organism = synthetic construct
SEQUENCE: 417
accatcccag tcgaggccaa                                              20

SEQ ID NO: 418          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 418
gaccatccca gtcgaggcca                                              20

SEQ ID NO: 419          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 419
agaccatccc agtcgaggcc                                              20

SEQ ID NO: 420          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 420
gagaccatcc cagtcgaggc                                              20

SEQ ID NO: 421          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 421
ggagaccatc ccagtcgagg                                              20

SEQ ID NO: 422          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 422
ttcgaaatcc ggtgtaaagg                                              20

SEQ ID NO: 423          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 423
cttcgaaatc cggtgtaaag                                              20

SEQ ID NO: 424          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 424
ccttcgaaat ccggtgtaaa                                              20

SEQ ID NO: 425          moltype = DNA  length = 20
FEATURE                 Location/Qualifiers
misc_feature            1..20
                        note = Synthetic oligonucleotide
source                  1..20
```

```
                        mol_type = other DNA
                        organism = synthetic construct
SEQUENCE: 425
accttcgaaa tccggtgtaa                                            20

SEQ ID NO: 426          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 426
caccttcgaa atccggtgta                                            20

SEQ ID NO: 427          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 427
gcaccttcga aatccggtgt                                            20

SEQ ID NO: 428          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 428
ggcaccttcg aaatccggtg                                            20

SEQ ID NO: 429          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 429
tggcaccttc gaaatccggt                                            20

SEQ ID NO: 430          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 430
gtggcacctt cgaaatccgg                                            20

SEQ ID NO: 431          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 431
ggtggcacct tcgaaatccg                                            20

SEQ ID NO: 432          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 432
cggtggcacc ttcgaaatcc                                            20

SEQ ID NO: 433          moltype = DNA  length = 20
FEATURE                 Location/Qualifiers
misc_feature            1..20
                        note = Synthetic oligonucleotide
```

```
source                  1..20
                        mol_type = other DNA
                        organism = synthetic construct
SEQUENCE: 433
tcggtggcac cttcgaaatc                                              20

SEQ ID NO: 434          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 434
gtcggtggca ccttcgaaat                                              20

SEQ ID NO: 435          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 435
tgtcggtggc accttcgaaa                                              20

SEQ ID NO: 436          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 436
gtgtcggtgg caccttcgaa                                              20

SEQ ID NO: 437          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 437
tgtgtcggtg gcaccttcga                                              20

SEQ ID NO: 438          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 438
atgtgtcggt ggcaccttcg                                              20

SEQ ID NO: 439          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 439
catgtgtcgg tggcaccttc                                              20

SEQ ID NO: 440          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 440
gcatgtgtcg gtggcacctt                                              20

SEQ ID NO: 441          moltype = DNA  length = 20
FEATURE                 Location/Qualifiers
misc_feature            1..20
```

```
                         note = Synthetic oligonucleotide
source                   1..20
                         mol_type = other DNA
                         organism = synthetic construct
SEQUENCE: 441
tgcatgtgtc ggtggcacct                                                 20

SEQ ID NO: 442           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 442
ttgcatgtgt cggtggcacc                                                 20

SEQ ID NO: 443           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 443
gttgcatgtg tcggtggcac                                                 20

SEQ ID NO: 444           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 444
agttgcatgt gtcggtggca                                                 20

SEQ ID NO: 445           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 445
aagttgcatg tgtcggtggc                                                 20

SEQ ID NO: 446           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 446
gaagttgcat gtgtcggtgg                                                 20

SEQ ID NO: 447           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 447
cgaagttgca tgtgtcggtg                                                 20

SEQ ID NO: 448           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 448
gtcgaagttg catgtgtcgg                                                 20

SEQ ID NO: 449           moltype = DNA  length = 20
FEATURE                  Location/Qualifiers
```

-continued

```
misc_feature            1..20
                        note = Synthetic oligonucleotide
source                  1..20
                        mol_type = other DNA
                        organism = synthetic construct
SEQUENCE: 449
agtcgaagtt gcatgtgtcg                                              20

SEQ ID NO: 450          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 450
aagtcgaagt tgcatgtgtc                                              20

SEQ ID NO: 451          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 451
caagtcgaag ttgcatgtgt                                              20

SEQ ID NO: 452          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 452
ccaagtcgaa gttgcatgtg                                              20

SEQ ID NO: 453          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 453
accaagtcga agttgcatgt                                              20

SEQ ID NO: 454          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 454
caccaagtcg aagttgcatg                                              20

SEQ ID NO: 455          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 455
ccaccaagtc gaagttgcat                                              20

SEQ ID NO: 456          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 456
tccaccaagt cgaagttgca                                              20

SEQ ID NO: 457          moltype = DNA  length = 20
```

```
FEATURE                Location/Qualifiers
misc_feature           1..20
                       note = Synthetic oligonucleotide
source                 1..20
                       mol_type = other DNA
                       organism = synthetic construct
SEQUENCE: 457
ctccaccaag tcgaagttgc                                              20

SEQ ID NO: 458         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 458
cctccaccaa gtcgaagttg                                              20

SEQ ID NO: 459         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 459
tcctccacca agtcgaagtt                                              20

SEQ ID NO: 460         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 460
gtcctccacc aagtcgaagt                                              20

SEQ ID NO: 461         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 461
cgtcctccac caagtcgaag                                              20

SEQ ID NO: 462         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 462
ccgtcctcca ccaagtcgaa                                              20

SEQ ID NO: 463         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 463
cccgtcctcc accaagtcga                                              20

SEQ ID NO: 464         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 464
gcccgtcctc caccaagtcg                                              20
```

```
SEQ ID NO: 465          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 465
agcccgtcct ccaccaagtc                                              20

SEQ ID NO: 466          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 466
gagcccgtcc tccaccaagt                                              20

SEQ ID NO: 467          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 467
tgagcccgtc ctccaccaag                                              20

SEQ ID NO: 468          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 468
ggttccgagc ctctgcctcg                                              20

SEQ ID NO: 469          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 469
cggttccgag cctctgcctc                                              20

SEQ ID NO: 470          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 470
ccggttccga gcctctgcct                                              20

SEQ ID NO: 471          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 471
cccggttccg agcctctgcc                                              20

SEQ ID NO: 472          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 472
tcccggttcc gagcctctgc                                              20
```

```
SEQ ID NO: 473          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 473
gtcccggttc cgagcctctg                                              20

SEQ ID NO: 474          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 474
aggtcccggt tccgagcctc                                              20

SEQ ID NO: 475          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 475
taggtcccgg ttccgagcct                                              20

SEQ ID NO: 476          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 476
ctaggtcccg gttccgagcc                                              20

SEQ ID NO: 477          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 477
tctaggtccc ggttccgagc                                              20

SEQ ID NO: 478          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 478
ctctaggtcc cggttccgag                                              20

SEQ ID NO: 479          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 479
cctctaggtc ccggttccga                                              20

SEQ ID NO: 480          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 480
```

-continued

```
gcctctaggt cccggttccg                                             20

SEQ ID NO: 481          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 481
catccgctcc tgcaactgcc                                             20

SEQ ID NO: 482          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 482
ccatccgctc ctgcaactgc                                             20

SEQ ID NO: 483          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 483
tccatccgct cctgcaactg                                             20

SEQ ID NO: 484          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 484
ctccatccgc tcctgcaact                                             20

SEQ ID NO: 485          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 485
actccatccg ctcctgcaac                                             20

SEQ ID NO: 486          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 486
aactccatcc gctcctgcaa                                             20

SEQ ID NO: 487          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 487
caactccatc cgctcctgca                                             20

SEQ ID NO: 488          moltype = DNA  length = 20
FEATURE                 Location/Qualifiers
misc_feature            1..20
                        note = Synthetic oligonucleotide
source                  1..20
                        mol_type = other DNA
                        organism = synthetic construct
```

```
SEQUENCE: 488
agcaactcca tccgctcctg                                              20

SEQ ID NO: 489          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 489
cagcaactcc atccgctcct                                              20

SEQ ID NO: 490          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 490
gcagcaactc catccgctcc                                              20

SEQ ID NO: 491          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 491
cagctgtggc tccctctgcc                                              20

SEQ ID NO: 492          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 492
acagctgtgg ctccctctgc                                              20

SEQ ID NO: 493          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 493
gacagctgtg gctccctctg                                              20

SEQ ID NO: 494          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 494
tgacagctgt ggctccctct                                              20

SEQ ID NO: 495          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 495
gtgacagctg tggctccctc                                              20

SEQ ID NO: 496          moltype = DNA  length = 20
FEATURE                 Location/Qualifiers
misc_feature            1..20
                        note = Synthetic oligonucleotide
source                  1..20
                        mol_type = other DNA
```

```
                       organism = synthetic construct
SEQUENCE: 496
cgtgacagct gtggctccct                                                20

SEQ ID NO: 497         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 497
ccgtgacagc tgtggctccc                                                20

SEQ ID NO: 498         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 498
cccgtgacag ctgtggctcc                                                20

SEQ ID NO: 499         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 499
ccccgtgaca gctgtggctc                                                20

SEQ ID NO: 500         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 500
cccccgtgac agctgtggct                                                20

SEQ ID NO: 501         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 501
acccccgtga cagctgtggc                                                20

SEQ ID NO: 502         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 502
gacccccgtg acagctgtgg                                                20

SEQ ID NO: 503         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 503
ggacccccgt gacagctgtg                                                20

SEQ ID NO: 504         moltype = DNA  length = 20
FEATURE                Location/Qualifiers
misc_feature           1..20
                       note = Synthetic oligonucleotide
source                 1..20
```

```
                         mol_type = other DNA
                         organism = synthetic construct
SEQUENCE: 504
gggacccccg tgacagctgt                                                  20

SEQ ID NO: 505           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 505
gaaggtggat ccgtggcccg                                                  20

SEQ ID NO: 506           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 506
ggaaggtgga tccgtggccc                                                  20

SEQ ID NO: 507           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 507
gggaaggtgg atccgtggcc                                                  20

SEQ ID NO: 508           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 508
tgggaaggtg gatccgtggc                                                  20

SEQ ID NO: 509           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 509
atgggaaggt ggatccgtgg                                                  20

SEQ ID NO: 510           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 510
gatgggaagg tggatccgtg                                                  20

SEQ ID NO: 511           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 511
tagatgggaa ggtggatccg                                                  20

SEQ ID NO: 512           moltype = DNA  length = 20
FEATURE                  Location/Qualifiers
misc_feature             1..20
                         note = Synthetic oligonucleotide
```

```
source                 1..20
                       mol_type = other DNA
                       organism = synthetic construct
SEQUENCE: 512
ctagatggga aggtggatcc                                              20

SEQ ID NO: 513         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 513
tctagatggg aaggtggatc                                              20

SEQ ID NO: 514         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 514
atctagatgg gaaggtggat                                              20

SEQ ID NO: 515         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 515
ccatctagat gggaaggtgg                                              20

SEQ ID NO: 516         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 516
gccatctaga tgggaaggtg                                              20

SEQ ID NO: 517         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 517
ggccatctag atgggaaggt                                              20

SEQ ID NO: 518         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 518
caccagcggg cactggccca                                              20

SEQ ID NO: 519         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 519
ccaccagcgg gcactggccc                                              20

SEQ ID NO: 520         moltype = DNA  length = 20
FEATURE                Location/Qualifiers
misc_feature           1..20
```

```
                         note = Synthetic oligonucleotide
source                   1..20
                         mol_type = other DNA
                         organism = synthetic construct
SEQUENCE: 520
cccaccagcg ggcactggcc                                                        20

SEQ ID NO: 521           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 521
ccccaccagc gggcactggc                                                        20

SEQ ID NO: 522           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 522
ggccccacca gcgggcactg                                                        20

SEQ ID NO: 523           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 523
tggccccacc agcgggcact                                                        20

SEQ ID NO: 524           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 524
ctggccccac cagcgggcac                                                        20

SEQ ID NO: 525           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 525
cctggcccca ccagcgggca                                                        20

SEQ ID NO: 526           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 526
gcctggcccc accagcgggc                                                        20

SEQ ID NO: 527           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 527
gggcctggcc ccaccagcgg                                                        20

SEQ ID NO: 528           moltype = DNA  length = 20
FEATURE                  Location/Qualifiers
```

```
misc_feature          1..20
                      note = Synthetic oligonucleotide
source                1..20
                      mol_type = other DNA
                      organism = synthetic construct
SEQUENCE: 528
aggtggcggc ggtgcatggg                                              20

SEQ ID NO: 529        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 529
caggtggcgg cggtgcatgg                                              20

SEQ ID NO: 530        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 530
gcaggtggcg gcggtgcatg                                              20

SEQ ID NO: 531        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 531
agcaggtggc ggcggtgcat                                              20

SEQ ID NO: 532        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 532
cagcaggtgg cggcggtgca                                              20

SEQ ID NO: 533        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 533
gcagcaggtg gcggcggtgc                                              20

SEQ ID NO: 534        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 534
agcagcaggt ggcggcggtg                                              20

SEQ ID NO: 535        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 535
gagcagcagg tggcggcggt                                              20

SEQ ID NO: 536        moltype = DNA  length = 20
```

```
FEATURE                Location/Qualifiers
misc_feature           1..20
                       note = Synthetic oligonucleotide
source                 1..20
                       mol_type = other DNA
                       organism = synthetic construct
SEQUENCE: 536
ggagcagcag gtggcggcgg                                                  20

SEQ ID NO: 537         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 537
gggagcagca ggtggcggcg                                                  20

SEQ ID NO: 538         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 538
agggagcagc aggtggcggc                                                  20

SEQ ID NO: 539         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 539
cagggagcag caggtggcgg                                                  20

SEQ ID NO: 540         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 540
gcagggagca gcaggtggcg                                                  20

SEQ ID NO: 541         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 541
ggcagggagc agcaggtggc                                                  20

SEQ ID NO: 542         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 542
tggcagggag cagcaggtgg                                                  20

SEQ ID NO: 543         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 543
ctggcaggga gcagcaggtg                                                  20
```

```
SEQ ID NO: 544          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 544
ccctggcagg gagcagcagg                                              20

SEQ ID NO: 545          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 545
accctggcag ggagcagcag                                              20

SEQ ID NO: 546          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 546
gaccctggca gggagcagca                                              20

SEQ ID NO: 547          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 547
ggaccctggc agggagcagc                                              20

SEQ ID NO: 548          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 548
ggcctaggga ccctggcagg                                              20

SEQ ID NO: 549          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 549
aggcctaggg accctggcag                                              20

SEQ ID NO: 550          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 550
ccaggcctag ggaccctggc                                              20

SEQ ID NO: 551          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 551
gccaggccta gggaccctgg                                              20
```

```
SEQ ID NO: 552          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 552
ggccaggcct agggaccctg                                              20

SEQ ID NO: 553          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 553
aggccaggcc tagggaccct                                              20

SEQ ID NO: 554          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 554
taggccaggc ctagggaccc                                              20

SEQ ID NO: 555          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 555
ataggccagg cctagggacc                                              20

SEQ ID NO: 556          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 556
gataggccag gcctagggac                                              20

SEQ ID NO: 557          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 557
cgataggcca ggcctaggga                                              20

SEQ ID NO: 558          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 558
ccgataggcc aggcctaggg                                              20

SEQ ID NO: 559          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 559
```

```
tccgataggc caggcctagg                                              20

SEQ ID NO: 560          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 560
ctccgatagg ccaggcctag                                              20

SEQ ID NO: 561          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 561
cctccgatag gccaggccta                                              20

SEQ ID NO: 562          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 562
gcctccgata ggccaggcct                                              20

SEQ ID NO: 563          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 563
gcgcctccga taggccaggc                                              20

SEQ ID NO: 564          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 564
aacaggagca gggaaagcgc                                              20

SEQ ID NO: 565          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 565
gaacaggagc agggaaagcg                                              20

SEQ ID NO: 566          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 566
cgaacaggag cagggaaagc                                              20

SEQ ID NO: 567          moltype = DNA  length = 20
FEATURE                 Location/Qualifiers
misc_feature            1..20
                        note = Synthetic oligonucleotide
source                  1..20
                        mol_type = other DNA
                        organism = synthetic construct
```

```
SEQUENCE: 567
gcgaacagga gcagggaaag                                                20

SEQ ID NO: 568          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 568
ggcgaacagg agcagggaaa                                                20

SEQ ID NO: 569          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 569
cggcgaacag gagcagggaa                                                20

SEQ ID NO: 570          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 570
acggcgaaca ggagcaggga                                                20

SEQ ID NO: 571          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 571
aacggcgaac aggagcaggg                                                20

SEQ ID NO: 572          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 572
caacggcgaa caggagcagg                                                20

SEQ ID NO: 573          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 573
gggcggcggc acgagacaga                                                20

SEQ ID NO: 574          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 574
agggcggcgg cacgagacag                                                20

SEQ ID NO: 575          moltype = DNA  length = 20
FEATURE                 Location/Qualifiers
misc_feature            1..20
                        note = Synthetic oligonucleotide
source                  1..20
                        mol_type = other DNA
```

```
                        organism = synthetic construct
SEQUENCE: 575
cagggcggcg gcacgagaca                                              20

SEQ ID NO: 576          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 576
ccagggcggc ggcacgagac                                              20

SEQ ID NO: 577          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 577
cccagggcgg cggcacgaga                                              20

SEQ ID NO: 578          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 578
gcccagggcg gcggcacgag                                              20

SEQ ID NO: 579          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 579
agcccagggc ggcggcacga                                              20

SEQ ID NO: 580          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 580
cagcccaggg cggcggcacg                                              20

SEQ ID NO: 581          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 581
gcagcccagg gcggcggcac                                              20

SEQ ID NO: 582          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 582
ctgcggtgag ttggccggcg                                              20

SEQ ID NO: 583          moltype = DNA  length = 20
FEATURE                 Location/Qualifiers
misc_feature            1..20
                        note = Synthetic oligonucleotide
source                  1..20
```

```
                         mol_type = other DNA
                         organism = synthetic construct
SEQUENCE: 583
actgcggtga gttggccggc                                               20

SEQ ID NO: 584           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 584
gactgcggtg agttggccgg                                               20

SEQ ID NO: 585           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 585
agactgcggt gagttggccg                                               20

SEQ ID NO: 586           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 586
cagactgcgg tgagttggcc                                               20

SEQ ID NO: 587           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 587
ccagactgcg gtgagttggc                                               20

SEQ ID NO: 588           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 588
gccagactgc ggtgagttgg                                               20

SEQ ID NO: 589           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 589
cgccagactg cggtgagttg                                               20

SEQ ID NO: 590           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 590
aagacagttc tagggttcag                                               20

SEQ ID NO: 591           moltype = DNA  length = 20
FEATURE                  Location/Qualifiers
misc_feature             1..20
                         note = Synthetic oligonucleotide
```

```
source                  1..20
                        mol_type = other DNA
                        organism = synthetic construct
SEQUENCE: 591
gaagacagtt ctagggttca                                              20

SEQ ID NO: 592          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 592
cgaagacagt tctagggttc                                              20

SEQ ID NO: 593          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 593
tcgaagacag ttctagggtt                                              20

SEQ ID NO: 594          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 594
gtcgaagaca gttctagggt                                              20

SEQ ID NO: 595          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 595
agtcgaagac agttctaggg                                              20

SEQ ID NO: 596          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 596
gagtcgaaga cagttctagg                                              20

SEQ ID NO: 597          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 597
ggagtcgaag acagttctag                                              20

SEQ ID NO: 598          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 598
cggagtcgaa gacagttcta                                              20

SEQ ID NO: 599          moltype = DNA  length = 20
FEATURE                 Location/Qualifiers
misc_feature            1..20
```

```
                        note = Synthetic oligonucleotide
source                  1..20
                        mol_type = other DNA
                        organism = synthetic construct
SEQUENCE: 599
ccggagtcga agacagttct                                          20

SEQ ID NO: 600          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 600
cccggagtcg aagacagttc                                          20

SEQ ID NO: 601          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 601
ccccggagtc gaagacagtt                                          20

SEQ ID NO: 602          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 602
gccccggagt cgaagacagt                                          20

SEQ ID NO: 603          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 603
ggccccggag tcgaagacag                                          20

SEQ ID NO: 604          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 604
gggccccgga gtcgaagaca                                          20

SEQ ID NO: 605          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 605
aggcggtggg cgcggcttct                                          20

SEQ ID NO: 606          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 606
caggcggtgg gcgcggcttc                                          20

SEQ ID NO: 607          moltype = DNA  length = 20
FEATURE                 Location/Qualifiers
```

```
misc_feature          1..20
                      note = Synthetic oligonucleotide
source                1..20
                      mol_type = other DNA
                      organism = synthetic construct
SEQUENCE: 607
gcaggcggtg ggcgcggctt                                              20

SEQ ID NO: 608        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 608
tggcaggcgg tgggcgcggc                                              20

SEQ ID NO: 609        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 609
actggcaggc ggtgggcgcg                                              20

SEQ ID NO: 610        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 610
gaactggcag gcggtgggcg                                              20

SEQ ID NO: 611        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 611
tgaactggca ggcggtgggc                                              20

SEQ ID NO: 612        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 612
tgtgaactgg caggcggtgg                                              20

SEQ ID NO: 613        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 613
tggagctggg cggagaccca                                              20

SEQ ID NO: 614        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 614
actggagctg ggcggagacc                                              20

SEQ ID NO: 615        moltype = DNA  length = 20
```

```
FEATURE                Location/Qualifiers
misc_feature           1..20
                       note = Synthetic oligonucleotide
source                 1..20
                       mol_type = other DNA
                       organism = synthetic construct
SEQUENCE: 615
gactggagct gggcggagac                                              20

SEQ ID NO: 616         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 616
aggactggag ctgggcggag                                              20

SEQ ID NO: 617         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 617
acaggactgg agctgggcgg                                              20

SEQ ID NO: 618         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 618
cacaggactg gagctgggcg                                              20

SEQ ID NO: 619         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 619
tcacaggact ggagctgggc                                              20

SEQ ID NO: 620         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 620
gcctcagcct ggccgaaaga                                              20

SEQ ID NO: 621         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 621
ggcctcagcc tggccgaaag                                              20

SEQ ID NO: 622         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 622
tggtggagcc aagccctccc                                              20
```

```
SEQ ID NO: 623          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 623
gggcaccctc agagcctgaa                                              20

SEQ ID NO: 624          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 624
accccactgc aagaagtcgg                                              20

SEQ ID NO: 625          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 625
gccccaggat gggaggatct                                              20

SEQ ID NO: 626          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 626
cataggacag agaaatgttg                                              20

SEQ ID NO: 627          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 627
tgctgacctt actctgcccc                                              20

SEQ ID NO: 628          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 628
taagccatgg ctctgagtca                                              20

SEQ ID NO: 629          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 629
agagaggcca tgggaggctg                                              20

SEQ ID NO: 630          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 630
ctggccctcc tggcttgccc                                              20
```

```
SEQ ID NO: 631          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 631
agctgcccca tgctggccct                                              20

SEQ ID NO: 632          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 632
gcccctggca gctgccccat                                              20

SEQ ID NO: 633          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 633
ctgtcggctg cgcccctggc                                              20

SEQ ID NO: 634          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 634
cgccgaacac ctgcctgtcg                                              20

SEQ ID NO: 635          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 635
cctcccagtg cctgggcacc                                              20

SEQ ID NO: 636          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 636
gcgcctgtct gcaaagctgg                                              20

SEQ ID NO: 637          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 637
cccaaagttg tccctcctgg                                              20

SEQ ID NO: 638          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 638
```

```
acacccagaa gaacccaaag                                              20

SEQ ID NO: 639          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 639
ctgacccaca cggctcatag                                              20

SEQ ID NO: 640          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 640
tggccccagg ccctggaaag                                              20

SEQ ID NO: 641          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 641
gacaaggcag ctggcagaag                                              20

SEQ ID NO: 642          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 642
aagaaaccag tgaccagtga                                              20

SEQ ID NO: 643          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 643
ctgtgaaatg ggaggaggag                                              20

SEQ ID NO: 644          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 644
gaaggttttt ccagaggctg                                              20

SEQ ID NO: 645          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 645
ggccaggaga gtcattaggg                                              20

SEQ ID NO: 646          moltype = DNA  length = 20
FEATURE                 Location/Qualifiers
misc_feature            1..20
                        note = Synthetic oligonucleotide
source                  1..20
                        mol_type = other DNA
                        organism = synthetic construct
```

```
SEQUENCE: 646
ccacaaaagg agtgctcctc                                           20

SEQ ID NO: 647          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 647
ccttttaagg cagcaggaac                                           20

SEQ ID NO: 648          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 648
ctaggactgt ctgcttccca                                           20

SEQ ID NO: 649          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 649
gtcattcatc aatttctaag                                           20

SEQ ID NO: 650          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 650
ggaggagctg cagccggaga                                           20

SEQ ID NO: 651          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 651
gcacccggag gagctgcagc                                           20

SEQ ID NO: 652          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 652
gcacgacacc tgcagggcac                                           20

SEQ ID NO: 653          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 653
agctcaccag gtagttctca                                           20

SEQ ID NO: 654          moltype = DNA  length = 20
FEATURE                 Location/Qualifiers
misc_feature            1..20
                        note = Synthetic oligonucleotide
source                  1..20
                        mol_type = other DNA
```

```
                       organism = synthetic construct
SEQUENCE: 654
gcttcctctc cccacctcct                                              20

SEQ ID NO: 655         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 655
gcagcacccc caatcctaga                                              20

SEQ ID NO: 656         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 656
gcccctcatc cacctgacac                                              20

SEQ ID NO: 657         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 657
ttccaggtaa gagacccccc                                              20

SEQ ID NO: 658         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 658
agaataggtc ccagacactc                                              20

SEQ ID NO: 659         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 659
ctccccctga gatgttctgg                                              20

SEQ ID NO: 660         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 660
ccccagccca gagataacca                                              20

SEQ ID NO: 661         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 661
cctgatccat cacggatggc                                              20

SEQ ID NO: 662         moltype = DNA  length = 20
FEATURE                Location/Qualifiers
misc_feature           1..20
                       note = Synthetic oligonucleotide
source                 1..20
```

```
                        mol_type = other DNA
                        organism = synthetic construct
SEQUENCE: 662
tactccatga ccaggtactg                                                20

SEQ ID NO: 663          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 663
gctctgacct tccaagaacc                                                20

SEQ ID NO: 664          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 664
ctcccttctg tggtcccacc                                                20

SEQ ID NO: 665          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 665
gtcgggtttg atgtccctgc                                                20

SEQ ID NO: 666          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 666
agggcactgg ctcaccgttc                                                20

SEQ ID NO: 667          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 667
gggccctcct tccaaccact                                                20

SEQ ID NO: 668          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 668
gcccacccct ctgggcccac                                                20

SEQ ID NO: 669          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 669
aggagcagag cgaggcttgg                                                20

SEQ ID NO: 670          moltype = DNA  length = 20
FEATURE                 Location/Qualifiers
misc_feature            1..20
                        note = Synthetic oligonucleotide
```

```
source                  1..20
                        mol_type = other DNA
                        organism = synthetic construct
SEQUENCE: 670
caccttgtag tggacgatct                                              20

SEQ ID NO: 671          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 671
ctaccccgcc cccgctcacc                                              20

SEQ ID NO: 672          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 672
ctaggtcact gctgggtcct                                              20

SEQ ID NO: 673          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 673
ctcagatagc tccccactcc                                              20

SEQ ID NO: 674          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 674
aattctctaa ttctctagac                                              20

SEQ ID NO: 675          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 675
tacctgaggg ccatgcagga                                              20

SEQ ID NO: 676          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 676
gttccaagac tgatcctgca                                              20

SEQ ID NO: 677          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 677
aggagggcgg tggcgcggcg                                              20

SEQ ID NO: 678          moltype = DNA  length = 20
FEATURE                 Location/Qualifiers
misc_feature            1..20
```

```
                        note = Synthetic oligonucleotide
source                  1..20
                        mol_type = other DNA
                        organism = synthetic construct
SEQUENCE: 678
tgacagctgg aaggagaaga                                              20

SEQ ID NO: 679          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 679
catgggaagg tggatccgtg                                              20

SEQ ID NO: 680          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 680
ggaggttatc tagggagatc                                              20

SEQ ID NO: 681          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 681
gaagggacag gtgacccgat                                              20

SEQ ID NO: 682          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 682
cgtaccctgg cagggagcag                                              20

SEQ ID NO: 683          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 683
ggactcgccc cgcctacgcc                                              20

SEQ ID NO: 684          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 684
ctcctgggac tcgccccgcc                                              20

SEQ ID NO: 685          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 685
gctcctggga ctcgccccgc                                              20

SEQ ID NO: 686          moltype = DNA  length = 20
FEATURE                 Location/Qualifiers
```

-continued

```
misc_feature          1..20
                      note = Synthetic oligonucleotide
source                1..20
                      mol_type = other DNA
                      organism = synthetic construct
SEQUENCE: 686
attggctcct gggactcgcc                                              20

SEQ ID NO: 687        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 687
gattggctcc tgggactcgc                                              20

SEQ ID NO: 688        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 688
gcctctgatt ggctcctggg                                              20

SEQ ID NO: 689        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 689
gcatgggcct ctgattggct                                              20

SEQ ID NO: 690        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 690
cacccggcat gggcctctga                                              20

SEQ ID NO: 691        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 691
gccaggccta gggacctgcg                                              20

SEQ ID NO: 692        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 692
ttcctccccc aaccctgatt                                              20

SEQ ID NO: 693        moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 693
aagtttgcag caacttttct                                              20

SEQ ID NO: 694        moltype = DNA  length = 20
```

```
FEATURE                 Location/Qualifiers
misc_feature            1..20
                        note = Synthetic oligonucleotide
source                  1..20
                        mol_type = other DNA
                        organism = synthetic construct
SEQUENCE: 694
gcccctcgga attcccggct                                               20

SEQ ID NO: 695          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 695
catctcggcc tgcgctccgc                                               20

SEQ ID NO: 696          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 696
gcaggccccc acattcccca                                               20

SEQ ID NO: 697          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 697
cttctgcacg cctccgtctc                                               20

SEQ ID NO: 698          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 698
tggcccacag ccacggccgg                                               20

SEQ ID NO: 699          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 699
ggcctggccc caccagcggg                                               20

SEQ ID NO: 700          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 700
cctggcaggg agcagcaggt                                               20

SEQ ID NO: 701          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 701
cagccgcact tcggctgaca                                               20
```

```
SEQ ID NO: 702          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 702
gcctgggtcc agcaccagct                                              20

SEQ ID NO: 703          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 703
gtcccaggaa gcctgggtcc                                              20

SEQ ID NO: 704          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 704
cgttagcagg tccccgccca                                              20

SEQ ID NO: 705          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 705
gtctatggcc atgacaatct                                              20

SEQ ID NO: 706          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 706
gtagcccagc cggtgcacgg                                              20

SEQ ID NO: 707          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 707
gggtgcccac agccaccagc                                              20

SEQ ID NO: 708          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 708
tggcccgtag ctgcctgccc                                              20

SEQ ID NO: 709          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 709
ggaaatcacc tgccccacct                                              20
```

```
SEQ ID NO: 710          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 710
ggatgtttct ggaaatcacc                                              20

SEQ ID NO: 711          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 711
gtggcaccct cgaagtctgg                                              20

SEQ ID NO: 712          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 712
ccccgctcac catggcagtg                                              20

SEQ ID NO: 713          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 713
ggtccgggac ctgattgtct                                              20

SEQ ID NO: 714          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 714
gctgcatgtc tgcccgtccc                                              20

SEQ ID NO: 715          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 715
ggccccagaa ccctagctgc                                              20

SEQ ID NO: 716          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 716
tcacagggcc tggctgcccc                                              20

SEQ ID NO: 717          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 717
```

```
ggctgacatg ttgggcaggc                                              20

SEQ ID NO: 718          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 718
tgtccaggcc ccagaaccct                                              20

SEQ ID NO: 719          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 719
ggccaggcct agggatctgc                                              20

SEQ ID NO: 720          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 720
cgcctcggat aggccaggcc                                              20

SEQ ID NO: 721          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 721
ggcttggagt cttagggttc                                              20

SEQ ID NO: 722          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 722
tccccggccg ccaggtggca                                              20

SEQ ID NO: 723          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 723
ggtgctgggc acgagccctg                                              20

SEQ ID NO: 724          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 724
gcccagctgc tgcagcagcg                                              20

SEQ ID NO: 725          moltype = DNA  length = 20
FEATURE                 Location/Qualifiers
misc_feature            1..20
                        note = Synthetic oligonucleotide
source                  1..20
                        mol_type = other DNA
                        organism = synthetic construct
```

```
SEQUENCE: 725
ccgtgtgtgc tggcagaggt                                           20

SEQ ID NO: 726          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 726
ataaataccg aggaatgtcg                                           20

SEQ ID NO: 727          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 727
gggacagaca ataaataccg                                           20

SEQ ID NO: 728          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 728
gtgcagccca gtgtggcggc                                           20

SEQ ID NO: 729          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 729
cctggagaag ttctggttgg                                           20

SEQ ID NO: 730          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 730
ggtgacccga tcggagccca                                           20

SEQ ID NO: 731          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 731
agctggagag agaagggaca                                           20

SEQ ID NO: 732          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 732
gtgagggact cgcctgcggc                                           20

SEQ ID NO: 733          moltype = DNA  length = 20
FEATURE                 Location/Qualifiers
misc_feature            1..20
                        note = Synthetic oligonucleotide
source                  1..20
                        mol_type = other DNA
```

```
                        organism = synthetic construct
SEQUENCE: 733
gcggctgcgg tgccccagcc                                             20

SEQ ID NO: 734          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 734
gggccatcta gctggagaga                                             20

SEQ ID NO: 735          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 735
ccccactgca agaagtcggc                                             20

SEQ ID NO: 736          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 736
ttgagccctt ttaaggcagc                                             20

SEQ ID NO: 737          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 737
tgaccaggta ctgggagcgg                                             20

SEQ ID NO: 738          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 738
cctggagctg gatcagtccc                                             20

SEQ ID NO: 739          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 739
acatgggaag gtggatccgt                                             20

SEQ ID NO: 740          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 740
gtgggacata ccctggcagg                                             20

SEQ ID NO: 741          moltype = DNA  length = 20
FEATURE                 Location/Qualifiers
misc_feature            1..20
                        note = Synthetic oligonucleotide
source                  1..20
```

```
                          mol_type = other DNA
                          organism = synthetic construct
SEQUENCE: 741
gccaggccta gggatctgca                                                20

SEQ ID NO: 742            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 742
ggaagcacga cacctcgcct                                                20

SEQ ID NO: 743            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 743
cctcaccatt ccatcaggct                                                20

SEQ ID NO: 744            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 744
cggcagcgac aagtgttccc                                                20

SEQ ID NO: 745            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 745
gtctctgaag gccatgcagc                                                20

SEQ ID NO: 746            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 746
cagccacttg atccggtggg                                                20

SEQ ID NO: 747            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 747
aggtcggcct cttcagccac                                                20

SEQ ID NO: 748            moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 748
gttggctgga gaagttctgg                                                20

SEQ ID NO: 749            moltype = DNA  length = 20
FEATURE                   Location/Qualifiers
misc_feature              1..20
                          note = Synthetic oligonucleotide
```

```
source                  1..20
                        mol_type = other DNA
                        organism = synthetic construct
SEQUENCE: 749
ccccgtgatg gctgcggctc                                              20

SEQ ID NO: 750          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 750
aggccaggcc tagggatcct                                              20

SEQ ID NO: 751          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 751
ggcgcggtgc cccagcctgg                                              20

SEQ ID NO: 752          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 752
gtcctggccc caccagcggg                                              20

SEQ ID NO: 753          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 753
ccaggcctag gaatcctggc                                              20

SEQ ID NO: 754          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 754
gcgcctcgga tagccaggcc                                              20

SEQ ID NO: 755          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 755
cccagtgtgg cgcagcagcc                                              20

SEQ ID NO: 756          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 756
gtgtttcatc ttcaccaccg                                              20

SEQ ID NO: 757          moltype = DNA  length = 20
FEATURE                 Location/Qualifiers
misc_feature            1..20
```

```
                        note = Synthetic oligonucleotide
source                  1..20
                        mol_type = other DNA
                        organism = synthetic construct
SEQUENCE: 757
aggtcagcct cttcagccac                                             20

SEQ ID NO: 758          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 758
ggccatatgg gaaggtggat                                             20

SEQ ID NO: 759          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 759
ggaggatttg gcgagaagca                                             20

SEQ ID NO: 760          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 760
cgaagtctgc cccacctcga                                             20

SEQ ID NO: 761          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 761
gtggcaccct cgaagtctgc                                             20

SEQ ID NO: 762          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 762
gggtccattg taaggaagct                                             20

SEQ ID NO: 763          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 763
ggtgcccaca gccaccaggg                                             20

SEQ ID NO: 764          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 764
tccatggcag tgagccggtc                                             20

SEQ ID NO: 765          moltype = DNA  length = 20
FEATURE                 Location/Qualifiers
```

```
misc_feature            1..20
                        note = Synthetic oligonucleotide
source                  1..20
                        mol_type = other DNA
                        organism = synthetic construct
SEQUENCE: 765
gggaccactt gatccggtgg                                              20

SEQ ID NO: 766          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 766
ggatcagagt tgggaccact                                              20

SEQ ID NO: 767          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 767
ccccgtgatg gctgcggttc                                              20

SEQ ID NO: 768          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 768
gtgtgtcctc ataccccgcc                                              20

SEQ ID NO: 769          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 769
gcaccctcga agtctcgacc                                              20

SEQ ID NO: 770          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 770
gctctgaagg ccatgcagca                                              20

SEQ ID NO: 771          moltype = DNA  length = 25
FEATURE                 Location/Qualifiers
misc_feature            1..25
                        note = Primer
source                  1..25
                        mol_type = other DNA
                        organism = synthetic construct
SEQUENCE: 771
gacatatgcc aagattgtgc actac                                        25

SEQ ID NO: 772          moltype = DNA  length = 21
FEATURE                 Location/Qualifiers
misc_feature            1..21
                        note = Primer
source                  1..21
                        mol_type = other DNA
                        organism = synthetic construct
SEQUENCE: 772
cacgaatgag gtcctgagct t                                            21

SEQ ID NO: 773          moltype = DNA  length = 22
```

```
FEATURE                Location/Qualifiers
misc_feature           1..22
                       note = Probe
source                 1..22
                       mol_type = other DNA
                       organism = synthetic construct
SEQUENCE: 773
aacacttgtc gctgccgctg gc                                              22

SEQ ID NO: 774         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 774
agcgaggctt cacttggcgc                                                 20

SEQ ID NO: 775         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 775
gggaagcgag gcttcacttg                                                 20

SEQ ID NO: 776         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 776
gcggtcagcg atcccagggt                                                 20

SEQ ID NO: 777         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 777
gggtgccagc gcggtgatct                                                 20

SEQ ID NO: 778         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 778
tgttacaaag aaagtgactg                                                 20

SEQ ID NO: 779         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 779
cgatggcagc aacggaagtt                                                 20

SEQ ID NO: 780         moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 780
gtcagtttac gatggcagca                                                 20
```

-continued

```
SEQ ID NO: 781          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 781
cagggctttg tttcgaaaaa                                         20

SEQ ID NO: 782          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 782
ccattttctt ccacagggct                                         20

SEQ ID NO: 783          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 783
atgcttcttc aagttttcca                                         20

SEQ ID NO: 784          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 784
cagaatgact ttaatgcttc                                         20

SEQ ID NO: 785          moltype = DNA  length = 21
FEATURE                 Location/Qualifiers
misc_feature            1..21
                        note = Primer
source                  1..21
                        mol_type = other DNA
                        organism = synthetic construct
SEQUENCE: 785
ccaccgcaaa tgcttctaga c                                       21

SEQ ID NO: 786          moltype = DNA  length = 20
FEATURE                 Location/Qualifiers
misc_feature            1..20
                        note = Primer
source                  1..20
                        mol_type = other DNA
                        organism = synthetic construct
SEQUENCE: 786
cccccccatt gagaagattc                                         20

SEQ ID NO: 787          moltype = DNA  length = 24
FEATURE                 Location/Qualifiers
misc_feature            1..24
                        note = Probe
source                  1..24
                        mol_type = other DNA
                        organism = synthetic construct
SEQUENCE: 787
ctccacctcc agcacgcgac ttct                                    24

SEQ ID NO: 788          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 788
gcggtcagcg atcccagggt                                         20
```

```
SEQ ID NO: 789          moltype = DNA  length = 25
FEATURE                 Location/Qualifiers
misc_feature            1..25
                        note = Synthetic oligonucleotide
source                  1..25
                        mol_type = other DNA
                        organism = synthetic construct
SEQUENCE: 789
agcagcagca gcagcagcag cagca                                   25

SEQ ID NO: 790          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 790
agcagcagca gcagcagcag                                         20

SEQ ID NO: 791          moltype = DNA  length = 15
FEATURE                 Location/Qualifiers
misc_feature            1..15
                        note = Synthetic oligonucleotide
source                  1..15
                        mol_type = other DNA
                        organism = synthetic construct
SEQUENCE: 791
gcagcagcag cagca                                              15

SEQ ID NO: 792          moltype =   length =
SEQUENCE: 792
000

SEQ ID NO: 793          moltype = DNA  length = 2611
FEATURE                 Location/Qualifiers
source                  1..2611
                        mol_type = genomic DNA
                        organism = Mus musculus
SEQUENCE: 793
cgggaagacc ccgagctccg gcccggggag gggccatggt gttgcctgcc caacatgtca  60
gccgaagtgc ggctgaggca gctccagcag ctggtgctgg acccaggctt cctgggactg  120
gagcccctgc tcgaccttct cctgggcgtc caccaggagc tgggtgcctc tcacctagcc  180
caggacaagt atgtggccga cttcttgcag tgggtggagc ccattgcagc aaggcttaag  240
gaggtccgac tgcagaggga tgattttgag attttgaagg tgatcgggcg tggggcgttc  300
agcgaggtag cggtggtgaa gatgaaacag acgggccaag tgtatgccat gaagattatg  360
aataagtggg acatgctgaa gagaggcgag gtgtcgtgct tccgggaaga aagggatgta  420
ttagtgaaag gggaccggcg ctggatcaca cagctgcact ttgccttcca ggatgagaac  480
tacctgtacc tggtcatgga atactacgtg ggcggggacc tgctaacgct gctgagcaag  540
tttggggagc ggatccccgc cgagatggct cgcttctacc tggccgagat tgtcatggcc  600
atagactccg tgcaccggct gggctacgtg cacagggaca tcaaaccaga taacattctg  660
ctggaccgat gtgggcacat tcgcctggca gacttcggct cctgcctcaa actgcagcct  720
gatggaatgg tgaggtcgct ggtggctgtg ggcaccccgg actacctgtc tcctgagatt  780
ctgcaggccg ttggtggagg gcctggggca ggcagctacg ggccagagtg tgactggtgg  840
gcactgggcg tgttcaccta tgagatgttc tatgggcaga ccccccttcta cgcggactcc  900
acagccgaga catatgccaa gattgtgcac tacagggaac acttgtcgct gccgctggca  960
gacacagttg tccccgagga agctcaggac ctcattcgtg ggctgctgtg tcctgctgag  1020
ataaggctag gtcgaggtgg ggcagacttc gagggtgcca cggacacatg caatttcgat  1080
gtggtggagg accggctcac tgccatggtg agcgggggcg gggagacgct gtcagacatg  1140
caggaagaca tgccccttgg ggtgcgcctg cccttcgtgg gctactccta ctgctgcatg  1200
gccttcagag acaatcaggt cccggacccc accctatgg aactagaggc cctgcagttg  1260
cctgtgtcag acttgcaagg gcttgacttg cagccccccag tgtccccacc ggatcaagtg  1320
gctgaagagg ctgacctagt ggctgtccct gcccctgtgg ctgaggcaga gaccacggta  1380
acgctgcagc agctccagga agccctggaa gaagaggttc tcacccggca gagcctgagc  1440
cgcgagctgg aggccatccg gaccgccaac cagaacttct ccagccaact acaggaggcc  1500
gaggtccgaa accgagacct ggaggcgcat gttcggcagc tacaggaacg gatggagatg  1560
ctgcaggccc caggagccgc agccatcacg gggtccccca gtccccgggc cacggatcca  1620
ccttcccatc tagatggccc cccggccgtg gctgtgggcc agtgcccgct ggtggggcca  1680
ggccccatgc accgccgtca cctgctgctc cctgccagga tccctaggcc tggcctatcc  1740
gaggcgcgtt gcctgctcct gttcgccgct gctctggctg ctgccgccac actgggctgc  1800
actgggttgg tggcctatac cggcggtctc accccagtct ggtgtttccc gggagccacc  1860
ttcgccccct gaaccctaag actccaagcc atctttcatt taggcctcct aggaaggtcg  1920
agcgaccagg gagcgaccca aagcgtctct gtgcccatcg cccccccccc cccccccacc  1980
gctccgctcc acacttctgt gagcctgggt ccccacccag ctccgctcct gtgatccagg  2040
cctgccacct ggcggccggg gagggaggaa cagggctcgt gcccagcacc cctggttcct  2100
gcagagctgg tagccaccgc tgctgcagca gctgggcatt cgccgacctt gctttactca  2160
gccccgacgt ggatgggcaa actgctcagc tcatccgatt tcacttttc actctcccag  2220
ccatcagtta caagccataa gcatgagccc cctatttcca gggacatccc attcccatag  2280
```

```
tgatggatca gcaagacctc tgccagcaca cacggagtct ttggcttcgg acagcctcac  2340
tcctgggggt tgctgcaact ccttccccgt gtacacgtct gcactctaac aacggagcca  2400
cagctgcact ccccctccc ccaaagcagt gtgggtattt attgatcttg ttatctgact  2460
cactgacaga ctccgggacc cacgttttag atgcattgag actcgacatt cctcggtatt  2520
tattgtctgt ccccacctac gacctccact cccgaccctt gcgaataaaa tacttctggt  2580
ctgccctaaa aaaaaaaaaa aaaaaaaaaa a                                 2611

SEQ ID NO: 794         moltype = DNA  length = 988
FEATURE                Location/Qualifiers
misc_feature           531
                       note = n is a, c, g, or t
misc_feature           942
                       note = n is a, c, g, or t
source                 1..988
                       mol_type = genomic DNA
                       organism = Mus musculus
SEQUENCE: 794
gctggaccgg tccggaattc tccggatcgc cagcctttgt gggccatatt cgtcatccct  60
cctggcttct catctgcttt tgtggtccta gctcaagacc tctaattcct ctgctgactt  120
aaatgccctt ccccagaggt cttctcaggc ctagtggaca agcttggagc cttatctgct  180
cctgcccaac attgagccaa agctccagct taccccagct tccttacaat ggaccccatt  240
gcagcaaggc ttaaggaggt ccgactgcag agggatgatt ttgagatttt gaaggtgatc  300
gggcgtgggg cgttcagcga ggtagcggtg gtgaagatga aacagacggg ccaagtgtat  360
gccatgaaga ttatgaataa gtgggacatg ctgaagagag gcgaggtgtc gtgcttccgg  420
gaagaaaggg atgtattagt gaaaggggac cggcgctgga tcacacagct gcactttgcc  480
ttccaggatg agaactacct gtacctggtc atggaatact acgtgggcgg ngacctgcta  540
acgctgctga gcaagttttg gggagcggat ccccgccgag atggctcgct tctacctggc  600
cgagattgtc atggccatag actccgtgca ccggctgggc tacgtgcaca gggacatcaa  660
accagataac attctgctgg accgatgtgg gcacattcgc ctggcagact tcggctcctg  720
gcctcaactg cagcctgatg gaatggtgga gtcccctggt ggctgtgggc acccccggac  780
tacctgtctc ctgaaattct gcagggcctt ggtgggaggc cctggggaag gcaactacgg  840
gccaaaagtt ggaagggggg ggcctggggg gggttcccct atgaaaagtt ctatggggag  900
gaccccccttt aagcggaatc ccaggccgaa aaatatgccc angattgggc cctaacaggg  960
aaaacttttc ccctgcccct gggacaat                                     988

SEQ ID NO: 795         moltype = DNA  length = 649
FEATURE                Location/Qualifiers
source                 1..649
                       mol_type = genomic DNA
                       organism = Mus musculus
SEQUENCE: 795
ggcgtgttcg cctatgagat gttctatggg cagacccccct tctacgcgga ctccacagcc  60
gagacatatg ccaagattgt gcactacagg gaacacttgt cgctgccgct ggcagacaca  120
gttgtccccg aggaagctca ggacctcatt cgtgggctgc tgtgtcctgc tgagataagg  180
ctaggtcgag gtggggcagg tgatttccag aaacatcctt tcttctttgg ccttgattgg  240
gagggtctcc gagacagtgt acccccccttt acaccagact tcgagggtgc cacggacaca  300
tgcaatttcg atgtggtgga ggaccggctc actgccatgg agacgctgtc agacatgcag  360
gaagacatgc cccttggggt gcgcctgccc ttcgtgggct actcctactg ctgcatggcc  420
ttcagagaca atcaggtccc ggaccccacc cctatggaac tagaggccct gcagttgcct  480
gtgtcagact tgcaagggct tgacttgcag cccccagtgt ccccaccgga tcaagtggtc  540
ccaactctga tccccaccga caggctgaag aggctgacct agtggctgtc cctgcccctg  600
tggctgaggc agagccacgg taacgctgca gcagctccag gaagccctg              649

SEQ ID NO: 796         moltype = DNA  length = 527
FEATURE                Location/Qualifiers
source                 1..527
                       mol_type = genomic DNA
                       organism = Mus musculus
SEQUENCE: 796
atttcgatgt ggtggaggac cggctcactg ccatggtgag cgggggcggg gagacgctgt  60
cagacatgca ggaagacatg ccccttgggg tgcgcctgcc cttcgtgggc tactcctact  120
gctgcatggc cttcagagac aatcaggtcc cggaccccac ccctatggaa ctagaggccc  180
tgcagttgcc tgtgtcagac ttgcaagggc ttgacttgca gcccccagtg tccccaccgg  240
atcaagtggc tgaagaggct gacctagtgg ctgtccctgc ccctgtggct gaggcagaga  300
ccacggtaac gctgcagcag ctccaggaag ccctggaaga agaggttctc acccggcaga  360
gcctgagccg cgagctggag gccatccgga ccgccaacca gaacttctcc aggaggccga  420
ggtccgaaac cgagacctgg aggcgcatgt tcggcagcta caggaacgga tggagatgct  480
gcaggcccca ggaaccgcag ccatcacggg ggtccccagt cccccgg                527

SEQ ID NO: 797         moltype = DNA  length = 567
FEATURE                Location/Qualifiers
source                 1..567
                       mol_type = genomic DNA
                       organism = Mus musculus
SEQUENCE: 797
atggtgaggt cgctggtggc tgtgggcacc ccggactacc tgtctcctga gattctgcag  60
gccgttggtg gagggcctgg ggcaggcagc tacgggccag agtgtgactg gtgggcactg  120
ggcgtgttcg cctatgagat gttctatggg cagacccccct tctacgcgga ctccacagcc  180
gagacatatg ccaagattgt gcactacagg gaacacttgt cgctgccgct ggcagacaca  240
```

-continued

```
gttgtccccg aggaagctca ggacctcatt cgtgggctgc tgtgtcctgc tgagataagg  300
ctaggtcgag gtggggcagg tgatttccag aaacatcctt tcttctttgg ccttgattgg  360
gagggtctcc gagacagtgt accccccttt acaccagact tcgagggtgc cacggacaca  420
tgcaatttcg atgtggtgga ggaccggctc actgccatgg tgagcggggg cggggtatga  480
ggacacacag gtgaccagtc cccaagacag tgagtgaggc ttcactcttg gcagtactaa  540
aattgaatgt agggggctgg gctcttg                                     567

SEQ ID NO: 798         moltype = DNA  length = 2474
FEATURE                Location/Qualifiers
source                 1..2474
                       mol_type = genomic DNA
                       organism = Mus musculus
SEQUENCE: 798
ccgggaagaa agggatgtat tagtgaaagg ggaccggcgc tggatcacac agctgcactt  60
tgccttccag gatgagaact acctgtacct ggtcatggaa tactacgtgg gcggggacct  120
gctaacgctg ctgagcaagt ttggggagcg gatccccgcc gagatggctc gcttctacct  180
ggccgagatt gtcatggcca tagactccgt gcaccggctg ggctacgtgc acagggacat  240
caaaccagat aacattctgc tggaccgatg tgggcacatt cgcctggcag acttcggctc  300
ctgcctcaaa ctgcagcctg atggaatggt gaggtcgctg gtggctgtgg gcaccccgga  360
ctacctgtct cctgagattc tgcaggccgt tggtggaggg cctggggcag gcagctacgg  420
gccagagtgt gactggtggg cactgggcgt gttcgcctat gagatgttct atgggcagac  480
ccccttctac gcggactcca cagccgagac atatgccaag attgtgcact acagggaaca  540
cttgtcgctg ccgctggcag acacagttgt ccccgaggaa gctcaggacc tcattcgtgg  600
gctgctgtgt cctgctgaga taaggctagg tcgagacttc gagggtgcca cggacacatg  660
caatttcgat gtggtggagg accggctcac tgccatggtg agcgggggcg gggagacgct  720
gtcagacatg caggaagaca tgccccttgg ggtgcgcctg cccttcgtgg gctactccta  780
ctgctgcatg gccttcagag acaatcaggt cccggacccc acccctatgg aactagaggc  840
cctgcagttg cctgtgtcag acttgcaagg gcttgacttg cagcccccag tgtccccacc  900
ggatcaagtg gctgaagagg ccgacctagt ggctgtccct gcccctgtgg ctgaggcaga  960
gaccacggta acgctgcagc agctccagga agccctggaa gaagaggttc tcacccggca  1020
gagcctgagc cgcgagctgg aggccatccg gaccgccaac cagaacttct ccagccaact  1080
acaggaggcc gaggtccgaa accgagacct ggaggcgcat gttcggcagc tacaggaacg  1140
gatggagatg ctgcaggccc caggagccgc aggcgagtcc ctcacctgct tccagccaag  1200
ggggcactgg gtggagatgg ggggcatgtt gggtgtgtga accctcgggg caggggagga  1260
gtccaggctg gggcaccgca gccgcgccac tgcctttctc ctccatcctc cacactccat  1320
acacctctct cttctccttc cagccatcac gggggtcccc agtccccggg ccacggatcc  1380
accttcccat gcttctcgcc aaatcctccc caagggaact ccctagactc ccgttctggc  1440
ctcgactaga ttcccgcact gcctctcgcc ctgctgctgg gctccgatcg ggtcacctgt  1500
cccttctctc tccagctaga tggccccccg gccgtggctg tgggccagtg cccgctggtg  1560
gggccaggcc ccatgcaccg ccgtcacctg ctgctccctg ccaggatccc taggcctggc  1620
ctatccgagg cgcgttgcct gctcctgttc gccgctgctc tggctgctgc cgccacactg  1680
ggctgcactg ggttggtggc ctataccggc ggtctcaccc cagtctggtg tttcccggga  1740
gccaccttcg ccccctgaac cctaagactc caagccatct ttcatttagg cctcctagga  1800
agatcgagcg accagggagc gacccaaagc gtctctgtgc ccatcgcccc cccccccccc  1860
cccaccgctc cgctccacac ttctgtgagc ctgggtcccc acccagctcc gctcctgtga  1920
tccaggcctg ccacctggcg gccggggagg gaggaacagg gctcgtgccc agcacccctg  1980
gttcctgcag agctggtagc caccgctgct gcagcagctg ggcattcgcc gaccttgctt  2040
tactcagccc tgacgtggat gggctaactg ctcagctcat ccgatttcac tttttcactc  2100
tcccagccat cagttacaag ccataagcat gagcccccta tttccaggga catcccattc  2160
ccatagtgat ggatcagcaa gacctctgcc agcacacacg gagtctttgg cttcggacag  2220
cctcactcct ggggggttgct gcaactcctt ccccgtgtac acgtctgcac tctaacaacg  2280
gagccacagc tgcactcccc cctcccccaa agcagtgtgg gtatttattg atcttgttat  2340
ctgactcact gacagactcc gggacccacg ttttagatgc attgagactc gacattcctc  2400
ggtatttatt gtctgtcccc acctacgacc tccactcccg acccttgcga ataaaatact  2460
tctggtctgc ccta                                                   2474

SEQ ID NO: 799         moltype = DNA  length = 2135
FEATURE                Location/Qualifiers
source                 1..2135
                       mol_type = genomic DNA
                       organism = Mus musculus
SEQUENCE: 799
ccgggaagaa agggatgtat tagtgaaagg ggaccggcgc tggatcacac agctgcactt  60
tgccttccag gatgagaact acctgtacct ggtcatggaa tactacgtgg gcggggacct  120
gctaacgctg ctgagcaagt ttggggagcg gatccccgcc gagatggctc gcttctacct  180
ggccgagatt gtcatggcca tagactccgt gcaccggctg ggctacgtgc acagggacat  240
caaaccagat aacattctgc tggaccgatg tgggcacatt cgcctggcag acttcggctc  300
ctgcctcaaa ctgcagcctg atggaatggt gaggtcgctg gtggctgtgg gcaccccgga  360
ctacctgtct cctgagattc tgcaggccgt tggtggaggg cctggggcag gcagctacgg  420
gccagagtgt gactggtggg cactgggcgt gttcgcctat gagatgttct atgggcagac  480
ccccttctac gcggactcca cagccgagac atatgccaag attgtgcact acagggaaca  540
cttgtcgctg ccgctggcag acacagttgt ccccgaggaa gctcaggacc tcattcgtgg  600
gctgctgtgt cctgctgaga taaggctagg tcgaggtggg gcaggtgatt tccagaaaca  660
tcctttcttc tttggccttg attgggaggg tctccgagac agtgtacccc cctttacacc  720
agacttcgag ggtgccacgg acacatgcaa tttcgatgtg gtggaggacc ggctcactgc  780
catggagacg ctgtcagaca tgcaggaaga catgcccctt ggggtgcgcc tgcccttcgt  840
gggctactcc tactgctgca tggccttcag agctgaagag gccgacctag tggctgtccc  900
tgcccctgtg gctgaggcag agaccacggt aacgctgcag cagctccagg aagccctgga  960
agaagaggtt ctcacccggc agagcctgag ccgcgagctg gaggccatcc ggaccgccaa  1020
```

-continued

```
ccagaacttc tccagccaac tacaggaggc cgaggtccga aaccgagacc tggaggcgca  1080
tgttcggcag ctacaggaac ggatggagat gctgcaggcc ccaggagccg cagccatcac  1140
gggggtcccc agtccccggg ccacggatcc accttcccat atggcccccc ggccgtggct  1200
gtgggccagt gcccgctggt ggggccaggc cccatgcacc gccgtcacct gctgctccct  1260
gccaggatcc ctaggcctgg cctatccgag gcgcgttgcc tgctcctgtt cgccgctgct  1320
ctggctgctg ccgccacact gggctgcact gggttggtgg cctataccgg cggtctcacc  1380
ccagtctggt gtttcccggg agccaccttc gccccctgaa ccctaagact ccaagccatc  1440
tttcatttag gcctcctagg aagatcgagc gaccagggag cgacccaaag cgtctctgtg  1500
cccatcgccc cccccccccc ccccaccgct ccgctccaca cttctgtgag cctgggtccc  1560
cacccagctc cgctcctgtg atccaggcct gccacctggc ggccggggag ggaggaacag  1620
ggctcgtgcc cagcacccct ggttcctgca gagctggtag ccaccgctgc tgcagcagct  1680
gggcattcgc cgaccttgct ttactcagcc ctgacgtgga tgggctaact gctcagctca  1740
tccgatttca ctttttcact ctcccagcca tcagttacaa gccataagca tgagcccccct  1800
atttccaggg acatcccatt cccatagtga tggatcagca agacctctgc cagcacacac  1860
ggagtctttg gcttcggaca gcctcactcc tgggggttgc tgcaactcct tccccgtgta  1920
cacgtctgca ctctaacaac ggagccacag ctgcactccc ccctccccca aagcagtgtg  1980
ggtatttatt gatcttgtta tctgactcac tgacagactc cgggacccac gttttagatg  2040
cattgagact cgacattcct cggtatttat tgtctgtccc cacctacgac ctccactccc  2100
gacccttgcg aataaaatac ttctggtctg cccta                             2135
```

```
SEQ ID NO: 800          moltype = DNA  length = 2873
FEATURE                 Location/Qualifiers
source                  1..2873
                        mol_type = genomic DNA
                        organism = Homo sapiens
SEQUENCE: 800
agggggggctg gaccaagggg tggggagaag gggaggaggc ctcggccggc cgcagagaga  60
agtggccaga gaggcccagg ggacagccag ggacaggcag acatgcagcc agggctccag  120
ggcctggaca ggggctgcca ggccctgtga caggaggacc ccgagccccc ggcccgggga  180
ggggccatgg tgctgcctgt ccaacatgtc agccgaggtg cggctgaggc ggctccagca  240
gctggtgttg gacccgggct tcctggggct ggagcccctg ctcgaccttc tcctgggcgt  300
ccaccaggag ctgggcgcct ccgaactggc ccaggacaag tacgtggccg acttcttgca  360
gtgggcggag cccatcgtgg tgaggcttaa ggaggtccga ctgcagaggg acgacttcga  420
gattctgaag gtgatcggac gcggggcgtt cagcgaggta gcggtagtga agatgaagca  480
gacgggccag gtgtatgcca tgaagatcat gaacaagtgg gacatgctga agaggggcga  540
ggtgtcgtgc ttccgtgagg agagggacgt gttggtgaat ggggaccggc ggtggatcac  600
gcagctgcac ttcgccttcc aggatgagaa ctacctgtac ctggtcatgg agtattacgt  660
gggcggggac ctgctgacac tgctgagcaa gtttggggag cggattccgg ccgagatggc  720
gcgcttctac ctggcggaga ttgtcatggc catagactcg gtgcaccggc ttggctacgt  780
gcacagggac atcaaacccg acaacatcct gctggaccgc tgtggccaca tccgcctggc  840
cgacttcggc tcttgcctca agctgcgggc agatggaacg gtgcggtcgc tggtggctgt  900
gggcacccca gactacctgt cccccgagat cctgcaggct gtgggcggtg ggcctgggac  960
aggcagctac gggcccgagt gtgactggtg ggcgctgggt gtattcgcct atgaaatgtt  1020
ctatgggcag acgcccttct acgcggattc cacggcggag acctatggca agatcgtcca  1080
ctacaaggag cacctctctc tgccgctggt ggacgaaggg gtccctgagg aggctcgaga  1140
cttcattcag cggttgctgt gtcccccgga gacacggctg ggccggggtg gagcaggcga  1200
cttccggaca catcccttct tctttggcct cgactgggat ggtctccggg acagcgtgcc  1260
ccccttaca ccggatttcg aaggtgccac cgacacatgc aacttcgact tggtggagga  1320
cgggctcact gccatggaga cactgtcgga cattcgggaa ggtgcgccgc tagggggtcca  1380
cctgcctttt gtgggctact cctactcctg catggccctc agggacagtg aggtcccagg  1440
ccccacaccc atggaactgg aggccgagca gctgcttgag ccacacgtgc aagcgcccag  1500
cctggagccc tcggtgtccc cacaggatga aacagctgaa gtggcagttc cagcggctgt  1560
ccctgcggca gaggctgagg ccgaggtgac gctgcgggag ctccaggaag ccctggagga  1620
ggaggtgctc acccggcaga gcctgagccg ggagatggag gccatccgca cggacaacca  1680
gaacttcgcc agtcaactac gcgaggcaga ggctcggaac cgggacctag aggcacacgt  1740
ccggcagttg caggagcgga tggagttgct gcaggcagag ggagccacag ctgtcacggg  1800
ggtccccagt ccccgggcca cggatccacc ttcccatatg gcccccggc cgtggctgtg  1860
ggccagtgcc cgctggtggg gccaggcccc atgcaccgcc gccacctgct gctccctgcc  1920
agggtcccta ggcctggcct atcggaggcg ctttccctgc tcctgttcgc cgttgttctg  1980
tctcgtgccg ccgccctggg ctgcattggg ttggtggccc acgccggcca actcaccgca  2040
gtctggcgcc gcccaggagc cgcccgcgct ccctgaaccc tagaactgtc ttcgactccg  2100
gggccccgtt ggaagactga gtgcccgggg cacggcacag aagccgcgcc caccgcctgc  2160
cagttcacaa ccgctccgag cgtgggtctc cgcccagctc cagtcctgtg atccgggccc  2220
gccccctagc ggccggggag ggaggggccg ggtccgcggc cggcgaacgg ggctcgaagg  2280
gtccttgtag ccgggaatgc tgctgctgct gctgctgctg ctgctgctgc tgctgctgct  2340
gctgctgctg ctgctgctgg ggggatcaca gaccatttct ttctttcggc caggctgagg  2400
ccctgacgtg gatgggcaaa ctgcaggcct gggaaggcag caagccgggc cgtccgtgtt  2460
ccatcctcca cgcaccccca cctatcgttg gttcgcaaag tgcaaagctt tcttgtgcat  2520
gacgccctgc tctggggagc gtctggcgcg atctctgcct gcttactcgg gaaatttgct  2580
tttgccaaac ccgctttttc ggggatcccg cgcccccctc ctcacttgcg ctgctctcgg  2640
agccccagcc ggctccgccc gcttcggcgg tttggatatt tattgacctc gtcctccgac  2700
tcgctgacag gctacaggac ccccaacaac cccaatccac gttttggatg cactgagacc  2760
ccgacattcc tcggtattta ttgtctgtcc ccacctagga cccccacccc cgaccctcgc  2820
gaataaaagg ccctccatct gcccaaaaaa aaaaaaaaaa aaaaaaaaaa aaa         2873
```

```
SEQ ID NO: 801          moltype = DNA  length = 1509
FEATURE                 Location/Qualifiers
source                  1..1509
                        mol_type = genomic DNA
```

```
                         organism = Homo sapiens
SEQUENCE: 801
ccaccgcagc ggacagcgcc aagtgaagcc tcgcttcccc tccgcggcga ccagggcccg  60
agccgagagt agcagttgta gctacccgcc cagaaactag acacaatgtg cgacgaagac  120
gagaccaccg ccctcgtgtg cgacaatggc tccggcctgg tgaaagccgg cttcgccggg  180
gatgacgccc ctagggccgt gttcccgtcc atcgtgggcc gcccccgaca ccagggcgtc  240
atggtcggta tgggtcagaa agattcctac gtgggcgacg aggctcagag caagagaggt  300
atcctgaccc tgaagtaccc tatcgagcac ggcatcatca ccaactggga tgacatggag  360
aagatctggc accacacctt ctacaacgag cttcgcgtgg ctcccgagga gcaccccacc  420
ctgctcaccg aggccccct caatcccaag gccaaccgcg agaagatgac ccagatcatg  480
tttgagacct tcaacgtgcc cgccatgtac gtggccatcc aggccgtgct gtccctctac  540
gcctccggca ggaccaccgg catcgtgctg gactccggcg acggcgtcac ccacaacgtg  600
cccatttatg agggctacgc gctgccgcac gccatcatgc gcctggacct ggcgggccgc  660
gatctcaccg actacctgat gaagatcctc actgagcgtg gctactcctt cgtgaccaca  720
gctgagcgcg agatcgtgcg cgacatcaag gagaagctgt gctacgtggc cctggacttc  780
gagaacgaga tggcgacggc cgcctcctcc tcctccctgg aaaagagcta cgagctgcca  840
gacgggcagg tcatcaccat cggcaacgag cgcttccgct gcccggagac gctcttccag  900
ccctccttca tcggtatgga gtcggcgggc attcacgaga ccacctacaa cagcatcatg  960
aagtgtgaca tcgacatcag gaaggacctg tatgccaaca acgtcatgtc ggggggcacc  1020
acgatgtacc ctgggatcgc tgaccgcatg cagaaagaga tcaccgcgct ggcacccagc  1080
accatgaaga tcaagatcat cgccccgccg gagcgcaaat actcggtgtg gatcggcggc  1140
tccatcctgg cctcgctgtc caccttccag cagatgtgga tcaccaagca ggagtacgac  1200
gaggccggcc cttccatcgt ccaccgcaaa tgcttctaga cacactccac ctccagcacg  1260
cgacttctca ggacgacgaa tcttctcaat ggggggggcgg ctgagctcca gccaccccgc  1320
agtcactttc tttgtaacaa cttccgttgc tgccatcgta aactgacaca gtgtttataa  1380
cgtgtacata cattaactta ttacctcatt ttgttatttt tcgaaacaaa gccctgtgga  1440
agaaaatgga aaacttgaag aagcattaaa gtcattctgt taagctgcgt aaaaaaaaaa  1500
aaaaaaaaa                                                          1509

SEQ ID NO: 802           moltype = DNA  length = 19
FEATURE                  Location/Qualifiers
misc_feature             1..19
                         note = Synthetic oligonucleotide
source                   1..19
                         mol_type = other DNA
                         organism = synthetic construct
SEQUENCE: 802
gcagcagcag cagcagcag                                               19

SEQ ID NO: 803           moltype = DNA  length = 19
FEATURE                  Location/Qualifiers
misc_feature             1..19
                         note = Synthetic oligonucleotide
source                   1..19
                         mol_type = other DNA
                         organism = synthetic construct
SEQUENCE: 803
gcagcagcag cagcagcag                                               19

SEQ ID NO: 804           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 804
agcagcagca gcagcagcag                                              20

SEQ ID NO: 805           moltype = DNA  length = 18
FEATURE                  Location/Qualifiers
misc_feature             1..18
                         note = Synthetic oligonucleotide
source                   1..18
                         mol_type = other DNA
                         organism = synthetic construct
SEQUENCE: 805
gcagcagcag cagcagca                                                18

SEQ ID NO: 806           moltype = DNA  length = 19
FEATURE                  Location/Qualifiers
misc_feature             1..19
                         note = Synthetic oligonucleotide
source                   1..19
                         mol_type = other DNA
                         organism = synthetic construct
SEQUENCE: 806
agcagcagca gcagcagca                                               19
```

```
SEQ ID NO: 807          moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 807
agcagcagca gcagca                                                  16

SEQ ID NO: 808          moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 808
ctcccgacaa gctcca                                                  16

SEQ ID NO: 809          moltype = DNA  length = 14
FEATURE                 Location/Qualifiers
misc_feature            1..14
                        note = Synthetic oligonucleotide
source                  1..14
                        mol_type = other DNA
                        organism = synthetic construct
SEQUENCE: 809
tcccgacaag ctcc                                                    14

SEQ ID NO: 810          moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 810
gcttgcacgt gtggct                                                  16

SEQ ID NO: 811          moltype = DNA  length = 14
FEATURE                 Location/Qualifiers
misc_feature            1..14
                        note = Synthetic oligonucleotide
source                  1..14
                        mol_type = other DNA
                        organism = synthetic construct
SEQUENCE: 811
cttgcacgtg tggc                                                    14

SEQ ID NO: 812          moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 812
ggttgtgaac tggcag                                                  16

SEQ ID NO: 813          moltype = DNA  length = 14
FEATURE                 Location/Qualifiers
misc_feature            1..14
                        note = Synthetic oligonucleotide
source                  1..14
                        mol_type = other DNA
                        organism = synthetic construct
SEQUENCE: 813
gttgtgaact ggca                                                    14

SEQ ID NO: 814          moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 814
gagcggttgt gaactg                                                  16
```

```
SEQ ID NO: 815          moltype = DNA  length = 14
FEATURE                 Location/Qualifiers
misc_feature            1..14
                        note = Synthetic oligonucleotide
source                  1..14
                        mol_type = other DNA
                        organism = synthetic construct
SEQUENCE: 815
agcggttgtg aact                                                    14

SEQ ID NO: 816          moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 816
gctgccttcc caggcc                                                  16

SEQ ID NO: 817          moltype = DNA  length = 14
FEATURE                 Location/Qualifiers
misc_feature            1..14
                        note = Synthetic oligonucleotide
source                  1..14
                        mol_type = other DNA
                        organism = synthetic construct
SEQUENCE: 817
ctgccttccc aggc                                                    14

SEQ ID NO: 818          moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 818
gcactttgcg aaccaa                                                  16

SEQ ID NO: 819          moltype = DNA  length = 14
FEATURE                 Location/Qualifiers
misc_feature            1..14
                        note = Synthetic oligonucleotide
source                  1..14
                        mol_type = other DNA
                        organism = synthetic construct
SEQUENCE: 819
cactttgcga acca                                                    14

SEQ ID NO: 820          moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 820
gaaagctttg cacttt                                                  16

SEQ ID NO: 821          moltype = DNA  length = 14
FEATURE                 Location/Qualifiers
misc_feature            1..14
                        note = Synthetic oligonucleotide
source                  1..14
                        mol_type = other DNA
                        organism = synthetic construct
SEQUENCE: 821
aaagctttgc actt                                                    14

SEQ ID NO: 822          moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 822
```

```
cggaggacga ggtcaa                                                  16

SEQ ID NO: 823         moltype = DNA  length = 14
FEATURE                Location/Qualifiers
misc_feature           1..14
                       note = Synthetic oligonucleotide
source                 1..14
                       mol_type = other DNA
                       organism = synthetic construct
SEQUENCE: 823
ggaggacgag gtca                                                    14

SEQ ID NO: 824         moltype = DNA  length = 16
FEATURE                Location/Qualifiers
misc_feature           1..16
                       note = Synthetic oligonucleotide
source                 1..16
                       mol_type = other DNA
                       organism = synthetic construct
SEQUENCE: 824
agcctgtcag cgagtc                                                  16

SEQ ID NO: 825         moltype = DNA  length = 14
FEATURE                Location/Qualifiers
misc_feature           1..14
                       note = Synthetic oligonucleotide
source                 1..14
                       mol_type = other DNA
                       organism = synthetic construct
SEQUENCE: 825
gcctgtcagc gagt                                                    14

SEQ ID NO: 826         moltype = DNA  length = 16
FEATURE                Location/Qualifiers
misc_feature           1..16
                       note = Synthetic oligonucleotide
source                 1..16
                       mol_type = other DNA
                       organism = synthetic construct
SEQUENCE: 826
tcctgtagcc tgtcag                                                  16

SEQ ID NO: 827         moltype = DNA  length = 14
FEATURE                Location/Qualifiers
misc_feature           1..14
                       note = Synthetic oligonucleotide
source                 1..14
                       mol_type = other DNA
                       organism = synthetic construct
SEQUENCE: 827
cctgtagcct gtca                                                    14

SEQ ID NO: 828         moltype = DNA  length = 16
FEATURE                Location/Qualifiers
misc_feature           1..16
                       note = Synthetic oligonucleotide
source                 1..16
                       mol_type = other DNA
                       organism = synthetic construct
SEQUENCE: 828
gaagcgaggc ttcact                                                  16

SEQ ID NO: 829         moltype = DNA  length = 14
FEATURE                Location/Qualifiers
misc_feature           1..14
                       note = Synthetic oligonucleotide
source                 1..14
                       mol_type = other DNA
                       organism = synthetic construct
SEQUENCE: 829
aagcgaggct tcac                                                    14

SEQ ID NO: 830         moltype = DNA  length = 16
FEATURE                Location/Qualifiers
misc_feature           1..16
                       note = Synthetic oligonucleotide
source                 1..16
                       mol_type = other DNA
                       organism = synthetic construct
```

```
SEQUENCE: 830
acctgcccgt ctggca                                                    16

SEQ ID NO: 831          moltype = DNA  length = 14
FEATURE                 Location/Qualifiers
misc_feature            1..14
                        note = Synthetic oligonucleotide
source                  1..14
                        mol_type = other DNA
                        organism = synthetic construct
SEQUENCE: 831
cctgcccgtc tggc                                                      14

SEQ ID NO: 832          moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 832
ggtcagcgat cccagg                                                    16

SEQ ID NO: 833          moltype = DNA  length = 14
FEATURE                 Location/Qualifiers
misc_feature            1..14
                        note = Synthetic oligonucleotide
source                  1..14
                        mol_type = other DNA
                        organism = synthetic construct
SEQUENCE: 833
gtcagcgatc ccag                                                      14

SEQ ID NO: 834          moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 834
attttcttcc acaggg                                                    16

SEQ ID NO: 835          moltype = DNA  length = 14
FEATURE                 Location/Qualifiers
misc_feature            1..14
                        note = Synthetic oligonucleotide
source                  1..14
                        mol_type = other DNA
                        organism = synthetic construct
SEQUENCE: 835
ttttcttcca cagg                                                      14

SEQ ID NO: 836          moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 836
gaatgacttt aatgct                                                    16

SEQ ID NO: 837          moltype = DNA  length = 14
FEATURE                 Location/Qualifiers
misc_feature            1..14
                        note = Synthetic oligonucleotide
source                  1..14
                        mol_type = other DNA
                        organism = synthetic construct
SEQUENCE: 837
aatgacttta atgc                                                      14
```

MODULATION OF DYSTROPHIA MYOTONICA-PROTEIN KINASE (DMPK) EXPRESSION

STATEMENT OF GOVERNMENT SUPPORT

This invention was made with government support under NS072323 awarded by the National Institutes of Health. The government has certain rights in the invention.

SEQUENCE LISTING

The present application is being filed along with a Sequence Listing in electronic format. The Sequence Listing is provided as a file entitled 2022 Jul. 19_01135-0068-06US ST26.xml created Jul. 19, 2022, which is 1,114,714 bytes in size. The information in the electronic format of the sequence listing is incorporated herein by reference in its entirety.

FIELD

Provided herein are methods, compounds, and compositions for reducing expression of DMPK mRNA and protein in an animal. Also, provided herein are methods, compounds, and compositions comprising a DMPK inhibitor for preferentially reducing CUGexp DMPK RNA, reducing myotonia, or reducing spliceopathy in an animal. Such methods, compounds, and compositions are useful, for example, to treat, prevent, or ameliorate type 1 myotonic dystrophy (DM1) in an animal.

BACKGROUND

Myotonic dystrophy type 1 (DM1) is the most common form of muscular dystrophy in adults with an estimated frequency of 1 in 7,500 (Harper P S., Myotonic Dystrophy. London: W. B. Saunders Company; 2001). DM1 is an autosomal dominant disorder caused by expansion of a non-coding CTG repeat in DMPK1. DMPK1 is a gene encoding a cytosolic serine/threonine kinase (Brook J D, et al., *Cell.,* 1992, 68 (4): 799-808). The physiologic functions and substrates of this kinase have not been fully determined. The expanded CTG repeat is located in the 3' untranslated region (UTR) of DMPK1. This mutation leads to RNA dominance, a process in which expression of RNA containing an expanded CUG repeat (CUGexp) induces cell dysfunction (Osborne R J and Thornton CA., *Human Molecular Genetics.,* 2006, 15 (2): R162-R169).

The DMPK gene normally has 5-37 CTG repeats in the 3' untranslated region. In myotonic dystrophy type 1, this number is significantly expanded and is, for example, in the range of 50 to greater than 3,500 (Harper, Myotonic Dystrophy (Saunders, London, ed. 3, 2001); Annu. Rev. Neurosci. 29:259, 2006; EMBO J. 19:4439, 2000; Curr Opin Neurol. 20:572, 2007).

The CUGexp tract interacts with RNA binding proteins including muscleblind-like (MBNL) protein, a splicing factor, and causes the mutant transcript to be retained in nuclear foci. The toxicity of this RNA stems from sequestration of RNA binding proteins and activation of signaling pathways. Studies in animal models have shown that phenotypes of DM1 can be reversed if toxicity of CUGexp RNA is reduced (Wheeler T M, et al., *Science.,* 2009, 325 (5938): 336-339; Mulders S A, et al., *Proc Natl Acad Sci USA.,* 2009, 106 (33): 13915-13920).

In DM1, skeletal muscle is the most severely affected tissue, but the disease also has important effects on cardiac and smooth muscle, ocular lens, and brain. The cranial, distal limb, and diaphragm muscles are preferentially affected. Manual dexterity is compromised early, which causes several decades of severe disability. The median age at death is 55 years, usually from respiratory failure (de Die-Smulders C E, et al., *Brain.,* 1998, 121 (Pt 8): 1557-1563).

Antisense technology is emerging as an effective means for modulating expression of certain gene products and may therefore prove to be uniquely useful in a number of therapeutic, diagnostic, and research applications for the modulation of DMPK1. Intramuscular injection of fully modified oligonucleotides targeting with the CAG-repeat were shown in mice to block formation of CUGexp-MBNL1 complexes, disperse nuclear foci of CUGexp transcripts, enhance the nucleocytoplasmic transport and translation of CUGexp transcripts, release MBNL proteins to the nucleoplasm, normalize alternative splicing of MBNL-dependent exons, and eliminate myotonia in CUGexp-expressing transgenic mice (Wheeler T M, et al., *Science.,* 2009, 325 (5938): 336-339; WO2008/036406).

Presently there is no treatment that can modify the course of DM1. The burden of disease, therefore, is significant. It is, therefore, an object herein to provide compounds, compositions, and methods for treating DM1

SUMMARY

Provided herein are methods, compounds, and compositions for inhibiting expression of DMPK and treating, preventing, delaying or ameliorating a DMPK related disease and or a symptom thereof. In certain embodiments, the compounds and compositions inhibit mutant DMPK or CUGexp DMPK.

Certain embodiments provide a method of reducing DMPK expression in an animal comprising administering to the animal a compound comprising a modified oligonucleotide as further described herein targeted to DMPK.

Certain embodiments provide a method of preferentially reducing CUGexp DMPK, reducing myotonia, or reducing spliceopathy in an animal comprising administering to the animal a compound comprising a modified oligonucleotide, as further described herein, targeted to CUGexp DMPK. CUGexp DMPK transcripts are believed to be particularly sensitive to antisense knockdown via nuclear ribonucleases, because of their longer residence time in the nucleus, and this sensitivity is thought to permit effective antisense inhibition of CUGexp DMPK transcripts in relevant tissues such as muscle despite the biodistribution barriers to tissue uptake of antisense oligonucleotides. Antisense mechanisms that do not elicit cleavage via nuclear ribonucleases, such as the CAG-repeat ASOs described in, for example, Wheeler T M, et al., Science., 2009, 325 (5938): 336-339 and WO2008/036406, do not provide the same therapeutic advantage.

Certain embodiments provide a method of treating an animal with type 1 myotonic dystrophy. In certain embodiments, the method includes administering to the animal a therapeutically effective amount of a compound comprising a modified oligonucleotide as further described herein targeted to DMPK. In certain embodiments, the method includes identifying an animal with type 1 myotonic dystrophy.

Certain embodiments provide a method of treating, preventing, delaying, or ameliorating symptoms and outcomes associated with development of DM1 including muscle stiffness, myotonia, disabling distal weakness, weakness in face and jaw muscles, difficulty in swallowing, drooping of the eyelids (ptosis), weakness of neck muscles, weakness in arm and leg muscles, persistent muscle pain, hypersomnia, muscle wasting, dysphagia, respiratory insufficiency, irregular heartbeat, heart muscle damage, apathy, insulin resistance, and cataracts. Certain embodiments provide a method of treating, preventing, delaying, or ameliorating symptoms and outcomes associated with development of DM1 in children, including, developmental delays, learning problems, language and speech issues, and personality development issues.

Certain embodiments provide a method of administering an antisense oligonucleotide to counteract RNA dominance by directing the cleavage of pathogenic transcripts.

In certain embodiments, the DMPK has a sequence as set forth in GenBank Accession No. NM_001081560.1 (incorporated herein as SEQ ID NO: 1). In certain embodiments, the DMPK has the sequence as set forth in GenBank Accession No. NT_011109.15 truncated from nucleotides 18540696 to U.S. Pat. No. 18,555,106 (incorporated herein as SEQ ID NO: 2). In certain embodiments, the DMPK has the sequence as set forth in GenBank Accession No. NT 039413.7 truncated from nucleotides 16666001 to U.S. Pat. No. 16,681,000 (incorporated herein as SEQ ID NO: 3). In certain embodiments, the DMPK has the sequence as set forth in GenBank Accession No. NM_032418.1 (incorporated herein as SEQ ID NO: 4). In certain embodiments, the DMPK has the sequence as set forth in GenBank Accession No. AI007148.1 (incorporated herein as SEQ ID NO: 5). In certain embodiments, the DMPK has the sequence as set forth in GenBank Accession No. AI304033.1 (incorporated herein as SEQ ID NO: 6). In certain embodiments, the DMPK has the sequence as set forth in GenBank Accession No. BC024150.1 (incorporated herein as SEQ ID NO: 7). In certain embodiments, the DMPK has the sequence as set forth in GenBank Accession No. BC056615.1 (incorporated herein as SEQ ID NO: 8). In certain embodiments, the DMPK has the sequence as set forth in GenBank Accession No. BC075715.1 (incorporated herein as SEQ ID NO: 793). In certain embodiments, the DMPK has the sequence as set forth in GenBank Accession No. BU519245.1 (incorporated herein as SEQ ID NO: 794). In certain embodiments, the DMPK has the sequence as set forth in GenBank Accession No. CB247909.1 (incorporated herein as SEQ ID NO: 795). In certain embodiments, the DMPK has the sequence as set forth in GenBank Accession No. CX208906.1 (incorporated herein as SEQ ID NO: 796). In certain embodiments, the DMPK has the sequence as set forth in GenBank Accession No. CX732022.1 (incorporated herein as SEQ ID NO: 797). In certain embodiments, the DMPK has the sequence as set forth in GenBank Accession No. S60315.1 (incorporated herein as SEQ ID NO: 798). In certain embodiments, the DMPK has the sequence as set forth in GenBank Accession No. S60316.1 (incorporated herein as SEQ ID NO: 799). In certain embodiments, the DMPK has the sequence as set forth in GenBank Accession No. NM_001081562.1 (incorporated herein as SEQ ID NO: 800). In certain embodiments, the DMPK has the sequence as set forth in GenBank Accession No. NM_001100.3 (incorporated herein as SEQ ID NO: 801).

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. Herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques can be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O$(CH_2)_2$—$OCH_3$) refers to an O-methoxy-ethyl modification of the 2' position of a furanosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to position 5. A 5-methylcytosine is a modified nucleobase.

"About" means within ±7% of a value. For example, if it is stated, "the compound affected at least 70% inhibition of DMPK", it is implied that the DMPK levels are inhibited within a range of 63% and 77%.

"Active pharmaceutical agent" means the substance or substances in a pharmaceutical composition that provide a therapeutic benefit when administered to an individual. For example, in certain embodiments an antisense oligonucleotide targeted to DMPK is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing an agent to an animal, and includes, but is not limited to, administering by a medical professional and self-administering.

"Agent" means an active substance that can provide a therapeutic benefit when administered to an animal. "First Agent" means a therapeutic compound of the invention. For example, a first agent can be an antisense oligonucleotide targeting DMPK. "Second agent" means a second therapeutic compound of the invention (e.g. a second antisense oligonucleotide targeting DMPK) and/or a non-DMPK therapeutic compound.

"Amelioration" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, snoRNAs, miRNAs, and satellite repeats.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furanosyl ring modified by the bridging of two non-geminal carbon ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"CUGexp DMPK" means mutant DMPK RNA containing an expanded CUG repeat (CUGexp). The wild-type DMPK gene has 5-37 CTG repeats in the 3' untranslated region. In a "CUGexp DMPK" (such as in a myotonic dystrophy type I patient) this number is significantly expanded and is, for example, in the range of 50 to greater than 3,500 (Harper, Myotonic Dystrophy (Saunders, London, ed. 3, 2001); Annu. Rev. Neurosci. 29:259, 2006; EMBO J. 19:4439, 2000; Curr Opin Neurol. 20:572, 2007).

"Diluent" means an ingredient in a composition that lacks pharmacological activity, but is pharmaceutically necessary or desirable. For example, the diluent in an injected composition can be a liquid, e.g. saline solution.

"DMPK" means any nucleic acid or protein of DMPK. DMPK can be a mutant DMPK including CUGexp DMPK nucleic acid.

"DMPK expression" means the level of mRNA transcribed from the gene encoding DMPK or the level of protein translated from the mRNA. DMPK expression can be determined by art known methods such as a Northern or Western blot.

"DMPK nucleic acid" means any nucleic acid encoding DMPK. For example, in certain embodiments, a DMPK nucleic acid includes a DNA sequence encoding DMPK, an RNA sequence transcribed from DNA encoding DMPK (including genomic DNA comprising introns and exons), and an mRNA or pre-mRNA sequence encoding DMPK. "DMPK mRNA" means an mRNA encoding a DMPK protein.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region can be referred to as a "gap segment" and the external regions can be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Identifying an animal with type 1 myotonic dystrophy" means identifying an animal having been diagnosed with a type 1 myotonic dystrophy, disorder or condition or identifying an animal predisposed to develop a type 1 myotonic dystrophy, disorder or condition. For example, individuals with a familial history can be predisposed to type 1 myotonic dystrophy, disorder or condition. Such identification can be accomplished by any method including evaluating an individual's medical history and standard clinical tests or assessments.

"Immediately adjacent" means there are no intervening elements between the immediately adjacent elements.

"Individual" means a human or non-human animal selected for treatment or therapy.

"Internucleoside linkage" refers to the chemical bond between nucleosides.

"Linked nucleosides" means adjacent nucleosides which are bonded or linked together by an internucleoside linkage.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"Myotonia" means an abnormally slow relaxation of a muscle after voluntary contraction or electrical stimulation.

"Nuclear ribonuclease" means a ribonuclease found in the nucleus. Nuclear ribonucleases include, but are not limited to, RNase H including RNase H1 and RNase H2, the double stranded RNase drosha and other double stranded RNases.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid can also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O—or other non-phosphodiester linkage).

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition can comprise one or more active agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Preferentially reducing CUG exp DMPK RNA" refers to a preferential reduction of RNA transcripts from a CUGexp DMPK allele relative to RNA transcripts from a normal DMPK allele.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum can indicate liver toxicity or liver function abnormality. For example, increased bilirubin can indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Spliceopathy" means a change in the alternative splicing of one or more RNAs that leads to the expression of altered splice products in a particular tissue.

"Subcutaneous administration" means administration just below the skin.

"Sugar surrogate" overlaps with the slightly broader term "nucleoside mimetic" but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of an agent that provides a therapeutic benefit to an individual.

"Treat" refers to administering a pharmaceutical composition to effect an alteration or improvement of a disease, disorder, or condition.

"Type 1 myotonic dystrophy" or "DM1" means an autosomal dominant disorder caused by expansion of a noncoding CTG repeat in DMPK. This mutation leads to RNA dominance, a process in which expression of RNA containing an expanded CUG repeat (CUGexp) induced cell dysfunction. The CUGexp tract interacts with RNA binding proteins and causes the mutant transcript to be retained in nuclear foci. The toxicity of this RNA stems from sequestration of RNA binding proteins and activation of signaling pathways.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds, and compositions for inhibiting DMPK expression.

Certain embodiments provide a method of reducing DMPK expression in an animal comprising administering to the animal a compound comprising a modified oligonucleotide targeting DMPK.

Certain embodiments provide a method of preferentially reducing CUGexp DMPK RNA, reducing myotonia or reducing spliceopathy in an animal comprising administering to the animal a compound comprising a modified oligonucleotide targeted to DMPK, wherein the modified oligonucleotide preferentially reduces CUGexp DMPK RNA, reduces myotonia or reduces spliceopathy in the animal.

Certain embodiments provide a method of administering an antisense oligonucleotide to counteract RNA dominance by directing the cleavage of pathogenic transcripts.

Certain embodiments provide a method of reducing spliceopathy of Serca1. In certain embodiments, methods provided herein result in exon 22 inclusion. In certain embodiments, the corrective splicing occurs in the tibialis anterior, gastrocnemius, and quadriceps muscles.

Certain embodiments provide a method of reducing spliceopathy of m-Titin. In certain embodiments, methods provided herein result in exon 5 inclusion. In certain embodiments, the corrective splicing occurs in the tibialis anterior, gastrocnemius, and quadriceps muscles.

Certain embodiments provide a method of reducing spliceopathy of Clcn1. In certain embodiments, methods provided herein result in exon 7a inclusion. In certain embodiments, the corrective splicing occurs in the tibialis anterior, gastrocnemius, and quadriceps muscles.

Certain embodiments provide a method of reducing spliceopathy of Zasp. In certain embodiments, methods provided herein result in exon 11 inclusion. In certain embodiments, the corrective splicing occurs in the tibialis anterior, gastrocnemius, and quadriceps muscles.

Certain embodiments provide a method for treating an animal with type 1 myotonic dystrophy comprising: a) identifying said animal with type 1 myotonic dystrophy, and b) administering to said animal a therapeutically effective amount of a compound comprising a modified oligonucleotide targeted to DMPK. In certain embodiments, the therapeutically effective amount of the compound administered to the animal preferentially reduces CUGexp DMPK RNA, reduces myotonia or reduces spliceopathy in the animal.

Certain embodiments provide a method of achieving a preferential reduction of CUGexp DMPK RNA, including administering to the subject suspected of having type 1 myotonic dystrophy or having a CUGexp DMPK RNA a modified antisense oligonucleotide complementary to a non-repeat region of said CUGexp DMPK RNA. The modified antisense oligonucleotide, when bound to said CUGexp DMPK RNA, achieves a preferential reduction of the CUGexp DMPK RNA.

Certain embodiments provide a method of achieving a preferential reduction of CUGexp DMPK RNA, including selecting a subject having type 1 myotonic dystrophy or having a CUGexp DMPK RNA and administering to said subject a modified antisense oligonucleotide complementary to a non-repeat region of said CUGexp DMPK RNA. The modified antisense oligonucleotide, when bound to the CUGexp DMPK RNA, activates a ribonuclease or nuclear ribonuclease, thereby achieving a preferential reduction of the CUGexp DMPK RNA in the nucleus.

Certain embodiments provide a method of achieving a preferential reduction of CUGexp DMPK RNA, including selecting a subject having type 1 myotonic dystrophy or having a mutant or CUGexp DMPK RNA and systemically administering to said subject a modified antisense oligonucleotide complementary to a non-repeat region of said CUGexp DMPK RNA. The modified antisense oligonucleotide, when bound to the mutant or CUGexp DMPK RNA, achieves a preferential reduction of the mutant or CUGexp DMPK RNA.

Certain embodiments provide a method of reducing myotonia in a subject in need thereof. The method includes administering to the subject a modified antisense oligonucleotide complementary to a non-repeat region of a DMPK RNA, wherein the modified antisense oligonucleotide, when bound to the DMPK RNA, activates a ribonuclease or nuclear ribonuclease, thereby reducing myotonia. In certain embodiments, the subject has or is suspected of having type 1 myotonic dystrophy or having a mutant DMPK RNA or CUGexp DMPK RNA. In certain embodiments, the DMPK RNA is nuclear retained.

Certain embodiments provide a method of reducing spliceopathy in a subject in need thereof. The method includes administering to the subject a modified antisense oligonucleotide complementary to a non-repeat region of a DMPK RNA, wherein the modified antisense oligonucleotide, when bound to the DMPK RNA, activates a ribonuclease or nuclear ribonuclease, thereby reducing spliceopathy. In certain embodiments, the subject has or is suspected of having type 1 myotonic dystrophy or having a nuclear retained CUGexp DMPK RNA. In certain embodiments, the DMPK RNA is nuclear retained. In certain embodiments, the spliceopathy is MBNL dependent spliceopathy.

In certain embodiments, the modified antisense oligonucleotide of the methods is chimeric. In certain embodiments, the modified antisense oligonucleotide of the methods is a gapmer.

In certain embodiments of the methods provided herein, the administering is subcutaneous. In certain embodiments, the administering is intravenous.

In certain embodiments, the modified antisense oligonucleotide of the methods targets a non-coding sequence within the non-repeat region of a DMPK RNA. In certain embodiments, the oligonucleotide targets a coding region, an intron, a 5'UTR, or a 3'UTR of the mutant DMPK RNA. In certain embodiments of the methods provided herein, the nuclear ribonuclease is RNase H1.

In certain embodiments of the methods, the DMPK RNA is reduced in muscle tissue. In certain embodiments, the mutant DMPK RNA CUGexp DMPK RNA is preferentially reduced.

In certain embodiments, the DMPK has the sequence as set forth in GenBank Accession No. NM_001081560.1 (incorporated herein as SEQ ID NO: 1). In certain embodiments, the DMPK has the sequence as set forth in GenBank Accession No. NT_011109.15 truncated from nucleotides 18540696 to U.S. Pat. No. 18,555,106 (incorporated herein as SEQ ID NO: 2). In certain embodiments, the DMPK has the sequence as set forth in GenBank Accession No. NT 039413.7 truncated from nucleotides 16666001 to U.S. Pat. No. 16,681,000 (incorporated herein as SEQ ID NO: 3). In certain embodiments, the DMPK has the sequence as set forth in GenBank Accession No. NM_032418.1 (incorporated herein as SEQ ID NO: 4). In certain embodiments, the DMPK has the sequence as set forth in GenBank Accession No. AI007148.1 (incorporated herein as SEQ ID NO: 5). In certain embodiments, the DMPK has the sequence as set forth in GenBank Accession No. AI304033.1 (incorporated herein as SEQ ID NO: 6). In certain embodiments, the DMPK has the sequence as set forth in GenBank Accession No. BC024150.1 (incorporated herein as SEQ ID NO: 7). In certain embodiments, the DMPK has the sequence as set forth in GenBank Accession No. BC056615.1 (incorporated herein as SEQ ID NO: 8). In certain embodiments, the DMPK has the sequence as set forth in GenBank Accession No. BC075715.1 (incorporated herein as SEQ ID NO: 793). In certain embodiments, the DMPK has the sequence as set forth in GenBank Accession No. BU519245.1 (incorporated herein as SEQ ID NO: 794). In certain embodiments, the DMPK has the sequence as set forth in GenBank Accession No. CB247909.1 (incorporated herein as SEQ ID NO: 795). In certain embodiments, the DMPK has the sequence as set forth in GenBank Accession No. CX208906.1 (incorporated herein as SEQ ID NO: 796). In certain embodiments, the DMPK has the sequence as set forth in GenBank Accession No. CX732022.1 (incorporated herein as SEQ ID NO: 797). In certain embodiments, the DMPK has the sequence as set forth in GenBank Accession No. S60315.1 (incorporated herein as SEQ ID NO: 798). In certain embodiments, the DMPK has the sequence as set forth in GenBank Accession No. S60316.1 (incorporated herein as SEQ ID NO: 799). In certain embodiments, the DMPK has the sequence as set forth in GenBank Accession No. NM_001081562.1 (incorporated herein as SEQ ID NO: 800). In certain embodiments, the DMPK has the sequence as set forth in GenBank Accession No. NM_001100.3 (incorporated herein as SEQ ID NO: 801).

In certain embodiments, the modified oligonucleotide has a nucleobase sequence comprising at least 8 contiguous nucleobases of a nucleobase sequence recited in any one of SEQ ID NOs: 12-156, 160-770, and 774-792. In certain embodiments, the modified oligonucleotide has a nucleobase sequence comprising at least 9, at least 10, or at least 11, contiguous nucleobases of a nucleobase sequence recited in any one of SEQ ID NOs: 12-156, 160-770, and 774-792.

In certain embodiments, the modified oligonucleotide has a nucleobase sequence comprising at least 12 contiguous nucleobases of a nucleobase sequence recited in any one of SEQ ID NOs: 12-156, 160-770, and 774-792. In certain embodiments, the modified oligonucleotide has a nucleobase sequence comprising at least 13, or at least 14, contiguous nucleobases of a nucleobase sequence recited in any one of SEQ ID NOs: 12-156, 160-770, and 774-792.

In certain embodiments, the modified oligonucleotide has a nucleobase sequence comprising at least 15 contiguous nucleobases of a nucleobase sequence recited in any one of SEQ ID NOs: 12-156, 160-770, and 774-792. In certain embodiments, the modified oligonucleotide has a nucleobase sequence comprising at least 16, or at least 17, contiguous nucleobases of a nucleobase sequence recited in any one of SEQ ID NOs: 12-156, 160-770, and 774-792.

In certain embodiments, the modified oligonucleotide has a nucleobase sequence comprising at least 18 contiguous nucleobases of a nucleobase sequence recited in any one of SEQ ID NOs: 12-156, 160-770, and 774-792. In certain embodiments, the modified oligonucleotide has a nucleobase sequence comprising at least 19 contiguous nucleobases of a nucleobase sequence recited in any one of SEQ ID NOs: 12-156, 160-770, and 774-792.

In certain embodiments, the modified oligonucleotides provided herein are targeted to any one of the following regions of SEQ ID NO: 1:1178-1206, 2159-2182, 2174-2196, 2426-2447, 2450-2518, 2679-2704, and 2697-2725.

In certain embodiments, the modified oligonucleotides provided herein are targeted to any one of the following regions of SEQ ID NO 1:178-223, 232-253, 279-299, 366-399, 519-541, 923-975, 1073-1105, 1171-1196, 1215-1246, 1263-1324, 1706-1734, 1743-1763, 1932-1979, 1981-2003, 2077-2108, and 2152-2173.

In certain embodiments, the modified oligonucleotides provided herein are targeted to any one of the following regions of SEQ ID NO: 2:1251-1303, 1305-1326, 1352-1372, 3762-3795, 4170-4192, 5800-5852, 6124-6149, 6168-6199, 6216-6277, 11979-12007, 12016-12036, 12993-13042, 13044-13066, 13140-13171, and 13215-13236.

In certain embodiments, the animal is a human.

In certain embodiments, the compounds or compositions of the invention are designated as a first agent and the methods of the invention further comprise administering a second agent. In certain embodiments, the first agent and the second agent are co-administered. In certain embodiments the first agent and the second agent are co-administered sequentially or concomitantly.

In certain embodiments, administration comprises parenteral administration.

In certain embodiments, the compound is a single-stranded modified oligonucleotide. In certain embodiments, the nucleobase sequence of the modified oligonucleotide is at least 95% complementary to any one of SEQ ID NOs: 1-8 and 793-801 as measured over the entirety of said modified oligonucleotide. In certain embodiments, the nucleobase sequence of the modified oligonucleotide is 100% complementary to any one of SEQ ID NOs: 1-8 and 793-801 as measured over the entirety of said modified oligonucleotide.

In certain embodiments, at least one internucleoside linkage of said modified oligonucleotide is a modified internucleoside linkage. In certain embodiments, each internucleoside linkage is a phosphorothioate internucleoside linkage.

In certain embodiments, at least one nucleoside of said modified oligonucleotide comprises a modified sugar. In certain embodiments, at least one modified sugar is a bicyclic sugar. In certain embodiments, at least one modified sugar comprises a 2'-O-methoxyethyl or a 4'-$(CH_2)_n$—O-2' bridge, wherein n is 1 or 2.

In certain embodiments, at least one nucleoside of said modified oligonucleotide comprises a modified nucleobase. In certain embodiments, the modified nucleobase is a 5-methylcytosine.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl sugar, each internucleoside linkage of said modified oligonucleotide is a phosphorothioate linkage, and each cytosine in said modified oligonucleotide is a 5'-methylcytosine.

In certain embodiments, the modified oligonucleotide consists of 20 linked nucleosides.

Certain embodiments provide a method of preferentially reducing CUGexp DMPK RNA, reducing myotonia or reducing spliceopathy in an animal comprising administering to the animal a compound comprising a modified oligonucleotide having a gap segment consisting of ten linked deoxynucleosides, a 5' wing segment consisting of five linked nucleosides and a 3' wing segment consisting of five linked nucleosides. The gap segment is positioned between the 5' wing segment and the 3' wing segment, each nucleoside of each wing segment comprises a 2'-O-methoxyethyl sugar, each internucleoside linkage of said modified oligonucleotide is a phosphorothioate linkage, each cytosine in said modified oligonucleotide is a 5'-methylcytosine.

Certain embodiments provide the use of any compound as described herein in the manufacture of a medicament for use in any of the therapeutic methods described herein. For example, certain embodiments provide the use of a compound as described herein in the manufacture of a medicament for treating, ameliorating, or preventing type 1 myotonic dystrophy. Certain embodiments provide the use of a compound as described herein in the manufacture of a medicament for inhibiting expression of DMPK and treating, preventing, delaying or ameliorating a DMPK related disease and or a symptom thereof. Certain embodiments provide the use of a compound as described herein in the manufacture of a medicament for reducing DMPK expression in an animal. Certain embodiments provide the use of a compound as described herein in the manufacture of a medicament for preferentially reducing CUGexp DMPK, reducing myotonia, or reducing spliceopathy in an animal. Certain embodiments provide the use of a compound as described herein in the manufacture of a medicament for treating an animal with type 1 myotonic dystrophy. Certain embodiments provide the use of a compound as described herein in the manufacture of a medicament for treating, preventing, delaying, or ameliorating symptoms and outcomes associated with development of DM1 including muscle stiffness, myotonia, disabling distal weakness, weakness in face and jaw muscles, difficulty in swallowing, drooping of the eyelids (ptosis), weakness of neck muscles, weakness in arm and leg muscles, persistent muscle pain, hypersomnia, muscle wasting, dysphagia, respiratory insufficiency, irregular heartbeat, heart muscle damage, apathy, insulin resistance, and cataracts. Certain embodiments provide the use of a compound as described herein in the manufacture of a medicament for counteracting RNA dominance by directing the cleavage of pathogenic transcripts.

Certain embodiments provide a kit for treating, preventing, or ameliorating type 1 myotonic dystrophy as described herein wherein the kit comprises: a) a compound as described herein; and optionally b) an additional agent or therapy as described herein. The kit can further include instructions or a label for using the kit to treat, prevent, or ameliorate type 1 myotonic dystrophy.

Certain embodiments provide any compound or composition as described herein, for use in any of the therapeutic methods described herein. For example, certain embodiments provide a compound or composition as described herein for inhibiting expression of DMPK and treating, preventing, delaying or ameliorating a DMPK related disease and or a symptom thereof. Certain embodiments provide a compound or composition as described herein for use in reducing DMPK expression in an animal. Certain embodiments provide a compound or composition as described herein for use in preferentially reducing CUGexp DMPK, reducing myotonia, or reducing spliceopathy in an animal. Certain embodiments provide a compound or composition as described herein for use in treating an animal with type 1 myotonic dystrophy. Certain embodiments provide a compound or composition as described herein for use in treating, preventing, delaying, or ameliorating symptoms and outcomes associated with development of DM1 including muscle stiffness, myotonia, disabling distal weakness, weakness in face and jaw muscles, difficulty in swallowing, drooping of the eyelids (ptosis), weakness of neck muscles, weakness in arm and leg muscles, persistent muscle pain, hypersomnia, muscle wasting, dysphagia, respiratory insufficiency, irregular heartbeat, heart muscle damage, apathy, insulin resistance, and cataracts. Certain embodiments provide a compound or composition as described herein for use in counteracting RNA dominance by directing the cleavage of pathogenic transcripts. Certain embodiments provide compounds comprising a modified oligonucleotide consisting of 12 to 30 linked nucleosides having a nucleobase sequence comprising at least 12 contiguous nucleobases of any of the nucleobase sequences of SEQ ID NOs: 12-156, 160-770, and 774-792.

Other compounds which can be used in the methods described herein are also provided.

For example, certain embodiments provide compounds comprising a modified oligonucleotide consisting of 10 to 80, 12 to 50, 12 to 30, 15 to 30, 18 to 24, 19 to 22, or 20 linked nucleosides having a nucleobase sequence comprising at least 8, at least 9, at least 10, at least 11, at least 12, at least 13, at least 14, at least 15, at least 16, at least 17, at least 18, or at least 19, contiguous nucleobases of any of the nucleobase sequences of SEQ ID NOs: 41, 44, 76, 109, 153, 320, 321, 322, 325, 329, 335, and 657.

Certain embodiments provide compounds comprising a modified oligonucleotide consisting of 10 to 80, 12 to 50, 12 to 30, 15 to 30, 18 to 24, 19 to 22, or 20, linked nucleosides having a nucleobase sequence comprising at least 8, at least 9, at least 10, at least 11, at least 12, at least 13, at least 14, at least 15, at least 16, at least 17, at least 18, at least 19, contiguous nucleobases of any of the nucleobase sequences of SEQ ID NOs: 15, 73, 77, 79, 83, 85, 130, 602, 648, 655, 674, and 680.

Certain embodiments provide compounds comprising a modified oligonucleotide consisting of 10 to 80, 12 to 50, 12 to 30, 15 to 30, 18 to 24, 19 to 22, or 20, linked nucleosides having a nucleobase sequence comprising a portion of at least 8, at least 9, at least 10, at least 11, at least 12, at least 13, at least 14, at least 15, at least 16, at least 17, at least 18, or at least 19, or more, contiguous nucleobases complementary to an equal length portion of nucleobases 664-683, 773-792, 926-945, 927-946, 928-947, 931-950, 935-954, 941-960, 2089-2108, 2163-2182, 2490-2509, 2499-2518, 2676-2695, 2685-2704, 2676-2695, 2688-2707, 2697-2716, 2764-2783, and 2770-2789 of SEQ ID NO: 1, wherein the nucleobase sequence is complementary to SEQ ID NO: 1.

Certain embodiments provide compounds comprising a modified oligonucleotide consisting of 10 to 80, 12 to 50, 12 to 30, 15 to 30, 18 to 24, 19 to 22, or 20, linked nucleosides having a nucleobase sequence comprising a portion of at least 8, at least 9, at least 10, at least 11, at least 12, at least 13, at least 14, at least 15, at least 16, at least 17, at least 18, or at least 19, or more, contiguous nucleobases complementary to an equal length portion of nucleobases 812-831, 3629-3648, 4447-4466, 4613-4632, 5803-5822, 5804-5823, 5805-5824, 5808-5827, 5818-5837, 6794-6813, 12463-12482, 13152-13171, and 13553-13572 of SEQ ID NO: 2, wherein the nucleobase sequence is complementary to SEQ ID NO: 2.

In certain embodiments, the modified oligonucleotide is a single-stranded oligonucleotide.

In certain embodiments, the nucleobase sequence of the modified oligonucleotide is at least 70%, at least 75%, at least 80%, at least 85%, at least 90%, at least 95%, or 100%, complementary to any of SEQ ID NOs: 1-8 and 793-801.

In certain embodiments, at least one internucleoside linkage is a modified internucleoside linkage.

In certain embodiments, each internucleoside linkage is a phosphorothioate internucleoside linkage.

In certain embodiments, at least one nucleoside comprises a modified sugar.

In certain embodiments, at least one modified sugar is a bicyclic sugar.

In certain embodiments, at least one modified sugar comprises a 2'-O-methoxyethyl.

In certain embodiments, at least one nucleoside comprises a modified nucleobase.

In certain embodiments, the modified nucleobase is a 5-methylcytosine.

In certain embodiments, the modified oligonucleotide comprises:

a gap segment consisting of linked deoxynucleosides;

a 5' wing segment consisting of linked nucleosides; and a 3' wing segment consisting of linked nucleosides;

wherein the gap segment is positioned between the 5' wing segment and the 3' wing segment and wherein each nucleoside of each wing segment comprises a modified sugar.

In certain embodiments, the modified oligonucleotide comprises:

a gap segment consisting of ten linked deoxynucleosides;

a 5' wing segment consisting of five linked nucleosides; and a 3' wing segment consisting of five linked nucleosides;

wherein the gap segment is positioned between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide consists of 14 linked nucleosides.

In certain embodiments, the modified oligonucleotide consists of 16 linked nucleosides.

In certain embodiments, the modified oligonucleotide consists of 20 linked nucleosides.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound can be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to DMPK as described herein is 10 to 30 nucleotides in length. In other words, the antisense compounds are in some embodiments from 10 to 30 linked nucleobases. In other embodiments, the antisense compound comprises a modified oligonucleotide consisting of 8 to 80, 10 to 80, 12 to 30, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values. In certain embodiments, antisense compounds of any of these lengths contain at least 8, at least 9, at least 10, at least 11, at least 12, at least 13, at least 14, at least 15, at least 16, at least 17, at least 18, or at least 19, contiguous nucleobases of the nucleobase sequence of any of the exemplary antisense compounds described herein (e.g., at least 8 contiguous nucleobases of a nucleobase sequence recited in any one of SEQ ID NOs: 12-156, 160-770, and 774-792.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide can have two nucleosides deleted from the 5' end, or alternatively can have two subunits deleted from the 3' end. Alternatively, the deleted nucleosides can be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside can be located at the 5' or 3' end of the oligonucleotide. When two or more additional nucleosides are present, the added nucleosides can be adjacent to each other, for example, in an oligonucleotide having two nucleosides added to the 5' end (5' addition), or alternatively to the 3' end (3' addition), of the oligonucleotide. Alternatively, the added nucleoside can be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bel-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a DMPK nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound can optionally serve as a substrate for the cellular endonuclease RNase H, which cleaves the RNA strand of an RNA: DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer can in some embodiments include β-D-ribonucleosides, β-D-deoxyribonucleosides, 2'-modified nucleosides (such 2'-modified nucleosides can include 2'-MOE, and 2'-O—$CH_3$, among others), and bicyclic sugar modified nucleosides (such bicyclic sugar modified nucleosides can include those having a 4'-$(CH_2)$ n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6, 5-8-5, 1-8-1, or 2-6-2.

In certain embodiments, the antisense compound as a "wingmer" motif, having a wing-gap or gap-wing configuration, i.e. an X-Y or Y—Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13, or 5-13.

In certain embodiments, antisense compounds targeted to a DMPK nucleic acid possess a 5-10-5 gapmer motif.

In certain embodiments, an antisense compound targeted to a DMPK nucleic acid has a gap-widened motif.

In certain embodiments, antisense compounds of any of these gapmer or wingmer motifs contain at least 8, at least 9, at least 10, at least 11, at least 12, at least 13, at least 14, at least 15, at least 16, at least 17, at least 18, or at least 19, contiguous nucleobases of the nucleobase sequence of any of the exemplary antisense compounds described herein (e.g., at least 8 contiguous nucleobases of a nucleobase sequence recited in any one of SEQ ID NOs: 12-156, 160-770, and 774-792.

Target Nucleic Acids, Target Regions and Nucleotide Sequences

Nucleotide sequences that encode DMPK include, without limitation, the following sequences as set forth in GenBank Accession No. NM_001081560.1 (incorporated herein as SEQ ID NO: 1), GenBank Accession No. NT_011109.15 truncated from nucleotides 18540696 to U.S. Pat. No. 18,555,106 (incorporated herein as SEQ ID NO: 2), GenBank Accession No. NT 039413.7 truncated from nucleotides 16666001 to U.S. Pat. No. 16,681,000 (incorporated herein as SEQ ID NO: 3), GenBank Accession No. NM_032418.1 (incorporated herein as SEQ ID NO: 4), GenBank Accession No. AI007148.1 (incorporated herein as SEQ ID NO: 5), GenBank Accession No. AI304033.1 (incorporated herein as SEQ ID NO: 6), GenBank Accession No. BC024150.1 (incorporated herein as SEQ ID NO: 7), GenBank Accession No. BC056615.1 (incorporated herein as SEQ ID NO: 8), GenBank Accession No. BC075715.1 (incorporated herein as SEQ ID NO: 793), GenBank Accession No. BU519245.1 (incorporated herein as SEQ ID NO: 794), GenBank Accession No. CB247909.1 (incorporated herein as SEQ ID NO: 795), GenBank Accession No. CX208906.1 (incorporated herein as SEQ ID NO: 796), GenBank Accession No. CX732022.1 (incorporated herein as SEQ ID NO: 797), GenBank Accession No. S60315.1 (incorporated herein as SEQ ID NO: 798), GenBank Accession No. S60316.1 (incorporated herein as SEQ ID NO: 799), GenBank Accession No. NM_001081562.1 (incorporated herein as SEQ ID NO: 800), and GenBank Accession No. NM_001100.3 (incorporated herein as SEQ ID NO: 801). It is understood that the sequence set forth in each SEQ ID NO in the Examples contained herein is independent of any modification to a sugar moiety, an internucleoside linkage, or a nucleobase. As such, antisense compounds defined by a SEQ ID NO can comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region can encompass a 3' UTR, a 5' UTR, an exon, an intron, an exon/intron junction, a coding region, a translation initiation region, translation termination region, or other defined nucleic acid region. The structurally defined regions for DMPK can be obtained by accession number from sequence databases such as NCBI and such information is incorporated herein by reference. In certain embodiments, a target region can encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region can contain one or more target segments. Multiple target segments within a target region can be overlapping. Alternatively, they can be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments can be found within a 5' UTR, a coding region, a 3' UTR, an intron, an exon, or an exon/intron junction. Target segments containing a start codon or a stop codon are also suitable target segments. A suitable target segment can specifically exclude a certain structurally defined region such as the start codon or stop codon.

The determination of suitable target segments can include a comparison of the sequence of a target nucleic acid to other sequences throughout the genome. For example, the BLAST algorithm can be used to identify regions of similarity amongst different nucleic acids. This comparison can prevent the selection of antisense compound sequences that can hybridize in a non-specific manner to sequences other than a selected target nucleic acid (i.e., non-target or off-target sequences).

There can be variation in activity (e.g., as defined by percent reduction of target nucleic acid levels) of the antisense compounds within an active target region. In certain embodiments, reductions in DMPK mRNA levels are indicative of inhibition of DMPK protein expression.

Reductions in levels of a DMPK protein are also indicative of inhibition of target mRNA expression. Further, phenotypic changes, such as a reducing myotonia or reducing spliceopathy, can be indicative of inhibition of DMPK mRNA and/or protein expression.

Hybridization

In some embodiments, hybridization occurs between an antisense compound disclosed herein and a DMPK nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrooke and Russell, Molecular Cloning: A Laboratory Manual, 3rd Ed., 2001). In certain embodiments, the antisense compounds provided herein are specifically hybridizable with a DMPK nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a DMPK nucleic acid).

An antisense compound can hybridize over one or more segments of a DMPK nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a DMPK nucleic acid, a target region, target segment, or specified portion thereof. In certain embodiments, the antisense compounds are at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to a DMPK nucleic acid, a target region, target segment, or specified portion thereof, and contain at least 8, at least 9, at least 10, at least 11, at least 12, at least 13, at least 14, at least 15, at least 16, at least 17, at least 18, or at least 19, contiguous nucleobases of the nucleobase sequence of any of the exemplary antisense compounds described herein (e.g., at least 8 contiguous nucleobases of a nucleobase sequence recited in any one of SEQ ID NOs: 12-156, 160-770, and 774-792). Percent complementarity of an antisense compound with a target nucleic acid can be determined using routine methods, and is measured over the entirety of the antisense compound.

For example, an antisense compound in which 18 of 20 nucleobases of the antisense compound are complementary to a target region, and would therefore specifically hybridize, would represent 90 percent complementarity. In this example, the remaining noncomplementary nucleobases can be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound can be fully complementary to a DMPK nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound can be fully complementary to the target sequence, depending on whether the remaining 10 nucleobases of the antisense compound are also complementary to the target sequence.

The location of a non-complementary nucleobase can be at the 5' end or 3' end of the antisense compound. Alternatively, the non-complementary nucleobase or nucleobases can be at an internal position of the antisense compound. When two or more non-complementary nucleobases are present, they can be either contiguous (i.e. linked) or non-contiguous. In one embodiment, a non-complementary nucleobase is located in the wing segment of a gapmer antisense oligonucleotide.

In certain embodiments, antisense compounds that are, or are up to 10, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a DMPK nucleic acid, or specified portion thereof.

In certain embodiments, antisense compounds that are, or are up to 10, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a DMPK nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 10 nucleobase portion of a target segment. In certain embodiments, the antisense compounds are complementary to at least a 15 nucleobase portion of a target segment. Also contemplated are antisense compounds that are complementary to at least an 8, at least a 9, at least a 10, at least an 11, at least a 12, at least a 13, at least a 14, at least a 15, at least a 16, at least a 17, at least an 18, at least a 19, at least a 20, or more nucleobase portion of a target segment, or a range defined by any two of these values.

Identity

The antisense compounds provided herein can also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases can be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, at least 75%, at least 80%, at least 85%, at least 90%, at least 95%, at least 96%, at least 97%, at least 98%, at least 99% or 100% identical to one or more of the exemplary antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a DMPK nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$(R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl(R or S), 4'-S, 2'-F, 2'—$OCH_3$, 2'—$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(=O)—$N(R_m)(R_n)$, and O—$CH_2$—C(=O)—N(Ri)-$(CH_2)_2$—$N(R_m)(R_n)$, where each $R_1$, $R_m$ and $R_n$ is, independently, H or substituted or unsubstituted $C_1$-$C_{10}$ alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-$(CH_2)$—O-2' (LNA); 4'-$(CH_2)$—S-2'; 4'—$(CH_2)_2$—O-2' (ENA); 4'-$CH(CH_3)$—O-2' and 4'-CH$(CH_2OCH_3)$—O-2' (and analogs thereof see U.S. Pat. No. 7,399,845, issued on Jul. 15, 2008); 4'-$C(CH_3)(CH_3)$—O-2' (and analogs thereof see PCT/US2008/068922 published as WO/2009/006478, published Jan. 8, 2009); 4'-$CH_2$—N$(OCH_3)$-2' (and analogs thereof see PCT/US2008/064591 published as WO/2008/150729, published Dec. 11, 2008); 4'-$CH_2$—O—$N(CH_3)$-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)$(CH_3)$-2' (see Chattopadhyaya et al., J. Org. Chem., 2009, 74, 118-134); and 4'-$CH_2$—C(—$CH_2$)-2' (and analogs thereof see PCT/US2008/066154 published as WO 2008/154401, published on Dec. 8, 2008).

Further bicyclic nucleosides have been reported in published literature (see for example: Srivastava et al., *J. Am. Chem. Soc.,* 2007, 129 (26) 8362-8379; Frieden et al., *Nucleic Acids Research,* 2003, 21, 6365-6372; Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; Wahlestedt et al., *Proc. Natl. Acad. Sci. U.S.A,* 2000, 97, 5633-5638; Singh et al., *Chem. Commun.,* 1998, 4, 455-456; Koshkin et al., *Tetrahedron,* 1998, 54, 3607-3630; Kumar et al., *Bioorg. Med. Chem. Lett.,* 1998, 8, 2219-2222; Singh et al., *J. Org. Chem.,* 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. Patent Applications, Serial Nos.: 12/129,154; 61/099,844; 61/097,787; 61/086,231; 61/056,564; 61/026,998; 61/026,995; 60/989,574; International applications WO 2007/134181; WO 2005/021570; WO 2004/106356; WO 94/14226; and PCT International Applications Nos.: PCT/US2008/068922; PCT/US2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic nucleosides comprise a bridge between the 4' and the 2' carbon atoms of the pentofuranosyl sugar moiety including without limitation, bridges comprising 1 or from 1 to 4 linked groups independently selected from $-[C(R_a)(R_b)]_n-$, $-C(R_a)=C(R_b)-$, $-C(R_a)=N-$, $-C(=NR_a)-$, $-C(=O)-$, $-C(=S)-$, $-O-$, $-Si(R_a)_2-$, $-S(=O)_x-$, and $-N(R_a)-$; wherein: x is 0, 1, or 2; n is 1, 2, 3, or 4; each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl(C(=O)—H), substituted acyl, CN, sulfonyl($S(=O)_2$-$J_1$), or sulfoxyl(S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl(C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is, $-[C(R_a)(R_b)]_n-$, $-[C(R_a)(R_b)]_n-O-$, $-C(R_aR_b)-N(R)-O-$ or $-C(R_aR_b)-O-N(R)-$. In certain embodiments, the bridge is 4'-$CH_2$-2', 4'—$(CH_2)_2$-2', 4'—$(CH_2)_3$-2', 4'—$CH_2$—O-2', 4'—$(CH_2)_2$—O-2', 4'—$CH_2$—O—N(R)-2' and 4'-$CH_2$—N(R)—O-2'— wherein each R is, independently, H, a protecting group or $C_1$-$C_{12}$ alkyl.

In certain embodiments, bicyclic nucleosides are further defined by isomeric configuration. For example, a nucleoside comprising a 4'-($CH_2$)—O-2' bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include those having a 4' to 2' bridge wherein such bridges include without limitation, α-L-4'-($CH_2$)—O-2', B-D-4'-$CH_2$—O-2', 4'—$(CH_2)_2$—O-2', 4'—$CH_2$—O—N(R)-2', 4'—$CH_2$—N(R)—O-2', 4'—$CH(CH_3)$—O-2', 4'—$CH_2$—S-2', 4'—$CH_2$—N(R)-2', 4'—$CH_2$—$CH(CH_3)$-2', and 4'-$(CH_2)_3$-2', wherein R is H, a protecting group or $C_1$-$C_{12}$ alkyl.

In certain embodiments, bicyclic nucleosides have the formula:

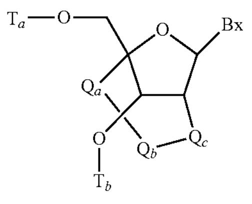

wherein:

Bx is a heterocyclic base moiety;

$Q_a$-$Q_b$-$Q_c$- is $-CH_2-N(R_c)-CH_2-$, $-C(=O)-N(R_c)-CH_2-$, $-CH_2-O-N(R_c)-$, $-CH_2-N(R_c)-O-$ or $-N(R_c)-O-CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides have the formula:

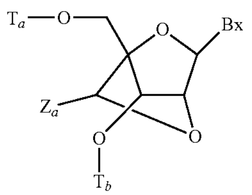

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

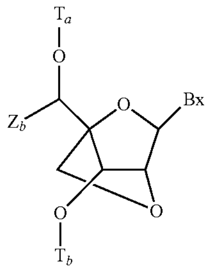

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl(C(=O)—).

In certain embodiments, bicyclic nucleosides have the formula:

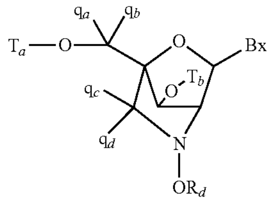

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium; $R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

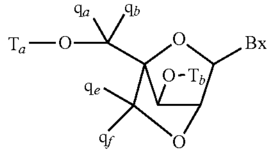

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O) $J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-$CH_2$—O-2' bridge, along with their oligomerization, and nucleic acid recognition properties have been described (Koshkin et al., Tetrahedron, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-$CH_2$—O-2' and 4'-$CH_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported. In certain embodiments, bicyclic nucleosides have the formula:

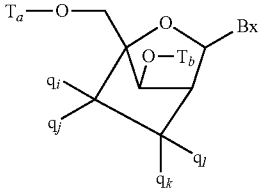

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O) $J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'—CH=CH—$CH_2$-2' have been described (Frier et al., *Nucleic Acids Research*, 1997, 25 (22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129 (26), 8362-8379).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-$(CH_2)_2$—O-2') BNA, (D) aminooxy (4'-$CH_2$—O—N(R)-2') BNA, (E) oxyamino (4'-$CH_2$—N(R)—O-2') BNA, (F) methyl(methyleneoxy)(4'—$CH(CH_3)$—O-2') BNA (also referred to as constrained ethyl or cEt), (G) methylene-thio(4'-$CH_2$—S-2') BNA, (H) methylene-amino (4'-$CH_2$—N(R)-2') BNA, (I) methyl carbocyclic (4'-$CH_2$—$CH(CH_3)$-2') BNA, (J) propylene carbocyclic (4'-$(CH_2)_3$-2') BNA, and (K) vinyl BNA as depicted below.

(A)

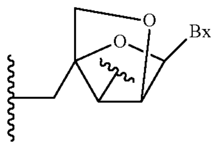

(B)

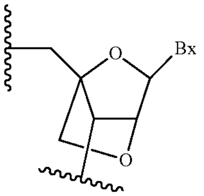

(C)

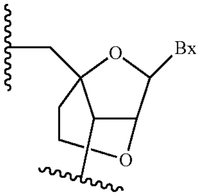

(D)

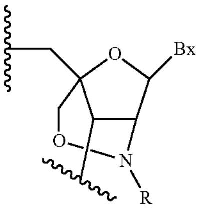

(E)

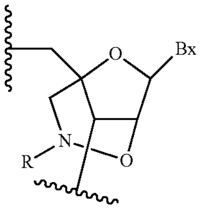

(F)

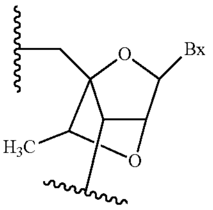

-continued (G)

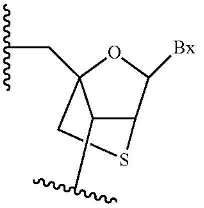

(H)

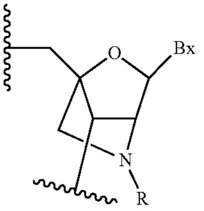

(I)

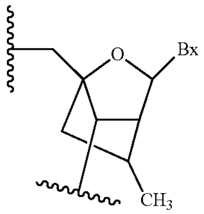

(J)

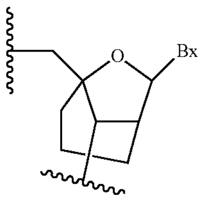

(K)

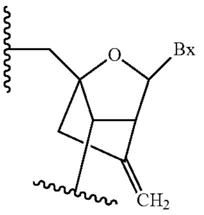

wherein Bx is the base moiety and R is, independently, H, a protecting group, $C_1$-$C_6$ alkyl or $C_1$-$C_6$ alkoxy.

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

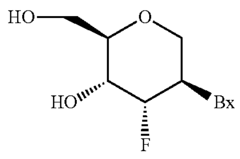

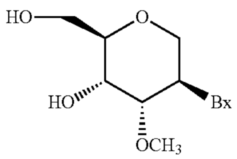

-continued

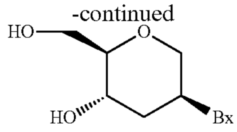

In certain embodiments, sugar surrogates are selected having the formula:

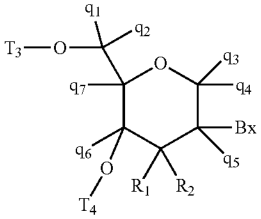

wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

Such sugar surrogates include, but are not limited to, what is referred to in the art as hexitol nucleic acid (HNA), altritol nucleic acid (ANA), and mannitol nucleic acid (MNA)(see Leumann, C. J., *Bioorg. & Med. Chem.,* 2002, 10, 841-854).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.,* 2008, 130 (6), 1979-1984; Horváth et al., *Tetrahedron Letters,* 2007, 48, 3621-3623; Nauwelaerts et al., *J. Am. Chem. Soc.,* 2007, 129 (30), 9340-9348; Gu et al., *Nucleosides, Nucleotides & Nucleic Acids,* 2005, 24 (5-7), 993-998; Nauwelaerts et al., *Nucleic Acids Research,* 2005, 33 (8), 2452-2463; Robeyns et al., *Acta Crystallographica, Section F: Structural Biology and Crystallization Communications,* 2005, F61 (6), 585-586; Gu et al., *Tetrahedron,* 2004, 60 (9), 2111-2123; Gu et al., *Oligonucleotides,* 2003, 13 (6), 479-489; Wang et al., *J. Org. Chem.,* 2003, 68, 4499-4505; Verbeure et al., *Nucleic Acids Research,* 2001, 29 (24), 4941-4947; Wang et al., *J. Org. Chem.,* 2001, 66, 8478-82; Wang et al., *Nucleosides, Nucleotides & Nucleic Acids,* 2001, 20 (4-7), 785-788; Wang et al., *J. Am. Chem.,* 2000, 122, 8595-8602; Published PCT application, WO 06/047842; and Published PCT Application WO 01/049687; the text of each is incorporated by reference herein, in their entirety). Certain modified cyclohexenyl nucleosides have the formula:

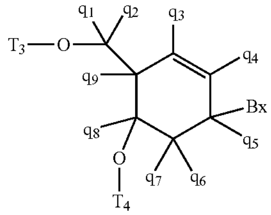

wherein:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other bicyclic and tricyclic sugar surrogate ring systems are also known in the art that can be used to modify nucleosides for incorporation into antisense compounds (see for example review article: Leumann, Christian J., *Bioorg. & Med. Chem.,* 2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds targeted to a DMPK nucleic acid comprise one or more nucleotides having modified sugar moieties. In certain embodiments, the modified sugar moiety is 2'-MOE. In certain embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a DMPK nucleic acid comprise one or more modified nucleobases. In certain embodiments, gap-widened antisense oligonucleotides targeted to a DMPK nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides can be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a DMPK nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a DMPK nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds can be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of DMPK nucleic acids can be tested in vitro in a variety of cell types. Cell types used for such analyses are available from commercial vendors (e.g. American Type Culture Collection, Manassas, VA; Zen-Bio, Inc., Research Triangle Park, NC; Clonetics Corporation, Walkersville, MD) and cells are cultured according to the vendor's instructions using commercially available reagents (e.g. Invitrogen Life Technologies, Carlsbad, CA). Illustrative cell types include, but are not limited to, HepG2 cells, Hep3B cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, CA). Antisense oligonucleotides are mixed with LIPOFEC- TIN® in OPTI-MEM® 1 (Invitrogen, Carlsbad, CA) to achieve the desired final concentration of antisense oligonucleotide and a LIPOFECTIN® concentration that typically ranges 2 to 12 μg/mL per 100 nM antisense oligonucleotide.

Another reagent used to introduce antisense oligonucleotides into cultured cells includes LIPOFECTAMINE 2000® (Invitrogen, Carlsbad, CA). Antisense oligonucleotide is mixed with LIPOFECTAMINE 2000® in OPTI-MEM® 1 reduced serum medium (Invitrogen, Carlsbad, CA) to achieve the desired concentration of antisense oligonucleotide and a LIPOFECTAMINE® concentration that typically ranges 2 to 12 μg/mL per 100 nM antisense oligonucleotide.

Another reagent used to introduce antisense oligonucleotides into cultured cells includes Cytofectin® (Invitrogen, Carlsbad, CA). Antisense oligonucleotide is mixed with Cytofectin® in OPTI-MEM® 1 reduced serum medium (Invitrogen, Carlsbad, CA) to achieve the desired concentration of antisense oligonucleotide and a Cytofectin® concentration that typically ranges 2 to 12 μg/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly (A)+mRNA. Methods of RNA isolation are well known in the art. RNA is prepared using methods well known in the art, for example, using the TRIZOL® Reagent (Invitrogen, Carlsbad, CA) according to the manufacturer's recommended protocols.

Analysis of Inhibition of Target Levels or Expression

Inhibition of levels or expression of a DMPK nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly (A)+mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, CA and used according to manufacturer's instructions.

Quantitative Real-Time PCR Analysis of Target RNA Levels

Quantitation of target RNA levels can be accomplished by quantitative real-time PCR using the ABI PRISM® 7600, 7700, or 7900 Sequence Detection System (PE-Applied Biosystems, Foster City, CA) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, CA). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, CA). Cyclophilin A expression is quantified by real time PCR, by being run simultaneously with the target, multiplexing, or separately. Total RNA is quantified using RIBOGREEN® RNA quantification reagent (Invitrogen, Inc. Eugene, OR). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a DMPK nucleic acid. Methods for designing real-time PCR probes and primers are well known in the art, and can include the use of software such as PRIMER EXPRESS® Software (Applied Biosystems, Foster City, CA).

Analysis of Protein Levels

Antisense inhibition of DMPK nucleic acids can be assessed by measuring DMPK protein levels. Protein levels of DMPK can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, MI), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of DMPK and produce phenotypic changes. Testing can be performed in normal animals, or in experimental disease models, for example, the $HSA^{LR}$ mouse model of myotonic dystrophy (DM1).

The $HSA^{LR}$ mouse model is an established model for DM1 (Mankodi, A. et al. Science. 289:1769, 2000). The mice carry a human skeletal actin (hACTA1) transgene with 220 CTG repeats inserted in the 3' UTR of the gene. The hACTA1-$CUG^{exp}$ transcript accumulates in nuclear foci in skeletal muscles and results in myotonia similar to that in human DM1 (Mankodi, A. et al. Mol. Cell 10:35, 2002; Lin, X. et al. Hum. Mol. Genet. 15:2087, 2006). Hence, it is expected that amelioration of DM1 symptoms in the $HSA^{LR}$ mouse by antisense inhibition of the hACTA1 transgene would predict amelioration of similar symptoms in human patients by antisense inhibition of the DMPK transcript.

Expression of CUGexp RNA in mice causes extensive remodeling of the muscle transcriptome, much of which is reproduced by ablation of MBNL1. Hence, it is expected that normalization of the transcriptome in $HSA^{LR}$ mice would predict normalization of the human transcriptome in DM1 patients by antisense inhibition of the DMPK transcript.

For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in DMPK nucleic acid expression are measured. Changes in DMPK protein levels are also measured.

Splicing

Myotonic dystrophy (DM1) is caused by CTG repeat expansions in the 3' untranslated region of the DMPK gene (Brook, J. D. et al. Cell. 68:799, 1992). This mutation leads to RNA dominance, a process in which expression of RNA containing an expanded CUG repeat (CUGexp) induces cell dysfunction (Osborne RJ and Thornton CA., *Human Molecular Genetics.,* 2006, 15(2): R162-R169). Such CUGexp are retained in the nuclear foci of skeletal muscles (Davis, B. M. et al. Proc. Natl. Acad. Sci. U.S.A. 94:7388, 1997). The accumulation of CUGexp in the nuclear foci leads to the sequestration of poly (CUG)-binding proteins, such as, Muscleblind-like 1 (MBLN1) (Miller, J. W. et al. EMBO J. 19:4439, 2000). MBLN1 is a splicing factor and regulates the splicing of genes such as Serca1, CIC-1, Titin, and Zasp. Therefore, sequestration of MBLN1 by CUGexp triggers misregulated alternative splicing of the exons of genes that MBLN1 normally controls (Lin, X. et al. Hum. Mol. Genet. 15:2087, 2006). Correction of alternative splicing in an animal displaying such disregulation, such as, for example, in a DM1 patient and the $HSA^{LR}$ mouse model, is a useful indicator for the efficacy of a treatment, including treatment with an antisense oligonucleotide.

Certain Biomarkers

DM1 severity in mouse models is determined, at least in part, by the level of CUGexp transcript accumulation in the nucleus or nuclear foci. A useful physiological marker for DM1 severity is the development of high-frequency runs of involuntary action potentials (myotonia).

Certain Indications

In certain embodiments, provided herein are methods of treating an individual comprising administering one or more pharmaceutical compositions as described herein. In certain embodiments, the individual has type 1 myotonic dystrophy (DM1).

Accordingly, provided herein are methods for ameliorating a symptom associated with type 1 myotonic dystrophy in a subject in need thereof. In certain embodiments, provided is a method for reducing the rate of onset of a symptom associated with type 1 myotonic dystrophy. In certain embodiments, provided is a method for reducing the severity of a symptom associated with type 1 myotonic dystrophy. In certain embodiments, symptoms associated with DM1 include muscle stiffness, myotonia, disabling distal weakness, weakness in face and jaw muscles, difficulty in swallowing, drooping of the eyelids (ptosis), weakness of neck muscles, weakness in arm and leg muscles, persistent muscle pain, hypersomnia, muscle wasting, dysphagia, respiratory insufficiency, irregular heartbeat, heart muscle damage, apathy, insulin resistance, and cataracts. In children, the symptoms may also be developmental delays, learning problems, language and speech issues, and personality development issues.

In certain embodiments, the methods comprise administering to an individual in need thereof a therapeutically effective amount of a compound targeted to a DMPK nucleic acid.

In certain embodiments, administration of an antisense compound targeted to a DMPK nucleic acid results in reduction of DMPK expression by at least about 15%, by at least about 20%, by at least about 25%, by at least about 30%, by at least about 35%, by at least about 40%, by at least about 45%, by at least about 50%, by at least about 55%, by at least about 60%, by least about 65%, by least about 70%, by least about 75%, by least about 80%, by at least about 85%, by at least about 90%, by at least about 95% or by at least about 99%, or a range defined by any two of these values.

In certain embodiments, pharmaceutical compositions comprising an antisense compound targeted to DMPK are used for the preparation of a medicament for treating a patient suffering or susceptible to type 1 myotonic dystrophy.

In certain embodiments, the methods described herein include administering a compound comprising a modified oligonucleotide having a contiguous nucleobases portion as described herein of a sequence recited in SEQ ID NO: 12-156, 160-770, and 774-792.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection (e.g., bolus injection). The injection can be delivered with a syringe.

Parenteral administration includes subcutaneous administration, intravenous administration, intramuscular administration, intraarterial administration, intraperitoneal administration, or intracranial administration, e.g., intrathecal or intracerebroventricular administration. Administration can be continuous, or chronic, or short, or intermittent.

In certain embodiments, the administering is subcutaneous, intravenous, intracerebral, intracerebroventricular, intrathecal or another administration that results in a systemic effect of the oligonucleotide (systemic administration is characterized by a systemic effect, i.e., an effect in more than one tissue) or delivery to the CNS or to the CSF.

The duration of action as measured by inhibition of alpha 1 actin and reduction of myotonia in the $HSA^{LR}$ mouse model of DM1 is prolonged in muscle tissue including quadriceps, gastrocnemius, and the tibialis anterior (see Examples, below). Subcutaneous injections of antisense oligonucleotide for 4 weeks results in inhibition of alpha 1 actin by at least 70% in quadriceps, gastrocnemius, and the tibialis anterior in $HSA^{LR}$ mice for at least 11 weeks (77 days) after termination of dosing. Subcutaneous injections of antisense oligonucleotide for 4 weeks results in elimination of myotonia in quadriceps, gastrocnemius, and the tibialis anterior in $HSA^{LR}$ mice for at least 11 weeks (77 days) after termination of dosing.

In certain embodiments, delivery of a compound of composition, as described herein, results in at least 70% down-regulation of a target mRNA and/or target protein for at least 77 days. In certain embodiments, delivery of a compound or composition, as described herein, results in 50%, 55%, 60%, 65%, 70%, 75%, 80%, 85%, 90%, 95%, or 100% down-regulation of a target mRNA and/or target protein for at least 30 days, at least 35 days, at least 40 days, at least 45 days, at least 50 days, at least 55 days, at least 60 days, at least 65 days, at least 70 days, at least 75 days, at least 76 days, at least 77 days, at least 78 days, at least 79 days, at least 80 days, at least 85 days, at least 90 days, at least 95 days, at least 100 days, at least 105 days, at least 110 days, at least 115 days, at least 120 days, at least 1 year.

In certain embodiments, an antisense oligonucleotide is delivered by injection or infusion once every 77 days. In certain embodiments, an antisense oligonucleotide is delivered by injection or infusion once every month, every two months, every three months, every 6 months, twice a year or once a year.

Certain Combination Therapies

In certain embodiments, a first agent comprising the modified oligonucleotide of the invention is co-administered with one or more secondary agents. In certain embodiments, such second agents are designed to treat the same type 1 myotonic dystrophy as the first agent described herein. In certain embodiments, such second agents are designed to treat a different disease, disorder, or condition as the first agent described herein. In certain embodiments, such second agents are designed to treat an undesired side effect of one or more pharmaceutical compositions as described herein. In certain embodiments, second agents are co-administered with the first agent to treat an undesired effect of the first agent. In certain embodiments, second agents are co-administered with the first agent to produce a combinational effect. In certain embodiments, second agents are co-administered with the first agent to produce a synergistic effect.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Dystrophia Myotonica Protein Kinase (DMPK) in Human Skeletal Muscle Cells (hSKMC)

Antisense oligonucleotides targeted to a human DMPK nucleic acid were tested for their effect on DMPK RNA transcript in vitro. Cultured hSKM cells at a density of 20,000 cells per well were transfected using electroporation with 100 nM antisense oligonucleotide. After approximately 24 hours, RNA was isolated from the cells and DMPK RNA transcript levels were measured by quantitative real-time PCR with human primer probe set RTS3164 (forward sequence AGCCTGAGCCGGGAGATG, designated herein as SEQ ID NO: 9; reverse sequence GCGTAGTTGACTGGCGAAGTT, designated herein as SEQ ID NO: 10; probe sequence AGGCCATCCGCACGGACAACCX, designated herein as SEQ ID NO: 11). DMPK RNA transcript levels were adjusted according to total RNA content, as measured by RIBOGREEN®. Results are presented as percent inhibition of hDMPK, relative to untreated control cells.

The antisense oligonucleotides in Tables 1 and 2 are 5-10-5 gapmers, where the gap segment comprises ten 2'-deoxynucleosides and each wing segment comprises five 2'-MOE nucleosides. The internucleoside linkages throughout each gapmer are phosphorothioate (P═S) linkages. All cytosine residues throughout each gapmer are 5-methylcytosines. 'Target start site' indicates the 5'-most nucleoside to which the antisense oligonucleotide is targeted. 'Target stop site' indicates the 3'-most nucleoside to which the antisense oligonucleotide is targeted. All the antisense oligonucleotides listed in Table 1 target SEQ ID NO: 1 (GENBANK Accession No. NM_001081560.1). All the antisense oligonucleotides listed in Table 2 target SEQ ID NO: 2 (the complement of GENBANK Accession No. NT_011109.15 truncated from nucleotides 18540696 to 18555106).

Several antisense oligonucleotides demonstrated significant inhibition of human DMPK mRNA levels under the conditions specified above.

TABLE 1

Inhibition of human DMPK RNA transcript in hSKMC by 5-10-5 gapmers targeting SEQ ID NO: 1

| Target Start Site | Target Stop Site | ISIS No | Sequence | % inhibition | SEQ ID NO. |
|---|---|---|---|---|---|
| 93 | 112 | 299476 | CTGGCTGCATGTCTGCCTGT | 81 | 12 |
| 277 | 296 | 299479 | CCAGGAGAAGGTCGAGCAGG | 57 | 13 |
| 737 | 756 | 299493 | TCTATGGCCATGACAATCTC | 57 | 14 |
| 773 | 792 | 299494 | ATGTCCCTGTGCACGTAGCC | 77 | 15 |
| 1194 | 1213 | 299501 | ATGTGTCCGGAAGTCGCCTG | 50 | 16 |
| 1628 | 1647 | 299511 | CTCAGGCTCTGCCGGGTGAG | 70 | 17 |
| 1855 | 1874 | 299517 | GGCACTGGCCCACAGCCACG | 78 | 18 |
| 2379 | 2398 | 299526 | CCTGGCCGAAAGAAAGAAAT | 31 | 19 |
| 2367 | 2386 | 444380 | AAAGAAATGGTCTGTGATCC | 56 | 20 |

TABLE 1-continued

Inhibition of human DMPK RNA transcript in hSKMC by 5-10-5 gapmers targeting SEQ ID NO: 1

| Target Start Site | Target Stop Site | ISIS No | Sequence | % inhibition | SEQ ID NO. |
|---|---|---|---|---|---|
| 2370 | 2389 | 444381 | AAGAAAGAAATGGTCTGTGA | 77 | 21 |
| 2376 | 2395 | 444382 | GGCCGAAAGAAAGAAATGGT | 61 | 22 |
| 2385 | 2404 | 444383 | CCTCAGCCTGGCCGAAAGAA | 57 | 23 |
| 2388 | 2407 | 444384 | GGGCCTCAGCCTGGCCGAAA | 65 | 24 |
| 2391 | 2410 | 444385 | TCAGGGCCTCAGCCTGGCCG | 61 | 25 |
| 2411 | 2430 | 444386 | CTGCAGTTTGCCCATCCACG | 68 | 26 |
| 2414 | 2433 | 444387 | GGCCTGCAGTTTGCCCATCC | 77 | 27 |
| 2417 | 2436 | 444388 | CCAGGCCTGCAGTTTGCCCA | 54 | 28 |
| 2423 | 2442 | 444389 | GCCTTCCCAGGCCTGCAGTT | 77 | 29 |
| 2426 | 2445 | 444390 | GCTGCCTTCCCAGGCCTGCA | 83 | 30 |
| 2429 | 2448 | 444391 | CTTGCTGCCTTCCCAGGCCT | 69 | 31 |
| 2435 | 2454 | 444392 | GCCCGGCTTGCTGCCTTCCC | 82 | 32 |
| 2438 | 2457 | 444393 | ACGGCCCGGCTTGCTGCCTT | 78 | 33 |
| 2441 | 2460 | 444394 | CGGACGGCCCGGCTTGCTGC | 57 | 34 |
| 2444 | 2463 | 444395 | ACACGGACGGCCCGGCTTGC | 73 | 35 |
| 2450 | 2469 | 444396 | GATGGAACACGGACGGCCCG | 80 | 36 |
| 2453 | 2472 | 444397 | GAGGATGGAACACGGACGGC | 86 | 37 |
| 2456 | 2475 | 444398 | GTGGAGGATGGAACACGGAC | 84 | 38 |
| 2481 | 2500 | 444399 | GCGAACCAACGATAGGTGGG | 80 | 39 |
| 2484 | 2503 | 444400 | TTTGCGAACCAACGATAGGT | 86 | 40 |
| 2490 | 2509 | 444401 | TTGCACTTTGCGAACCAACG | 89 | 41 |
| 2493 | 2512 | 444402 | GCTTTGCACTTTGCGAACCA | 89 | 42 |
| 2496 | 2515 | 444403 | AAAGCTTTGCACTTTGCGAA | 83 | 43 |
| 2499 | 2518 | 444404 | AAGAAAGCTTTGCACTTTGC | 91 | 44 |
| 2502 | 2521 | 444405 | CACAAGAAAGCTTTGCACTT | 70 | 45 |
| 2508 | 2527 | 444406 | GTCATGCACAAGAAAGCTTT | 34 | 46 |
| 2527 | 2546 | 444407 | ACGCTCCCCAGAGCAGGGCG | 39 | 47 |
| 2543 | 2562 | 444408 | GCAGAGATCGCGCCAGACGC | 85 | 48 |
| 2546 | 2565 | 444409 | CAGGCAGAGATCGCGCCAGA | 65 | 49 |
| 2549 | 2568 | 444410 | AAGCAGGCAGAGATCGCGCC | 84 | 50 |
| 2555 | 2574 | 444411 | CCGAGTAAGCAGGCAGAGAT | 58 | 51 |
| 2558 | 2577 | 444412 | TTCCCGAGTAAGCAGGCAGA | 70 | 52 |
| 2564 | 2583 | 444413 | GCAAATTTCCCGAGTAAGCA | 62 | 53 |
| 2567 | 2586 | 444414 | AAAGCAAATTTCCCGAGTAA | 53 | 54 |
| 2573 | 2592 | 444415 | TTGGCAAAAGCAAATTTCCC | 64 | 55 |
| 2576 | 2595 | 444416 | GGTTTGGCAAAAGCAAATTT | 23 | 56 |

TABLE 1-continued

Inhibition of human DMPK RNA transcript in hSKMC by 5-10-5 gapmers targeting SEQ ID NO: 1

| Target Start Site | Target Stop Site | ISIS No | Sequence | % inhibition | SEQ ID NO. |
|---|---|---|---|---|---|
| 2579 | 2598 | 444417 | GCGGGTTTGGCAAAAGCAAA | 70 | 57 |
| 2582 | 2601 | 444418 | AAAGCGGGTTTGGCAAAAGC | 43 | 58 |
| 2588 | 2607 | 444419 | CCCGAAAAAGCGGGTTTGGC | 71 | 59 |
| 2591 | 2610 | 444420 | ATCCCCGAAAAAGCGGGTTT | 53 | 60 |
| 2595 | 2614 | 444421 | CGGGATCCCCGAAAAAGCGG | 45 | 61 |
| 2598 | 2617 | 444422 | GCGCGGGATCCCCGAAAAAG | 48 | 62 |
| 2623 | 2642 | 444423 | GAGAGCAGCGCAAGTGAGGA | 77 | 63 |
| 2626 | 2645 | 444424 | TCCGAGAGCAGCGCAAGTGA | 62 | 64 |
| 2629 | 2648 | 444425 | GGCTCCGAGAGCAGCGCAAG | 79 | 65 |
| 2649 | 2668 | 444426 | AAGCGGGCGGAGCCGGCTGG | 20 | 66 |
| 2652 | 2671 | 444427 | CCGAAGCGGGCGGAGCCGGC | 0 | 67 |
| 2658 | 2677 | 444428 | AAACCGCCGAAGCGGGCGGA | 0 | 68 |
| 2661 | 2680 | 444429 | TCCAAACCGCCGAAGCGGGC | 45 | 69 |
| 2664 | 2683 | 444430 | ATATCCAAACCGCCGAAGCG | 31 | 70 |
| 2667 | 2686 | 444431 | TAAATATCCAAACCGCCGAA | 42 | 71 |
| 2670 | 2689 | 444432 | CAATAAATATCCAAACCGCC | 53 | 72 |
| 2676 | 2695 | 444433 | CGAGGTCAATAAATATCCAA | 63 | 73 |
| 2679 | 2698 | 444434 | GGACGAGGTCAATAAATATC | 83 | 74 |
| 2682 | 2701 | 444435 | GGAGGACGAGGTCAATAAAT | 82 | 75 |
| 2685 | 2704 | 444436 | GTCGGAGGACGAGGTCAATA | 86 | 76 |
| 2688 | 2707 | 444437 | CGAGTCGGAGGACGAGGTCA | 73 | 77 |
| 2694 | 2713 | 444438 | TGTCAGCGAGTCGGAGGACG | 79 | 78 |
| 2697 | 2716 | 444439 | GCCTGTCAGCGAGTCGGAGG | 83 | 79 |
| 2700 | 2719 | 444440 | GTAGCCTGTCAGCGAGTCGG | 94 | 80 |
| 2703 | 2722 | 444441 | CCTGTAGCCTGTCAGCGAGT | 90 | 81 |
| 2706 | 2725 | 444442 | GGTCCTGTAGCCTGTCAGCG | 90 | 82 |
| 2764 | 2783 | 444443 | AAATACCGAGGAATGTCGGG | 82 | 83 |
| 2767 | 2786 | 444444 | AATAAATACCGAGGAATGTC | 66 | 84 |
| 2770 | 2789 | 444445 | GACAATAAATACCGAGGAAT | 67 | 85 |
| 2093 | 2112 | 445546 | CGGGGCCCCGGAGTCGAAGA | 0 | 86 |
| 2097 | 2116 | 445547 | CCAACGGGGCCCCGGAGTCG | 38 | 87 |
| 2099 | 2118 | 445548 | TTCCAACGGGGCCCCGGAGT | 22 | 88 |
| 2102 | 2121 | 445549 | GTCTTCCAACGGGGCCCCGG | 50 | 89 |
| 2104 | 2123 | 445550 | CAGTCTTCCAACGGGGCCCC | 27 | 90 |
| 2106 | 2125 | 445551 | CTCAGTCTTCCAACGGGGCC | 57 | 91 |
| 2109 | 2128 | 445552 | GCACTCAGTCTTCCAACGGG | 69 | 92 |
| 2115 | 2134 | 445553 | CCCCGGGCACTCAGTCTTCC | 76 | 93 |

TABLE 1-continued

Inhibition of human DMPK RNA transcript in hSKMC by 5-10-5 gapmers targeting SEQ ID NO: 1

| Target Start Site | Target Stop Site | ISIS No | Sequence | % inhibition | SEQ ID NO. |
|---|---|---|---|---|---|
| 2117 | 2136 | 445554 | TGCCCCGGGCACTCAGTCTT | 59 | 94 |
| 2119 | 2138 | 445555 | CGTGCCCCGGGCACTCAGTC | 61 | 95 |
| 2123 | 2142 | 445556 | GTGCCGTGCCCCGGGCACTC | 26 | 96 |
| 2126 | 2145 | 445557 | TCTGTGCCGTGCCCCGGGCA | 50 | 97 |
| 2129 | 2148 | 445558 | GCTTCTGTGCCGTGCCCCGG | 57 | 98 |
| 2132 | 2151 | 445559 | GCGGCTTCTGTGCCGTGCCC | 27 | 99 |
| 2134 | 2153 | 445560 | GCGCGGCTTCTGTGCCGTGC | 0 | 100 |
| 2136 | 2155 | 445561 | GGGCGCGGCTTCTGTGCCGT | 8 | 101 |
| 2142 | 2161 | 445562 | GGCGGTGGGCGCGGCTTCTG | 62 | 102 |
| 2146 | 2165 | 445563 | GGCAGGCGGTGGGCGCGGCT | 49 | 103 |
| 2148 | 2167 | 445564 | CTGGCAGGCGGTGGGCGCGG | 51 | 104 |
| 2150 | 2169 | 445565 | AACTGGCAGGCGGTGGGCGC | 38 | 105 |
| 2153 | 2172 | 445566 | GTGAACTGGCAGGCGGTGGG | 64 | 106 |
| 2157 | 2176 | 445567 | GGTTGTGAACTGGCAGGCGG | 66 | 107 |
| 2159 | 2178 | 445568 | GCGGTTGTGAACTGGCAGGC | 85 | 108 |
| 2163 | 2182 | 445569 | CGGAGCGGTTGTGAACTGGC | 92 | 109 |
| 2167 | 2186 | 445570 | CGCTCGGAGCGGTTGTGAAC | 51 | 110 |
| 2171 | 2190 | 445571 | CCCACGCTCGGAGCGGTTGT | 74 | 111 |
| 2174 | 2193 | 445572 | AGACCCACGCTCGGAGCGGT | 80 | 112 |
| 2177 | 2196 | 445573 | CGGAGACCCACGCTCGGAGC | 83 | 113 |
| 2180 | 2199 | 445574 | GGGCGGAGACCCACGCTCGG | 62 | 114 |
| 2183 | 2202 | 445575 | GCTGGGCGGAGACCCACGCT | 11 | 115 |
| 2186 | 2205 | 445576 | GGAGCTGGGCGGAGACCCAC | 42 | 116 |
| 2188 | 2207 | 445577 | CTGGAGCTGGGCGGAGACCC | 17 | 117 |
| 2191 | 2210 | 445578 | GGACTGGAGCTGGGCGGAGA | 53 | 118 |
| 2193 | 2212 | 445579 | CAGGACTGGAGCTGGGCGGA | 46 | 119 |
| 2197 | 2216 | 445580 | ATCACAGGACTGGAGCTGGG | 66 | 120 |
| 2209 | 2228 | 445581 | GGGCGGGCCCGGATCACAGG | 85 | 121 |
| 2211 | 2230 | 445582 | GGGGGCGGGCCCGGATCACA | 96 | 122 |
| 179 | 198 | 445583 | AGGCAGCACCATGGCCCCTC | 88 | 123 |
| 235 | 254 | 445584 | GGTCCAACACCAGCTGCTGG | 84 | 124 |
| 418 | 437 | 445585 | CGATCACCTTCAGAATCTCG | 11 | 125 |
| 498 | 517 | 445586 | CTTGTTCATGATCTTCATGG | 0 | 126 |
| 565 | 584 | 445587 | CCCCATTCACCAACACGTCC | 83 | 127 |
| 583 | 602 | 445588 | GCGTGATCCACCGCCGGTCC | 59 | 128 |
| 639 | 658 | 445589 | GTAATACTCCATGACCAGGT | 86 | 129 |

TABLE 1-continued

Inhibition of human DMPK RNA transcript in hSKMC by 5-10-5 gapmers targeting SEQ ID NO: 1

| Target Start Site | Target Stop Site | ISIS No | Sequence | % inhibition | SEQ ID NO. |
|---|---|---|---|---|---|
| 664 | 683 | 445590 | GCAGTGTCAGCAGGTCCCCG | 83 | 130 |
| 744 | 763 | 445591 | CACCGAGTCTATGGCCATGA | 60 | 131 |
| 761 | 780 | 445592 | ACGTAGCCAAGCCGGTGCAC | 68 | 132 |
| 812 | 831 | 445593 | ATGTGGCCACAGCGGTCCAG | 56 | 133 |
| 1099 | 1118 | 445594 | CTTCGTCCACCAGCGGCAGA | 32 | 134 |
| 1104 | 1123 | 445595 | GACCCCTTCGTCCACCAGCG | 83 | 135 |
| 1178 | 1197 | 445596 | CCTGCTCCACCCCGGCCCAG | 82 | 136 |
| 1187 | 1206 | 445597 | CGGAAGTCGCCTGCTCCACC | 81 | 137 |
| 1229 | 1248 | 445598 | CGGAGACCATCCCAGTCGAG | 67 | 138 |
| 1402 | 1421 | 445599 | TGAGGGCCATGCAGGAGTAG | 26 | 139 |
| 1443 | 1462 | 445600 | CTCCAGTTCCATGGGTGTGG | 80 | 140 |
| 1477 | 1496 | 445601 | GCGCTTGCACGTGTGGCTCA | 94 | 141 |
| 1526 | 1545 | 445602 | GCCACTTCAGCTGTTTCATC | 54 | 142 |
| 1562 | 1581 | 445603 | GCCTCAGCCTCTGCCGCAGG | 71 | 143 |
| 1576 | 1595 | 445604 | GCAGCGTCACCTCGGCCTCA | 31 | 144 |
| 1630 | 1649 | 445605 | GGCTCAGGCTCTGCCGGGTG | 86 | 145 |
| 1700 | 1719 | 445606 | TTCCGAGCCTCTGCCTCGCG | 73 | 146 |
| 1708 | 1727 | 445607 | GGTCCCGGTTCCGAGCCTCT | 76 | 147 |
| 1742 | 1761 | 445608 | ATCCGCTCCTGCAACTGCCG | 93 | 148 |
| 1750 | 1769 | 445609 | GCAACTCCATCCGCTCCTGC | 60 | 149 |
| 1812 | 1831 | 445610 | AGGTGGATCCGTGGCCCGGG | 48 | 150 |
| 2133 | 2152 | 445611 | CGCGGCTTCTGTGCCGTGCC | 24 | 151 |
| 2428 | 2447 | 445612 | TTGCTGCCTTCCCAGGCCTG | 80 | 152 |

TABLE 2

Inhibition of human DMPK RNA transcript in hSKMC by 5-10-5 gapmers targeting SEQ ID NO: 2

| Target Start Site | Target Stop Site | ISIS No | Sequence | % inhibition | SEQ ID NO. |
|---|---|---|---|---|---|
| 812 | 831 | 299471 | TGCTCCCGACAAGCTCCAGA | 95 | 153 |
| 876 | 895 | 299473 | AGAACCTGCCCATTGCTGAA | 68 | 154 |
| 2381 | 2400 | 299535 | CACTGAGGGCCAGACATATG | 68 | 155 |
| 3289 | 3308 | 299544 | CTCTAGATTCAGATGCAGGT | 88 | 156 |

The antisense oligonucleotides from Tables 1 and 2 were also tested in an assay with similar conditions as described above, and mRNA levels measured with the human primer probe RTS3162 (forward sequence CGGGCCGTCCGTGTT, designated herein as SEQ ID NO: 157; reverse sequence CTTTGCACTTTGCGAACCAA, designated herein as SEQ ID NO: 158; probe sequence CATCCTCCACGCACCCCCACCX, designated herein as SEQ ID NO: 159). The results are presented in Table 3. DMPK mRNA expression was also assessed by RTS3162 which targets the DMPK gene near the 3'UTR. The use of a second primer probe was employed to confirm that the expression of the entire DMPK gene had been inhibited

TABLE 3

Inhibition of human DMPK RNA transcript in hSKMC by 5-10-5 gapmers measured using primer probe set RTS3162

| ISIS No | % inhibition |
|---|---|
| 299471 | 91 |
| 299473 | 65 |
| 299476 | 76 |
| 299479 | 53 |
| 299493 | 60 |
| 299494 | 66 |
| 299501 | 44 |
| 299511 | 39 |
| 299517 | 71 |
| 299526 | 39 |
| 299535 | 75 |
| 299544 | 84 |
| 444380 | 72 |
| 444381 | 82 |
| 444382 | 67 |
| 444383 | 63 |
| 444384 | 66 |
| 444385 | 66 |
| 444386 | 74 |
| 444387 | 85 |
| 444388 | 60 |
| 444389 | 81 |
| 444390 | 88 |
| 444391 | 79 |
| 444392 | 94 |
| 444393 | 88 |
| 444394 | 94 |
| 444395 | 96 |
| 444396 | 96 |
| 444397 | 95 |
| 444398 | 96 |
| 444399 | 95 |
| 444400 | 95 |
| 444401 | 95 |
| 444402 | 91 |
| 444403 | 84 |
| 444404 | 89 |
| 444405 | 71 |
| 444406 | 47 |
| 444407 | 42 |
| 444408 | 80 |
| 444409 | 56 |
| 444410 | 79 |
| 444411 | 66 |
| 444412 | 67 |
| 444413 | 55 |
| 444414 | 45 |
| 444415 | 57 |
| 444416 | 18 |
| 444417 | 64 |
| 444418 | 51 |
| 444419 | 66 |
| 444420 | 0 |
| 444421 | 46 |
| 444422 | 33 |
| 444423 | 74 |
| 444424 | 73 |
| 444425 | 78 |
| 444426 | 0 |
| 444427 | 0 |
| 444428 | 0 |
| 444429 | 75 |
| 444430 | 28 |
| 444431 | 58 |
| 444432 | 52 |
| 444433 | 60 |
| 444434 | 87 |
| 444435 | 76 |
| 444436 | 83 |

TABLE 3-continued

Inhibition of human DMPK RNA transcript in hSKMC by 5-10-5 gapmers measured using primer probe set RTS3162

| ISIS No | % inhibition |
|---|---|
| 444437 | 71 |
| 444438 | 76 |
| 444439 | 73 |
| 444440 | 91 |
| 444441 | 87 |
| 444442 | 93 |
| 444443 | 77 |
| 444444 | 64 |
| 444445 | 67 |
| 445546 | 0 |
| 445547 | 59 |
| 445548 | 49 |
| 445549 | 77 |
| 445550 | 62 |
| 445551 | 74 |
| 445552 | 84 |
| 445553 | 70 |
| 445554 | 63 |
| 445555 | 75 |
| 445556 | 52 |
| 445557 | 78 |
| 445558 | 81 |
| 445559 | 58 |
| 445560 | 12 |
| 445561 | 42 |
| 445562 | 70 |
| 445563 | 76 |
| 445564 | 69 |
| 445565 | 60 |
| 445566 | 86 |
| 445567 | 84 |
| 445568 | 92 |
| 445569 | 93 |
| 445570 | 59 |
| 445571 | 84 |
| 445572 | 88 |
| 445573 | 84 |
| 445574 | 74 |
| 445575 | 26 |
| 445576 | 56 |
| 445577 | 38 |
| 445578 | 69 |
| 445579 | 70 |
| 445580 | 75 |
| 445581 | 85 |
| 445582 | 95 |
| 445583 | 88 |
| 445584 | 87 |
| 445585 | 34 |
| 445586 | 0 |
| 445587 | 82 |
| 445588 | 66 |
| 445589 | 87 |
| 445590 | 82 |
| 445591 | 68 |
| 445592 | 64 |
| 445593 | 54 |
| 445594 | 52 |
| 445595 | 77 |
| 445596 | 84 |
| 445597 | 78 |
| 445598 | 73 |
| 445599 | 29 |
| 445600 | 68 |
| 445601 | 92 |
| 445602 | 53 |
| 445603 | 70 |
| 445604 | 32 |
| 445605 | 61 |
| 445606 | 84 |
| 445607 | 80 |
| 445608 | 91 |
| 445609 | 68 |

TABLE 3-continued

| Inhibition of human DMPK RNA transcript in hSKMC by 5-10-5 gapmers measured using primer probe set RTS3162 | |
|---|---|
| ISIS No | % inhibition |
| 445610 | 63 |
| 445611 | 44 |
| 445612 | 91 |

Example 2: Design of Antisense Oligonucleotides Targeting CUG Repeats

Antisense oligonucleotides were designed targeting mRNA transcripts that contain multiple CUG repeats. The chemistry of these oligonucleotides as well as their sequence is shown in Table 4. The symbols designated to the sugar type are shown after the base in subscript and are as follows: b=2'-O—N-[2-(dimethylamino)ethyl]acetamido ribose; d=2'-deoxyribose; e=2'-O-methoxyethyl ribose; f=2'-alpha-fluoro-2'-deoxyribose; g=2'-O-2 [2-(2-methoxyethoxy) ethoxy]ethyl ribose; h=3'-fluoro-HNA; k=(S)-cEt; 1=LNA (Locked Nucleic Acids); n=2'-O—(N-methylacetamide) ribose; o=2'-O-dimethylaminooxyethyl (DMAOE) ribose; p=PNA; r=propylribose; and x=amino acid core. The heterocycle names are defined with standard symbols for adenine, cytosine, thymine and guanine, 'mC' for 5-methylcytosine, and 'K' for Lysine Side Chain. Linkers are shown after the sugar type in subscript and designated with the following symbols: g=PNA-glycine full; a=amino acid; and s=thioate ester.

TABLE 4

| Design of antisense oligonucleotides targeting CUG repeats | | | | |
|---|---|---|---|---|
| ISIS No | Sequence | Chemistry | Backbone | SEQ ID NO |
| 431896 | $G_{ds}C_{ds}A_{ls}G_{ds}C_{ds}A_{ls}G_{ds}C_{ds}A_{ls}$ $G_{ds}C_{ds}A_{ls}G_{ds}C_{ds}A_{ls}G_{ds}C_{ds}A_{ls}G_{d}$ | Deoxy and LNA units | Phosphorothioate | 802 |
| 433804 | $K_{xa}G_{pg}C_{pg}A_{pg}G_{pg}C_{pg}A_{pg}G_{pg}C_{pg}A_{pg}G_{pg}C_{pg}A_{pg}G_{pg}$ $C_{pg}A_{pg}G_{pg}C_{pg}A_{pg}G_{pg}K_{xa}K_{xa}K_{xa}K_{xa}K_{xa}K_{xa}K_{xa}K_{xa}$ | PNA and Amino Acid Core units with a Carboxy-amide endcap | mixed | 803 |
| 444745 | $A_{es}G_{es}mC_{es}A_{es}G_{es}mC_{es}A_{es}G_{es}mC_{es}A_{es}G_{es}mC_{es}$ $A_{es}G_{es}mC_{es}A_{es}G_{es}mC_{es}A_{es}G_{es}mC_{es}A_{es}G_{es}mC_{es}A_{e}$ | Uniform MOE | Phosphorothioate | 789 |
| 444746 | $A_{es}G_{es}mC_{es}A_{es}G_{es}mC_{es}A_{es}G_{es}mC_{es}A_{es}$ $G_{es}mC_{es}A_{es}G_{es}mC_{es}A_{es}G_{es}mC_{es}A_{es}G_{e}$ | Uniform MOE | Phosphorothioate | 804 |
| 444747 | $G_{es}mC_{es}A_{es}G_{es}mC_{es}A_{es}G_{es}mC_{es}A_{es}$ $G_{es}mC_{es}A_{es}G_{es}mC_{es}A_{es}G_{es}mC_{es}A_{es}G_{es}$ | Uniform MOE | Phosphorothioate | 802 |
| 444748 | $G_{es}mC_{es}A_{es}G_{es}mC_{es}A_{es}G_{es}mC_{es}A_{es}$ $G_{es}mC_{es}A_{es}G_{es}mC_{es}A_{es}G_{es}mC_{es}A_{e}$ | Uniform MOE | Phosphorothioate | 805 |
| 444750 | $G_{ks}C_{ks}A_{ds}G_{ds}C_{ks}A_{ds}G_{ds}C_{ks}A_{ds}$ $G_{ds}C_{ks}A_{ds}G_{ds}C_{ks}A_{ds}G_{ds}C_{ks}A_{k}$ | Deoxy and (S)-cEt units | Phosphorothioate | 805 |
| 444752 | $G_{ks}C_{ks}A_{es}G_{es}C_{ks}A_{es}G_{es}C_{ks}A_{es}$ $G_{es}C_{ks}A_{es}G_{es}C_{ks}A_{es}G_{es}C_{ks}A_{k}$ | MOE and (S)-cEt units | Phosphorothioate | 805 |
| 444754 | $G_{es}mC_{es}A_{fs}G_{fs}C_{fs}A_{fs}G_{fs}C_{fs}A_{fs}$ $G_{fs}C_{fs}A_{fs}G_{fs}C_{fs}A_{fs}G_{fs}mC_{es}A_{es}$ | MOE and 2'-alpha-flouro units | Phosphorothioate | 805 |
| 444759 | $G_{hs}mC_{hs}A_{hs}G_{hs}mC_{hs}A_{hs}G_{hs}mC_{hs}A_{hs}$ $G_{hs}mC_{hs}A_{hs}G_{hs}mC_{hs}A_{hs}G_{hs}mC_{hs}A_{h}$ | Uniform 3'-fluoro-HNA | Phosphorothioate | 805 |
| 444761 | $G_{rs}mC_{rs}A_{rs}G_{rs}mC_{rs}A_{rs}G_{rs}mC_{rs}A_{rs}$ $G_{rs}mC_{rs}A_{rs}G_{rs}mC_{rs}A_{rs}G_{rs}mC_{rs}A_{r}$ | Uniform 2'-O-propylribose | Phosphorothioate | 805 |
| 444762 | $G_{ns}mC_{ns}A_{ns}G_{ns}mC_{ns}A_{ns}G_{ns}mC_{ns}A_{ns}$ $G_{ns}mC_{ns}A_{ns}G_{ns}mC_{ns}A_{ns}G_{ns}mC_{ns}A_{n}$ | Uniform 2'-O-(N-methylacetamide) ribose | Phosphorothioate | 805 |
| 444763 | $G_{os}mC_{es}A_{os}G_{os}mC_{es}A_{os}G_{os}mC_{es}A_{os}$ $G_{os}mC_{es}A_{os}G_{os}mC_{es}A_{os}G_{os}mC_{es}A_{o}$ | MOE and 2'-O-dimethylaminooxyethyl (DMAOE) ribose units | Phosphorothioate | 805 |
| 444764 | $G_{gs}mC_{es}A_{es}G_{gs}mC_{es}A_{es}G_{gs}mC_{es}A_{es}$ $G_{gs}mC_{es}A_{es}G_{gs}mC_{es}A_{es}G_{gs}mC_{es}A_{es}G_{g}$ | MOE and 2'-O-2[2-(2-methoxyethoxy)ethoxy]ethyl ribose units | Phosphorothioate | 802 |
| 444765 | $G_{bs}mC_{es}A_{es}G_{bs}mC_{es}A_{es}G_{bs}mC_{es}A_{es}$ $G_{bs}mC_{es}A_{es}G_{bs}mC_{es}A_{es}G_{bs}mC_{es}A_{es}G_{b}$ | MOE and 2'-O-N-[2-(dimethylamino)ethyl]acetamido ribose units | Phosphorothioate | 802 |
| 473810 | $A_{ks}G_{ds}mC_{ds}A_{ks}G_{ds}mC_{ds}A_{ks}G_{as}mC_{ds}$ $A_{ks}G_{ds}mC_{ds}A_{ks}G_{ds}mC_{ds}A_{ks}G_{ds}mC_{ds}A_{k}$ | Deoxy and (S)-cEt units | Phosphorothioate | 806 |

TABLE 4-continued

| Design of antisense oligonucleotides targeting CUG repeats | | | | |
|---|---|---|---|---|
| ISIS No | Sequence | Chemistry | Backbone | SEQ ID NO |
| 473811 | $A_{ks}G_{ds}mC_{ds}A_{ks}G_{ds}mC_{ds}A_{ks}G_{ds}$ $mC_{ds}A_{ks}G_{ds}mC_{ds}A_{ks}G_{ds}mC_{ds}A_{k}$ | Deoxy and (S)-cEt units | Phosphorothioate | 807 |

Example 3: Dose-Dependent Antisense Inhibition of Human DMPK in Human Skeletal Muscle Cells Several of the antisense oligonucleotides exhibiting in vitro inhibition of DMPK in hSKMC (see Example 1) were tested at various doses. Cells were plated at a density of 20,000 cells per well and transfected using electroporation with 1,250 nM, 2,500 nM, 5,000 nM, 10,000 nM and 20,000 nM concentrations of each antisense oligonucleotide. After approximately 16 hours, RNA was isolated from the cells and DMPK mRNA transcript levels were measured by quantitative real-time PCR using primer probe set RTS3164, described hereinabove. DMPK mRNA transcript levels were normalized to total RNA content, as measured by RIBOGREEN®. Results are presented in Table 5 as percent inhibition of DMPK, relative to untreated control cells.

The tested antisense oligonucleotides demonstrated dose-dependent inhibition of DMPK mRNA levels under the conditions specified above.

TABLE 5

Dose-dependent antisense inhibition of human DMPK in hSKMC tested with primer probe set RTS3164

| ISIS No. | 1,250 nM | 2,500 nM | 5,000 nM | 10,000 nM | 20,000 nM | $IC_{50}$ (μM) |
|---|---|---|---|---|---|---|
| 299471 | 34 | 65 | 87 | 91 | 94 | 1.60 |
| 299473 | 2 | 33 | 60 | 89 | 92 | 4.31 |
| 299476 | 15 | 17 | 49 | 81 | 91 | 4.89 |
| 299535 | 0 | 12 | 34 | 62 | 59 | 9.95 |
| 299535 | 20 | 33 | 47 | 67 | 80 | 5.11 |
| 299544 | 32 | 63 | 81 | 85 | 87 | 1.82 |
| 444397 | 10 | 30 | 58 | 85 | 82 | 4.51 |
| 444398 | 33 | 57 | 74 | 85 | 87 | 2.07 |
| 444400 | 52 | 46 | 63 | 82 | 88 | 1.76 |
| 444401 | 51 | 71 | 84 | 89 | 91 | 0.71 |
| 444402 | 53 | 79 | 83 | 87 | 84 | <1.25 |
| 444404 | 48 | 68 | 77 | 86 | 90 | 0.95 |
| 444408 | 26 | 47 | 70 | 87 | 87 | 2.80 |
| 444410 | 22 | 47 | 67 | 83 | 87 | 3.12 |
| 444436 | 28 | 67 | 76 | 89 | 92 | 1.94 |
| 444440 | 70 | 77 | 83 | 89 | 85 | <1.25 |
| 444441 | 33 | 55 | 81 | 87 | 86 | 1.99 |
| 444442 | 54 | 73 | 84 | 89 | 88 | <1.25 |
| 445568 | 65 | 83 | 85 | 84 | 76 | <1.25 |
| 445569 | 60 | 77 | 87 | 93 | 91 | <1.25 |
| 445581 | 16 | 44 | 78 | 86 | 94 | 3.13 |
| 445582 | 0 | 7 | 26 | 96 | 99 | 5.60 |
| 445583 | 39 | 53 | 73 | 89 | 94 | 2.00 |
| 445584 | 20 | 26 | 61 | 81 | 93 | 4.02 |
| 445589 | 42 | 61 | 81 | 91 | 87 | 1.36 |
| 445601 | 49 | 79 | 87 | 93 | 94 | 0.66 |
| 445608 | 26 | 59 | 71 | 85 | 97 | 2.41 |
| 445612 | 46 | 59 | 72 | 88 | 93 | 1.51 |

The antisense oligonucleotides from Table 5 were also tested with primer probe set RTS3162, described hereinabove. The results are presented in Table 6. DMPK mRNA expression was also assessed by RTS3162 which targets the DMPK gene near the 3'UTR. The use of a second primer probe was employed to confirm that the expression of the entire DMPK gene had been inhibited.

TABLE 6

Dose-dependent antisense inhibition of human DMPK in hSKMC tested with primer probe set RTS3164

| ISIS No. | 1,250 nM | 2,500 nM | 5,000 nM | 10,000 nM | 20,000 nM | $IC_{50}$ (μM) |
|---|---|---|---|---|---|---|
| 299471 | 40 | 72 | 86 | 91 | 93 | 1.17 |
| 299473 | 6 | 43 | 63 | 87 | 89 | 3.86 |
| 299476 | 3 | 21 | 48 | 74 | 86 | 5.58 |
| 299535 | 9 | 22 | 36 | 62 | 77 | 7.05 |
| 299535 | 6 | 19 | 49 | 68 | 70 | 6.70 |
| 299544 | 35 | 66 | 81 | 84 | 87 | 1.52 |
| 444397 | 88 | 90 | 95 | 97 | 96 | <1.25 |
| 444398 | 91 | 97 | 97 | 97 | 98 | <1.25 |
| 444400 | 72 | 87 | 93 | 96 | 96 | <1.25 |
| 444401 | 86 | 92 | 97 | 98 | 97 | <1.25 |
| 444402 | 83 | 91 | 94 | 95 | 95 | <1.25 |
| 444404 | 49 | 69 | 81 | 90 | 93 | 0.92 |
| 444408 | 21 | 46 | 70 | 84 | 86 | 3.10 |
| 444410 | 35 | 55 | 77 | 89 | 91 | 2.02 |
| 444436 | 37 | 66 | 81 | 89 | 92 | 1.50 |
| 444440 | 66 | 79 | 89 | 92 | 89 | <1.25 |
| 444441 | 40 | 62 | 85 | 89 | 89 | 1.40 |
| 444442 | 55 | 75 | 86 | 90 | 91 | <1.25 |
| 445568 | 74 | 92 | 91 | 92 | 91 | <1.25 |
| 445569 | 68 | 83 | 90 | 94 | 93 | <1.25 |
| 445581 | 8 | 48 | 77 | 85 | 92 | 3.33 |
| 445582 | 15 | 22 | 44 | 97 | 99 | 4.29 |
| 445583 | 36 | 58 | 71 | 87 | 92 | 1.96 |
| 445584 | 25 | 43 | 66 | 86 | 94 | 3.05 |
| 445589 | 38 | 56 | 77 | 85 | 81 | 1.74 |
| 445601 | 55 | 76 | 84 | 93 | 93 | <1.25 |
| 445608 | 22 | 56 | 72 | 86 | 94 | 2.66 |
| 445612 | 61 | 75 | 85 | 91 | 94 | <1.25 |

Example 4: Dose-Dependent Antisense Inhibition of Human DMPK in Human Skeletal Muscle Cells Several of the antisense oligonucleotides exhibiting in vitro inhibition of DMPK in hSKMC (see Example 3) were tested at various doses. Cells were plated at a density of 20,000 cells per well and transfected using electroporation with 1,250 nM, 2,500 nM, 5,000 nM, 10,000 nM and 20,000 nM concentrations of each antisense oligonucleotide. After approximately 16 hours, RNA was isolated from the cells and DMPK mRNA transcript levels were measured by quantitative real-time PCR using primer probe set RTS3164, described hereinabove. DMPK mRNA transcript levels were normalized to total RNA content, as measured by RIBOGREEN®. Results are presented in Table 7 as percent inhibition of DMPK, relative to untreated control cells.

The majority of the tested antisense oligonucleotides demonstrated dose-dependent inhibition of DMPK mRNA levels under the conditions specified above.

TABLE 7

Dose-dependent antisense inhibition of human DMPK in hSKMC tested with primer probe set RTS3164

| ISIS No. | 1,250 nM | 2,500 nM | 5,000 nM | 10,000 nM | 20,000 nM | $IC_{50}$ (μM) |
|---|---|---|---|---|---|---|
| 299471 | 34 | 65 | 87 | 91 | 94 | 1.59 |
| 299473 | 2 | 33 | 60 | 89 | 92 | 4.31 |
| 299476 | 15 | 17 | 49 | 81 | 91 | 4.89 |
| 299535 | 0 | 12 | 34 | 62 | 59 | 9.95 |
| 299535 | 20 | 33 | 47 | 67 | 80 | 5.11 |
| 299544 | 32 | 63 | 81 | 85 | 87 | 1.82 |
| 444397 | 10 | 30 | 58 | 85 | 82 | 4.51 |
| 444398 | 33 | 57 | 74 | 85 | 87 | 2.07 |
| 444400 | 52 | 46 | 63 | 82 | 88 | 1.76 |
| 444401 | 51 | 71 | 84 | 89 | 91 | <1.25 |
| 444402 | 53 | 79 | 83 | 87 | 84 | <1.25 |
| 444404 | 48 | 68 | 77 | 86 | 90 | 0.95 |
| 444408 | 26 | 47 | 70 | 87 | 87 | 2.80 |
| 444410 | 22 | 47 | 67 | 83 | 87 | 3.12 |
| 444436 | 28 | 67 | 76 | 89 | 92 | 1.94 |
| 444440 | 66 | 77 | 83 | 89 | 85 | <1.25 |
| 444441 | 33 | 55 | 81 | 87 | 86 | 1.99 |
| 444442 | 54 | 73 | 84 | 89 | 88 | <1.25 |
| 445568 | 65 | 83 | 85 | 84 | 76 | <1.25 |
| 445569 | 60 | 77 | 87 | 93 | 91 | <1.25 |
| 445581 | 16 | 44 | 78 | 86 | 94 | 3.13 |
| 445582 | 0 | 7 | 26 | 96 | 99 | 5.62 |
| 445583 | 39 | 53 | 73 | 89 | 94 | 1.97 |
| 445584 | 20 | 26 | 61 | 81 | 93 | 4.20 |
| 445589 | 42 | 61 | 81 | 91 | 87 | 1.36 |
| 445601 | 49 | 79 | 87 | 93 | 94 | 0.66 |
| 445608 | 26 | 59 | 71 | 85 | 97 | 2.41 |
| 445612 | 46 | 59 | 72 | 88 | 93 | 1.51 |

Example 5: Dose-Dependent Antisense Inhibition of Human DMPK in Human Skeletal Muscle Cells Several antisense oligonucleotides were designed to target human DMPK mRNA and were tested in hSKMC at various doses. Several other antisense oligonucleotides were designed to target human actin mRNA and were also tested in hSKMC at various doses. The newly designed gapmers are 2-10-2 MOE or 3-10-3 MOE gapmers. The 2-10-2 MOE gapmers are 14 nucleosides in length and where the gap segment comprises ten 2'-deoxynucleosides and each wing segment comprises two 2'-MOE nucleosides. The 3-10-3 MOE gapmers are 16 nucleosides in length and where the gap segment comprises ten 2'-deoxynucleosides and each wing segment comprises three 2'-MOE nucleosides. The internucleoside linkages throughout each gapmer are phosphorothioate (P=S) linkages. All cytosine residues throughout each gapmer are 5-methylcytosines. 'Target start site' indicates the 5'-most nucleoside to which the antisense oligonucleotide is targeted. 'Target stop site' indicates the 3'-most nucleoside to which the antisense oligonucleotide is targeted. The antisense oligonucleotides listed in Table 8 target either the human DMPK genomic sequence, designated herein as SEQ ID NO: 2 (the complement of GENBANK Accession No. NT_011109.15 truncated from nucleotides 18540696 to 18555106) or the human actin sequence, designated herein as SEQ ID NO: 801 (GENBANK Accession No. NM_001100.3).

Cells were plated at a density of 20,000 cells per well and transfected using electroporation with 1,250 nM, 2,500 nM, 5,000 nM, 10,000 nM and 20,000 nM concentrations of each antisense oligonucleotide. After approximately 16 hours, RNA was isolated from the cells and DMPK mRNA transcript levels were measured by quantitative real-time PCR using primer probe set RTS3162, described hereinabove. DMPK mRNA transcript levels were normalized to total RNA content, as measured by RIBOGREEN®. Results are presented in Table 8 as percent inhibition of DMPK, relative to untreated control cells. The antisense oligonucleotides were also tested under similar conditions with RTS3164. The results are presented in Table 9.

Many of the tested antisense oligonucleotides demonstrated dose-dependent inhibition of DMPK mRNA levels under the conditions specified above.

TABLE 8

Dose-dependent antisense inhibition of human DMPK and human actin in hSKMC tested with primer probe set RTS3162

| ISIS No | Sequence | Motif | Target SEQ ID NO | Start Site | 1,250 nM | 2,500 nM | 5,000 nM | 10,000 nM | 20,000 nM | $IC_{50}$ (nM) | SEQ ID NO |
|---|---|---|---|---|---|---|---|---|---|---|---|
| 468787 | CTCCCGACAAGCTCCA | 3-10-3 | 2 | 814 | 28 | 47 | 51 | 84 | 88 | 3.27 | 808 |
| 468772 | TCCCGACAAGCTCC | 2-10-2 | 2 | 815 | 17 | 39 | 67 | 72 | 80 | 4.04 | 809 |
| 468795 | GCTTGCACGTGTGGCT | 3-10-3 | 2 | 10935 | 32 | 58 | 77 | 85 | 75 | 1.94 | 810 |
| 468780 | CTTGCACGTGTGGC | 2-10-2 | 2 | 10936 | 22 | 17 | 43 | 66 | 77 | 6.23 | 811 |
| 468793 | GGTTGTGAACTGGCAG | 3-10-3 | 2 | 13224 | 69 | 77 | 93 | 96 | 96 | <1.25 | 812 |
| 468778 | GTTGTGAACTGGCA | 2-10-2 | 2 | 13225 | 60 | 69 | 89 | 95 | 97 | <1.25 | 813 |
| 468794 | GAGCGGTTGTGAACTG | 3-10-3 | 2 | 13228 | 21 | 32 | 61 | 70 | 86 | 4.27 | 814 |
| 468779 | AGCGGTTGTGAACT | 2-10-2 | 2 | 13229 | 40 | 45 | 72 | 91 | 97 | 2.20 | 815 |
| 468796 | GCTGCCTTCCCAGGCC | 3-10-3 | 2 | 13493 | 73 | 79 | 91 | 96 | 95 | <1.25 | 816 |
| 468781 | CTGCCTTCCCAGGC | 2-10-2 | 2 | 13494 | 36 | 53 | 66 | 86 | 90 | 2.28 | 817 |
| 468788 | GCACTTTGCGAACCAA | 3-10-3 | 2 | 13555 | 55 | 80 | 84 | 94 | 96 | <1.25 | 818 |
| 468773 | CACTTTGCGAACCA | 2-10-2 | 2 | 13556 | 31 | 52 | 82 | 91 | 93 | 2.16 | 819 |
| 468789 | GAAAGCTTTGCACTTT | 3-10-3 | 2 | 13564 | 42 | 66 | 83 | 91 | 98 | 1.31 | 820 |

TABLE 8-continued

Dose-dependent antisense inhibition of human DMPK and human actin in hSKMC tested with primer probe set RTS3162

| ISIS No | Sequence | Motif | Target SEQ ID NO | Start Site | 1,250 nM | 2,500 nM | 5,000 nM | 10,000 nM | 20,000 nM | $IC_{50}$ (nM) | SEQ ID NO |
|---|---|---|---|---|---|---|---|---|---|---|---|
| 468774 | AAAGCTTTGCACTT | 2-10-2 | 2 | 13565 | 21 | 0 | 31 | 41 | 55 | 1.87 | 821 |
| 468790 | CGGAGGACGAGGTCAA | 3-10-3 | 2 | 13750 | 43 | 57 | 79 | 87 | 89 | 1.51 | 822 |
| 468775 | GGAGGACGAGGTCA | 2-10-2 | 2 | 13751 | 27 | 51 | 58 | 78 | 81 | 3.18 | 823 |
| 468791 | AGCCTGTCAGCGAGTC | 3-10-3 | 2 | 13765 | 49 | 63 | 85 | 62 | 95 | 1.04 | 824 |
| 468776 | GCCTGTCAGCGAGT | 2-10-2 | 2 | 13766 | 65 | 47 | 81 | 88 | 93 | <1.25 | 825 |
| 468792 | TCCTGTAGCCTGTCAG | 3-10-3 | 2 | 13771 | 38 | 57 | 73 | 85 | 93 | 1.91 | 826 |
| 468777 | CCTGTAGCCTGTCA | 2-10-2 | 2 | 13772 | 15 | 58 | 66 | 85 | 92 | 2.99 | 827 |
| 468783 | GAAGCGAGGCTTCACT | 3-10-3 | 801 | 22 | 0 | 20 | 5 | 0 | 0 | >20.00 | 828 |
| 468768 | AAGCGAGGCTTCAC | 2-10-2 | 801 | 23 | 25 | 22 | 5 | 17 | 0 | >20.00 | 829 |
| 468784 | ACCTGCCCGTCTGGCA | 3-10-3 | 801 | 836 | 15 | 25 | 32 | 18 | 25 | >20.00 | 830 |
| 468769 | CCTGCCCGTCTGGC | 2-10-2 | 801 | 837 | 32 | 11 | 11 | 20 | 32 | >20.00 | 831 |
| 468782 | GGTCAGCGATCCCAGG | 3-10-3 | 801 | 1030 | 0 | 0 | 0 | 0 | 0 | >20.00 | 832 |
| 468767 | GTCAGCGATCCCAG | 2-10-2 | 801 | 1031 | 15 | 0 | 11 | 0 | 0 | >20.00 | 833 |
| 468785 | ATTTTCTTCCACAGGG | 3-10-3 | 801 | 1432 | 12 | 0 | 0 | 0 | 0 | >20.00 | 834 |
| 468770 | TTTTCTTCCACAGG | 2-10-2 | 801 | 1433 | 36 | 2 | 0 | 0 | 28 | >20.00 | 835 |
| 468786 | GAATGACTTTAATGCT | 3-10-3 | 801 | 1462 | 0 | 0 | 0 | 4 | 0 | >20.00 | 836 |
| 468771 | AATGACTTTAATGC | 2-10-2 | 801 | 1463 | 8 | 16 | 0 | 5 | 0 | >20.00 | 837 |

TABLE 9

Dose-dependent antisense inhibition of human DMPK in hSKMC tested with primer probe set RTS3164

| ISIS No | 1,250 nM | 2,500 nM | 5,000 nM | 10,000 nM | 20,000 nM | $IC_{50}$ (μM) |
|---|---|---|---|---|---|---|
| 468777 | 20 | 66 | 72 | 87 | 96 | 2.41 |
| 468776 | 68 | 48 | 86 | 90 | 96 | <1.25 |
| 468794 | 18 | 23 | 58 | 65 | 86 | 4.97 |
| 468787 | 36 | 50 | 51 | 88 | 92 | 2.69 |
| 468772 | 12 | 47 | 69 | 80 | 86 | 3.57 |
| 468773 | 33 | 48 | 82 | 91 | 96 | 2.21 |
| 468774 | 21 | 0 | 30 | 42 | 59 | 1.60 |
| 468790 | 50 | 57 | 77 | 91 | 91 | 1.26 |
| 468780 | 23 | 22 | 55 | 73 | 85 | 4.69 |
| 468775 | 29 | 52 | 55 | 79 | 84 | 3.03 |
| 468782 | 9 | 0 | 0 | 0 | 0 | >20.00 |
| 468786 | 2 | 0 | 0 | 0 | 0 | >20.00 |
| 468785 | 15 | 0 | 1 | 0 | 5 | >20.00 |
| 468788 | 57 | 74 | 76 | 94 | 96 | <1.25 |
| 468791 | 45 | 66 | 88 | 61 | 97 | 1.10 |
| 468789 | 26 | 65 | 82 | 90 | 97 | 2.02 |
| 468781 | 28 | 46 | 59 | 82 | 84 | 3.08 |
| 468779 | 26 | 31 | 66 | 90 | 97 | 3.29 |
| 468784 | 7 | 23 | 26 | 7 | 18 | >20.00 |
| 468783 | 0 | 16 | 8 | 0 | 0 | >20.00 |
| 468792 | 26 | 49 | 73 | 84 | 92 | 2.72 |
| 468795 | 30 | 53 | 83 | 86 | 85 | 2.14 |
| 468793 | 49 | 66 | 90 | 96 | 95 | 0.93 |
| 468768 | 23 | 3 | 5 | 9 | 0 | >20.00 |
| 468767 | 0 | 0 | 14 | 0 | 0 | >20.00 |
| 468769 | 31 | 0 | 0 | 16 | 25 | >20.00 |
| 468771 | 4 | 0 | 0 | 0 | 0 | >20.00 |
| 468770 | 33 | 0 | 0 | 0 | 32 | >20.00 |
| 468796 | 62 | 72 | 84 | 96 | 95 | <1.25 |
| 468778 | 44 | 58 | 86 | 96 | 98 | 1.44 |

Example 6: Dose Response Studies with Antisense Oligonucleotides Targeting Human Dystrophia Myotonica-Protein Kinase (DMPK) in DM1 Fibroblast Cells The mutant form of the DMPK mRNA, harboring large CUG repeats, are fully transcribed and polyadenylated, but remain trapped in the nucleus (Davis et al, 1997, *Proc. Natl. Acad. Sci. U.S.A* 94, 7388-7393). These mutant nuclear-retained mRNAs are one of the most important pathological features of myotonic dystrophy 1 (DM1). Antisense inhibition of mutant DMPK mRNA in DM1 fibroblast cells was studied.

The DMPK gene normally has 5-37 CTG repeats in the 3' untranslated region. In myotonic dystrophy type I, this number is significantly expanded and may be in the range of 50 to greater than 3,500 (Harper, Myotonic Dystrophy (Saunders, London, ed. 3, 2001); Annu. Rev. Neurosci.

29:259, 2006; EMBO J. 19:4439, 2000; Curr Opin Neurol. 20:572, 2007).DM1 fibroblast cells were plated at a density of 4,500 cells per well and transfected using Cytofectin reagent with 9.4 nM, 18.8 nM, 37.5 nM, 75.0 nM, 150.0 nM, and 300.0 nM concentrations of each antisense oligonucleotide. After approximately 16 hours, RNA was isolated from the cells and DMPK RNA transcript levels were measured by quantitative real-time PCR using primer probe set RTS3164, described hereinabove. DMPK RNA transcript levels were normalized to total RNA content, as measured by RIBOGREEN®. Results are presented in Table 10 as percent inhibition of DMPK, relative to untreated control cells.

An assay with similar conditions was also performed with primer probe set RTS3162, described hereinabove, which targets the 3'-end of the DMPK transcript. Results are presented in Table 11 as percent inhibition of DMPK, relative to untreated control cells.

The tested antisense oligonucleotides demonstrated dose-dependent inhibition of DMPK mRNA levels under the conditions specified above.

TABLE 10

Dose-dependent antisense inhibition of DMPK mRNA in DM1 fibroblast cells with RTS3164

| ISIS No. | 9.4 nM | 18.8 nM | 37.5 nM | 75.0 nM | 150.0 nM | 300.0 nM | $IC_{50}$ (nM) |
|---|---|---|---|---|---|---|---|
| 299471 | 10 | 25 | 31 | 47 | 61 | 73 | 86.3 |
| 444401 | 8 | 27 | 41 | 60 | 67 | 74 | 64.3 |
| 444404 | 10 | 21 | 31 | 43 | 55 | 73 | 100.0 |
| 444436 | 7 | 17 | 36 | 64 | 68 | 70 | 72.3 |
| 445569 | 19 | 31 | 41 | 59 | 46 | 77 | 72.2 |

TABLE 11

Dose-dependent antisense inhibition of DMPK mRNA in DM1 fibroblast cells with RTS3162

| ISIS No | 9.4 nM | 18.8 nM | 37.5 nM | 75.0 nM | 150.0 nM | 300.0 nM | $IC_{50}$ (nM) |
|---|---|---|---|---|---|---|---|
| 299471 | 7 | 25 | 29 | 46 | 48 | 69 | 115.3 |
| 444401 | 20 | 34 | 52 | 72 | 83 | 89 | 35.8 |
| 444404 | 5 | 20 | 28 | 42 | 54 | 77 | 98.8 |
| 444436 | 12 | 15 | 27 | 61 | 68 | 75 | 74.3 |
| 445569 | 5 | 25 | 33 | 53 | 50 | 76 | 89.6 |

Example 7: Antisense Inhibition of Human DMPK in Human Skeletal Muscle Cells (hSKMc)

Antisense oligonucleotides targeted to a human DMPK nucleic acid were tested for their effect on DMPK RNA transcript in vitro. Cultured hSKMc at a density of 20,000 cells per well were transfected using electroporation with 10,000 nM antisense oligonucleotide. After approximately 24 hours, RNA was isolated from the cells and DMPK transcript levels were measured by quantitative real-time PCR. DMPK RNA transcript levels were adjusted according to total RNA content, as measured by RIBOGREEN®. Results are presented as percent inhibition of DMPK, relative to untreated control cells.

The antisense oligonucleotides in Tables 12 and 13 are 5-10-5 gapmers, where the gap segment comprises ten 2'-deoxynucleosides and each wing segment comprises five 2'-MOE nucleosides. The internucleoside linkages throughout each gapmer are phosphorothioate (P═S) linkages. All cytsoine residues throughout each gapmer are 5-methylcytosines. 'Target start site' indicates the 5'-most nucleoside to which the antisense oligonucleotide is targeted in the human genomic gene sequence. 'Target stop site' indicates the 3'-most nucleoside to which the antisense oligonucleotide is targeted in the human genomic sequence. All the antisense oligonucleotides listed in Table 12 target SEQ ID NO: 1 (GENBANK Accession No. NM_001081560.1). All the antisense oligonucleotides listed in Table 13 target SEQ ID NO: 2 (the complement of GENBANK Accession No. NT 011109.15 truncated from nucleotides 18540696 to 18555106).

Several of the antisense oligonucleotides demonstrated significant inhibition of DMPK mRNA levels under the conditions specified above.

TABLE 12

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 124 | 143 | 502369 | GCCTGGCAGCCCCTGTCCAG | 16 | 160 |
| 125 | 144 | 502370 | GGCCTGGCAGCCCCTGTCCA | 58 | 161 |
| 126 | 145 | 502371 | GGGCCTGGCAGCCCCTGTCC | 62 | 162 |
| 169 | 188 | 502372 | ATGGCCCCTCCCCGGGCCGG | 41 | 163 |
| 170 | 189 | 502373 | CATGGCCCCTCCCCGGGCCG | 29 | 164 |
| 171 | 190 | 502374 | CCATGGCCCCTCCCCGGGCC | 34 | 165 |
| 172 | 191 | 502375 | ACCATGGCCCCTCCCCGGGC | 60 | 166 |
| 173 | 192 | 502376 | CACCATGGCCCCTCCCCGGG | 68 | 167 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 174 | 193 | 502377 | GCACCATGGCCCCTCCCCGG | 75 | 168 |
| 175 | 194 | 502378 | AGCACCATGGCCCCTCCCCG | 65 | 169 |
| 176 | 195 | 502379 | CAGCACCATGGCCCCTCCCC | 63 | 170 |
| 177 | 196 | 502380 | GCAGCACCATGGCCCCTCCC | 73 | 171 |
| 178 | 197 | 502381 | GGCAGCACCATGGCCCCTCC | 80 | 172 |
| 180 | 199 | 502382 | CAGGCAGCACCATGGCCCCT | 82 | 173 |
| 181 | 200 | 502383 | ACAGGCAGCACCATGGCCCC | 72 | 174 |
| 183 | 202 | 502384 | GGACAGGCAGCACCATGGCC | 70 | 175 |
| 184 | 203 | 502385 | TGGACAGGCAGCACCATGGC | 71 | 176 |
| 185 | 204 | 502386 | TTGGACAGGCAGCACCATGG | 73 | 177 |
| 186 | 205 | 502387 | GTTGGACAGGCAGCACCATG | 73 | 178 |
| 187 | 206 | 502388 | TGTTGGACAGGCAGCACCAT | 60 | 179 |
| 188 | 207 | 502389 | ATGTTGGACAGGCAGCACCA | 75 | 180 |
| 189 | 208 | 502390 | CATGTTGGACAGGCAGCACC | 81 | 181 |
| 190 | 209 | 502391 | ACATGTTGGACAGGCAGCAC | 67 | 182 |
| 191 | 210 | 502392 | GACATGTTGGACAGGCAGCA | 71 | 183 |
| 192 | 211 | 502393 | TGACATGTTGGACAGGCAGC | 81 | 184 |
| 193 | 212 | 502394 | CTGACATGTTGGACAGGCAG | 76 | 185 |
| 194 | 213 | 502395 | GCTGACATGTTGGACAGGCA | 70 | 186 |
| 195 | 214 | 502396 | GGCTGACATGTTGGACAGGC | 77 | 187 |
| 196 | 215 | 502397 | CGGCTGACATGTTGGACAGG | 74 | 188 |
| 197 | 216 | 502398 | TCGGCTGACATGTTGGACAG | 63 | 189 |
| 198 | 217 | 502399 | CTCGGCTGACATGTTGGACA | 80 | 190 |
| 199 | 218 | 502400 | CCTCGGCTGACATGTTGGAC | 71 | 191 |
| 200 | 219 | 502401 | ACCTCGGCTGACATGTTGGA | 64 | 192 |
| 201 | 220 | 502402 | CACCTCGGCTGACATGTTGG | 71 | 193 |
| 202 | 221 | 502403 | GCACCTCGGCTGACATGTTG | 77 | 194 |
| 203 | 222 | 502404 | CGCACCTCGGCTGACATGTT | 80 | 195 |
| 204 | 223 | 502405 | CCGCACCTCGGCTGACATGT | 80 | 196 |
| 205 | 224 | 502406 | GCCGCACCTCGGCTGACATG | 79 | 197 |
| 206 | 225 | 502407 | AGCCGCACCTCGGCTGACAT | 74 | 198 |
| 207 | 226 | 502408 | CAGCCGCACCTCGGCTGACA | 66 | 199 |
| 208 | 227 | 502409 | TCAGCCGCACCTCGGCTGAC | 15 | 200 |
| 209 | 228 | 502410 | CTCAGCCGCACCTCGGCTGA | 32 | 201 |
| 210 | 229 | 502411 | CCTCAGCCGCACCTCGGCTG | 65 | 202 |
| 211 | 230 | 502412 | GCCTCAGCCGCACCTCGGCT | 81 | 203 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 232 | 251 | 502413 | CCAACACCAGCTGCTGGAGC | 90 | 204 |
| 233 | 252 | 502414 | TCCAACACCAGCTGCTGGAG | 78 | 205 |
| 234 | 253 | 502415 | GTCCAACACCAGCTGCTGGA | 84 | 206 |
| 236 | 255 | 502416 | GGGTCCAACACCAGCTGCTG | 69 | 207 |
| 257 | 276 | 502417 | GGCTCCAGCCCCAGGAAGCC | 46 | 208 |
| 258 | 277 | 502418 | GGGCTCCAGCCCCAGGAAGC | 28 | 209 |
| 276 | 295 | 502419 | CAGGAGAAGGTCGAGCAGGG | 41 | 210 |
| 278 | 297 | 502420 | CCCAGGAGAAGGTCGAGCAG | 71 | 211 |
| 279 | 298 | 502421 | GCCCAGGAGAAGGTCGAGCA | 85 | 212 |
| 280 | 299 | 451363 | CGCCCAGGAGAAGGTCGAGC | 84 | 213 |
| 281 | 300 | 502422 | ACGCCCAGGAGAAGGTCGAG | 67 | 214 |
| 317 | 336 | 502423 | TCCTGGGCCAGTTCGGAGGC | 58 | 215 |
| 318 | 337 | 502424 | GTCCTGGGCCAGTTCGGAGG | 71 | 216 |
| 319 | 338 | 502425 | TGTCCTGGGCCAGTTCGGAG | 69 | 217 |
| 320 | 339 | 502426 | TTGTCCTGGGCCAGTTCGGA | 71 | 218 |
| 321 | 340 | 502427 | CTTGTCCTGGGCCAGTTCGG | 66 | 219 |
| 322 | 341 | 502428 | ACTTGTCCTGGGCCAGTTCG | 59 | 220 |
| 323 | 342 | 502429 | TACTTGTCCTGGGCCAGTTC | 75 | 221 |
| 324 | 343 | 502430 | GTACTTGTCCTGGGCCAGTT | 78 | 222 |
| 325 | 344 | 502431 | CGTACTTGTCCTGGGCCAGT | 74 | 223 |
| 343 | 362 | 502432 | ACTGCAAGAAGTCGGCCACG | 73 | 224 |
| 345 | 364 | 502433 | CCACTGCAAGAAGTCGGCCA | 65 | 225 |
| 346 | 365 | 451364 | CCCACTGCAAGAAGTCGGCC | 32 | 226 |
| 347 | 366 | 502434 | GCCCACTGCAAGAAGTCGGC | 70 | 227 |
| 348 | 367 | 502435 | CGCCCACTGCAAGAAGTCGG | 61 | 228 |
| 349 | 368 | 502436 | CCGCCCACTGCAAGAAGTCG | 54 | 229 |
| 350 | 369 | 502437 | TCCGCCCACTGCAAGAAGTC | 40 | 230 |
| 351 | 370 | 502438 | CTCCGCCCACTGCAAGAAGT | 33 | 231 |
| 352 | 371 | 502439 | GCTCCGCCCACTGCAAGAAG | 23 | 232 |
| 353 | 372 | 502440 | GGCTCCGCCCACTGCAAGAA | 23 | 233 |
| 354 | 373 | 502441 | GGGCTCCGCCCACTGCAAGA | 17 | 234 |
| 355 | 374 | 502442 | TGGGCTCCGCCCACTGCAAG | 22 | 235 |
| 356 | 375 | 502443 | ATGGGCTCCGCCCACTGCAA | 14 | 236 |
| 357 | 376 | 502444 | GATGGGCTCCGCCCACTGCA | 43 | 237 |
| 358 | 377 | 502445 | CGATGGGCTCCGCCCACTGC | 37 | 238 |
| 359 | 378 | 502446 | ACGATGGGCTCCGCCCACTG | 0 | 239 |
| 360 | 379 | 502447 | CACGATGGGCTCCGCCCACT | 59 | 240 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 361 | 380 | 502448 | CCACGATGGGCTCCGCCCAC | 69 | 241 |
| 362 | 381 | 502449 | ACCACGATGGGCTCCGCCCA | 63 | 242 |
| 363 | 382 | 502450 | CACCACGATGGGCTCCGCCC | 73 | 243 |
| 364 | 383 | 502451 | TCACCACGATGGGCTCCGCC | 77 | 244 |
| 365 | 384 | 502452 | CTCACCACGATGGGCTCCGC | 66 | 245 |
| 366 | 385 | 502453 | CCTCACCACGATGGGCTCCG | 81 | 246 |
| 367 | 386 | 502454 | GCCTCACCACGATGGGCTCC | 77 | 247 |
| 368 | 387 | 502455 | AGCCTCACCACGATGGGCTC | 63 | 248 |
| 369 | 388 | 502456 | AAGCCTCACCACGATGGGCT | 70 | 249 |
| 370 | 389 | 502457 | TAAGCCTCACCACGATGGGC | 78 | 250 |
| 371 | 390 | 502458 | TTAAGCCTCACCACGATGGG | 76 | 251 |
| 372 | 391 | 502459 | CTTAAGCCTCACCACGATGG | 78 | 252 |
| 373 | 392 | 502460 | CCTTAAGCCTCACCACGATG | 68 | 253 |
| 374 | 393 | 502461 | TCCTTAAGCCTCACCACGAT | 67 | 254 |
| 375 | 394 | 502462 | CTCCTTAAGCCTCACCACGA | 84 | 255 |
| 376 | 395 | 502463 | CCTCCTTAAGCCTCACCACG | 76 | 256 |
| 377 | 396 | 502464 | ACCTCCTTAAGCCTCACCAC | 64 | 257 |
| 378 | 397 | 502465 | GACCTCCTTAAGCCTCACCA | 72 | 258 |
| 379 | 398 | 502466 | GGACCTCCTTAAGCCTCACC | 69 | 259 |
| 380 | 399 | 502467 | CGGACCTCCTTAAGCCTCAC | 81 | 260 |
| 381 | 400 | 502468 | TCGGACCTCCTTAAGCCTCA | 78 | 261 |
| 382 | 401 | 502469 | GTCGGACCTCCTTAAGCCTC | 57 | 262 |
| 384 | 403 | 502470 | CAGTCGGACCTCCTTAAGCC | 62 | 263 |
| 385 | 404 | 502471 | GCAGTCGGACCTCCTTAAGC | 45 | 264 |
| 386 | 405 | 502472 | TGCAGTCGGACCTCCTTAAG | 60 | 265 |
| 412 | 431 | 502473 | CCTTCAGAATCTCGAAGTCG | 67 | 266 |
| 413 | 432 | 502474 | ACCTTCAGAATCTCGAAGTC | 50 | 267 |
| 415 | 434 | 502475 | TCACCTTCAGAATCTCGAAG | 54 | 268 |
| 416 | 435 | 502476 | ATCACCTTCAGAATCTCGAA | 38 | 269 |
| 417 | 436 | 502477 | GATCACCTTCAGAATCTCGA | 35 | 270 |
| 419 | 438 | 502478 | CCGATCACCTTCAGAATCTC | 52 | 271 |
| 420 | 439 | 502479 | TCCGATCACCTTCAGAATCT | 50 | 272 |
| 421 | 440 | 502480 | GTCCGATCACCTTCAGAATC | 44 | 273 |
| 422 | 441 | 502481 | CGTCCGATCACCTTCAGAAT | 41 | 274 |
| 467 | 486 | 502482 | CCCGTCTGCTTCATCTTCAC | 67 | 275 |
| 468 | 487 | 502483 | GCCCGTCTGCTTCATCTTCA | 76 | 276 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 469 | 488 | 502484 | GGCCCGTCTGCTTCATCTTC | 57 | 277 |
| 470 | 489 | 502485 | TGGCCCGTCTGCTTCATCTT | 64 | 278 |
| 471 | 490 | 502486 | CTGGCCCGTCTGCTTCATCT | 64 | 279 |
| 472 | 491 | 502487 | CCTGGCCCGTCTGCTTCATC | 73 | 280 |
| 473 | 492 | 502488 | ACCTGGCCCGTCTGCTTCAT | 64 | 281 |
| 474 | 493 | 502489 | CACCTGGCCCGTCTGCTTCA | 80 | 282 |
| 475 | 494 | 502490 | ACACCTGGCCCGTCTGCTTC | 71 | 283 |
| 476 | 495 | 502491 | TACACCTGGCCCGTCTGCTT | 74 | 284 |
| 497 | 516 | 502492 | TTGTTCATGATCTTCATGGC | 56 | 285 |
| 499 | 518 | 502493 | ACTTGTTCATGATCTTCATG | 23 | 286 |
| 500 | 519 | 502494 | CACTTGTTCATGATCTTCAT | 43 | 287 |
| 501 | 520 | 502495 | CCACTTGTTCATGATCTTCA | 43 | 288 |
| 502 | 521 | 502496 | CCCACTTGTTCATGATCTTC | 47 | 289 |
| 503 | 522 | 502497 | TCCCACTTGTTCATGATCTT | 34 | 290 |
| 504 | 523 | 502498 | GTCCCACTTGTTCATGATCT | 34 | 291 |
| 505 | 524 | 502499 | TGTCCCACTTGTTCATGATC | 27 | 292 |
| 506 | 525 | 502500 | ATGTCCCACTTGTTCATGAT | 23 | 293 |
| 507 | 526 | 502501 | CATGTCCCACTTGTTCATGA | 51 | 294 |
| 508 | 527 | 502502 | GCATGTCCCACTTGTTCATG | 20 | 295 |
| 509 | 528 | 502503 | AGCATGTCCCACTTGTTCAT | 52 | 296 |
| 510 | 529 | 502504 | CAGCATGTCCCACTTGTTCA | 72 | 297 |
| 511 | 530 | 502505 | TCAGCATGTCCCACTTGTTC | 70 | 298 |
| 512 | 531 | 502506 | TTCAGCATGTCCCACTTGTT | 53 | 299 |
| 513 | 532 | 502507 | CTTCAGCATGTCCCACTTGT | 52 | 300 |
| 514 | 533 | 502508 | TCTTCAGCATGTCCCACTTG | 45 | 301 |
| 516 | 535 | 502509 | CCTCTTCAGCATGTCCCACT | 68 | 302 |
| 517 | 536 | 502510 | CCCTCTTCAGCATGTCCCAC | 68 | 303 |
| 518 | 537 | 502511 | CCCCTCTTCAGCATGTCCCA | 79 | 304 |
| 519 | 538 | 502512 | GCCCCTCTTCAGCATGTCCC | 85 | 305 |
| 520 | 539 | 502513 | CGCCCCTCTTCAGCATGTCC | 84 | 306 |
| 521 | 540 | 502514 | TCGCCCCTCTTCAGCATGTC | 80 | 307 |
| 522 | 541 | 502515 | CTCGCCCCTCTTCAGCATGT | 82 | 308 |
| 523 | 542 | 502516 | CCTCGCCCCTCTTCAGCATG | 78 | 309 |
| 524 | 543 | 502517 | ACCTCGCCCCTCTTCAGCAT | 73 | 310 |
| 525 | 544 | 502518 | CACCTCGCCCCTCTTCAGCA | 76 | 311 |
| 526 | 545 | 502519 | ACACCTCGCCCCTCTTCAGC | 79 | 312 |
| 527 | 546 | 502520 | GACACCTCGCCCCTCTTCAG | 73 | 313 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 821 | 840 | 502521 | GCCAGGCGGATGTGGCCACA | 57 | 314 |
| 868 | 887 | 502522 | ACCGCACCGTTCCATCTGCC | 62 | 315 |
| 869 | 888 | 502523 | GACCGCACCGTTCCATCTGC | 29 | 316 |
| 923 | 942 | 502524 | ACAGCCTGCAGGATCTCGGG | 86 | 317 |
| 924 | 943 | 502525 | CACAGCCTGCAGGATCTCGG | 81 | 318 |
| 925 | 944 | 502526 | CCACAGCCTGCAGGATCTCG | 83 | 319 |
| 926 | 945 | 502527 | CCCACAGCCTGCAGGATCTC | 84 | 320 |
| 927 | 946 | 502528 | GCCCACAGCCTGCAGGATCT | 91 | 321 |
| 928 | 947 | 502529 | CGCCCACAGCCTGCAGGATC | 90 | 322 |
| 929 | 948 | 502530 | CCGCCCACAGCCTGCAGGAT | 82 | 323 |
| 930 | 949 | 502531 | ACCGCCCACAGCCTGCAGGA | 83 | 324 |
| 931 | 950 | 502532 | CACCGCCCACAGCCTGCAGG | 85 | 325 |
| 932 | 951 | 502533 | CCACCGCCCACAGCCTGCAG | 84 | 326 |
| 933 | 952 | 502534 | CCCACCGCCCACAGCCTGCA | 80 | 327 |
| 934 | 953 | 502535 | GCCCACCGCCCACAGCCTGC | 90 | 328 |
| 935 | 954 | 502536 | GGCCCACCGCCCACAGCCTG | 94 | 329 |
| 936 | 955 | 502537 | AGGCCCACCGCCCACAGCCT | 88 | 330 |
| 937 | 956 | 502538 | CAGGCCCACCGCCCACAGCC | 91 | 331 |
| 938 | 957 | 502539 | CCAGGCCCACCGCCCACAGC | 73 | 332 |
| 939 | 958 | 502540 | CCCAGGCCCACCGCCCACAG | 86 | 333 |
| 940 | 959 | 502541 | TCCCAGGCCCACCGCCCACA | 88 | 334 |
| 941 | 960 | 502542 | GTCCCAGGCCCACCGCCCAC | 84 | 335 |
| 942 | 961 | 502543 | TGTCCCAGGCCCACCGCCCA | 85 | 336 |
| 943 | 962 | 502544 | CTGTCCCAGGCCCACCGCCC | 65 | 337 |
| 944 | 963 | 502545 | CCTGTCCCAGGCCCACCGCC | 81 | 338 |
| 945 | 964 | 502546 | GCCTGTCCCAGGCCCACCGC | 90 | 339 |
| 946 | 965 | 502547 | TGCCTGTCCCAGGCCCACCG | 85 | 340 |
| 947 | 966 | 502548 | CTGCCTGTCCCAGGCCCACC | 89 | 341 |
| 948 | 967 | 502549 | GCTGCCTGTCCCAGGCCCAC | 91 | 342 |
| 949 | 968 | 502550 | AGCTGCCTGTCCCAGGCCCA | 94 | 343 |
| 950 | 969 | 502551 | TAGCTGCCTGTCCCAGGCCC | 92 | 344 |
| 951 | 970 | 502552 | GTAGCTGCCTGTCCCAGGCC | 88 | 345 |
| 952 | 971 | 502553 | CGTAGCTGCCTGTCCCAGGC | 85 | 346 |
| 953 | 972 | 502554 | CCGTAGCTGCCTGTCCCAGG | 83 | 347 |
| 954 | 973 | 502555 | CCCGTAGCTGCCTGTCCCAG | 64 | 348 |
| 955 | 974 | 502556 | GCCCGTAGCTGCCTGTCCCA | 83 | 349 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 956 | 975 | 502557 | GGCCCGTAGCTGCCTGTCCC | 89 | 350 |
| 1004 | 1023 | 502558 | TAGAACATTTCATAGGCGAA | 68 | 351 |
| 1042 | 1061 | 502559 | TCTCCGCCGTGGAATCCGCG | 75 | 352 |
| 1043 | 1062 | 502560 | GTCTCCGCCGTGGAATCCGC | 79 | 353 |
| 1044 | 1063 | 502561 | GGTCTCCGCCGTGGAATCCG | 66 | 354 |
| 1045 | 1064 | 502562 | AGGTCTCCGCCGTGGAATCC | 50 | 355 |
| 1046 | 1065 | 502563 | TAGGTCTCCGCCGTGGAATC | 71 | 356 |
| 1067 | 1086 | 502564 | TTGTAGTGGACGATCTTGCC | 68 | 357 |
| 1068 | 1087 | 502565 | CTTGTAGTGGACGATCTTGC | 70 | 358 |
| 1069 | 1088 | 502566 | CCTTGTAGTGGACGATCTTG | 61 | 359 |
| 1070 | 1089 | 502567 | TCCTTGTAGTGGACGATCTT | 72 | 360 |
| 1071 | 1090 | 502568 | CTCCTTGTAGTGGACGATCT | 75 | 361 |
| 1072 | 1091 | 502569 | GCTCCTTGTAGTGGACGATC | 75 | 362 |
| 1073 | 1092 | 502570 | TGCTCCTTGTAGTGGACGAT | 83 | 363 |
| 1074 | 1093 | 502571 | GTGCTCCTTGTAGTGGACGA | 72 | 364 |
| 1075 | 1094 | 502572 | GGTGCTCCTTGTAGTGGACG | 66 | 365 |
| 1076 | 1095 | 502573 | AGGTGCTCCTTGTAGTGGAC | 51 | 366 |
| 1077 | 1096 | 502574 | GAGGTGCTCCTTGTAGTGGA | 46 | 367 |
| 1078 | 1097 | 502575 | AGAGGTGCTCCTTGTAGTGG | 70 | 368 |
| 1079 | 1098 | 502576 | GAGAGGTGCTCCTTGTAGTG | 47 | 369 |
| 1080 | 1099 | 502577 | AGAGAGGTGCTCCTTGTAGT | 65 | 370 |
| 1081 | 1100 | 502578 | GAGAGAGGTGCTCCTTGTAG | 45 | 371 |
| 1082 | 1101 | 502579 | AGAGAGAGGTGCTCCTTGTA | 63 | 372 |
| 1083 | 1102 | 502580 | CAGAGAGAGGTGCTCCTTGT | 77 | 373 |
| 1085 | 1104 | 502581 | GGCAGAGAGAGGTGCTCCTT | 70 | 374 |
| 1086 | 1105 | 502582 | CGGCAGAGAGAGGTGCTCCT | 80 | 375 |
| 1087 | 1106 | 502583 | GCGGCAGAGAGAGGTGCTCC | 62 | 376 |
| 1088 | 1107 | 502584 | AGCGGCAGAGAGAGGTGCTC | 44 | 377 |
| 1089 | 1108 | 502585 | CAGCGGCAGAGAGAGGTGCT | 78 | 378 |
| 1090 | 1109 | 502586 | CCAGCGGCAGAGAGAGGTGC | 71 | 379 |
| 1165 | 1184 | 502587 | GGCCCAGCCGTGTCTCCGGG | 77 | 380 |
| 1166 | 1185 | 502588 | CGGCCCAGCCGTGTCTCCGG | 69 | 381 |
| 1167 | 1186 | 502589 | CCGGCCCAGCCGTGTCTCCG | 70 | 382 |
| 1168 | 1187 | 502590 | CCCGGCCCAGCCGTGTCTCC | 75 | 383 |
| 1169 | 1188 | 502591 | CCCCGGCCCAGCCGTGTCTC | 77 | 384 |
| 1170 | 1189 | 502592 | ACCCCGGCCCAGCCGTGTCT | 73 | 385 |
| 1171 | 1190 | 502593 | CACCCCGGCCCAGCCGTGTC | 84 | 386 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 1172 | 1191 | 502594 | CCACCCCGGCCCAGCCGTGT | 78 | 387 |
| 1173 | 1192 | 502595 | TCCACCCCGGCCCAGCCGTG | 71 | 388 |
| 1174 | 1193 | 502596 | CTCCACCCCGGCCCAGCCGT | 81 | 389 |
| 1175 | 1194 | 502597 | GCTCCACCCCGGCCCAGCCG | 86 | 390 |
| 1176 | 1195 | 502598 | TGCTCCACCCCGGCCCAGCC | 83 | 391 |
| 1177 | 1196 | 502599 | CTGCTCCACCCCGGCCCAGC | 88 | 392 |
| 1199 | 1218 | 502600 | AAGGGATGTGTCCGGAAGTC | 60 | 393 |
| 1200 | 1219 | 502601 | GAAGGGATGTGTCCGGAAGT | 58 | 394 |
| 1201 | 1220 | 502602 | AGAAGGGATGTGTCCGGAAG | 63 | 395 |
| 1202 | 1221 | 502603 | AAGAAGGGATGTGTCCGGAA | 62 | 396 |
| 1203 | 1222 | 502604 | GAAGAAGGGATGTGTCCGGA | 61 | 397 |
| 1204 | 1223 | 502605 | AGAAGAAGGGATGTGTCCGG | 62 | 398 |
| 1205 | 1224 | 502606 | AAGAAGAAGGGATGTGTCCG | 56 | 399 |
| 1206 | 1225 | 502607 | AAAGAAGAAGGGATGTGTCC | 58 | 400 |
| 1207 | 1226 | 502608 | CAAAGAAGAAGGGATGTGTC | 50 | 401 |
| 1208 | 1227 | 502609 | CCAAAGAAGAAGGGATGTGT | 61 | 402 |
| 1210 | 1229 | 502610 | GGCCAAAGAAGAAGGGATGT | 73 | 403 |
| 1211 | 1230 | 502611 | AGGCCAAAGAAGAAGGGATG | 56 | 404 |
| 1212 | 1231 | 502612 | GAGGCCAAAGAAGAAGGGAT | 73 | 405 |
| 1213 | 1232 | 502613 | CGAGGCCAAAGAAGAAGGGA | 75 | 406 |
| 1214 | 1233 | 502614 | TCGAGGCCAAAGAAGAAGGG | 75 | 407 |
| 1215 | 1234 | 502615 | GTCGAGGCCAAAGAAGAAGG | 83 | 408 |
| 1216 | 1235 | 502616 | AGTCGAGGCCAAAGAAGAAG | 58 | 409 |
| 1217 | 1236 | 502617 | CAGTCGAGGCCAAAGAAGAA | 52 | 410 |
| 1218 | 1237 | 502618 | CCAGTCGAGGCCAAAGAAGA | 68 | 411 |
| 1219 | 1238 | 502619 | CCCAGTCGAGGCCAAAGAAG | 78 | 412 |
| 1220 | 1239 | 502620 | TCCCAGTCGAGGCCAAAGAA | 66 | 413 |
| 1221 | 1240 | 502621 | ATCCCAGTCGAGGCCAAAGA | 75 | 414 |
| 1222 | 1241 | 502622 | CATCCCAGTCGAGGCCAAAG | 70 | 415 |
| 1223 | 1242 | 502623 | CCATCCCAGTCGAGGCCAAA | 81 | 416 |
| 1224 | 1243 | 502624 | ACCATCCCAGTCGAGGCCAA | 82 | 417 |
| 1225 | 1244 | 502625 | GACCATCCCAGTCGAGGCCA | 88 | 418 |
| 1226 | 1245 | 502626 | AGACCATCCCAGTCGAGGCC | 79 | 419 |
| 1227 | 1246 | 502627 | GAGACCATCCCAGTCGAGGC | 82 | 420 |
| 1228 | 1247 | 502628 | GGAGACCATCCCAGTCGAGG | 60 | 421 |
| 1263 | 1282 | 502629 | TTCGAAATCCGGTGTAAAGG | 84 | 422 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 1264 | 1283 | 502630 | CTTCGAAATCCGGTGTAAAG | 57 | 423 |
| 1265 | 1284 | 502631 | CCTTCGAAATCCGGTGTAAA | 64 | 424 |
| 1266 | 1285 | 502632 | ACCTTCGAAATCCGGTGTAA | 73 | 425 |
| 1267 | 1286 | 502633 | CACCTTCGAAATCCGGTGTA | 77 | 426 |
| 1268 | 1287 | 502634 | GCACCTTCGAAATCCGGTGT | 59 | 427 |
| 1269 | 1288 | 502635 | GGCACCTTCGAAATCCGGTG | 85 | 428 |
| 1270 | 1289 | 502636 | TGGCACCTTCGAAATCCGGT | 86 | 429 |
| 1271 | 1290 | 502637 | GTGGCACCTTCGAAATCCGG | 74 | 430 |
| 1272 | 1291 | 502638 | GGTGGCACCTTCGAAATCCG | 79 | 431 |
| 1273 | 1292 | 502639 | CGGTGGCACCTTCGAAATCC | 85 | 432 |
| 1274 | 1293 | 502640 | TCGGTGGCACCTTCGAAATC | 71 | 433 |
| 1275 | 1294 | 502641 | GTCGGTGGCACCTTCGAAAT | 88 | 434 |
| 1276 | 1295 | 502642 | TGTCGGTGGCACCTTCGAAA | 89 | 435 |
| 1277 | 1296 | 502643 | GTGTCGGTGGCACCTTCGAA | 88 | 436 |
| 1278 | 1297 | 502644 | TGTGTCGGTGGCACCTTCGA | 87 | 437 |
| 1279 | 1298 | 502645 | ATGTGTCGGTGGCACCTTCG | 88 | 438 |
| 1280 | 1299 | 502646 | CATGTGTCGGTGGCACCTTC | 88 | 439 |
| 1281 | 1300 | 502647 | GCATGTGTCGGTGGCACCTT | 91 | 440 |
| 1282 | 1301 | 502648 | TGCATGTGTCGGTGGCACCT | 87 | 441 |
| 1283 | 1302 | 502649 | TTGCATGTGTCGGTGGCACC | 86 | 442 |
| 1284 | 1303 | 502650 | GTTGCATGTGTCGGTGGCAC | 83 | 443 |
| 1285 | 1304 | 502651 | AGTTGCATGTGTCGGTGGCA | 81 | 444 |
| 1286 | 1305 | 502652 | AAGTTGCATGTGTCGGTGGC | 79 | 445 |
| 1287 | 1306 | 502653 | GAAGTTGCATGTGTCGGTGG | 58 | 446 |
| 1288 | 1307 | 502654 | CGAAGTTGCATGTGTCGGTG | 85 | 447 |
| 1290 | 1309 | 502655 | GTCGAAGTTGCATGTGTCGG | 77 | 448 |
| 1291 | 1310 | 502656 | AGTCGAAGTTGCATGTGTCG | 79 | 449 |
| 1292 | 1311 | 502657 | AAGTCGAAGTTGCATGTGTC | 74 | 450 |
| 1293 | 1312 | 502658 | CAAGTCGAAGTTGCATGTGT | 82 | 451 |
| 1294 | 1313 | 502659 | CCAAGTCGAAGTTGCATGTG | 82 | 452 |
| 1295 | 1314 | 502660 | ACCAAGTCGAAGTTGCATGT | 70 | 453 |
| 1296 | 1315 | 502661 | CACCAAGTCGAAGTTGCATG | 76 | 454 |
| 1297 | 1316 | 502662 | CCACCAAGTCGAAGTTGCAT | 79 | 455 |
| 1298 | 1317 | 502663 | TCCACCAAGTCGAAGTTGCA | 68 | 456 |
| 1299 | 1318 | 502664 | CTCCACCAAGTCGAAGTTGC | 71 | 457 |
| 1300 | 1319 | 502665 | CCTCCACCAAGTCGAAGTTG | 67 | 458 |
| 1301 | 1320 | 502666 | TCCTCCACCAAGTCGAAGTT | 70 | 459 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 1302 | 1321 | 502667 | GTCCTCCACCAAGTCGAAGT | 80 | 460 |
| 1303 | 1322 | 502668 | CGTCCTCCACCAAGTCGAAG | 76 | 461 |
| 1304 | 1323 | 502669 | CCGTCCTCCACCAAGTCGAA | 78 | 462 |
| 1305 | 1324 | 502670 | CCCGTCCTCCACCAAGTCGA | 83 | 463 |
| 1306 | 1325 | 502671 | GCCCGTCCTCCACCAAGTCG | 76 | 464 |
| 1307 | 1326 | 502672 | AGCCCGTCCTCCACCAAGTC | 72 | 465 |
| 1308 | 1327 | 502673 | GAGCCCGTCCTCCACCAAGT | 71 | 466 |
| 1309 | 1328 | 502674 | TGAGCCCGTCCTCCACCAAG | 60 | 467 |
| 1702 | 1721 | 502675 | GGTTCCGAGCCTCTGCCTCG | 44 | 468 |
| 1703 | 1722 | 502676 | CGGTTCCGAGCCTCTGCCTC | 74 | 469 |
| 1704 | 1723 | 502677 | CCGGTTCCGAGCCTCTGCCT | 72 | 470 |
| 1705 | 1724 | 502678 | CCCGGTTCCGAGCCTCTGCC | 73 | 471 |
| 1706 | 1725 | 502679 | TCCCGGTTCCGAGCCTCTGC | 84 | 472 |
| 1707 | 1726 | 502680 | GTCCCGGTTCCGAGCCTCTG | 66 | 473 |
| 1709 | 1728 | 502681 | AGGTCCCGGTTCCGAGCCTC | 82 | 474 |
| 1710 | 1729 | 502682 | TAGGTCCCGGTTCCGAGCCT | 83 | 475 |
| 1711 | 1730 | 502683 | CTAGGTCCCGGTTCCGAGCC | 81 | 476 |
| 1712 | 1731 | 502684 | TCTAGGTCCCGGTTCCGAGC | 74 | 477 |
| 1713 | 1732 | 502685 | CTCTAGGTCCCGGTTCCGAG | 78 | 478 |
| 1714 | 1733 | 502686 | CCTCTAGGTCCCGGTTCCGA | 75 | 479 |
| 1715 | 1734 | 502687 | GCCTCTAGGTCCCGGTTCCG | 80 | 480 |
| 1743 | 1762 | 502688 | CATCCGCTCCTGCAACTGCC | 89 | 481 |
| 1744 | 1763 | 502689 | CCATCCGCTCCTGCAACTGC | 81 | 482 |
| 1745 | 1764 | 502690 | TCCATCCGCTCCTGCAACTG | 71 | 483 |
| 1746 | 1765 | 502691 | CTCCATCCGCTCCTGCAACT | 75 | 484 |
| 1747 | 1766 | 502692 | ACTCCATCCGCTCCTGCAAC | 64 | 485 |
| 1748 | 1767 | 502693 | AACTCCATCCGCTCCTGCAA | 52 | 486 |
| 1749 | 1768 | 502694 | CAACTCCATCCGCTCCTGCA | 45 | 487 |
| 1751 | 1770 | 502695 | AGCAACTCCATCCGCTCCTG | 78 | 488 |
| 1752 | 1771 | 502696 | CAGCAACTCCATCCGCTCCT | 64 | 489 |
| 1753 | 1772 | 502697 | GCAGCAACTCCATCCGCTCC | 56 | 490 |
| 1774 | 1793 | 502698 | CAGCTGTGGCTCCCTCTGCC | 60 | 491 |
| 1775 | 1794 | 502699 | ACAGCTGTGGCTCCCTCTGC | 45 | 492 |
| 1776 | 1795 | 502700 | GACAGCTGTGGCTCCCTCTG | 49 | 493 |
| 1777 | 1796 | 502701 | TGACAGCTGTGGCTCCCTCT | 26 | 494 |
| 1778 | 1797 | 502702 | GTGACAGCTGTGGCTCCCTC | 32 | 495 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 1779 | 1798 | 502703 | CGTGACAGCTGTGGCTCCCT | 28 | 496 |
| 1780 | 1799 | 502704 | CCGTGACAGCTGTGGCTCCC | 35 | 497 |
| 1781 | 1800 | 502705 | CCCGTGACAGCTGTGGCTCC | 33 | 498 |
| 1782 | 1801 | 502706 | CCCCGTGACAGCTGTGGCTC | 53 | 499 |
| 1783 | 1802 | 502707 | CCCCCGTGACAGCTGTGGCT | 39 | 500 |
| 1784 | 1803 | 502708 | ACCCCCGTGACAGCTGTGGC | 53 | 501 |
| 1785 | 1804 | 502709 | GACCCCCGTGACAGCTGTGG | 51 | 502 |
| 1786 | 1805 | 502710 | GGACCCCCGTGACAGCTGTG | 58 | 503 |
| 1787 | 1806 | 502711 | GGGACCCCCGTGACAGCTGT | 71 | 504 |
| 1814 | 1833 | 502712 | GAAGGTGGATCCGTGGCCCG | 73 | 505 |
| 1815 | 1834 | 502713 | GGAAGGTGGATCCGTGGCCC | 70 | 506 |
| 1816 | 1835 | 502714 | GGGAAGGTGGATCCGTGGCC | 72 | 507 |
| 1817 | 1836 | 502715 | TGGGAAGGTGGATCCGTGGC | 50 | 508 |
| 1818 | 1837 | 502716 | ATGGGAAGGTGGATCCGTGG | 62 | 509 |
| 1819 | 1838 | 502717 | GATGGGAAGGTGGATCCGTG | 75 | 510 |
| 1821 | 1840 | 502718 | TAGATGGGAAGGTGGATCCG | 52 | 511 |
| 1822 | 1841 | 502719 | CTAGATGGGAAGGTGGATCC | 56 | 512 |
| 1823 | 1842 | 502720 | TCTAGATGGGAAGGTGGATC | 21 | 513 |
| 1824 | 1843 | 502721 | ATCTAGATGGGAAGGTGGAT | 34 | 514 |
| 1826 | 1845 | 502722 | CCATCTAGATGGGAAGGTGG | 43 | 515 |
| 1827 | 1846 | 502723 | GCCATCTAGATGGGAAGGTG | 17 | 516 |
| 1828 | 1847 | 451383 | GGCCATCTAGATGGGAAGGT | 0 | 517 |
| 1863 | 1882 | 502724 | CACCAGCGGGCACTGGCCCA | 51 | 518 |
| 1864 | 1883 | 502725 | CCACCAGCGGGCACTGGCCC | 55 | 519 |
| 1865 | 1884 | 502726 | CCCACCAGCGGGCACTGGCC | 61 | 520 |
| 1866 | 1885 | 502727 | CCCCACCAGCGGGCACTGGC | 43 | 521 |
| 1868 | 1887 | 502728 | GGCCCCACCAGCGGGCACTG | 16 | 522 |
| 1869 | 1888 | 502729 | TGGCCCCACCAGCGGGCACT | 43 | 523 |
| 1870 | 1889 | 502730 | CTGGCCCCACCAGCGGGCAC | 43 | 524 |
| 1871 | 1890 | 502731 | CCTGGCCCCACCAGCGGGCA | 41 | 525 |
| 1872 | 1891 | 502732 | GCCTGGCCCCACCAGCGGGC | 30 | 526 |
| 1874 | 1893 | 502733 | GGGCCTGGCCCCACCAGCGG | 66 | 527 |
| 1892 | 1911 | 502734 | AGGTGGCGGCGGTGCATGGG | 31 | 528 |
| 1893 | 1912 | 502735 | CAGGTGGCGGCGGTGCATGG | 23 | 529 |
| 1894 | 1913 | 502736 | GCAGGTGGCGGCGGTGCATG | 57 | 530 |
| 1895 | 1914 | 502737 | AGCAGGTGGCGGCGGTGCAT | 54 | 531 |
| 1896 | 1915 | 502738 | CAGCAGGTGGCGGCGGTGCA | 61 | 532 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 1897 | 1916 | 502739 | GCAGCAGGTGGCGGCGGTGC | 57 | 533 |
| 1898 | 1917 | 502740 | AGCAGCAGGTGGCGGCGGTG | 36 | 534 |
| 1899 | 1918 | 502741 | GAGCAGCAGGTGGCGGCGGT | 53 | 535 |
| 1900 | 1919 | 502742 | GGAGCAGCAGGTGGCGGCGG | 39 | 536 |
| 1901 | 1920 | 502743 | GGGAGCAGCAGGTGGCGGCG | 36 | 537 |
| 1902 | 1921 | 502744 | AGGGAGCAGCAGGTGGCGGC | 62 | 538 |
| 1903 | 1922 | 502745 | CAGGGAGCAGCAGGTGGCGG | 56 | 539 |
| 1904 | 1923 | 502746 | GCAGGGAGCAGCAGGTGGCG | 58 | 540 |
| 1905 | 1924 | 502747 | GGCAGGGAGCAGCAGGTGGC | 65 | 541 |
| 1906 | 1925 | 502748 | TGGCAGGGAGCAGCAGGTGG | 47 | 542 |
| 1907 | 1926 | 502749 | CTGGCAGGGAGCAGCAGGTG | 41 | 543 |
| 1909 | 1928 | 451432 | CCCTGGCAGGGAGCAGCAGG | 53 | 544 |
| 1910 | 1929 | 502750 | ACCCTGGCAGGGAGCAGCAG | 52 | 545 |
| 1911 | 1930 | 502751 | GACCCTGGCAGGGAGCAGCA | 77 | 546 |
| 1912 | 1931 | 502752 | GGACCCTGGCAGGGAGCAGC | 0 | 547 |
| 1919 | 1938 | 502753 | GGCCTAGGGACCCTGGCAGG | 39 | 548 |
| 1920 | 1939 | 502754 | AGGCCTAGGGACCCTGGCAG | 35 | 549 |
| 1922 | 1941 | 502755 | CCAGGCCTAGGGACCCTGGC | 44 | 550 |
| 1923 | 1942 | 502756 | GCCAGGCCTAGGGACCCTGG | 60 | 551 |
| 1924 | 1943 | 502757 | GGCCAGGCCTAGGGACCCTG | 58 | 552 |
| 1925 | 1944 | 502758 | AGGCCAGGCCTAGGGACCCT | 57 | 553 |
| 1926 | 1945 | 502759 | TAGGCCAGGCCTAGGGACCC | 52 | 554 |
| 1927 | 1946 | 502760 | ATAGGCCAGGCCTAGGGACC | 51 | 555 |
| 1928 | 1947 | 502761 | GATAGGCCAGGCCTAGGGAC | 41 | 556 |
| 1929 | 1948 | 502762 | CGATAGGCCAGGCCTAGGGA | 69 | 557 |
| 1930 | 1949 | 502763 | CCGATAGGCCAGGCCTAGGG | 80 | 558 |
| 1931 | 1950 | 502764 | TCCGATAGGCCAGGCCTAGG | 78 | 559 |
| 1932 | 1951 | 502765 | CTCCGATAGGCCAGGCCTAG | 89 | 560 |
| 1933 | 1952 | 502766 | CCTCCGATAGGCCAGGCCTA | 79 | 561 |
| 1934 | 1953 | 502767 | GCCTCCGATAGGCCAGGCCT | 73 | 562 |
| 1936 | 1955 | 502768 | GCGCCTCCGATAGGCCAGGC | 83 | 563 |
| 1952 | 1971 | 502769 | AACAGGAGCAGGGAAAGCGC | 83 | 564 |
| 1953 | 1972 | 502770 | GAACAGGAGCAGGGAAAGCG | 70 | 565 |
| 1954 | 1973 | 502771 | CGAACAGGAGCAGGGAAAGC | 43 | 566 |
| 1955 | 1974 | 502772 | GCGAACAGGAGCAGGGAAAG | 47 | 567 |
| 1956 | 1975 | 502773 | GGCGAACAGGAGCAGGGAAA | 61 | 568 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 1957 | 1976 | 502774 | CGGCGAACAGGAGCAGGGAA | 74 | 569 |
| 1958 | 1977 | 502775 | ACGGCGAACAGGAGCAGGGA | 60 | 570 |
| 1959 | 1978 | 502776 | AACGGCGAACAGGAGCAGGG | 86 | 571 |
| 1960 | 1979 | 502777 | CAACGGCGAACAGGAGCAGG | 84 | 572 |
| 1981 | 2000 | 502778 | GGGCGGCGGCACGAGACAGA | 80 | 573 |
| 1982 | 2001 | 502779 | AGGGCGGCGGCACGAGACAG | 76 | 574 |
| 1983 | 2002 | 502780 | CAGGGCGGCGGCACGAGACA | 58 | 575 |
| 1984 | 2003 | 502781 | CCAGGGCGGCGGCACGAGAC | 80 | 576 |
| 1985 | 2004 | 502782 | CCCAGGGCGGCGGCACGAGA | 59 | 577 |
| 1986 | 2005 | 502783 | GCCCAGGGCGGCGGCACGAG | 68 | 578 |
| 1987 | 2006 | 502784 | AGCCCAGGGCGGCGGCACGA | 75 | 579 |
| 1988 | 2007 | 502785 | CAGCCCAGGGCGGCGGCACG | 76 | 580 |
| 1989 | 2008 | 502786 | GCAGCCCAGGGCGGCGGCAC | 70 | 581 |
| 2026 | 2045 | 502787 | CTGCGGTGAGTTGGCCGGCG | 68 | 582 |
| 2027 | 2046 | 502788 | ACTGCGGTGAGTTGGCCGGC | 67 | 583 |
| 2028 | 2047 | 502789 | GACTGCGGTGAGTTGGCCGG | 58 | 584 |
| 2029 | 2048 | 502790 | AGACTGCGGTGAGTTGGCCG | 71 | 585 |
| 2030 | 2049 | 502791 | CAGACTGCGGTGAGTTGGCC | 70 | 586 |
| 2031 | 2050 | 502792 | CCAGACTGCGGTGAGTTGGC | 79 | 587 |
| 2032 | 2051 | 502793 | GCCAGACTGCGGTGAGTTGG | 76 | 588 |
| 2033 | 2052 | 502794 | CGCCAGACTGCGGTGAGTTG | 66 | 589 |
| 2077 | 2096 | 502795 | AAGACAGTTCTAGGGTTCAG | 87 | 590 |
| 2078 | 2097 | 502796 | GAAGACAGTTCTAGGGTTCA | 78 | 591 |
| 2079 | 2098 | 502797 | CGAAGACAGTTCTAGGGTTC | 85 | 592 |
| 2080 | 2099 | 502798 | TCGAAGACAGTTCTAGGGTT | 78 | 593 |
| 2081 | 2100 | 502799 | GTCGAAGACAGTTCTAGGGT | 92 | 594 |
| 2082 | 2101 | 502800 | AGTCGAAGACAGTTCTAGGG | 85 | 595 |
| 2083 | 2102 | 502801 | GAGTCGAAGACAGTTCTAGG | 83 | 596 |
| 2084 | 2103 | 502802 | GGAGTCGAAGACAGTTCTAG | 86 | 597 |
| 2085 | 2104 | 502803 | CGGAGTCGAAGACAGTTCTA | 91 | 598 |
| 2086 | 2105 | 502804 | CCGGAGTCGAAGACAGTTCT | 76 | 599 |
| 2087 | 2106 | 502805 | CCCGGAGTCGAAGACAGTTC | 90 | 600 |
| 2088 | 2107 | 502806 | CCCCGGAGTCGAAGACAGTT | 83 | 601 |
| 2089 | 2108 | 502807 | GCCCCGGAGTCGAAGACAGT | 82 | 602 |
| 2090 | 2109 | 502808 | GGCCCCGGAGTCGAAGACAG | 73 | 603 |
| 2091 | 2110 | 502809 | GGGCCCCGGAGTCGAAGACA | 67 | 604 |
| 2143 | 2162 | 502810 | AGGCGGTGGGCGCGGCTTCT | 73 | 605 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 2144 | 2163 | 502811 | CAGGCGGTGGGCGCGGCTTC | 57 | 606 |
| 2145 | 2164 | 502812 | GCAGGCGGTGGGCGCGGCTT | 69 | 607 |
| 2147 | 2166 | 502813 | TGGCAGGCGGTGGGCGCGGC | 73 | 608 |
| 2149 | 2168 | 502814 | ACTGGCAGGCGGTGGGCGCG | 56 | 609 |
| 2151 | 2170 | 502815 | GAACTGGCAGGCGGTGGGCG | 71 | 610 |
| 2152 | 2171 | 502816 | TGAACTGGCAGGCGGTGGGC | 80 | 611 |
| 2154 | 2173 | 502817 | TGTGAACTGGCAGGCGGTGG | 85 | 612 |
| 2187 | 2206 | 502818 | TGGAGCTGGGCGGAGACCCA | 55 | 613 |
| 2189 | 2208 | 502819 | ACTGGAGCTGGGCGGAGACC | 53 | 614 |
| 2190 | 2209 | 502820 | GACTGGAGCTGGGCGGAGAC | 55 | 615 |
| 2192 | 2211 | 502821 | AGGACTGGAGCTGGGCGGAG | 76 | 616 |
| 2194 | 2213 | 502822 | ACAGGACTGGAGCTGGGCGG | 77 | 617 |
| 2195 | 2214 | 502823 | CACAGGACTGGAGCTGGGCG | 74 | 618 |
| 2196 | 2215 | 502824 | TCACAGGACTGGAGCTGGGC | 90 | 619 |
| 2386 | 2405 | 502825 | GCCTCAGCCTGGCCGAAAGA | 80 | 620 |
| 2387 | 2406 | 502826 | GGCCTCAGCCTGGCCGAAAG | 72 | 621 |
| 2490 | 2509 | 444401 | TTGCACTTTGCGAACCAACG | 97 | 41 |

TABLE 13

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 503 | 522 | 502983 | TGGTGGAGCCAAGCCCTCCC | 83 | 622 |
| 561 | 580 | 502984 | GGGCACCCTCAGAGCCTGAA | 82 | 623 |
| 1197 | 1216 | 502369 | GCCTGGCAGCCCCTGTCCAG | 16 | 160 |
| 1198 | 1217 | 502370 | GGCCTGGCAGCCCCTGTCCA | 58 | 161 |
| 1199 | 1218 | 502371 | GGGCCTGGCAGCCCCTGTCC | 62 | 162 |
| 1242 | 1261 | 502372 | ATGGCCCCTCCCCGGGCCGG | 41 | 163 |
| 1243 | 1262 | 502373 | CATGGCCCCTCCCCGGGCCG | 29 | 164 |
| 1244 | 1263 | 502374 | CCATGGCCCCTCCCCGGGCC | 34 | 165 |
| 1245 | 1264 | 502375 | ACCATGGCCCCTCCCCGGGC | 60 | 166 |
| 1246 | 1265 | 502376 | CACCATGGCCCCTCCCCGGG | 68 | 167 |
| 1247 | 1266 | 502377 | GCACCATGGCCCCTCCCCGG | 75 | 168 |
| 1248 | 1267 | 502378 | AGCACCATGGCCCCTCCCCG | 65 | 169 |
| 1249 | 1268 | 502379 | CAGCACCATGGCCCCTCCCC | 63 | 170 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 1250 | 1269 | 502380 | GCAGCACCATGGCCCCTCCC | 73 | 171 |
| 1251 | 1270 | 502381 | GGCAGCACCATGGCCCCTCC | 80 | 172 |
| 1253 | 1272 | 502382 | CAGGCAGCACCATGGCCCCT | 82 | 173 |
| 1254 | 1273 | 502383 | ACAGGCAGCACCATGGCCCC | 72 | 174 |
| 1256 | 1275 | 502384 | GGACAGGCAGCACCATGGCC | 70 | 175 |
| 1257 | 1276 | 502385 | TGGACAGGCAGCACCATGGC | 71 | 176 |
| 1258 | 1277 | 502386 | TTGGACAGGCAGCACCATGG | 73 | 177 |
| 1259 | 1278 | 502387 | GTTGGACAGGCAGCACCATG | 73 | 178 |
| 1260 | 1279 | 502388 | TGTTGGACAGGCAGCACCAT | 60 | 179 |
| 1261 | 1280 | 502389 | ATGTTGGACAGGCAGCACCA | 75 | 180 |
| 1262 | 1281 | 502390 | CATGTTGGACAGGCAGCACC | 81 | 181 |
| 1263 | 1282 | 502391 | ACATGTTGGACAGGCAGCAC | 67 | 182 |
| 1264 | 1283 | 502392 | GACATGTTGGACAGGCAGCA | 71 | 183 |
| 1265 | 1284 | 502393 | TGACATGTTGGACAGGCAGC | 81 | 184 |
| 1266 | 1285 | 502394 | CTGACATGTTGGACAGGCAG | 76 | 185 |
| 1267 | 1286 | 502395 | GCTGACATGTTGGACAGGCA | 70 | 186 |
| 1268 | 1287 | 502396 | GGCTGACATGTTGGACAGGC | 77 | 187 |
| 1269 | 1288 | 502397 | CGGCTGACATGTTGGACAGG | 74 | 188 |
| 1270 | 1289 | 502398 | TCGGCTGACATGTTGGACAG | 63 | 189 |
| 1271 | 1290 | 502399 | CTCGGCTGACATGTTGGACA | 80 | 190 |
| 1272 | 1291 | 502400 | CCTCGGCTGACATGTTGGAC | 71 | 191 |
| 1273 | 1292 | 502401 | ACCTCGGCTGACATGTTGGA | 64 | 192 |
| 1274 | 1293 | 502402 | CACCTCGGCTGACATGTTGG | 71 | 193 |
| 1275 | 1294 | 502403 | GCACCTCGGCTGACATGTTG | 77 | 194 |
| 1276 | 1295 | 502404 | CGCACCTCGGCTGACATGTT | 80 | 195 |
| 1277 | 1296 | 502405 | CCGCACCTCGGCTGACATGT | 80 | 196 |
| 1278 | 1297 | 502406 | GCCGCACCTCGGCTGACATG | 79 | 197 |
| 1279 | 1298 | 502407 | AGCCGCACCTCGGCTGACAT | 74 | 198 |
| 1280 | 1299 | 502408 | CAGCCGCACCTCGGCTGACA | 66 | 199 |
| 1281 | 1300 | 502409 | TCAGCCGCACCTCGGCTGAC | 15 | 200 |
| 1282 | 1301 | 502410 | CTCAGCCGCACCTCGGCTGA | 32 | 201 |
| 1283 | 1302 | 502411 | CCTCAGCCGCACCTCGGCTG | 65 | 202 |
| 1284 | 1303 | 502412 | GCCTCAGCCGCACCTCGGCT | 81 | 203 |
| 1305 | 1324 | 502413 | CCAACACCAGCTGCTGGAGC | 90 | 204 |
| 1306 | 1325 | 502414 | TCCAACACCAGCTGCTGGAG | 78 | 205 |
| 1307 | 1326 | 502415 | GTCCAACACCAGCTGCTGGA | 84 | 206 |
| 1309 | 1328 | 502416 | GGGTCCAACACCAGCTGCTG | 69 | 207 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 1330 | 1349 | 502417 | GGCTCCAGCCCCAGGAAGCC | 46 | 208 |
| 1331 | 1350 | 502418 | GGGCTCCAGCCCCAGGAAGC | 28 | 209 |
| 1349 | 1368 | 502419 | CAGGAGAAGGTCGAGCAGGG | 41 | 210 |
| 1351 | 1370 | 502420 | CCCAGGAGAAGGTCGAGCAG | 71 | 211 |
| 1352 | 1371 | 502421 | GCCCAGGAGAAGGTCGAGCA | 85 | 212 |
| 1353 | 1372 | 451363 | CGCCCAGGAGAAGGTCGAGC | 84 | 213 |
| 1354 | 1373 | 502422 | ACGCCCAGGAGAAGGTCGAG | 67 | 214 |
| 1390 | 1409 | 502423 | TCCTGGGCCAGTTCGGAGGC | 58 | 215 |
| 1391 | 1410 | 502424 | GTCCTGGGCCAGTTCGGAGG | 71 | 216 |
| 1392 | 1411 | 502425 | TGTCCTGGGCCAGTTCGGAG | 69 | 217 |
| 1393 | 1412 | 502426 | TTGTCCTGGGCCAGTTCGGA | 71 | 218 |
| 1394 | 1413 | 502427 | CTTGTCCTGGGCCAGTTCGG | 66 | 219 |
| 1395 | 1414 | 502428 | ACTTGTCCTGGGCCAGTTCG | 59 | 220 |
| 1396 | 1415 | 502429 | TACTTGTCCTGGGCCAGTTC | 75 | 221 |
| 1397 | 1416 | 502430 | GTACTTGTCCTGGGCCAGTT | 78 | 222 |
| 1398 | 1417 | 502431 | CGTACTTGTCCTGGGCCAGT | 74 | 223 |
| 1416 | 1435 | 502432 | ACTGCAAGAAGTCGGCCACG | 73 | 224 |
| 1418 | 1437 | 502433 | CCACTGCAAGAAGTCGGCCA | 65 | 225 |
| 1419 | 1438 | 451364 | CCCACTGCAAGAAGTCGGCC | 32 | 226 |
| 1421 | 1440 | 502985 | ACCCCACTGCAAGAAGTCGG | 60 | 624 |
| 1551 | 1570 | 502986 | GCCCCAGGATGGGAGGATCT | 58 | 625 |
| 1597 | 1616 | 502987 | CATAGGACAGAGAAATGTTG | 70 | 626 |
| 1630 | 1649 | 502988 | TGCTGACCTTACTCTGCCCC | 86 | 627 |
| 1666 | 1685 | 502989 | TAAGCCATGGCTCTGAGTCA | 51 | 628 |
| 1712 | 1731 | 502990 | AGAGAGGCCATGGGAGGCTG | 42 | 629 |
| 1841 | 1860 | 502991 | CTGGCCCTCCTGGCTTGCCC | 72 | 630 |
| 1853 | 1872 | 502992 | AGCTGCCCCATGCTGGCCCT | 76 | 631 |
| 1862 | 1881 | 502993 | GCCCCTGGCAGCTGCCCCAT | 70 | 632 |
| 1873 | 1892 | 502994 | CTGTCGGCTGCGCCCCTGGC | 78 | 633 |
| 1887 | 1906 | 502995 | CGCCGAACACCTGCCTGTCG | 68 | 634 |
| 1931 | 1950 | 502996 | CCTCCCAGTGCCTGGGCACC | 52 | 635 |
| 1981 | 2000 | 502998 | GCGCCTGTCTGCAAAGCTGG | 84 | 636 |
| 2025 | 2044 | 502999 | CCCAAAGTTGTCCCTCCTGG | 83 | 637 |
| 2038 | 2057 | 503000 | ACACCCAGAAGAACCCAAAG | 75 | 638 |
| 2117 | 2136 | 503001 | CTGACCCACACGGCTCATAG | 65 | 639 |
| 2235 | 2254 | 503002 | TGGCCCCAGGCCCTGGAAAG | 67 | 640 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 2278 | 2297 | 503003 | GACAAGGCAGCTGGCAGAAG | 79 | 641 |
| 2331 | 2350 | 503004 | AAGAAACCAGTGACCAGTGA | 85 | 642 |
| 2523 | 2542 | 503005 | CTGTGAAATGGGAGGAGGAG | 0 | 643 |
| 2578 | 2597 | 503006 | GAAGGTTTTTCCAGAGGCTG | 88 | 644 |
| 2615 | 2634 | 503007 | GGCCAGGAGAGTCATTAGGG | 84 | 645 |
| 2710 | 2729 | 503008 | CCACAAAAGGAGTGCTCCTC | 79 | 646 |
| 2789 | 2808 | 503009 | CCTTTTAAGGCAGCAGGAAC | 78 | 647 |
| 3629 | 3648 | 503010 | CTAGGACTGTCTGCTTCCCA | 88 | 648 |
| 3761 | 3780 | 502452 | CTCACCACGATGGGCTCCGC | 66 | 245 |
| 3762 | 3781 | 502453 | CCTCACCACGATGGGCTCCG | 81 | 246 |
| 3763 | 3782 | 502454 | GCCTCACCACGATGGGCTCC | 77 | 247 |
| 3764 | 3783 | 502455 | AGCCTCACCACGATGGGCTC | 63 | 248 |
| 3765 | 3784 | 502456 | AAGCCTCACCACGATGGGCT | 70 | 249 |
| 3766 | 3785 | 502457 | TAAGCCTCACCACGATGGGC | 78 | 250 |
| 3767 | 3786 | 502458 | TTAAGCCTCACCACGATGGG | 76 | 251 |
| 3768 | 3787 | 502459 | CTTAAGCCTCACCACGATGG | 78 | 252 |
| 3769 | 3788 | 502460 | CCTTAAGCCTCACCACGATG | 68 | 253 |
| 3770 | 3789 | 502461 | TCCTTAAGCCTCACCACGAT | 67 | 254 |
| 3771 | 3790 | 502462 | CTCCTTAAGCCTCACCACGA | 84 | 255 |
| 3772 | 3791 | 502463 | CCTCCTTAAGCCTCACCACG | 76 | 256 |
| 3773 | 3792 | 502464 | ACCTCCTTAAGCCTCACCAC | 64 | 257 |
| 3774 | 3793 | 502465 | GACCTCCTTAAGCCTCACCA | 72 | 258 |
| 3775 | 3794 | 502466 | GGACCTCCTTAAGCCTCACC | 69 | 259 |
| 3776 | 3795 | 502467 | CGGACCTCCTTAAGCCTCAC | 81 | 260 |
| 3777 | 3796 | 502468 | TCGGACCTCCTTAAGCCTCA | 78 | 261 |
| 3778 | 3797 | 502469 | GTCGGACCTCCTTAAGCCTC | 57 | 262 |
| 3780 | 3799 | 502470 | CAGTCGGACCTCCTTAAGCC | 62 | 263 |
| 3781 | 3800 | 502471 | GCAGTCGGACCTCCTTAAGC | 45 | 264 |
| 3782 | 3801 | 502472 | TGCAGTCGGACCTCCTTAAG | 60 | 265 |
| 3808 | 3827 | 502473 | CCTTCAGAATCTCGAAGTCG | 67 | 266 |
| 3809 | 3828 | 502474 | ACCTTCAGAATCTCGAAGTC | 50 | 267 |
| 3811 | 3830 | 502475 | TCACCTTCAGAATCTCGAAG | 54 | 268 |
| 3812 | 3831 | 502476 | ATCACCTTCAGAATCTCGAA | 38 | 269 |
| 3813 | 3832 | 502477 | GATCACCTTCAGAATCTCGA | 35 | 270 |
| 3815 | 3834 | 502478 | CCGATCACCTTCAGAATCTC | 52 | 271 |
| 3816 | 3835 | 502479 | TCCGATCACCTTCAGAATCT | 50 | 272 |
| 3817 | 3836 | 502480 | GTCCGATCACCTTCAGAATC | 44 | 273 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 3818 | 3837 | 502481 | CGTCCGATCACCTTCAGAAT | 41 | 274 |
| 3921 | 3940 | 503011 | GTCATTCATCAATTTCTAAG | 44 | 649 |
| 4118 | 4137 | 502482 | CCCGTCTGCTTCATCTTCAC | 67 | 275 |
| 4119 | 4138 | 502483 | GCCCGTCTGCTTCATCTTCA | 76 | 276 |
| 4120 | 4139 | 502484 | GGCCCGTCTGCTTCATCTTC | 57 | 277 |
| 4121 | 4140 | 502485 | TGGCCCGTCTGCTTCATCTT | 64 | 278 |
| 4122 | 4141 | 502486 | CTGGCCCGTCTGCTTCATCT | 64 | 279 |
| 4123 | 4142 | 502487 | CCTGGCCCGTCTGCTTCATC | 73 | 280 |
| 4124 | 4143 | 502488 | ACCTGGCCCGTCTGCTTCAT | 64 | 281 |
| 4125 | 4144 | 502489 | CACCTGGCCCGTCTGCTTCA | 80 | 282 |
| 4126 | 4145 | 502490 | ACACCTGGCCCGTCTGCTTC | 71 | 283 |
| 4127 | 4146 | 502491 | TACACCTGGCCCGTCTGCTT | 74 | 284 |
| 4148 | 4167 | 502492 | TTGTTCATGATCTTCATGGC | 56 | 285 |
| 4150 | 4169 | 502493 | ACTTGTTCATGATCTTCATG | 23 | 286 |
| 4151 | 4170 | 502494 | CACTTGTTCATGATCTTCAT | 43 | 287 |
| 4152 | 4171 | 502495 | CCACTTGTTCATGATCTTCA | 43 | 288 |
| 4153 | 4172 | 502496 | CCCACTTGTTCATGATCTTC | 47 | 289 |
| 4154 | 4173 | 502497 | TCCCACTTGTTCATGATCTT | 34 | 290 |
| 4155 | 4174 | 502498 | GTCCCACTTGTTCATGATCT | 34 | 291 |
| 4156 | 4175 | 502499 | TGTCCCACTTGTTCATGATC | 27 | 292 |
| 4157 | 4176 | 502500 | ATGTCCCACTTGTTCATGAT | 23 | 293 |
| 4158 | 4177 | 502501 | CATGTCCCACTTGTTCATGA | 51 | 294 |
| 4159 | 4178 | 502502 | GCATGTCCCACTTGTTCATG | 20 | 295 |
| 4160 | 4179 | 502503 | AGCATGTCCCACTTGTTCAT | 52 | 296 |
| 4161 | 4180 | 502504 | CAGCATGTCCCACTTGTTCA | 72 | 297 |
| 4162 | 4181 | 502505 | TCAGCATGTCCCACTTGTTC | 70 | 298 |
| 4163 | 4182 | 502506 | TTCAGCATGTCCCACTTGTT | 53 | 299 |
| 4164 | 4183 | 502507 | CTTCAGCATGTCCCACTTGT | 52 | 300 |
| 4165 | 4184 | 502508 | TCTTCAGCATGTCCCACTTG | 45 | 301 |
| 4167 | 4186 | 502509 | CCTCTTCAGCATGTCCCACT | 68 | 302 |
| 4168 | 4187 | 502510 | CCCTCTTCAGCATGTCCCAC | 68 | 303 |
| 4169 | 4188 | 502511 | CCCCTCTTCAGCATGTCCCA | 79 | 304 |
| 4170 | 4189 | 502512 | GCCCCTCTTCAGCATGTCCC | 85 | 305 |
| 4171 | 4190 | 502513 | CGCCCCTCTTCAGCATGTCC | 84 | 306 |
| 4172 | 4191 | 502514 | TCGCCCCTCTTCAGCATGTC | 80 | 307 |
| 4173 | 4192 | 502515 | CTCGCCCCTCTTCAGCATGT | 82 | 308 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 4174 | 4193 | 502516 | CCTCGCCCCTCTTCAGCATG | 78 | 309 |
| 4175 | 4194 | 502517 | ACCTCGCCCCTCTTCAGCAT | 73 | 310 |
| 4176 | 4195 | 502518 | CACCTCGCCCCTCTTCAGCA | 76 | 311 |
| 4239 | 4258 | 503012 | GGAGGAGCTGCAGCCGGAGA | 7 | 650 |
| 4245 | 4264 | 503013 | GCACCCGGAGGAGCTGCAGC | 0 | 651 |
| 4261 | 4280 | 503014 | GCACGACACCTGCAGGGCAC | 23 | 652 |
| 4355 | 4374 | 503015 | AGCTCACCAGGTAGTTCTCA | 49 | 653 |
| 4427 | 4446 | 503016 | GCTTCCTCTCCCCACCTCCT | 65 | 654 |
| 4447 | 4466 | 503017 | GCAGCACCCCCAATCCTAGA | 67 | 655 |
| 4508 | 4527 | 503018 | GCCCCTCATCCACCTGACAC | 62 | 656 |
| 4613 | 4632 | 503019 | TTCCAGGTAAGAGACCCCCC | 87 | 657 |
| 4679 | 4698 | 503020 | AGAATAGGTCCCAGACACTC | 81 | 658 |
| 4731 | 4750 | 503021 | CTCCCCCTGAGATGTTCTGG | 53 | 659 |
| 4858 | 4877 | 503022 | CCCCAGCCCAGAGATAACCA | 74 | 660 |
| 4927 | 4946 | 503023 | CCTGATCCATCACGGATGGC | 69 | 661 |
| 4987 | 5006 | 503024 | TACTCCATGACCAGGTACTG | 81 | 662 |
| 5185 | 5204 | 503025 | GCTCTGACCTTCCAAGAACC | 56 | 663 |
| 5354 | 5373 | 503026 | CTCCCTTCTGTGGTCCCACC | 0 | 664 |
| 5407 | 5426 | 503027 | GTCGGGTTTGATGTCCCTGC | 75 | 665 |
| 5445 | 5464 | 502521 | GCCAGGCGGATGTGGCCACA | 57 | 314 |
| 5500 | 5519 | 503028 | AGGGCACTGGCTCACCGTTC | 45 | 666 |
| 5681 | 5700 | 503029 | GGGCCCTCCTTCCAACCACT | 28 | 667 |
| 5708 | 5727 | 503030 | GCCCACCCCTCTGGGCCCAC | 45 | 668 |
| 5728 | 5747 | 503031 | AGGAGCAGAGCGAGGCTTGG | 38 | 669 |
| 5800 | 5819 | 502524 | ACAGCCTGCAGGATCTCGGG | 86 | 317 |
| 5801 | 5820 | 502525 | CACAGCCTGCAGGATCTCGG | 81 | 318 |
| 5802 | 5821 | 502526 | CCACAGCCTGCAGGATCTCG | 83 | 319 |
| 5803 | 5822 | 502527 | CCCACAGCCTGCAGGATCTC | 84 | 320 |
| 5804 | 5823 | 502528 | GCCCACAGCCTGCAGGATCT | 91 | 321 |
| 5805 | 5824 | 502529 | CGCCCACAGCCTGCAGGATC | 90 | 322 |
| 5806 | 5825 | 502530 | CCGCCCACAGCCTGCAGGAT | 82 | 323 |
| 5807 | 5826 | 502531 | ACCGCCCACAGCCTGCAGGA | 83 | 324 |
| 5808 | 5827 | 502532 | CACCGCCCACAGCCTGCAGG | 85 | 325 |
| 5809 | 5828 | 502533 | CCACCGCCCACAGCCTGCAG | 84 | 326 |
| 5810 | 5829 | 502534 | CCCACCGCCCACAGCCTGCA | 80 | 327 |
| 5811 | 5830 | 502535 | GCCCACCGCCCACAGCCTGC | 90 | 328 |
| 5812 | 5831 | 502536 | GGCCCACCGCCCACAGCCTG | 94 | 329 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 5813 | 5832 | 502537 | AGGCCCACCGCCCACAGCCT | 88 | 330 |
| 5814 | 5833 | 502538 | CAGGCCCACCGCCCACAGCC | 91 | 331 |
| 5815 | 5834 | 502539 | CCAGGCCCACCGCCCACAGC | 73 | 332 |
| 5816 | 5835 | 502540 | CCCAGGCCCACCGCCCACAG | 86 | 333 |
| 5817 | 5836 | 502541 | TCCCAGGCCCACCGCCCACA | 88 | 334 |
| 5818 | 5837 | 502542 | GTCCCAGGCCCACCGCCCAC | 84 | 335 |
| 5819 | 5838 | 502543 | TGTCCCAGGCCCACCGCCCA | 85 | 336 |
| 5820 | 5839 | 502544 | CTGTCCCAGGCCCACCGCCC | 65 | 337 |
| 5821 | 5840 | 502545 | CCTGTCCCAGGCCCACCGCC | 81 | 338 |
| 5822 | 5841 | 502546 | GCCTGTCCCAGGCCCACCGC | 90 | 339 |
| 5823 | 5842 | 502547 | TGCCTGTCCCAGGCCCACCG | 85 | 340 |
| 5824 | 5843 | 502548 | CTGCCTGTCCCAGGCCCACC | 89 | 341 |
| 5825 | 5844 | 502549 | GCTGCCTGTCCCAGGCCCAC | 91 | 342 |
| 5826 | 5845 | 502550 | AGCTGCCTGTCCCAGGCCCA | 94 | 343 |
| 5827 | 5846 | 502551 | TAGCTGCCTGTCCCAGGCCC | 92 | 344 |
| 5828 | 5847 | 502552 | GTAGCTGCCTGTCCCAGGCC | 88 | 345 |
| 5829 | 5848 | 502553 | CGTAGCTGCCTGTCCCAGGC | 85 | 346 |
| 5830 | 5849 | 502554 | CCGTAGCTGCCTGTCCCAGG | 83 | 347 |
| 5831 | 5850 | 502555 | CCCGTAGCTGCCTGTCCCAG | 64 | 348 |
| 5832 | 5851 | 502556 | GCCCGTAGCTGCCTGTCCCA | 83 | 349 |
| 5833 | 5852 | 502557 | GGCCCGTAGCTGCCTGTCCC | 89 | 350 |
| 5881 | 5900 | 502558 | TAGAACATTTCATAGGCGAA | 68 | 351 |
| 5919 | 5938 | 502559 | TCTCCGCCGTGGAATCCGCG | 75 | 352 |
| 5920 | 5939 | 502560 | GTCTCCGCCGTGGAATCCGC | 79 | 353 |
| 5921 | 5940 | 502561 | GGTCTCCGCCGTGGAATCCG | 66 | 354 |
| 5922 | 5941 | 502562 | AGGTCTCCGCCGTGGAATCC | 50 | 355 |
| 5923 | 5942 | 502563 | TAGGTCTCCGCCGTGGAATC | 71 | 356 |
| 5944 | 5963 | 502564 | TTGTAGTGGACGATCTTGCC | 68 | 357 |
| 5945 | 5964 | 502565 | CTTGTAGTGGACGATCTTGC | 70 | 358 |
| 5946 | 5965 | 502566 | CCTTGTAGTGGACGATCTTG | 61 | 359 |
| 5948 | 5967 | 503032 | CACCTTGTAGTGGACGATCT | 62 | 670 |
| 6039 | 6058 | 502582 | CGGCAGAGAGAGGTGCTCCT | 80 | 375 |
| 6040 | 6059 | 502583 | GCGGCAGAGAGAGGTGCTCC | 62 | 376 |
| 6041 | 6060 | 502584 | AGCGGCAGAGAGAGGTGCTC | 44 | 377 |
| 6042 | 6061 | 502585 | CAGCGGCAGAGAGAGGTGCT | 78 | 378 |
| 6043 | 6062 | 502586 | CCAGCGGCAGAGAGAGGTGC | 71 | 379 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 6118 | 6137 | 502587 | GGCCCAGCCGTGTCTCCGGG | 77 | 380 |
| 6119 | 6138 | 502588 | CGGCCCAGCCGTGTCTCCGG | 69 | 381 |
| 6120 | 6139 | 502589 | CCGGCCCAGCCGTGTCTCCG | 70 | 382 |
| 6121 | 6140 | 502590 | CCCGGCCCAGCCGTGTCTCC | 75 | 383 |
| 6122 | 6141 | 502591 | CCCCGGCCCAGCCGTGTCTC | 77 | 384 |
| 6123 | 6142 | 502592 | ACCCCGGCCCAGCCGTGTCT | 73 | 385 |
| 6124 | 6143 | 502593 | CACCCCGGCCCAGCCGTGTC | 84 | 386 |
| 6125 | 6144 | 502594 | CCACCCCGGCCCAGCCGTGT | 78 | 387 |
| 6126 | 6145 | 502595 | TCCACCCCGGCCCAGCCGTG | 71 | 388 |
| 6127 | 6146 | 502596 | CTCCACCCCGGCCCAGCCGT | 81 | 389 |
| 6128 | 6147 | 502597 | GCTCCACCCCGGCCCAGCCG | 86 | 390 |
| 6129 | 6148 | 502598 | TGCTCCACCCCGGCCCAGCC | 83 | 391 |
| 6130 | 6149 | 502599 | CTGCTCCACCCCGGCCCAGC | 88 | 392 |
| 6152 | 6171 | 502600 | AAGGGATGTGTCCGGAAGTC | 60 | 393 |
| 6153 | 6172 | 502601 | GAAGGGATGTGTCCGGAAGT | 58 | 394 |
| 6154 | 6173 | 502602 | AGAAGGGATGTGTCCGGAAG | 63 | 395 |
| 6155 | 6174 | 502603 | AAGAAGGGATGTGTCCGGAA | 62 | 396 |
| 6156 | 6175 | 502604 | GAAGAAGGGATGTGTCCGGA | 61 | 397 |
| 6157 | 6176 | 502605 | AGAAGAAGGGATGTGTCCGG | 62 | 398 |
| 6158 | 6177 | 502606 | AAGAAGAAGGGATGTGTCCG | 56 | 399 |
| 6159 | 6178 | 502607 | AAAGAAGAAGGGATGTGTCC | 58 | 400 |
| 6160 | 6179 | 502608 | CAAAGAAGAAGGGATGTGTC | 50 | 401 |
| 6161 | 6180 | 502609 | CCAAAGAAGAAGGGATGTGT | 61 | 402 |
| 6163 | 6182 | 502610 | GGCCAAAGAAGAAGGGATGT | 73 | 403 |
| 6164 | 6183 | 502611 | AGGCCAAAGAAGAAGGGATG | 56 | 404 |
| 6165 | 6184 | 502612 | GAGGCCAAAGAAGAAGGGAT | 73 | 405 |
| 6166 | 6185 | 502613 | CGAGGCCAAAGAAGAAGGGA | 75 | 406 |
| 6167 | 6186 | 502614 | TCGAGGCCAAAGAAGAAGGG | 75 | 407 |
| 6168 | 6187 | 502615 | GTCGAGGCCAAAGAAGAAGG | 83 | 408 |
| 6169 | 6188 | 502616 | AGTCGAGGCCAAAGAAGAAG | 58 | 409 |
| 6170 | 6189 | 502617 | CAGTCGAGGCCAAAGAAGAA | 52 | 410 |
| 6171 | 6190 | 502618 | CCAGTCGAGGCCAAAGAAGA | 68 | 411 |
| 6172 | 6191 | 502619 | CCCAGTCGAGGCCAAAGAAG | 78 | 412 |
| 6173 | 6192 | 502620 | TCCCAGTCGAGGCCAAAGAA | 66 | 413 |
| 6174 | 6193 | 502621 | ATCCCAGTCGAGGCCAAAGA | 75 | 414 |
| 6175 | 6194 | 502622 | CATCCCAGTCGAGGCCAAAG | 70 | 415 |
| 6176 | 6195 | 502623 | CCATCCCAGTCGAGGCCAAA | 81 | 416 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 6177 | 6196 | 502624 | ACCATCCCAGTCGAGGCCAA | 82 | 417 |
| 6178 | 6197 | 502625 | GACCATCCCAGTCGAGGCCA | 88 | 418 |
| 6179 | 6198 | 502626 | AGACCATCCCAGTCGAGGCC | 79 | 419 |
| 6180 | 6199 | 502627 | GAGACCATCCCAGTCGAGGC | 82 | 420 |
| 6181 | 6200 | 502628 | GGAGACCATCCCAGTCGAGG | 60 | 421 |
| 6216 | 6235 | 502629 | TTCGAAATCCGGTGTAAAGG | 84 | 422 |
| 6217 | 6236 | 502630 | CTTCGAAATCCGGTGTAAAG | 57 | 423 |
| 6218 | 6237 | 502631 | CCTTCGAAATCCGGTGTAAA | 64 | 424 |
| 6219 | 6238 | 502632 | ACCTTCGAAATCCGGTGTAA | 73 | 425 |
| 6220 | 6239 | 502633 | CACCTTCGAAATCCGGTGTA | 77 | 426 |
| 6221 | 6240 | 502634 | GCACCTTCGAAATCCGGTGT | 59 | 427 |
| 6222 | 6241 | 502635 | GGCACCTTCGAAATCCGGTG | 85 | 428 |
| 6223 | 6242 | 502636 | TGGCACCTTCGAAATCCGGT | 86 | 429 |
| 6224 | 6243 | 502637 | GTGGCACCTTCGAAATCCGG | 74 | 430 |
| 6225 | 6244 | 502638 | GGTGGCACCTTCGAAATCCG | 79 | 431 |
| 6226 | 6245 | 502639 | CGGTGGCACCTTCGAAATCC | 85 | 432 |
| 6227 | 6246 | 502640 | TCGGTGGCACCTTCGAAATC | 71 | 433 |
| 6228 | 6247 | 502641 | GTCGGTGGCACCTTCGAAAT | 88 | 434 |
| 6229 | 6248 | 502642 | TGTCGGTGGCACCTTCGAAA | 89 | 435 |
| 6230 | 6249 | 502643 | GTGTCGGTGGCACCTTCGAA | 88 | 436 |
| 6231 | 6250 | 502644 | TGTGTCGGTGGCACCTTCGA | 87 | 437 |
| 6232 | 6251 | 502645 | ATGTGTCGGTGGCACCTTCG | 88 | 438 |
| 6233 | 6252 | 502646 | CATGTGTCGGTGGCACCTTC | 88 | 439 |
| 6234 | 6253 | 502647 | GCATGTGTCGGTGGCACCTT | 91 | 440 |
| 6235 | 6254 | 502648 | TGCATGTGTCGGTGGCACCT | 87 | 441 |
| 6236 | 6255 | 502649 | TTGCATGTGTCGGTGGCACC | 86 | 442 |
| 6237 | 6256 | 502650 | GTTGCATGTGTCGGTGGCAC | 83 | 443 |
| 6238 | 6257 | 502651 | AGTTGCATGTGTCGGTGGCA | 81 | 444 |
| 6239 | 6258 | 502652 | AAGTTGCATGTGTCGGTGGC | 79 | 445 |
| 6240 | 6259 | 502653 | GAAGTTGCATGTGTCGGTGG | 58 | 446 |
| 6241 | 6260 | 502654 | CGAAGTTGCATGTGTCGGTG | 85 | 447 |
| 6243 | 6262 | 502655 | GTCGAAGTTGCATGTGTCGG | 77 | 448 |
| 6244 | 6263 | 502656 | AGTCGAAGTTGCATGTGTCG | 79 | 449 |
| 6245 | 6264 | 502657 | AAGTCGAAGTTGCATGTGTC | 74 | 450 |
| 6246 | 6265 | 502658 | CAAGTCGAAGTTGCATGTGT | 82 | 451 |
| 6247 | 6266 | 502659 | CCAAGTCGAAGTTGCATGTG | 82 | 452 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 6248 | 6267 | 502660 | ACCAAGTCGAAGTTGCATGT | 70 | 453 |
| 6249 | 6268 | 502661 | CACCAAGTCGAAGTTGCATG | 76 | 454 |
| 6250 | 6269 | 502662 | CCACCAAGTCGAAGTTGCAT | 79 | 455 |
| 6251 | 6270 | 502663 | TCCACCAAGTCGAAGTTGCA | 68 | 456 |
| 6252 | 6271 | 502664 | CTCCACCAAGTCGAAGTTGC | 71 | 457 |
| 6253 | 6272 | 502665 | CCTCCACCAAGTCGAAGTTG | 67 | 458 |
| 6254 | 6273 | 502666 | TCCTCCACCAAGTCGAAGTT | 70 | 459 |
| 6255 | 6274 | 502667 | GTCCTCCACCAAGTCGAAGT | 80 | 460 |
| 6256 | 6275 | 502668 | CGTCCTCCACCAAGTCGAAG | 76 | 461 |
| 6257 | 6276 | 502669 | CCGTCCTCCACCAAGTCGAA | 78 | 462 |
| 6258 | 6277 | 502670 | CCCGTCCTCCACCAAGTCGA | 83 | 463 |
| 6259 | 6278 | 502671 | GCCCGTCCTCCACCAAGTCG | 76 | 464 |
| 6260 | 6279 | 502672 | AGCCCGTCCTCCACCAAGTC | 72 | 465 |
| 6261 | 6280 | 502673 | GAGCCCGTCCTCCACCAAGT | 71 | 466 |
| 6262 | 6281 | 502674 | TGAGCCCGTCCTCCACCAAG | 60 | 467 |
| 6289 | 6308 | 503033 | CTACCCCGCCCCCGCTCACC | 60 | 671 |
| 6445 | 6464 | 503034 | CTAGGTCACTGCTGGGTCCT | 86 | 672 |
| 6596 | 6615 | 503035 | CTCAGATAGCTCCCCACTCC | 55 | 673 |
| 6794 | 6813 | 503036 | AATTCTCTAATTCTCTAGAC | 19 | 674 |
| 8666 | 8685 | 503037 | TACCTGAGGGCCATGCAGGA | 51 | 675 |
| 8765 | 8784 | 503038 | GTTCCAAGACTGATCCTGCA | 69 | 676 |
| 11975 | 11994 | 502675 | GGTTCCGAGCCTCTGCCTCG | 44 | 468 |
| 11976 | 11995 | 502676 | CGGTTCCGAGCCTCTGCCTC | 74 | 469 |
| 11977 | 11996 | 502677 | CCGGTTCCGAGCCTCTGCCT | 72 | 470 |
| 11978 | 11997 | 502678 | CCCGGTTCCGAGCCTCTGCC | 73 | 471 |
| 11979 | 11998 | 502679 | TCCCGGTTCCGAGCCTCTGC | 84 | 472 |
| 11980 | 11999 | 502680 | GTCCCGGTTCCGAGCCTCTG | 66 | 473 |
| 11982 | 12001 | 502681 | AGGTCCCGGTTCCGAGCCTC | 82 | 474 |
| 11983 | 12002 | 502682 | TAGGTCCCGGTTCCGAGCCT | 83 | 475 |
| 11984 | 12003 | 502683 | CTAGGTCCCGGTTCCGAGCC | 81 | 476 |
| 11985 | 12004 | 502684 | TCTAGGTCCCGGTTCCGAGC | 74 | 477 |
| 11986 | 12005 | 502685 | CTCTAGGTCCCGGTTCCGAG | 78 | 478 |
| 11987 | 12006 | 502686 | CCTCTAGGTCCCGGTTCCGA | 75 | 479 |
| 11988 | 12007 | 502687 | GCCTCTAGGTCCCGGTTCCG | 80 | 480 |
| 12016 | 12035 | 502688 | CATCCGCTCCTGCAACTGCC | 89 | 481 |
| 12017 | 12036 | 502689 | CCATCCGCTCCTGCAACTGC | 81 | 482 |
| 12018 | 12037 | 502690 | TCCATCCGCTCCTGCAACTG | 71 | 483 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 12019 | 12038 | 502691 | CTCCATCCGCTCCTGCAACT | 75 | 484 |
| 12020 | 12039 | 502692 | ACTCCATCCGCTCCTGCAAC | 64 | 485 |
| 12021 | 12040 | 502693 | AACTCCATCCGCTCCTGCAA | 52 | 486 |
| 12022 | 12041 | 502694 | CAACTCCATCCGCTCCTGCA | 45 | 487 |
| 12024 | 12043 | 502695 | AGCAACTCCATCCGCTCCTG | 78 | 488 |
| 12025 | 12044 | 502696 | CAGCAACTCCATCCGCTCCT | 64 | 489 |
| 12026 | 12045 | 502697 | GCAGCAACTCCATCCGCTCC | 56 | 490 |
| 12173 | 12192 | 503039 | AGGAGGGCGGTGGCGCGGCG | 0 | 677 |
| 12221 | 12240 | 503040 | TGACAGCTGGAAGGAGAAGA | 41 | 678 |
| 12258 | 12277 | 502712 | GAAGGTGGATCCGTGGCCCG | 73 | 505 |
| 12259 | 12278 | 502713 | GGAAGGTGGATCCGTGGCCC | 70 | 506 |
| 12260 | 12279 | 502714 | GGGAAGGTGGATCCGTGGCC | 72 | 507 |
| 12261 | 12280 | 502715 | TGGGAAGGTGGATCCGTGGC | 50 | 508 |
| 12262 | 12281 | 502716 | ATGGGAAGGTGGATCCGTGG | 62 | 509 |
| 12263 | 12282 | 451417 | CATGGGAAGGTGGATCCGTG | 77 | 679 |
| 12463 | 12482 | 503041 | GGAGGTTATCTAGGGAGATC | 42 | 680 |
| 12542 | 12561 | 503042 | GAAGGGACAGGTGACCCGAT | 69 | 681 |
| 12596 | 12615 | 502724 | CACCAGCGGGCACTGGCCCA | 51 | 518 |
| 12597 | 12616 | 502725 | CCACCAGCGGGCACTGGCCC | 55 | 519 |
| 12598 | 12617 | 502726 | CCCACCAGCGGGCACTGGCC | 61 | 520 |
| 12599 | 12618 | 502727 | CCCCACCAGCGGGCACTGGC | 43 | 521 |
| 12601 | 12620 | 502728 | GGCCCCACCAGCGGGCACTG | 16 | 522 |
| 12602 | 12621 | 502729 | TGGCCCCACCAGCGGGCACT | 43 | 523 |
| 12603 | 12622 | 502730 | CTGGCCCCACCAGCGGGCAC | 43 | 524 |
| 12604 | 12623 | 502731 | CCTGGCCCCACCAGCGGGCA | 41 | 525 |
| 12605 | 12624 | 502732 | GCCTGGCCCCACCAGCGGGC | 30 | 526 |
| 12607 | 12626 | 502733 | GGGCCTGGCCCCACCAGCGG | 66 | 527 |
| 12625 | 12644 | 502734 | AGGTGGCGGCGGTGCATGGG | 31 | 528 |
| 12626 | 12645 | 502735 | CAGGTGGCGGCGGTGCATGG | 23 | 529 |
| 12627 | 12646 | 502736 | GCAGGTGGCGGCGGTGCATG | 57 | 530 |
| 12628 | 12647 | 502737 | AGCAGGTGGCGGCGGTGCAT | 54 | 531 |
| 12629 | 12648 | 502738 | CAGCAGGTGGCGGCGGTGCA | 61 | 532 |
| 12630 | 12649 | 502739 | GCAGCAGGTGGCGGCGGTGC | 57 | 533 |
| 12631 | 12650 | 502740 | AGCAGCAGGTGGCGGCGGTG | 36 | 534 |
| 12632 | 12651 | 502741 | GAGCAGCAGGTGGCGGCGGT | 53 | 535 |
| 12633 | 12652 | 502742 | GGAGCAGCAGGTGGCGGCGG | 39 | 536 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 12634 | 12653 | 502743 | GGGAGCAGCAGGTGGCGGCG | 36 | 537 |
| 12635 | 12654 | 502744 | AGGGAGCAGCAGGTGGCGGC | 62 | 538 |
| 12636 | 12655 | 502745 | CAGGGAGCAGCAGGTGGCGG | 56 | 539 |
| 12637 | 12656 | 502746 | GCAGGGAGCAGCAGGTGGCG | 58 | 540 |
| 12638 | 12657 | 502747 | GGCAGGGAGCAGCAGGTGGC | 65 | 541 |
| 12639 | 12658 | 502748 | TGGCAGGGAGCAGCAGGTGG | 47 | 542 |
| 12640 | 12659 | 502749 | CTGGCAGGGAGCAGCAGGTG | 41 | 543 |
| 12642 | 12661 | 451432 | CCCTGGCAGGGAGCAGCAGG | 53 | 544 |
| 12643 | 12662 | 502750 | ACCCTGGCAGGGAGCAGCAG | 52 | 545 |
| 12646 | 12665 | 503043 | CGTACCCTGGCAGGGAGCAG | 59 | 682 |
| 12918 | 12937 | 502977 | GGACTCGCCCCGCCTACGCC | 71 | 683 |
| 12924 | 12943 | 502978 | CTCCTGGGACTCGCCCCGCC | 67 | 684 |
| 12925 | 12944 | 503044 | GCTCCTGGGACTCGCCCCGC | 66 | 685 |
| 12929 | 12948 | 503045 | ATTGGCTCCTGGGACTCGCC | 77 | 686 |
| 12930 | 12949 | 502979 | GATTGGCTCCTGGGACTCGC | 70 | 687 |
| 12936 | 12955 | 502980 | GCCTCTGATTGGCTCCTGGG | 56 | 688 |
| 12942 | 12961 | 502981 | GCATGGGCCTCTGATTGGCT | 20 | 689 |
| 12948 | 12967 | 502982 | CACCCGGCATGGGCCTCTGA | 20 | 690 |
| 12986 | 13005 | 503046 | GCCAGGCCTAGGGACCTGCG | 58 | 691 |
| 12990 | 13009 | 502760 | ATAGGCCAGGCCTAGGGACC | 51 | 555 |
| 12991 | 13010 | 502761 | GATAGGCCAGGCCTAGGGAC | 41 | 556 |
| 12992 | 13011 | 502762 | CGATAGGCCAGGCCTAGGGA | 69 | 557 |
| 12993 | 13012 | 502763 | CCGATAGGCCAGGCCTAGGG | 80 | 558 |
| 12994 | 13013 | 502764 | TCCGATAGGCCAGGCCTAGG | 78 | 559 |
| 12995 | 13014 | 502765 | CTCCGATAGGCCAGGCCTAG | 89 | 560 |
| 12996 | 13015 | 502766 | CCTCCGATAGGCCAGGCCTA | 79 | 561 |
| 12997 | 13016 | 502767 | GCCTCCGATAGGCCAGGCCT | 73 | 562 |
| 12999 | 13018 | 502768 | GCGCCTCCGATAGGCCAGGC | 83 | 563 |
| 13015 | 13034 | 502769 | AACAGGAGCAGGGAAAGCGC | 83 | 564 |
| 13016 | 13035 | 502770 | GAACAGGAGCAGGGAAAGCG | 70 | 565 |
| 13017 | 13036 | 502771 | CGAACAGGAGCAGGGAAAGC | 43 | 566 |
| 13018 | 13037 | 502772 | GCGAACAGGAGCAGGGAAAG | 47 | 567 |
| 13019 | 13038 | 502773 | GGCGAACAGGAGCAGGGAAA | 61 | 568 |
| 13020 | 13039 | 502774 | CGGCGAACAGGAGCAGGGAA | 74 | 569 |
| 13021 | 13040 | 502775 | ACGGCGAACAGGAGCAGGGA | 60 | 570 |
| 13022 | 13041 | 502776 | AACGGCGAACAGGAGCAGGG | 86 | 571 |
| 13023 | 13042 | 502777 | CAACGGCGAACAGGAGCAGG | 84 | 572 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 13044 | 13063 | 502778 | GGGCGGCGGCACGAGACAGA | 80 | 573 |
| 13045 | 13064 | 502779 | AGGGCGGCGGCACGAGACAG | 76 | 574 |
| 13046 | 13065 | 502780 | CAGGGCGGCGGCACGAGACA | 58 | 575 |
| 13047 | 13066 | 502781 | CCAGGGCGGCGGCACGAGAC | 80 | 576 |
| 13048 | 13067 | 502782 | CCCAGGGCGGCGGCACGAGA | 59 | 577 |
| 13049 | 13068 | 502783 | GCCCAGGGCGGCGGCACGAG | 68 | 578 |
| 13050 | 13069 | 502784 | AGCCCAGGGCGGCGGCACGA | 75 | 579 |
| 13051 | 13070 | 502785 | CAGCCCAGGGCGGCGGCACG | 76 | 580 |
| 13052 | 13071 | 502786 | GCAGCCCAGGGCGGCGGCAC | 70 | 581 |
| 13089 | 13108 | 502787 | CTGCGGTGAGTTGGCCGGCG | 68 | 582 |
| 13090 | 13109 | 502788 | ACTGCGGTGAGTTGGCCGGC | 67 | 583 |
| 13091 | 13110 | 502789 | GACTGCGGTGAGTTGGCCGG | 58 | 584 |
| 13092 | 13111 | 502790 | AGACTGCGGTGAGTTGGCCG | 71 | 585 |
| 13093 | 13112 | 502791 | CAGACTGCGGTGAGTTGGCC | 70 | 586 |
| 13094 | 13113 | 502792 | CCAGACTGCGGTGAGTTGGC | 79 | 587 |
| 13095 | 13114 | 502793 | GCCAGACTGCGGTGAGTTGG | 76 | 588 |
| 13096 | 13115 | 502794 | CGCCAGACTGCGGTGAGTTG | 66 | 589 |
| 13140 | 13159 | 502795 | AAGACAGTTCTAGGGTTCAG | 87 | 590 |
| 13141 | 13160 | 502796 | GAAGACAGTTCTAGGGTTCA | 78 | 591 |
| 13142 | 13161 | 502797 | CGAAGACAGTTCTAGGGTTC | 85 | 592 |
| 13143 | 13162 | 502798 | TCGAAGACAGTTCTAGGGTT | 78 | 593 |
| 13144 | 13163 | 502799 | GTCGAAGACAGTTCTAGGGT | 92 | 594 |
| 13145 | 13164 | 502800 | AGTCGAAGACAGTTCTAGGG | 85 | 595 |
| 13146 | 13165 | 502801 | GAGTCGAAGACAGTTCTAGG | 83 | 596 |
| 13147 | 13166 | 502802 | GGAGTCGAAGACAGTTCTAG | 86 | 597 |
| 13148 | 13167 | 502803 | CGGAGTCGAAGACAGTTCTA | 91 | 598 |
| 13149 | 13168 | 502804 | CCGGAGTCGAAGACAGTTCT | 76 | 599 |
| 13150 | 13169 | 502805 | CCCGGAGTCGAAGACAGTTC | 90 | 600 |
| 13151 | 13170 | 502806 | CCCCGGAGTCGAAGACAGTT | 83 | 601 |
| 13152 | 13171 | 502807 | GCCCCGGAGTCGAAGACAGT | 82 | 602 |
| 13153 | 13172 | 502808 | GGCCCCGGAGTCGAAGACAG | 73 | 603 |
| 13154 | 13173 | 502809 | GGGCCCCGGAGTCGAAGACA | 67 | 604 |
| 13206 | 13225 | 502810 | AGGCGGTGGGCGCGGCTTCT | 73 | 605 |
| 13207 | 13226 | 502811 | CAGGCGGTGGGCGCGGCTTC | 57 | 606 |
| 13208 | 13227 | 502812 | GCAGGCGGTGGGCGCGGCTT | 69 | 607 |
| 13210 | 13229 | 502813 | TGGCAGGCGGTGGGCGCGGC | 73 | 608 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 13212 | 13231 | 502814 | ACTGGCAGGCGGTGGGCGCG | 56 | 609 |
| 13214 | 13233 | 502815 | GAACTGGCAGGCGGTGGGCG | 71 | 610 |
| 13215 | 13234 | 502816 | TGAACTGGCAGGCGGTGGGC | 80 | 611 |
| 13217 | 13236 | 502817 | TGTGAACTGGCAGGCGGTGG | 85 | 612 |
| 13250 | 13269 | 502818 | TGGAGCTGGGCGGAGACCCA | 55 | 613 |
| 13252 | 13271 | 502819 | ACTGGAGCTGGGCGGAGACC | 53 | 614 |
| 13253 | 13272 | 502820 | GACTGGAGCTGGGCGGAGAC | 55 | 615 |
| 13255 | 13274 | 502821 | AGGACTGGAGCTGGGCGGAG | 76 | 616 |
| 13257 | 13276 | 502822 | ACAGGACTGGAGCTGGGCGG | 77 | 617 |
| 13258 | 13277 | 502823 | CACAGGACTGGAGCTGGGCG | 74 | 618 |
| 13259 | 13278 | 502824 | TCACAGGACTGGAGCTGGGC | 90 | 619 |
| 13449 | 13468 | 502825 | GCCTCAGCCTGGCCGAAAGA | 80 | 620 |
| 13450 | 13469 | 502826 | GGCCTCAGCCTGGCCGAAAG | 72 | 621 |
| 13553 | 13572 | 444401 | TTGCACTTTGCGAACCAACG | 97 | 41 |
| 14037 | 14056 | 503047 | TTCCTCCCCCAACCCTGATT | 34 | 692 |
| 14255 | 14274 | 503048 | AAGTTTGCAGCAACTTTTCT | 0 | 693 |
| 14325 | 14344 | 503049 | GCCCCTCGGAATTCCCGGCT | 0 | 694 |
| 14343 | 14362 | 503050 | CATCTCGGCCTGCGCTCCGC | 39 | 695 |
| 14361 | 14380 | 503051 | GCAGGCCCCCACATTCCCCA | 0 | 696 |
| 14392 | 14411 | 503052 | CTTCTGCACGCCTCCGTCTC | 30 | 697 |

Example 8: Antisense Inhibition of Murine DMPK in Mouse Primary Hepatocytes

Antisense oligonucleotides targeted to a murine DMPK nucleic acid were tested for their effect on DMPK RNA transcript in vitro. Cultured mouse primary hepatocytes at a density of 35,000 cells per well were transfected using electroporation with 8,000 nM antisense oligonucleotide. After approximately 24 hours, RNA was isolated from the cells and DMPK transcript levels were measured by quantitative real-time PCR. DMPK RNA transcript levels were adjusted according to total RNA content, as measured by RIBOGREEN®. Results are presented as percent inhibition of DMPK, relative to untreated control cells.

The antisense oligonucleotides in Tables 14, 15, and 16 are 5-10-5 gapmers, where the gap segment comprises ten 2'-deoxynucleosides and each wing segment comprises five 2'-MOE nucleosides. The internucleoside linkages throughout each gapmer are phosphorothioate (P=S) linkages. All cytosine residues throughout each gapmer are 5-methylcytosines. 'Murine Target start site' indicates the 5'-most nucleoside to which the antisense oligonucleotide is targeted in the murine gene sequence. 'Murine Target stop site' indicates the 3'-most nucleoside to which the antisense oligonucleotide is targeted in the murine gene sequence. All the antisense oligonucleotides listed in Table 12 target SEQ ID NO: 3 (GENBANK Accession No. NT_039413.7 truncated from nucleotides 16666001 to 16681000). All the antisense oligonucleotides listed in Table 13 target SEQ ID NO: 4 (GENBANK Accession No. NM_032418.1). The antisense oligonucleotides of Table 14 target SEQ ID NO: 5 (GENBANK Accession No. AI007148.1), SEQ ID NO: 6 (GENBANK Accession No. AI304033.1), SEQ ID NO: 7 (GENBANK Accession No. BC024150.1), SEQ ID NO: 8 (GENBANK Accession No. BC056615.1), SEQ ID NO: 793 (GENBANK Accession No. BC075715.1), SEQ ID NO: 794 (GENBANK Accession No. BU519245.1), SEQ ID NO: 795 (GENBANK Accession No. CB247909.1), SEQ ID NO: 796 (GENBANK Accession No. CX208906.1), SEQ ID NO: 797 (GENBANK Accession No. CX732022.1), SEQ ID NO: 798 (GENBANK Accession No. S60315.1), or SEQ ID NO: 799 (GENBANK Accession No. S60316.1). In addition, the human antisense oligonucleotide ISIS 451421 targeting SEQ ID NO: 800 (GENBANK Accession No. NM_001081562.1) was also included in this assay and is listed in Table 14.

The murine oligonucleotides of Tables 14, 15, and 16 may also be cross-reactive with human gene sequences. 'Mismatches' indicate the number of nucleobases by which the murine oligonucleotide is mismatched with a human gene sequence. The greater the complementarity between the murine oligonucleotide and the human sequence, the more likely the murine oligonucleotide can cross-react with the human sequence. The murine oligonucleotides in Tables 14, 15, and 16 were compared to SEQ ID NO: 800 (GENBANK Accession No. NM_001081562.1). "Human Target start site" indicates the 5'-most nucleoside to which the gapmer is targeted in the human gene sequence. "Human Target stop site" indicates the 3'-most nucleoside to which the gapmer is targeted human gene sequence.

Several of the tested antisense oligonucleotides demonstrated significant inhibition of DMPK mRNA levels under the conditions specified above. Certain of the tested antisense oligonucleotides are cross-reactive with human gene sequences.

TABLE 14

Inhibition of murine DMPK RNA transcript in mouse primary hepatocytes by 5-10-5 gapmers targeting SEQ ID NO: 800

| Murine Target Start Site | Murine Target Stop Site | ISIS No | Sequence | % inhibition | SEQ ID NO. | Human Target Start Site | Human Target Stop Site | Mismatches |
|---|---|---|---|---|---|---|---|---|
| 11904 | 11923 | 299516 | TGGCCCACAGCCACGGCCGG | 47 | 698 | 1850 | 1869 | 0 |
| 11927 | 11946 | 299520 | GGCCTGGCCCCACCAGCGGG | 58 | 699 | 1873 | 1892 | 0 |
| 11962 | 11981 | 299521 | CCTGGCAGGGAGCAGCAGGT | 44 | 700 | 1908 | 1927 | 0 |
| 3345 | 3364 | 451360 | CAGCCGCACTTCGGCTGACA | 29 | 701 | 207 | 226 | 1 |
| 3378 | 3397 | 451361 | GCCTGGGTCCAGCACCAGCT | 67 | 702 | 240 | 259 | 2 |
| 3388 | 3407 | 451362 | GTCCCAGGAAGCCTGGGTCC | 62 | 703 | 250 | 269 | 2 |
| 3418 | 3437 | 451363 | CGCCCAGGAGAAGGTCGAGC | 69 | 213 | 280 | 299 | 0 |
| 3484 | 3503 | 451364 | CCCACTGCAAGAAGTCGGCC | 69 | 226 | 346 | 365 | 0 |
| 6264 | 6283 | 451366 | CGTTAGCAGGTCCCCGCCCA | 73 | 704 | 660 | 679 | 2 |
| 6342 | 6361 | 451367 | GTCTATGGCCATGACAATCT | 61 | 705 | 738 | 757 | 0 |
| 6363 | 6382 | 451368 | GTAGCCCAGCCGGTGCACGG | 54 | 706 | 759 | 778 | 2 |
| 6851 | 6870 | 451370 | GGGTGCCCACAGCCACCAGC | 72 | 707 | 889 | 908 | 0 |
| 6919 | 6938 | 451371 | TGGCCCGTAGCTGCCTGCCC | 80 | 708 | 957 | 976 | 2 |
| 7448 | 7467 | 451373 | GGAAATCACCTGCCCCACCT | 80 | 709 | n/a | n/a | n/a |
| 7458 | 7477 | 451374 | GGATGTTTCTGGAAATCACC | 84 | 710 | n/a | n/a | n/a |
| 7533 | 7552 | 451375 | GTGGCACCCTCGAAGTCTGG | 77 | 711 | 1271 | 1290 | 3 |
| 7589 | 7608 | 451376 | CCCCGCTCACCATGGCAGTG | 31 | 712 | n/a | n/a | n/a |
| 10278 | 10297 | 451378 | GGTCCGGGACCTGATTGTCT | 85 | 713 | n/a | n/a | n/a |
| 3229 | 3248 | 451385 | GCTGCATGTCTGCCCGTCCC | 74 | 714 | 90 | 109 | 1 |
| 3244 | 3263 | 451386 | GGCCCCAGAACCCTAGCTGC | 73 | 715 | n/a | n/a | n/a |
| 3270 | 3289 | 451387 | TCACAGGGCCTGGCTGCCCC | 62 | 716 | 131 | 150 | 1 |
| 3333 | 3352 | 451388 | GGCTGACATGTTGGGCAGGC | 60 | 717 | 195 | 214 | 1 |
| 3250 | 3269 | 451389 | TGTCCAGGCCCCAGAACCCT | 68 | 718 | 111 | 130 | 3 |
| 12295 | 12314 | 451391 | GGCCAGGCCTAGGGATCTGC | 51 | 719 | n/a | n/a | n/a |
| 12306 | 12325 | 451392 | CGCCTCGGATAGGCCAGGCC | 52 | 720 | 1935 | 1954 | 1 |
| 12450 | 12469 | 451393 | GGCTTGGAGTCTTAGGGTTC | 85 | 721 | n/a | n/a | n/a |
| 12623 | 12642 | 451394 | TCCCCGGCCGCCAGGTGGCA | 43 | 722 | 2224 | 2243 | 3 |
| 12651 | 12670 | 451395 | GGTGCTGGGCACGAGCCCTG | 62 | 723 | n/a | n/a | n/a |
| 12698 | 12717 | 451396 | GCCCAGCTGCTGCAGCAGCG | 66 | 724 | n/a | n/a | n/a |
| 12876 | 12895 | 451397 | CCGTGTGTGCTGGCAGAGGT | 76 | 725 | n/a | n/a | n/a |
| 13084 | 13103 | 451398 | ATAAATACCGAGGAATGTCG | 77 | 726 | 2766 | 2785 | 0 |

TABLE 14-continued

Inhibition of murine DMPK RNA transcript in mouse primary hepatocytes by 5-10-5 gapmers targeting SEQ ID NO: 800

| Murine Target Start Site | Murine Target Stop Site | ISIS No | Sequence | % inhibition | SEQ ID NO. | Human Target Start Site | Human Target Stop Site | Mismatches |
|---|---|---|---|---|---|---|---|---|
| 13094 | 13113 | 451399 | GGGACAGACAATAAATACCG | 80 | 727 | 2776 | 2795 | 0 |
| 12362 | 12381 | 451405 | GTGCAGCCCAGTGTGGCGGC | 69 | 728 | 1991 | 2010 | 3 |
| 11175 | 11194 | 451415 | CCTGGAGAAGTTCTGGTTGG | 48 | 729 | 1674 | 1693 | 3 |
| 11585 | 11604 | 451417 | CATGGGAAGGTGGATCCGTG | 65 | 679 | 1819 | 1838 | 1 |
| 11854 | 11873 | 451419 | GGTGACCCGATCGGAGCCCA | 11 | 730 | n/a | n/a | n/a |
| 11874 | 11893 | 451420 | AGCTGGAGAGAGAAGGGACA | 37 | 731 | n/a | n/a | n/a |
| 11379 | 11398 | 451422 | GTGAGGGACTCGCCTGCGGC | 36 | 732 | n/a | n/a | n/a |
| 11479 | 11498 | 451423 | GCGGCTGCGGTGCCCCAGCC | 50 | 733 | n/a | n/a | n/a |
| 11883 | 11902 | 451424 | GGGCCATCTAGCTGGAGAGA | 45 | 734 | n/a | n/a | n/a |
| 3485 | 3504 | 451427 | CCCCACTGCAAGAAGTCGGC | 57 | 735 | 347 | 366 | 1 |
| 4621 | 4640 | 451428 | TTGAGCCCTTTTAAGGCAGC | 43 | 736 | n/a | n/a | n/a |
| 6232 | 6251 | 451429 | TGACCAGGTACTGGGAGCGG | 47 | 737 | n/a | n/a | n/a |
| 10985 | 11004 | 451430 | CCTGGAGCTGGATCAGTCCC | 6 | 738 | n/a | n/a | n/a |
| 11586 | 11605 | 451431 | ACATGGGAAGGTGGATCCGT | 70 | 739 | 1820 | 1839 | 1 |
| 11963 | 11982 | 451432 | CCCTGGCAGGGAGCAGCAGG | 42 | 544 | 1909 | 1928 | 0 |
| 11973 | 11992 | 451433 | GTGGGACATACCCTGGCAGG | 34 | 740 | n/a | n/a | n/a |
| 12294 | 12313 | 451434 | GCCAGGCCTAGGGATCTGCA | 35 | 741 | n/a | n/a | n/a |

TABLE 15

Inhibition of murine DMPK RNA transcript in mouse primary hepatocytes by 5-10-5 gapmers targeting SEQ ID NO: 800

| Murine Target Start Site | Murine Target Stop Site | ISIS No | Sequence | % inhibition | SEQ ID NO. | Human Target Start Site | Human Target Stop Site | Mismatches |
|---|---|---|---|---|---|---|---|---|
| 330 | 349 | 451365 | GGAAGCACGACACCTCGCCT | 67 | 742 | 535 | 554 | 1 |
| 662 | 681 | 451369 | CCTCACCATTCCATCAGGCT | 81 | 743 | n/a | n/a | n/a |
| 881 | 900 | 451372 | CGGCAGCGACAAGTGTTCCC | 90 | 744 | n/a | n/a | n/a |
| 1217 | 1236 | 451377 | GTCTCTGAAGGCCATGCAGC | 69 | 745 | 1407 | 1426 | 3 |
| 1329 | 1348 | 451379 | CAGCCACTTGATCCGGTGGG | 62 | 746 | n/a | n/a | n/a |
| 1342 | 1361 | 451380 | AGGTCGGCCTCTTCAGCCAC | 74 | 747 | n/a | n/a | n/a |
| 1494 | 1513 | 451381 | GTTGGCTGGAGAAGTTCTGG | 39 | 748 | 1678 | 1697 | 2 |
| 1598 | 1617 | 451382 | CCCCGTGATGGCTGCGGCTC | 54 | 749 | 1782 | 1801 | 3 |
| 1644 | 1663 | 451383 | GGCCATCTAGATGGGAAGGT | 21 | 517 | 1828 | 1847 | 0 |
| 1741 | 1760 | 451384 | AGGCCAGGCCTAGGGATCCT | 39 | 750 | 1925 | 1944 | 1 |

TABLE 16

Inhibition of murine DMPK RNA transcript in mouse primary hepatocytes by 5-10-5 gapmers targeting SEQ ID NOs: 5-8 and 793-799

| Murine Target Start Site | Murine Target Stop Site | Murine Target SEQ ID NO | ISIS No | Sequence | % inhibition | SEQ ID NO. | Human Target Start Site | Human Target Stop Site | Mismatches |
|---|---|---|---|---|---|---|---|---|---|
| 324 | 343 | 5 | 451410 | GGCGCGGTGCCCCAGCCTGG | 67 | 751 | n/a | n/a | n/a |
| 485 | 504 | 5 | 451411 | GTCCTGGCCCCACCAGCGGG | 66 | 752 | 1873 | 1892 | 1 |
| 534 | 553 | 5 | 451412 | CCAGGCCTAGGAATCCTGGC | 17 | 753 | 1922 | 1941 | 2 |
| 547 | 566 | 5 | 451413 | GCGCCTCGGATAGCCAGGCC | 51 | 754 | n/a | n/a | n/a |
| 594 | 613 | 5 | 451414 | CCCAGTGTGGCGCAGCAGCC | 65 | 755 | n/a | n/a | n/a |
| 393 | 412 | 6 | 451402 | GTGTTTCATCTTCACCACCG | 80 | 756 | 462 | 481 | 3 |
| 1475 | 1494 | 7 | 451390 | AGGTCAGCCTCTTCAGCCAC | 60 | 757 | n/a | n/a | n/a |
| n/a | n/a | n/a | 451425 | GGCCATATGGGAAGGTGGAT | 48 | 758 | 1824 | 1843 | 0 |
| 1763 | 1782 | 8 | 451418 | GGAGGATTTGGCGAGAAGCA | 48 | 759 | n/a | n/a | n/a |
| 1032 | 1051 | 793 | 451403 | CGAAGTCTGCCCCACCTCGA | 58 | 760 | n/a | n/a | n/a |
| 1042 | 1061 | 793 | 451404 | GTGGCACCCTCGAAGTCTGC | 72 | 761 | n/a | n/a | n/a |
| 217 | 236 | 794 | 451400 | GGGTCCATTGTAAGGAAGCT | 4 | 762 | n/a | n/a | n/a |
| 754 | 773 | 794 | 451401 | GGTGCCCACAGCCACCAGGG | 82 | 763 | 888 | 907 | 1 |
| 322 | 341 | 795 | 451406 | TCCATGGCAGTGAGCCGGTC | 55 | 764 | 1319 | 1338 | 1 |
| 523 | 542 | 795 | 451407 | GGGACCACTTGATCCGGTGG | 63 | 765 | n/a | n/a | n/a |
| 534 | 553 | 795 | 451408 | GGATCAGAGTTGGGACCACT | 0 | 766 | n/a | n/a | n/a |
| 492 | 511 | 796 | 451416 | CCCCGTGATGGCTGCGGTTC | 49 | 767 | n/a | n/a | n/a |
| 469 | 488 | 797 | 451409 | GTGTGTCCTCATACCCCGCC | 60 | 768 | n/a | n/a | n/a |
| 629 | 648 | 798 | 451421 | GCACCCTCGAAGTCTCGACC | 72 | 769 | n/a | n/a | n/a |
| 854 | 873 | 799 | 451426 | GCTCTGAAGGCCATGCAGCA | 52 | 770 | n/a | n/a | n/a |

Example 9: Dose-Dependent Antisense Inhibition of Murine DMPK in Mouse Primary Hepatocytes Several of the antisense oligonucleotides exhibiting in vitro inhibition of DMPK in mouse primary hepatocytes (see Example 8) were tested at various doses. Cells were plated at a density of 35,000 cells per well and transfected using electroporation with 1,000 nM, 2,000 nM, 4,000 nM, 8,000 nM, and 16,000 nM concentrations of each antisense oligonucleotide. After approximately 16 hours, RNA was isolated from the cells and DMPK transcript levels were measured by quantitative real-time PCR using primer probe set RTS3181 (forward sequence GACATATGCCAAGATTGTGCACTAC, designated herein as SEQ ID NO: 771; reverse sequence CACGAATGAGGTCCTGAGCTT, designated herein as SEQ ID NO: 772; probe sequence AACACTTGTCGCTGCCGCTGGCX, designated herein as SEQ ID NO: 773). DMPK transcript levels were normalized to total RNA content, as measured by RIBOGREEN®. Results are presented in Table 17 as percent inhibition of DMPK, relative to untreated control cells.

The majority of the tested antisense oligonucleotides demonstrated dose-dependent inhibition of DMPK mRNA levels under the conditions specified above.

TABLE 17

Dose-dependent antisense inhibition of murine DMPK in mouse primary hepatocytes

| ISIS No | 1,000 nM | 2,000 nM | 4,000 nM | 8,000 nM | 16,000 nM | $IC_{50}$ (nM) |
|---|---|---|---|---|---|---|
| 451369 | 33 | 59 | 78 | 87 | 94 | 1.57 |
| 451371 | 60 | 77 | 84 | 90 | 91 | 0.24 |
| 451373 | 53 | 62 | 82 | 89 | 92 | 0.74 |
| 451374 | 33 | 42 | 76 | 88 | 94 | 2.00 |
| 451375 | 43 | 62 | 81 | 89 | 88 | 1.05 |
| 451378 | 39 | 79 | 80 | 87 | 94 | 0.87 |
| 451385 | 22 | 57 | 80 | 78 | 93 | 2.01 |
| 451393 | 49 | 63 | 86 | 80 | 80 | 0.59 |
| 451397 | 63 | 75 | 74 | 81 | 92 | 0.22 |
| 451398 | 29 | 72 | 84 | 83 | 90 | 1.29 |
| 451399 | 27 | 53 | 81 | 68 | 80 | 2.07 |
| 451401 | 34 | 71 | 87 | 86 | 92 | 1.12 |
| 451402 | 34 | 69 | 75 | 86 | 74 | 1.14 |

Example 10: Antisense Inhibition of Human Alpha1 Skeletal Actin in HepG2 Cells Antisense oligonucleotides targeted to a human alpha1 skeletal actin nucleic acid, a gene which may carry an expanded CTG repeat capable of causing symptoms of DM1 when inserted into mouse models, were tested for their effect on alpha1 actin RNA transcript in vitro. Cultured HepG2 cells at a density of 20,000 cells per well were transfected using electroporation with 10,000 nM antisense oligonucleotide. After approximately 24 hours, RNA was isolated from the cells and alpha1 actin RNA transcript levels were measured by quantitative real-time PCR. Alpha1 actin RNA transcript levels were adjusted according to total RNA content, as measured by RIBOGREEN®. Results are presented as percent inhibition of alpha1 actin, relative to untreated control cells.

The antisense oligonucleotides in Table 18 are 5-10-5 gapmers, where the gap segment comprises ten 2'-deoxynucleosides and each wing segment comprises five 2'-MOE nucleosides. The internucleoside linkages throughout each gapmer are phosphorothioate (P=S) linkages. All cytosine residues throughout each gapmer are 5-methylcytosines. ‘Target start site’ indicates the 5'-most nucleoside to which the antisense oligonucleotide is targeted. ‘Target stop site’ indicates the 3'-most nucleoside to which the antisense oligonucleotide is targeted. All the antisense oligonucleotides listed in Table 18 target SEQ ID NO: 801 (GENBANK Accession No. NM_001100.3).

The tested antisense oligonucleotide sequences demonstrated dose-dependent inhibition of alpha 1 actin mRNA levels under the conditions specified above.

TABLE 18

Inhibition of human alpha 1 actin RNA transcript in HepG2 cells by 5-10-5 gapmers targeting SEQ ID NO: 801

| Target Start Site | Target Stop Site | ISIS No | Sequence | % inhibition | SEQ ID NO. |
|---|---|---|---|---|---|
| 16 | 35 | 445205 | AGCGAGGCTTCACTTGGCGC | 74 | 774 |
| 20 | 39 | 190403 | GGGAAGCGAGGCTTCACTTG | 75 | 775 |
| 1028 | 1047 | 190401 | GCGGTCAGCGATCCCAGGGT | 78 | 776 |
| 1058 | 1077 | 445225 | GGGTGCCAGCGCGGTGATCT | 73 | 777 |
| 1320 | 1339 | 445231 | TGTTACAAAGAAAGTGACTG | 74 | 778 |
| 1339 | 1358 | 445232 | CGATGGCAGCAACGGAAGTT | 96 | 779 |
| 1348 | 1367 | 445233 | GTCAGTTTACGATGGCAGCA | 100 | 780 |
| 1417 | 1436 | 445235 | CAGGGCTTTGTTTCGAAAAA | 91 | 781 |
| 1430 | 1449 | 445236 | CCATTTTCTTCCACAGGGCT | 99 | 782 |
| 1447 | 1466 | 445237 | ATGCTTCTTCAAGTTTTCCA | 97 | 783 |
| 1460 | 1479 | 445238 | CAGAATGACTTTAATGCTTC | 95 | 784 |

Example 11: Dose-Dependent Antisense Inhibition of Human Alpha1 Actin in HepG2 Cells Several of the antisense oligonucleotides exhibiting in vitro inhibition of alpha1 actin in HepG2 cells (see Example 8) were tested at various doses. Cells were plated at a density of 20,000 cells per well and transfected using electroporation with 625 nM, 1,250 nM, 2,500 nM, 5,000 nM, 10,000 nM and 20,000 nM concentrations of each antisense oligonucleotide. After approximately 16 hours, RNA was isolated from the cells and alpha1 actin RNA transcript levels were measured by quantitative real-time PCR using primer probe set RTS3154 (forward sequence CCACCGCAAATGCTTCTAGAC, designated herein as SEQ ID NO: 785; reverse sequence CCCCCCCATTGAGAAGATTC, designated herein as SEQ ID NO: 786; probe sequence CTCCACCTCCAGCACGCGACTTCTX, designated herein as SEQ ID NO: 787). Alpha1 actin RNA transcript levels were normalized to total RNA content, as measured by RIBOGREEN®. Results are presented in Table 19 as percent inhibition of alpha1 actin, relative to untreated control cells.

Several of the antisense oligonucleotides demonstrated dose-dependent inhibition of alpha 1 actin mRNA levels under the conditions specified above.

TABLE 19

Dose-dependent antisense inhibition of human alpha1 actin in HepG2 cells

| ISIS No. | 625 nM | 1,250 nM | 2,500 nM | 5,000 nM | 10,000 nM | 20,000 nM | $IC_{50}$ (nM) |
|---|---|---|---|---|---|---|---|
| 445233 | 21 | 72 | 63 | 82 | 96 | 83 | 1.1 |
| 445236 | 26 | 68 | 82 | 91 | 90 | 91 | 0.8 |
| 445237 | 36 | 59 | 76 | 84 | 83 | 90 | 0.8 |
| 445232 | 14 | 42 | 54 | 59 | 80 | 91 | 2.6 |
| 445238 | 27 | 43 | 54 | 73 | 76 | 90 | 2.0 |
| 445235 | 26 | 52 | 29 | 58 | 59 | 24 | 0.7 |
| 190403 | 25 | 29 | 36 | 25 | 61 | 54 | 11.9 |
| 190401 | 17 | 14 | 40 | 68 | 76 | 72 | 3.9 |

TABLE 19-continued

Dose-dependent antisense inhibition of human alpha1 actin in HepG2 cells

| ISIS No. | 625 nM | 1,250 nM | 2,500 nM | 5,000 nM | 10,000 nM | 20,000 nM | $IC_{50}$ (nM) |
|---|---|---|---|---|---|---|---|
| 445225 | 25 | 23 | 49 | 28 | 52 | 50 | 15.8 |
| 445205 | 26 | 31 | 34 | 28 | 55 | 36 | 7.6 |
| 445231 | 30 | 25 | 39 | 26 | 42 | 36 | >20.0 |

Example 12: In Vivo Antisense Inhibition of Human Alpha1 Actin by Intramuscular Administration in Transgenic Mice To test the effect of antisense inhibition for the treatment of myotonic dystrophy, an appropriate mouse model was required. The $HSA^{LR}$ mouse model is an established model for DM1 (Mankodi, A. et al. Science. 289:1769, 2000). The mice carry a human skeletal actin (hACTA1) transgene with 220 CTG repeats inserted in the 3' UTR of the gene. The hACTA1-CUGexp transcript accumulates in nuclear foci in skeletal muscles and results in myotonia similar to that in human DM1 (Mankodi, A. et al. Mol. Cell 10:35, 2002; Lin, X. et al. Hum. Mol. Genet. 15:2087, 2006). Hence, it was expected that amelioration of DM1 symptoms in the $HSA^{LR}$ mouse by antisense inhibition of the hACTA1 transgene would predict amelioration of similar symptoms in human patients by antisense inhibition of the DMPK transcript.

HSA (human skeletal actin) LR (long repeat) DM1 mice were generated by insertion in FVB/N mice of a transgene with 250 CUG repeats in the 3' UTR of human skeletal actin. The transgene is expressed in the mice as a CUG repeat RNA, which is retained in the nucleus, forming nuclear inclusions or foci, similar to that seen in human tissue samples of patients with myotonic dystrophy (DM1).

ISIS 190403 and ISIS 445238, which demonstrated statistically significant dose-dependent inhibition in vitro (see Example 11), were evaluated for their ability to reduce human alpha1 actin RNA transcript in vivo.

Treatment $HSA^{LR}$ mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

The mice were divided into two treatment groups. The two groups received direct intramuscular injections of ISIS 190403 or ISIS 445238 at a dose of 0.8 nM into the tibialis anterior muscle on one side. The contralateral tibialis anterior muscle in each mouse received a single dose intramuscular injection of PBS. The PBS-injected muscle acted as the control.

Inhibition of Alpha1 Actin RNA

Twenty four hours after the final dose, the animals were sacrificed and tissue from the tibialis anterior muscles of both sides was isolated. RNA was isolated for real-time PCR analysis of alpha1 actin and normalized to 18s RNA. As presented in Table 20, treatment with antisense oligonucleotides reduced human alpha1 actin RNA transcript expression. The results are expressed as percent inhibition of alpha1 actin transcript, relative to the PBS control.

The results indicate that treatment with ISIS 190403 and ISIS 445238 resulted in inhibition of alpha 1 actin RNA levels in the mice.

TABLE 20

Percent inhibition of human alpha1 actin RNA transcript in $HSA^{LR}$ mice

| ISIS No. | % inhibition |
|---|---|
| 190403 | 38 |
| 445238 | 40 |

Example 13: Dose Dependent Antisense Inhibition of Human Alpha1 Actin by Intramuscular Administration in Transgenic Mice ISIS 445236, which demonstrated statistically significant dose-dependent inhibition in vitro (see Example 11), was evaluated for its ability to reduce human alpha1 actin RNA transcript in vivo.

Treatment $HSA^{LR}$ mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

The mice were divided into three treatment groups. The groups received direct intramuscular injections of ISIS 445236 at doses of 0.2 nM, 0.4 nM or 0.8 nM into the tibialis anterior muscle of one side. The contralateral tibialis anterior muscle in each mouse received a single dose intramuscular injection of PBS. The PBS-injected muscle acted as the control.

Inhibition of Alpha1 Actin RNA

Twenty four hours after the final dose, the animals were sacrificed and tissue from the tibialis anterior muscles of both sides was isolated. RNA was isolated for real-time PCR analysis of alpha1 actin and normalized to 18s RNA. As presented in Table 21, treatment with ISIS 445236 reduced human alpha1 actin RNA transcript expression at all dosages. The results are expressed as percent inhibition of alpha1 actin transcript, relative to the control.

The results indicate that treatment with ISIS 445236 resulted in significant inhibition of alpha 1 actin mRNA levels under the conditions specified above.

TABLE 21

Inhibition of human alpha1 actin RNA transcript by ISIS 445236 in $HSA^{LR}$ mice

| Dose (nM) | % inhibition |
|---|---|
| 0.2 | 70 |
| 0.4 | 54 |
| 0.8 | 78 |

Assessment of Myotonia by Electromyography

Myotonia refers to repetitive action potential that is due to delayed relaxation of muscle fibers. This phenomenon is observed in patients of myotonic dystrophy as well as in the $HSA^{LR}$ mice. When the EMG needle is inserted into a myotonic muscle, the electrical activity is prolonged for up to several seconds past when the insertional activity should normally cease. The frequency of myotonic discharges ranges from 50 to 100 impulses per second.

Myotonia was measured via electromyography and graded in the following manner: grade 0 refers to no myotonia elicited by any needle insertion (0%); grade 1 refers to myotonia elicited by less than 50% needle insertions; grade 2 refers to myotonia elicited by more than 50% needle insertions; and grade 3 refers to mytonia elicited by 100% needle insertions.

Before electromyography, mice were anesthetized by using i.p. a cocktail of 100 mg/kg ketamine, 10 mg/kg xylazine, and 3 mg/kg acepromazine. Electromyography on left and right quadriceps, left and right gastrocnemius muscles, left and right tibialis anterior muscles and lumbar paraspinals muscles was performed as previously described (Kanadia et al, 2003, Science, 302:1978-1980) by using 30 gauge concentric needle electrodes and a minimum of 10 needle insertions for each muscle. The data is presented in Table 22 as the average myotonia grade observed in four mice of each group and demonstrates significant reduction of myotonia in mice treated with ISIS 445236.

TABLE 22

Average reduction of myotonia in various muscles of antisense oligonucleotide-treated $HSA^{LR}$ mice

| Treatment | Dose (nM) | Myotonia grade |
|---|---|---|
| PBS | | 2.7 |
| ISIS | 0.2 | 1.3 |
| 455236 | 0.4 | 1.0 |
| | 0.8 | 1.0 |

Correction of Alternative Splicing

In DM1/$HSA^{LR}$ mouse model, the accumulation of expanded CUG RNA in the nucleus leads to the sequestration of poly (CUG)-binding proteins, such as Muscleblind-like 1 (MBLN1) (Miller, J. W. et al. EMBO J. 19:4439, 2000). The splicing factor MBNL1, which controls alternative splicing of the Serca1 gene is sequestered in expanded CUG foci. This triggers dysregulation of the alternative splicing of this gene. To evaluate the effect of antisense inhibition of human alpha 1 actin on such alternative splicing, total RNA was purified from the tibialis anterior, gastrocnemius, and quadriceps muscle using RNeasy Lipid Tissue Mini Kit (Qiagen), according to the manufacturer's instructions. RT-PCR was performed with the SuperScript III One-Step RT-PCR System and Platinum Taq Polymerase (Invitrogen), using gene-specific primers for cDNA synthesis and PCR amplification. The forward and reverse primers for Serca-1 have been described in Bennett and Swayze (Annu. Rev. Pharmacol. 2010; 50:259-93). PCR products were separated on agarose gels, stained with SybrGreen I Nucleic Acid Gel Stain (Invitrogen), and imaged using a Fujifilm LAS-3000 Intelligent Dark Box.

The PCR products of Serca1 splicing in the PBS control demonstrated exon 22 exclusion as a result of dysregulation of MBLN1. Treatment with ISIS 445236 resulted in exon 22 inclusion and normalization of alternative splicing of the Serca1 gene in the tibialis anterior, gastrocnemius, and quadriceps muscles.

Therefore, antisense inhibition of alpha1 actin corrected Serca1 splicing dysregulation, which indicates that treatment with antisense oligonucleotide reduced accumulation of CUGexp in the nuclear foci. Reduced accumulation of CUGexp in the nuclear foci corrects MBLN1 sequestration thereby allowing normal splicing to occur.

Example 14: In Vivo Antisense Inhibition of Human Alpha1 Actin by Subcutaneous Administration in Transgenic Mice ISIS 190403, ISIS 445236 and ISIS 445238 were evaluated for their ability to reduce human alpha1 actin RNA transcript in vivo.

Treatment $HSA^{LR}$ mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

The mice were divided into four treatment groups. The first three groups received subcutaneous injections of ISIS 190403, ISIS 445236 or ISIS 445238 at a dose of 25 mg/kg twice per week for 4 weeks. The fourth group received subcutaneous injections of PBS twice weekly for 4 weeks. The PBS-injected group served as the control group to which the oligonucleotide-treated group was compared.

Inhibition of Alpha1 Actin RNA

Twenty four hours after the final dose, the animals were sacrificed and tissue from the quadriceps muscles (left and right), gastrocnemius muscles (left and right), and tibialis anterior muscles (left and right) was isolated. RNA was isolated for real-time PCR analysis of alpha1 actin and normalized to 18s RNA. As presented in Table 23, treatment with antisense oligonucleotides reduced human alpha1 actin RNA transcript expression. The results are expressed as percent inhibition of alpha1 actin transcript, relative to the control.

Both ISIS 445236 and ISIS 445238 demonstrated significant inhibition of alpha1 actin mRNA levels under the conditions specified above.

TABLE 23

Percent inhibition of human alpha1 actin RNA transcript in $HSA^{LR}$ mice

| Muscle Type | ISIS 190403 | ISIS 445236 | ISIS 445238 |
|---|---|---|---|
| Quadriceps | 16 | 83 | 72 |
| Gastrocnemius | 0 | 85 | 73 |
| Tibialis anterior | 2 | 81 | 71 |

Fluorescence In Situ Hybridization of Alpha1 Actin in Muscles

Frozen muscle tissue sections were fixed in fresh 3% paraformaldehyde in PBS solution for 15-20 minutes, after which they were rinsed twice with PBS for 5 minutes. The nuclei were permeabilized with 0.5% Triton X-100 for 5 minutes after which the tissue was blocked with normal goat serum for 30 minutes. The sections were incubated a 2'-O-methyl RNA targeted to alpha1 actin that is 5'-labeled with Texas Red (Integrated DNA Technologies). The sections were counter-stained with DAPI to label the nuclei. The sections were mounted and viewed with a standard fluorescence microscope. Image acquisition was by Metavue software and deconvolution was achieved by Autoquant software.

All muscle tissue sections from mice treated with ISIS 445236 and ISIS 445238 displayed reduced fluorescent intensity of alpha1 actin signal at the ribonuclear foci, indicating antisense inhibition of human alpha1 actin mRNA and reduction of the RNA in the nuclear foci.

Assessment of Myotonia by Electromyography

Myotonia refers to repetitive action potential that is due to delayed relaxation of muscle fibers. This phenomenon is observed in patients of myotonic dystrophy as well as in the $HSA^{LR}$ mice. When the EMG needle is inserted into a myotonic muscle, the electrical activity is prolonged for up to several seconds past when the insertional activity should normally cease. The frequency of myotonic discharges ranges from 50 to 100 impulses per second.

Myotonia may be measured via electromyography and is graded in the following manner: grade 0 refers to no myotonia elicited by any needle insertion (0%); grade 1 refers to myotonia elicited by less than 50% needle insertions; grade 2 refers to myotonia elicited by more than 50% needle insertions; and grade 3 refers to mytonia elicited by 100% needle insertions.

Before electromyography, mice were anesthetized by using i.p. 100 mg/kg ketamine, 10 mg/kg xylazine, and 3 mg/kg acepromazine or 250 mg/kg 2,2,2-tribromoethanol. Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 24 as the average myotonia grade observed in four mice of each group and demonstrates significant reduction of myotonia in mice treated with ISIS 445236 and ISIS 445238.

TABLE 24

Average reduction of myotonia in various muscles of antisense oligonucleotide-treated $HSA^{LR}$ mice

| | PBS | ISIS 190403 | ISIS 445236 | ISIS 445238 |
|---|---|---|---|---|
| Left quadriceps | 3.00 | 3.00 | 0.00 | 0.25 |
| Right quadriceps | 3.00 | 3.00 | 0.00 | 0.00 |
| Left gastrocnemius | 3.00 | 3.00 | 0.00 | 0.25 |
| Right gastrocnemius | 3.00 | 3.00 | 0.00 | 0.25 |
| Left Tibialis anterior | 2.75 | 2.50 | 0.00 | 0.00 |
| Right Tibialis anterior | 2.75 | 2.50 | 0.00 | 0.00 |
| Lumbar paraspinals | 3.00 | 3.00 | 0.00 | 0.75 |

Correction of Alternative Splicing

The splicing factor MBNL1, which controls Serca1 splicing, m-Titin splicing, CIC-1 chloride channel gene (Clen1) splicing, and Zasp splicing, is sequestered in expanded CUG foci. MBNL1 sequestration triggers dysregulated splicing in each of these genes. To evaluate the effect of antisense inhibition of human alpha 1 actin on splicing, total RNA was purified from the tibialis anterior, gastrocnemius, and quadriceps muscle and RT-PCR was performed, as described in Example 13. The forward and reverse primers for Serca-1, m-Titin, Clen1, and ZASP have been described in Bennett and Swayze, Annu. Rev. Pharmacol. 2010; 50:259-93.

In PBS treated $HSA^{LR}$ mice, Serca1 splicing is dysregulated as demonstrated by exon 22 exclusion. Treatment with each of ISIS 445236 and ISIS 445238 resulted in exon 22 inclusion and normalization of alternative splicing of the Serca1 gene in the tibialis anterior, gastrocnemius, and quadriceps muscles.

In PBS treated $HSA^{LR}$ mice, m-Titin splicing is dysregulated as demonstrated by exon 5 inclusion. Treatment with each of ISIS 445236 and ISIS 445238 resulted in skipping of exon 5 and normalization of alternative splicing of the m-Titin gene in the tibialis anterior, gastrocnemius, and quadriceps muscles.

In PBS treated $HSA^{LR}$ mice, Clen1 splicing is dysregulated as demonstrated by exon 7a inclusion. Treatment with each of ISIS 445236 and ISIS 445238 resulted in skipping of exon 7a and normalization of alternative splicing of the Clen1 gene in the tibialis anterior, gastrocnemius, and quadriceps muscles.

In PBS treated $HSA^{LR}$ mice, Zasp splicing is dysregulated as demonstrated by exon 11 inclusion. Treatment with each of ISIS 445236 and ISIS 445238 resulted in skipping of exon 11 and normalization of alternative splicing of the Zasp gene in the tibialis anterior, gastrocnemius, and quadriceps muscles.

Therefore, antisense inhibition of alpha1 actin corrected Serca1, m-Titin, Clon1, and Zasp splicing dysregulation, which indicates that treatment with antisense oligonucleotide reduced accumulation of CUGexp in the nuclear foci. Reduced accumulation of CUGexp in the nuclear foci correct MBLN1 sequestration thereby allowing normal splicing to occur.

Example 15: In Vivo Antisense Inhibition of Human Alpha1 Actin in Transgenic Mice Antisense inhibition of human alpha1 actin RNA transcript by ISIS 445236 and ISIS 445238 on myotonia in $HSA^{LR}$ mice was further evaluated.

Treatment $HSA^{LR}$ mice were divided into three treatment groups. The first two groups received subcutaneous injections of ISIS 445236 or ISIS 445238 at a dose of 25 mg/kg twice per week for 2 weeks. The third group received subcutaneous injections of PBS twice per week for 2 weeks. The PBS-injected group served as the control group to which the oligonucleotide-treated group was compared.

Inhibition of Alpha1 Actin RNA

Twenty four hours after the final dose, the animals were sacrificed and tissue from the quadriceps muscles, gastrocnemius muscles, and tibialis anterior muscles was isolated. RNA was isolated for real-time PCR analysis of alpha1 actin and normalized to 18s RNA. As presented in Table 25, treatment with antisense oligonucleotides reduced human alpha1 actin RNA transcript expression. The results are expressed as percent inhibition of alpha1 actin transcript, relative to the PBS control.

Both ISIS 445236 and ISIS 445238 demonstrated significant inhibition of alpha1 actin mRNA levels under the conditions specified above.

TABLE 25

Percent inhibition of human alpha1 actin RNA transcript in $HSA^{LR}$ mice

| Muscle Type | ISIS 445236 | ISIS 445238 |
|---|---|---|
| Quadriceps | 61 | 64 |
| Gastrocnemius | 68 | 37 |
| Tibialis anterior | 68 | 41 |

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 26 as the average myotonia grade observed in four mice of each group and demonstrates significant reduction of myotonia in mice treated with ISIS 445236 and ISIS 445238.

TABLE 26

| Average reduction of myotonia in various muscles of antisense oligonucleotide-treated $HSA^{LR}$ mice | PBS | ISIS 445236 | ISIS 445238 |
|---|---|---|---|
| Left quadriceps | 3.00 | 0.00 | 1.75 |
| Right quadriceps | 3.00 | 0.00 | 1.75 |
| Left gastrocnemius | 3.00 | 0.25 | 1.5 |
| Right gastrocnemius | 3.00 | 0.25 | 1.00 |
| Left Tibialis anterior | 2.75 | 0.00 | 0.00 |
| Right Tibialis anterior | 2.75 | 0.00 | 0.00 |
| Lumbar paraspinals | 3.00 | 0.50 | 2.00 |

Correction of Alternative Splicing

To evaluate the effect of ISIS 190401 on alternative splicing of Serca1, total RNA purified from the tibialis anterior gastrocnemius, and quadriceps muscle was analyzed in a procedure similar to that described in Example 13.

In PBS treated $HSA^{LR}$ mice, Serca1 splicing is dysregulated as demonstrated by exon 22 exclusion, as a result of MBLN1 dysregulation. Treatment with each of ISIS 445236 and ISIS 445238 resulted in near-complete inclusion and normalization of alternative splicing of exon 22 of the Serca1 gene in the tibialis anterior and quadriceps muscles.

Therefore, antisense inhibition of alpha1 actin corrected Serca1 splicing dysregulation, which indicates that treatment with antisense oligonucleotide reduced accumulation of CUGexp in the nuclear foci. Reduced accumulation of CUGexp in the nuclear foci correct MBLN1 sequestration thereby allowing normal splicing to occur.

Example 16: Dose-Dependent Antisense Inhibition of Human Alpha1 Actin in Transgenic Mice Dose-dependent inhibition of human alpha1 actin RNA transcript by ISIS 445236 and ISIS 445238 on myotonia in $HSA^{LR}$ mice was evaluated.

Treatment $HSA^{LR}$ mice were subcutaneously injected with ISIS 445236 or ISIS 445238 at doses of 2.5 mg/kg, 8.5 mg/kg or 25.0 mg/kg twice per week for 4 weeks. The control group received subcutaneous injections of PBS twice per week for 4 weeks. The PBS-injected group served as the control group to which the oligonucleotide-treated group was compared.

Inhibition of Alpha1 Actin RNA

Twenty four hours after the final dose, the animals were sacrificed and tissue from the quadriceps muscles (Quad), gastrocnemius muscles (Gastroc), and tibialis anterior muscles (TA) was isolated. RNA was isolated for real-time PCR analysis of alpha1 actin and normalized to 18s RNA. As presented in Table 27, treatment with antisense oligonucleotides reduced human alpha1 actin RNA transcript expression. The results are expressed as percent inhibition of alpha1 actin transcript, relative to the PBS control.

Both the antisense oligonucleotides demonstrated dose-dependent inhibition of alpha1 actin mRNA levels in quadriceps muscles, gastrocnemius muscles, and tibialis anterior muscles under the conditions specified above.

TABLE 27

Dose-dependent inhibition of human alpha1 actin RNA transcript in $HSA^{LR}$ mice

| | mg/kg/wk | Quad | Gastroc | TA |
|---|---|---|---|---|
| ISIS 445236 | 5 | 24 | 36 | 46 |
| | 17 | 53 | 57 | 59 |
| | 50 | 86 | 86 | 90 |
| ISIS 445238 | 5 | 21 | 37 | 3 |
| | 17 | 30 | 39 | 60 |
| | 50 | 59 | 81 | 70 |

Assessment of Myotonia by Electromyography

Electromyography on left and right quadriceps (Quad), left and right gastrocnemius muscles (Gastroc), left and right tibialis anterior (TA) muscles and lumbar paraspinals muscles was performed as previously described (Kanadia et al, 2003, Science, 302:1978-1980) by using 30 gauge concentric needle electrodes and a minimum of 10 needle insertions for each muscle. The data is presented in Table 28 as the average myotonia grade observed in four mice of each group and demonstrates significant dose-dependent reduction of myotonia in mice treated with ISIS 445236 and ISIS 445238.

TABLE 28

Average reduction of myotonia in various muscles of antisense oligonucleotide-treated $HSA^{LR}$ mice

| | mg/kg/wk | Left Quad | Right Quad | Left Gastroc | Right Gastroc | Left TA | Right TA | Lumbar paraspinals |
|---|---|---|---|---|---|---|---|---|
| PBS | — | 3.00 | 3.00 | 3.00 | 3.00 | 2.75 | 2.75 | 3.00 |
| ISIS | 5 | 3.00 | 3.00 | 3.00 | 3.00 | 2.25 | 2.25 | 3.00 |
| 445236 | 17 | 0.75 | 0.75 | 0.75 | 1.00 | 0.00 | 0.00 | 1.75 |
| | 50 | 0.00 | 0.00 | 0.00 | 0.00 | 0.00 | 0.00 | 0.00 |
| ISIS | 5 | 2.75 | 2.75 | 2.50 | 2.50 | 2.00 | 1.75 | 2.75 |
| 445238 | 17 | 3.00 | 3.00 | 2.00 | 2.25 | 0.00 | 0.00 | 2.75 |
| | 50 | 0.75 | 0.75 | 0.25 | 0.25 | 0.00 | 0.00 | 1.00 |

Correction of Alternative Splicing

To evaluate the effect of ISIS 190401 on alternative splicing of Serca1, total RNA purified from the tibialis anterior gastrocnemius, and quadriceps muscle was analyzed in a procedure similar to that described in Example 13.

In PBS treated $HSA^{LR}$ mice, Serca1 splicing is dysregulated as demonstrated by exon 22 exclusion, as a result of MBLN1 dysregulation. Treatment with either ISIS 445236 or ISIS 445238 at doses of 8.5 mg/kg or 25.0 mg/kg twice a week (or 17.0 mg/kg/week and 50.0 mg/kg/week) resulted in complete inclusion and normalization of alternative splicing of exon 22 of the Serca1 gene in all three muscle types.

Therefore, antisense inhibition of alpha1 actin corrected Serca1 splicing dysregulation, which indicates that treatment with antisense oligonucleotide reduced accumulation of CUGexp in the nuclear foci. Reduced accumulation of CUGexp in the nuclear foci correct MBLN1 sequestration thereby allowing normal splicing to occur.

Example 17: In Vivo Antisense Inhibition by an Oligonucleotide Targeting the HSA Coding Region of Human Alpha1 Actin in Transgenic Mice Antisense inhibition of human alpha1 actin RNA transcript by ISIS 190401 (5'-GCGGTCAGCGATCCCAGGGT-3' (SEQ ID NO: 788), target start site 1028 of SEQ ID NO: 1) on myotonia in $HSA^{LR}$ mice was evaluated.

Treatment $HSA^{LR}$ mice received subcutaneous injections of ISIS 190401 at a dose of 25 mg/kg twice per week for 4 weeks. A control group received subcutaneous injections of PBS twice per week for 2 weeks. The PBS-injected group served as the control group to which the oligonucleotide-treated group was compared.

Inhibition of Alpha1 Actin RNA

Twenty four hours after the final dose, the animals were sacrificed and tissue from the quadriceps muscles, gastrocnemius muscles, and tibialis anterior muscles was isolated. RNA was isolated for real-time PCR analysis of alpha1 actin and normalized to 18s RNA. As presented in Table 29, treatment with antisense oligonucleotides reduced human alpha1 actin RNA transcript expression. The results are expressed as percent inhibition of alpha1 actin transcript, relative to the PBS control.

Treatment with ISIS 190401 resulted in significant inhibition of alpha1 actin mRNA levels in quadriceps muscle, gastrocnemius muscle, and tibialis anterior muscle under the conditions specified above.

TABLE 29

Antisense inhibition of human alpha1 actin RNA transcript in $HSA^{LR}$ mice

| Muscle Type | % inhibition |
|---|---|
| Quadriceps | 85 |
| Gastrocnemius | 86 |
| Tibialis anterior | 89 |

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 30 as the average myotonia grade observed in four mice of each group and demonstrates significant reduction of myotonia in mice treated with ISIS 190401.

TABLE 30

Average reduction of myotonia in various muscles of antisense oligonucleotide-treated $HSA^{LR}$ mice

| | PBS | ISIS 190401 |
|---|---|---|
| Left quadriceps | 3.00 | 0.00 |
| Right quadriceps | 3.00 | 0.00 |
| Left gastrocnemius | 3.00 | 0.00 |
| Right gastrocnemius | 3.00 | 0.00 |
| Left Tibialis anterior | 2.50 | 0.00 |
| Right Tibialis anterior | 2.50 | 0.00 |
| Lumbar paraspinals | 3.00 | 0.50 |

Correction of Alternative Splicing

To evaluate the effect of ISIS 190401 on alternative splicing of Serca1, total RNA purified from the tibialis anterior gastrocnemius, and quadriceps muscle was analyzed in a procedure similar to that described in Example 13.

In PBS treated $HSA^{LR}$ mice, Serca1 splicing is dysregulated as demonstrated by exon 22 exclusion, as a result of MBLN1 dysregulation. Treatment with ISIS 190401 resulted in complete inclusion and normalization of alternative splicing of exon 22 of the Serca1 gene in all three muscle types.

Therefore, antisense inhibition of alpha1 actin corrected Serca1 splicing dysregulation, which indicates that treatment with antisense oligonucleotide reduced accumulation of CUGexp in the nuclear foci. Reduced accumulation of CUGexp in the nuclear foci corrects MBLN1 sequestration thereby allowing normal splicing to occur.

Example 18: Duration of Action of Antisense Inhibition by an Oligonucleotide Targeting Human Alpha1 Actin in Transgenic Mice The duration of action of antisense inhibition of human alpha1 actin RNA transcript by ISIS 445236 in $HSA^{LR}$ mice was evaluated.

Treatment $HSA^{LR}$ mice received subcutaneous injections of ISIS 445236 at a dose of 25 mg/kg twice per week for 4 weeks. A control group received subcutaneous injections of PBS twice per week for 2 weeks. The PBS-injected group served as the control group to which the oligonucleotide-treated group was compared. The mice were analyzed 6 weeks after administration of the last dose.

Inhibition of Alpha1 Actin RNA

Six weeks after the final dose, the animals were sacrificed and tissue from the quadriceps muscles, gastrocnemius muscles, and tibialis anterior muscles was isolated. RNA was isolated for real-time PCR analysis of alpha1 actin and normalized to 18s RNA. As presented in Table 31, treatment with ISIS 445236 reduced human alpha1 actin RNA transcript expression, and this effect was sustained at least for 6 weeks. The results are expressed as percent inhibition of alpha1 actin transcript, relative to the PBS control.

Treatment with ISIS 445236 resulted in significant inhibition of alpha1 actin mRNA levels in quadriceps muscle, gastrocnemius muscle, and tibialis anterior muscle under the conditions specified above.

TABLE 31

| Antisense inhibition of human alpha1 actin RNA transcript in $HSA^{LR}$ mice | |
|---|---|
| Muscle Type | % inhibition |
| Quadriceps | 88 |
| Gastrocnemius | 76 |
| Tibialis anterior | 67 |

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 32 as the average myotonia grade observed in four mice of each group and demonstrates significant reduction of myotonia in mice treated with ISIS 445236. Therefore, the effect of antisense inhibition of alpha actin by ISIS 445236 was sustained at least for 6 weeks.

TABLE 32

| Average reduction of myotonia in various muscles of antisense oligonucleotide-treated $HSA^{LR}$ mice | | |
|---|---|---|
| | PBS | ISIS 445236 |
| Left quadriceps | 3.00 | 0.00 |
| Right quadriceps | 3.00 | 0.00 |
| Left gastrocnemius | 3.00 | 0.00 |
| Right gastrocnemius | 3.00 | 0.00 |
| Left Tibialis anterior | 2.50 | 0.00 |
| Right Tibialis anterior | 2.50 | 0.00 |
| Lumbar paraspinals | 3.00 | 0.00 |

Example 19: In Vivo Effect of Antisense Inhibition of mRNA with CUG Repeats by Intramuscular Administration in Transgenic Mice The effect of antisense inhibition of mRNA transcripts containing multiple CUG repeats on myotonia in $HSA^{LR}$ mice was evaluated. Three antisense oligonucleotides targeting the CUG repeats and with varying lengths were assayed for their effectiveness in inhibiting myotonia in the mice. ISIS 444745 (AGCAGCAGCAGCAGCAGCAGCAGCA (SEQ ID NO: 789) is a uniform 2'-O-methoxyethyl oligonucleotide, 25 nucleotides in length and with a phosphorothioate backbone. ISIS 444746 (AGCAGCAGCAGCAGCAGCAG (SEQ ID NO: 790) is a uniform 2'-O-methoxyethyl oligonucleotide, 20 nucleotides in length and with a phosphorothioate backbone. ISIS 444749 (GCAGCAGCAGCAGCA (SEQ ID NO: 791) is a uniform 2'-O-methoxyethyl oligonucleotide, 15 nucleotides in length and with a phosphorothioate backbone. ISIS 445236 was included in the assay as a positive control.

Treatment $HSA^{LR}$ mice were divided into three treatment groups. The groups received direct intramuscular injections of ISIS 444745, ISIS 444746 or ISIS 444749 at a dose of 0.4 nM into the tibialis anterior muscle. The contralateral tibialis anterior muscle in each mouse received a single dose intramuscular injection of PBS. The PBS-injected muscle acted as the control.

Inhibition of Alpha1 Actin RNA

Twenty four hours after the final dose, the animals were sacrificed and tissue from the tibialis anterior (left and right) was isolated. RNA was isolated for real-time PCR analysis of alpha1 actin and normalized to 18s RNA. As presented in Table 33, only treatment with ISIS 444745 reduced human alpha1 actin RNA transcript expression. The results are expressed as percent inhibition of alpha1 actin transcript, relative to the PBS control.

TABLE 33

| Percent inhibition of human alpha1 actin RNA transcript in $HSA^{LR}$ mice | |
|---|---|
| ISIS No. | % inhibition |
| 444745 | 51 |
| 444746 | 0 |
| 444749 | 12 |

Example 20: In Vivo Dose Dependent Inhibition of mRNA with CUG Repeats by Intramuscular Administration in Transgenic Mice ISIS 444745 and ISIS 444746 were further evaluated for their ability to reduce human alpha 1 actin mRNA in vivo.

Treatment $HSA^{LR}$ mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

The mice were divided into 6 treatment groups. Three of the groups received direct intramuscular injections of ISIS 444745 at doses of 0.2 nM, 0.5 nM, or 1.0 nM into the tibialis anterior muscle on one side. Another three groups direct intramuscular injections of ISIS 444746 at doses of 0.2 nM, 0.5 nM, or 1.0 nM into the tibialis anterior muscle on one side. The contralateral tibialis anterior muscle in each mouse received a single dose intramuscular injection of PBS. The PBS-injected muscle acted as the control for the corresponding muscle treated with ISIS oligonucleotide.

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 34 as the average myotonia grade observed in four mice of each group and demonstrates significant reduction of myotonia in mice treated with either ISIS 444745 or ISIS 444746. The effect of antisense inhibition of alpha actin by ISIS 444745 and 444746 was sustained at least for 6 weeks.

TABLE 34

| Dose-dependent reduction of myotonia in muscles of antisense oligonucleotide-treated $HSA^{LR}$ mice | | | |
|---|---|---|---|
| | 0.2 nM | 0.5 nM | 1.0 nM |
| PBS | 3.00 | 3.00 | 2.33 |
| ISIS 444745 | 1.67 | 1.00 | 0.33 |

TABLE 34-continued

| Dose-dependent reduction of myotonia in muscles of antisense oligonucleotide-treated $HSA^{LR}$ mice | | | |
|---|---|---|---|
| | 0.2 nM | 0.5 nM | 1.0 nM |
| PBS | 2.50 | 2.00 | 3.00 |
| ISIS444746 | 2.00 | 0.00 | 1.00 |

Example 21: In Vivo Effect of Antisense Inhibition of mRNA with CUG Repeats by Subcutaneous Administration in Transgenic Mice The effect of antisense inhibition of mRNA transcripts containing multiple CUG repeats on myotonia in $HSA^{LR}$ mice was evaluated. ISIS 445236 was included in the assay as a positive control.

Treatment $HSA^{LR}$ mice were divided into five treatment groups. The first three groups received subcutaneous injections of ISIS 444745, ISIS 444746 or ISIS 444749 at a dose of 25 mg/kg twice per week for 4 weeks. The fourth group received subcutaneous injections of PBS twice per week for 4 weeks. The fifth group received subcutaneous injections of ISIS 445236 at a dose of 25 mg/kg twice per week for 4 weeks. The PBS-injected group served as the control group to which the oligonucleotide-treated group was compared.

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 35 as the average myotonia grade observed in four mice of each group.

Treatment with ISIS 445236 led to significant reduction in myotonia. Treatment with ISIS 444745 and ISIS 444746 also resulted in reduced myotonia in some of the tissues tested.

TABLE 35

| Average reduction of myotonia in various muscles of antisense oligonucleotide-treated $HSA^{LR}$ mice | | | | | |
|---|---|---|---|---|---|
| | PBS | ISIS 444745 | ISIS 444746 | ISIS 444749 | ISIS 445236 |
| Left quadriceps | 3.00 | 3.00 | 3.00 | 3.00 | 0.00 |
| Right quadriceps | 3.00 | 3.00 | 3.00 | 3.00 | 0.00 |
| Left gastrocnemius | 3.00 | 2.75 | 3.00 | 3.00 | 0.00 |
| Right gastrocnemius | 3.00 | 2.75 | 2.75 | 3.00 | 0.00 |
| Left Tibialis anterior | 3.00 | 2.25 | 2.75 | 2.75 | 0.00 |
| Right Tibialis anterior | 3.00 | 2.25 | 2.50 | 2.75 | 0.00 |
| Lumbar paraspinals | 3.00 | 3.00 | 3.00 | 3.00 | 0.00 |

Example 22: Dose-Dependent Inhibition of Long CUG Repeat mRNA ($HSA^{LR}$ Mice) and a Short CUG Repeat ($HSA^{SR}$ Mice) by Subcutaneous Administration in Transgenic Mice Dose-dependent inhibition of mRNA transcripts containing a long CUG repeat ($HSA^{LR}$ mice) and a short CUG repeat ($HSA^{SR}$ mice), was evaluated. HSA-short repeat ($HSA^{SR}$) mice express the identical transgene as the $HSA^{LR}$ mice, except that 5 instead of 250 CUG repeats are inserted in the 3' UTR. $HSA^{SR}$ mice do not have myotonia, splicing changes, or any other observable myotonia phenotype. ISIS 445236 was used in this assay.

Treatment $HSA^{LR}$ mice were divided into four treatment groups. The first three groups received subcutaneous injections of ISIS 445236 at doses of 2.5 mg/kg, 8.5 mg/kg or 25.0 mg/kg twice per week for 4 weeks. The fourth group received subcutaneous injections of PBS twice per week for 4 weeks. The PBS-injected group served as the control group to which the oligonucleotide-treated group was compared. $HSA^{SR}$ mice were also divided into four groups and similarly treated.

Inhibition of Alpha1 Actin RNA

Twenty four hours after the final dose, the animals were sacrificed and tissue from the quadriceps muscles (left and right), gastrocnemius muscles (left and right), and tibialis anterior muscles (left and right) was isolated. RNA was isolated for real-time PCR analysis of alpha1 actin and normalized to 18s RNA. The results are presented in Tables 36 and 37 and are expressed as percent inhibition of alpha1 actin transcript, relative to the control. Greater inhibition of the nuclear-retained long repeat in the muscle of $HSA^{LR}$ mice was achieved compared with the non-nuclear-retained short repeat in the muscle of $HSA^{SR}$ mice.

TABLE 36

| Percent inhibition of human alpha1 actin RNA transcript in $HSA^{LR}$ mice | | | |
|---|---|---|---|
| Dose (mg/kg) | Quadriceps | Gastrocnemius | Tibialis anterior |
| 2.5 | 24 | 36 | 46 |
| 8.5 | 53 | 66 | 59 |
| 25 | 86 | 86 | 90 |

TABLE 37

| Percent inhibition of human alpha1 actin RNA transcript in $HSA^{SR}$ mice | | | |
|---|---|---|---|
| Dose (mg/kg) | Quadriceps | Gastrocnemius | Tibialis anterior |
| 2.5 | 15 | 14 | 0 |
| 8.5 | 30 | 11 | 0 |
| 25 | 59 | 48 | 54 |

Example 23: In Vivo Antisense Inhibition of Human DMPK in Transgenic Mice

LC15 mice, Line A, are transgenic mice containing the entire human DMPK 3'UTR (developed by Wheeler et al, University of Rochester). The mice are the second generation of mice backcrossed to an FVB background. The transgene is expressed in the mice as a CUG repeat RNA, which is retained in the nucleus, forming nuclear inclusions or foci, similar to that seen in human tissue samples of patients with myotonic dystrophy (DM1). There are 350-400 CUG repeats in the DMPK transgene. These mice display early signs of DM1 and do not display any myotonia in their muscle tissues.

ISIS 445569, ISIS 444404, ISIS 444436 and ISIS 473810, which demonstrated statistically significant dose-dependent inhibition in vitro (see Example 5), were evaluated for their ability to reduce human DMPK RNA transcript in vivo.

Treatment

LC15, Line A mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

The mice were divided into five treatment groups. The first three groups received subcutaneous injections of ISIS 445569, ISIS 444404 or ISIS 444436 at a dose of 25 mg/kg twice per week for 4 weeks. The fourth group received subcutaneous injections of ISIS 473810 at a dose of 12.5 mg/kg twice per week for 4 weeks. The fifth group received subcutaneous injections of PBS twice weekly for 4 weeks. The PBS-injected group served as the control group to which the oligonucleotide-treated group was compared.

Inhibition of DMPK RNA

Twenty four hours after the final dose, the animals were sacrificed and tissue from the quadriceps muscles was isolated. RNA was isolated for real-time PCR analysis of DMPK and normalized to 18s RNA. As presented in Table 38, treatment with antisense oligonucleotides reduced human DMPK RNA transcript expression. The results are expressed as percent inhibition of DMPK transcript, relative to the PBS control.

TABLE 38

Antisense inhibition of human DMPK RNA transcript in LC15 mice

| ISIS No | mg/kg/wk | % inhibition |
|---|---|---|
| 444404 | 50 | 20 |
| 444404 | 50 | 55 |
| 444436 | 50 | 41 |
| 473810 | 25 | 56 |

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. Since LC15 mice do not have myotonia, neither the control group nor the treatment groups displayed any myotonia in any muscle tested.

Example 24: In Vivo Antisense Inhibition of Human DMPK in Transgenic Mice

LC15 mice, Line D, are transgenic mice containing the entire human DMPK 3'UTR (developed by Wheeler et al, University of Rochester). The mice are the third generation of mice backcrossed to an FVB background. The transgene is expressed in the mice as a CUG repeat RNA, which is retained in the nucleus, forming nuclear inclusions or foci, similar to that seen in human tissue samples of patients with myotonic dystrophy (DM1). There are 350-400 CUG repeats in the DMPK transgene. These mice display early signs of DM1 and do not display any myotonia in their muscle tissues.

ISIS 445569, ISIS 444404, ISIS 444436 and ISIS 473810 were further evaluated for their ability to reduce human DMPK RNA transcript in vivo.

Treatment

LC15, Line D mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

The mice were divided into six treatment groups. The first three groups received subcutaneous injections of ISIS 445569, ISIS 444404 or ISIS 444436 at a dose of 25.00 mg/kg twice per week for 4 weeks. The fourth group received subcutaneous injections of ISIS 473810 at a dose of 12.50 mg/kg twice per week for 4 weeks. The fifth group received subcutaneous injections of ISIS 473810 at a dose of 6.25 mg/kg twice per week for 4 weeks. The sixth group received subcutaneous injections of PBS twice weekly for 4 weeks. The PBS-injected group served as the control group to which the oligonucleotide-treated group was compared.

Inhibition of DMPK RNA

Twenty four hours after the final dose, the animals were sacrificed and tissue from the quadriceps muscles was isolated. RNA was isolated for real-time PCR analysis of DMPK and normalized to 18s RNA. As presented in Table 39, treatment with antisense oligonucleotides reduced human DMPK RNA transcript expression. The results are expressed as percent inhibition of DMPK transcript, relative to the PBS control.

The results indicate that treatment with the antisense oligonucleotides resulted in inhibition of DMPK mRNA in the mice.

TABLE 39

Antisense inhibition of human DMPK RNA transcript in LC15 mice

| ISIS No | mg/kg/wk | % inhibition |
|---|---|---|
| 444404 | 50.00 | 24 |
| 444404 | 50.00 | 30 |
| 444436 | 50.00 | 17 |
| 473810 | 25.00 | 7 |
| 473810 | 12.50 | 18 |

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. Since LC15 mice do not have myotonia, neither the control group nor the treatment groups displayed any myotonia in any muscle tested.

Example 25: In Vivo Antisense Inhibition of Human DMPK in SXL Transgenic Mouse Model Using hDMPK-targeting ASOs 444401 and 299471 target knockdown in soleus muscle was measured in SXL mice. The SXL mouse is transgenic for the entire DMPK gene and promoter and contains a 1000 CUG repeat sequence in the 3'UTR of DMPK gene. Mice were dosed 50 mg/kg twice weekly for 4 weeks (n=3 mice per group, except n=2 for saline-injected controls). Results of Taqman assays demonstrated that treatment with either ISISI 444401 or ISIS 299471 significantly reduced mut-hDMPK mRNA levels but had negligible effect on endogenous mouse Dmpk mRNA levels.

Therefore, ISIS 444401 and ISIS 299471 selectively target human DMPK mRNA transcript.

Example 26: Duration of Action of Antisense Inhibition by an Oligonucleotide Targeting Human Alpha1 Actin in Transgenic Mice The duration of action of antisense inhibition of human alpha1 actin RNA transcript by ISIS 190401 in HSA$^{LR}$ mice was evaluated.

Treatment

HSA$^{LR}$ mice received subcutaneous injections of ISIS 190401 at a dose of 25 mg/kg twice per week for 4 weeks. A control group received subcutaneous injections of PBS twice per week for 4 weeks. The PBS-injected group served as the control group to which the oligonucleotide-treated group was compared. The mice were analyzed 15 weeks after administration of the last dose.

Inhibition of Alpha1 Actin RNA

Fifteen weeks after the final dose, the animals were sacrificed and tissue from the quadriceps muscles, gastrocnemius muscles, and tibialis anterior muscles was isolated. RNA was isolated for real-time PCR analysis of alpha1 actin and normalized to 18s RNA. As presented in Table 40, treatment with ISIS 190401 reduced human alpha1 actin RNA transcript expression, and this effect was sustained at least for 15 weeks. The results are expressed as percent inhibition of alpha1 actin transcript, relative to the PBS control.

Treatment with ISIS 190401 resulted in significant inhibition of alpha1 actin mRNA levels under the conditions specified above.

TABLE 40

Antisense inhibition of human alpha1 actin RNA transcript in HSA$^{LR}$ mice

| Muscle Type | % inhibition |
|---|---|
| Quadriceps | 74 |
| Gastrocnemius | 81 |
| Tibialis anterior | 75 |

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 41 as the average myotonia grade observed in four mice of each group and demonstrates significant reduction of myotonia in mice treated with ISIS 190401. Therefore, the effect of antisense inhibition of alpha actin by ISIS 190401 was sustained at least for 15 weeks.

TABLE 41

Average reduction of myotonia in various muscles of antisense oligonucleotide-treated HSA$^{LR}$ mice

| | PBS | ISIS 190401 |
|---|---|---|
| Left quadriceps | 3.0 | 0.0 |
| Right quadriceps | 3.0 | 0.0 |
| Left gastrocnemius | 2.5 | 0.0 |
| Right gastrocnemius | 2.5 | 0.0 |
| Left Tibialis anterior | 2.5 | 0.0 |
| Right Tibialis anterior | 2.5 | 0.0 |
| Lumbar paraspinals | 2.5 | 0.0 |

Correction of Alternative Splicing

To evaluate the effect of ISIS 190401 on alternative splicing of Serca1, total RNA purified from the tibialis anterior gastrocnemius, and quadriceps muscle was analyzed in a procedure similar to that described in Example 13.

In PBS treated HSA$^{LR}$ mice, Serca1 splicing is dysregulated as demonstrated by exon 22 exclusion. Treatment with ISIS 190401 resulted in complete inclusion and normalization of alternative splicing of exon 22 of the Serca1 gene in all three muscle types, which was sustained even after 15 weeks.

Therefore, antisense inhibition of alpha1 actin corrected Serca1 splicing dysregulation, which indicates that treatment with antisense oligonucleotide reduced accumulation of CUGexp in the nuclear foci. Reduced accumulation of CUGexp in the nuclear foci corrects MBLN1 sequestration thereby allowing normal splicing to occur.

Example 27: Microarray Analysis of Transcriptomic Effect of Antisense Inhibition of Human Actin Expression of actin mRNA with expanded CUG repeats causes extensive remodeling of the muscle transcriptome. To evaluate the overall transcriptomic effects of ISIS 190401 and ISIS 445236, microarray analyses was utilized in HSA$^{LR}$ mice.

Treatment

HSA$^{LR}$ mice received subcutaneous injections of ISIS 190401 or ISIS 445236 at a dose of 25 mg/kg twice per week for 4 weeks. A control group received subcutaneous injections of PBS twice per week for 4 weeks. The PBS-injected group served as the control group to which the oligonucleotide-treated group was compared.

Transcriptome Analysis by Microarray

RNA was isolated from the quadriceps muscle of wild-type or HSA$^{LR}$ mice. RNA integrity was verified using an Agilent Bioanalyzer (RNA integrity number >7.5). RNA was processed to complementary RNA (cRNA) and hybridized on microbeads using MouseRef-8 v2.0 Expression BeadChip Kits (Illumina, San Diego), according to the manufacturer's recommendations. Image data were quantified using BeadStudio software (Illumina). Signal intensities were quantile normalized. Row-specific offsets were used to avoid any values of less than 2 prior to normalization. Data from all probe sets with 6 or more nucleotides of CUG, UGC, or GCU repeats was suppressed to eliminate the possibility that expanded repeats in the hybridization mixture (CAG repeats in cRNA originating from CUG repeats in the mRNA) could cross-hybridize with repeat sequences in the probes. To eliminate genes whose expression was not readily quantified on the arrays, probes showing a P value for detection probability of <0.1 were suppressed in all samples. Comparisons between groups were summarized and rank-ordered by fold-changes of mean expression level and t tests. The software package R(Butler et al. *Diabetes.* 2002; 51:1028-34) was used to perform principal components analysis (Levin et al. In *Antisense Drug Technology: Principles, Strategies, and Applications*, S. T. Crooke, Ed. (CRC Press, Boca Raton, 2008), pp 183-215; Geary et al. *Drug Metab. Dispos.* 2003; 31:1419-28) on wild-type, ISIS oligonucleotide-treated, and PBS-treated microarray samples. The principle components allowed the capture of the majority of the expression variation in each sample within 3 dimensions. The first three principal components of each sample were plotted.

The principle component analysis of untreated wild-type and $HSA^{LR}$ mice demonstrated segregation of $HSA^{LR}$ away from wild-type mice, in widely separated clusters. In contrast, antisense oligonucleotide-treated $HSA^{LR}$ mice clustered more closely to wild-type mice, suggesting an overall trend for transcriptome normalization. Comparisons of $HSA^{LR}$ transgenic mice with wild-type mice identified 93 transcripts whose expression levels were altered more than two-fold (P<0.0001), as presented in Table 42, below. The extent of dysregulation for these transcripts was reduced or normalized for antisense oligonucleotides (88% dysregulated transcripts responded to ISIS 445236, P<0.05 for ISIS 445236 vs. PBS control, whereas 90% responded to ISIS 190401).

In order to consider transcripts that have off-target knockdown, all transcripts whose expression was reduced in antisense oligonucleotide-treated $HSA^{LR}$ mice were identified (>two-fold reduction by either oligonucleotide, P<0.0001, n=41 transcripts). All transcripts that were down-regulated by these criteria demonstrated upregulation in $HSA^{LR}$ mice. The only exception, collagen 6 alpha2, is unlikely to result from off-target cleavage because it was down-regulated by the two antisense oligonucleotides with non-overlapping sequences.

These results indicate that treatment with antisense oligonucleotides for 4 weeks resulted in a general improvement of the muscle transcriptome without any evidence for off-target effects.

TABLE 42

Comparisons of HSALR transgenic mice with wild-type mice identified 93 transcripts

| Transcript | Fold-change HSALR-saline vs. WT | t test HSALR-Saline vs. WT | Fold-change HSALR-190104 vs. HSALR-saline | t test HASLR 190401 vs. HSALR-saline | Fold-change HSALR-190401 vs. WT | t test HSALR-190401 vs. WT | Fold-change HSALR-445236 vs. HSALR-saline | t test HSALR-445236 vs. HSALR-saline | Fold-change HSALR-445236 vs. WT | t test HSALR-445236 vs. WT |
|---|---|---|---|---|---|---|---|---|---|---|
| OSBPL10 | 15.11 | 0.0000 | 0.46 | 0.0023 | 6.95 | 0.0008 | 0.39 | 0.0007 | 5.92 | 0.0002 |
| FBXL13 | 12.12 | 0.0000 | 0.49 | 0.0159 | 5.91 | 0.0385 | 0.65 | 0.0255 | 7.93 | 0.0026 |
| NGFR | 11.57 | 0.0000 | 0.23 | 0.0001 | 2.66 | 0.0314 | 0.16 | 0.0000 | 1.84 | 0.0133 |
| SLC1A1 | 9.39 | 0.0000 | 0.39 | 0.0001 | 3.66 | 0.0001 | 0.30 | 0.0001 | 2.85 | 0.0116 |
| CXADR | 9.13 | 0.0000 | 0.14 | 0.0000 | 1.30 | 0.6119 | 0.21 | 0.0001 | 1.94 | 0.2244 |
| NFATC2 | 8.48 | 0.0000 | 0.32 | 0.0002 | 2.67 | 0.0043 | 0.22 | 0.0001 | 1.84 | 0.0394 |
| ATP1B4 | 7.02 | 0.0000 | 0.24 | 0.0000 | 1.68 | 0.0021 | 0.24 | 0.0000 | 1.70 | 0.0091 |
| UCHL1 | 6.80 | 0.0000 | 0.71 | 0.0168 | 4.86 | 0.0005 | 0.72 | 0.1187 | 4.91 | 0.0090 |
| TEAD4 | 6.76 | 0.0000 | 0.50 | 0.0030 | 3.39 | 0.0085 | 0.30 | 0.0004 | 2.06 | 0.1213 |
| TAS1R1 | 6.72 | 0.0000 | 0.28 | 0.0003 | 1.91 | 0.1857 | 0.43 | 0.0002 | 2.88 | 0.0047 |
| MUSTN1 | 6.52 | 0.0000 | 0.31 | 0.0000 | 2.01 | 0.0006 | 0.33 | 0.0000 | 2.15 | 0.0115 |
| IRF5 | 6.01 | 0.0000 | 0.21 | 0.0000 | 1.28 | 0.0556 | 0.33 | 0.0001 | 1.96 | 0.0035 |
| CRIP3 | 5.82 | 0.0000 | 0.33 | 0.0000 | 1.92 | 0.0151 | 0.29 | 0.0001 | 1.67 | 0.1470 |
| TAL2 | 5.75 | 0.0000 | 0.20 | 0.0001 | 1.13 | 0.7717 | 0.36 | 0.0002 | 2.08 | 0.0274 |
| ORF63 | 5.39 | 0.0000 | 0.27 | 0.0001 | 1.45 | 0.0206 | 0.47 | 0.0018 | 2.51 | 0.0066 |
| COPG | 5.05 | 0.0000 | 0.30 | 0.0000 | 1.53 | 0.0218 | 0.25 | 0.0001 | 1.25 | 0.3617 |
| CAMK1D | 4.92 | 0.0000 | 0.23 | 0.0002 | 1.12 | 0.8157 | 0.27 | 0.0000 | 1.32 | 0.2449 |
| HSPA2 | 4.76 | 0.0000 | 0.43 | 0.0000 | 2.02 | 0.0079 | 0.42 | 0.0000 | 2.02 | 0.0197 |
| CAMK2D | 4.70 | 0.0000 | 0.36 | 0.0001 | 1.70 | 0.0493 | 0.45 | 0.0004 | 2.12 | 0.0095 |
| CNTNAP2 | 4.49 | 0.0000 | 0.58 | 0.0001 | 2.59 | 0.0000 | 0.67 | 0.0007 | 3.02 | 0.0000 |
| TTC7 | 4.33 | 0.0000 | 0.38 | 0.0000 | 1.63 | 0.0085 | 0.68 | 0.0468 | 2.96 | 0.0126 |
| CD276 | 4.08 | 0.0001 | 0.36 | 0.0001 | 1.47 | 0.1613 | 0.59 | 0.0029 | 2.39 | 0.0072 |
| USH1C | 4.07 | 0.0000 | 0.50 | 0.0011 | 2.04 | 0.0077 | 0.38 | 0.0029 | 1.55 | 0.2881 |
| LRP11 | 4.03 | 0.0000 | 0.55 | 0.0017 | 2.24 | 0.0011 | 0.55 | 0.0006 | 2.23 | 0.0000 |
| PHLDA3 | 3.96 | 0.0000 | 0.40 | 0.0001 | 1.60 | 0.0019 | 0.36 | 0.0001 | 1.42 | 0.0609 |
| HSPB7 | 3.80 | 0.0000 | 0.30 | 0.0000 | 1.14 | 0.5358 | 0.30 | 0.0000 | 1.15 | 0.4474 |
| TRIT1 | 3.74 | 0.0000 | 0.43 | 0.0000 | 1.62 | 0.0003 | 0.31 | 0.0000 | 1.16 | 0.1043 |
| PCNX | 3.66 | 0.0000 | 0.37 | 0.0002 | 1.34 | 0.1628 | 0.42 | 0.0001 | 1.53 | 0.0105 |
| 3632451O06RIK | 3.51 | 0.0000 | 0.81 | 0.1094 | 2.83 | 0.0025 | 0.71 | 0.0015 | 2.51 | 0.0002 |
| AMHR2 | 3.46 | 0.0000 | 0.45 | 0.0001 | 1.56 | 0.0037 | 0.52 | 0.0003 | 1.79 | 0.0016 |
| SNX13 | 3.27 | 0.0000 | 0.47 | 0.0000 | 1.55 | 0.0007 | 0.44 | 0.0000 | 1.42 | 0.0003 |
| ATP9A | 3.26 | 0.0000 | 0.60 | 0.0001 | 1.96 | 0.0024 | 0.42 | 0.0002 | 1.38 | 0.2009 |
| D030028O16RIK | 3.22 | 0.0000 | 0.53 | 0.0011 | 1.70 | 0.0104 | 0.48 | 0.0001 | 1.56 | 0.0007 |
| RPS6KA3 | 3.09 | 0.0000 | 0.38 | 0.0000 | 1.17 | 0.1845 | 0.44 | 0.0001 | 1.37 | 0.0321 |
| GCA | 3.00 | 0.0000 | 0.70 | 0.0031 | 2.09 | 0.0005 | 0.74 | 0.0103 | 2.22 | 0.0006 |
| PACRG | 2.89 | 0.0001 | 0.51 | 0.0002 | 1.46 | 0.0063 | 0.46 | 0.0001 | 1.34 | 0.0229 |
| SPSB2 | 2.88 | 0.0001 | 0.33 | 0.0000 | 0.95 | 0.6599 | 0.37 | 0.0000 | 1.07 | 0.6216 |
| POU4F1 | 2.83 | 0.0000 | 0.42 | 0.0000 | 1.19 | 0.2046 | 0.60 | 0.0007 | 1.68 | 0.0074 |
| STRN4 | 2.72 | 0.0000 | 0.38 | 0.0000 | 1.03 | 0.8900 | 0.46 | 0.0000 | 1.25 | 0.2128 |
| NCAM1 | 2.67 | 0.0001 | 0.70 | 0.0259 | 1.87 | 0.0135 | 0.54 | 0.0006 | 1.43 | 0.0343 |
| A930018M24Rik | 2.65 | 0.0001 | 0.58 | 0.0058 | 1.53 | 0.0727 | 0.43 | 0.0002 | 1.13 | 0.3919 |
| TUBA4A | 2.60 | 0.0000 | 0.42 | 0.0000 | 1.09 | 0.1806 | 0.50 | 0.0000 | 1.31 | 0.0041 |
| 1AP | 2.57 | 0.0000 | 0.57 | 0.0002 | 1.46 | 0.0108 | 0.59 | 0.0016 | 1.52 | 0.0333 |
| ANKRD40 | 2.56 | 0.0000 | 0.63 | 0.0155 | 1.60 | 0.0683 | 0.57 | 0.0002 | 1.46 | 0.0047 |
| UVRAG | 2.48 | 0.0000 | 0.59 | 0.0000 | 1.48 | 0.0005 | 0.52 | 0.0000 | 1.28 | 0.0165 |

TABLE 42-continued

Comparisons of HSALR transgenic mice with wild-type mice identified 93 transcripts

| Transcript | Fold-change HSALR-saline vs. WT | t test HSALR-Saline vs. WT | Fold-change HSALR-190104 vs. HSALR-saline | t test HASLR 190401 vs. HSALR-saline | Fold-change HSALR-190401 vs. WT | t test HSALR-190401 vs. WT | Fold-change HSALR-445236 vs. HSALR-saline | t test HSALR-445236 vs. HSALR-saline | Fold-change HSALR-445236 vs. WT | t test HSALR-445236 vs. WT |
|---|---|---|---|---|---|---|---|---|---|---|
| HIST1H4H | 2.46 | 0.0001 | 0.55 | 0.0001 | 1.34 | 0.0474 | 0.65 | 0.0014 | 1.60 | 0.0125 |
| EPS15 | 2.44 | 0.0000 | 0.61 | 0.0001 | 1.50 | 0.0057 | 0.77 | 0.0043 | 1.87 | 0.0007 |
| PANX1 | 2.41 | 0.0001 | 0.46 | 0.0004 | 1.11 | 0.4311 | 0.36 | 0.0000 | 0.87 | 0.0561 |
| CALML4 | 2.41 | 0.0001 | 0.45 | 0.0008 | 1.10 | 0.6994 | 0.67 | 0.0154 | 1.62 | 0.0538 |
| ASPH | 2.40 | 0.0000 | 0.40 | 0.0000 | 0.95 | 0.6969 | 0.44 | 0.0000 | 1.05 | 0.7267 |
| CREB3L2 | 2.37 | 0.0001 | 0.71 | 0.0287 | 1.67 | 0.0416 | 0.65 | 0.0051 | 1.54 | 0.0410 |
| TRAF3 | 2.32 | 0.0001 | 0.50 | 0.0001 | 1.16 | 0.2851 | 0.57 | 0.0001 | 1.32 | 0.0481 |
| CMYA1 | 2.30 | 0.0000 | 0.44 | 0.0007 | 1.02 | 0.9450 | 0.44 | 0.0000 | 1.01 | 0.9265 |
| ADAMTSL5 | 2.30 | 0.0001 | 0.48 | 0.0000 | 1.11 | 0.3365 | 0.53 | 0.0004 | 1.22 | 0.1827 |
| HS2ST1 | 2.27 | 0.0001 | 0.64 | 0.0002 | 1.44 | 0.0223 | 0.74 | 0.0041 | 1.68 | 0.0062 |
| HIST1H4J | 2.21 | 0.0000 | 0.59 | 0.0000 | 1.31 | 0.0283 | 0.72 | 0.0002 | 1.60 | 0.0023 |
| SPSB1 | 2.20 | 0.0000 | 0.53 | 0.0005 | 1.16 | 0.2409 | 0.48 | 0.0000 | 1.05 | 0.3088 |
| LANCL1 | 2.20 | 0.0000 | 0.63 | 0.0002 | 1.39 | 0.0002 | 0.66 | 0.0006 | 1.46 | 0.0005 |
| KCNC4 | 2.16 | 0.0000 | 0.91 | 0.3892 | 1.96 | 0.0036 | 0.98 | 0.8712 | 2.12 | 0.0029 |
| PRRC1 | 2.16 | 0.0000 | 0.57 | 0.0001 | 1.23 | 0.0324 | 0.59 | 0.0000 | 1.26 | 0.0070 |
| MID1IP1 | 2.13 | 0.0001 | 1.27 | 0.0161 | 2.70 | 0.0001 | 1.09 | 0.4336 | 2.32 | 0.0014 |
| DICER1 | 2.13 | 0.0000 | 0.65 | 0.0006 | 1.39 | 0.0051 | 0.69 | 0.0018 | 1.47 | 0.0035 |
| IKBKB | 2.10 | 0.0001 | 0.74 | 0.0240 | 1.56 | 0.0262 | 0.78 | 0.0039 | 1.64 | 0.0015 |
| D5WSU178E | 2.10 | 0.0000 | 0.86 | 0.1447 | 1.80 | 0.0049 | 0.88 | 0.0352 | 1.84 | 0.0002 |
| ZFP106 | 2.08 | 0.0000 | 0.53 | 0.0000 | 1.11 | 0.1324 | 0.58 | 0.0002 | 1.20 | 0.0706 |
| B930041F14RIK | 2.06 | 0.0000 | 0.71 | 0.0002 | 1.47 | 0.0000 | 0.72 | 0.0030 | 1.49 | 0.0025 |
| FHL1 | 2.04 | 0.0000 | 0.58 | 0.0000 | 1.17 | 0.1332 | 0.40 | 0.0000 | 0.81 | 0.0815 |
| UHRFIBP1L | 2.04 | 0.0001 | 0.78 | 0.0315 | 1.59 | 0.0071 | 0.68 | 0.0024 | 1.38 | 0.0151 |
| PHCA | 2.02 | 0.0000 | 0.64 | 0.0001 | 1.29 | 0.0354 | 0.74 | 0.0070 | 1.50 | 0.0145 |
| B230312A22RIK | 2.02 | 0.0000 | 0.79 | 0.0022 | 1.59 | 0.0004 | 0.77 | 0.0019 | 1.56 | 0.0007 |
| PPP2R5C | 2.01 | 0.0000 | 0.59 | 0.0001 | 1.16 | 0.0161 | 0.66 | 0.0017 | 1.32 | 0.0177 |
| UCK2 | 2.01 | 0.0001 | 0.70 | 0.0004 | 1.41 | 0.0129 | 0.64 | 0.0001 | 1.28 | 0.0510 |
| LEPROTL1 | 0.50 | 0.0000 | 1.45 | 0.0013 | 0.72 | 0.0004 | 1.47 | 0.0011 | 0.73 | 0.0005 |
| COPS7A | 0.49 | 0.0000 | 1.35 | 0.0645 | 0.66 | 0.0039 | 1.49 | 0.0026 | 0.73 | 0.0016 |
| PRM17 | 0.48 | 0.0001 | 1.51 | 0.2023 | 0.73 | 0.1585 | 1.34 | 0.0445 | 0.65 | 0.0002 |
| LDB3 | 0.47 | 0.0000 | 1.55 | 0.0550 | 0.73 | 0.0607 | 1.57 | 0.0010 | 0.74 | 0.0055 |
| LOC100046120 | 0.47 | 0.0000 | 1.31 | 0.0077 | 0.61 | 0.0000 | 1.27 | 0.0381 | 0.60 | 0.0002 |
| LOC677317 | 0.45 | 0.0001 | 1.49 | 0.0004 | 0.68 | 0.0012 | 1.93 | 0.0011 | 0.88 | 0.2082 |
| LDB2 | 0.45 | 0.0000 | 1.73 | 0.0424 | 0.78 | 0.1234 | 1.23 | 0.0817 | 0.56 | 0.0000 |
| SUM03 | 0.44 | 0.0000 | 1.70 | 0.0123 | 0.74 | 0.0223 | 1.37 | 0.0960 | 0.60 | 0.0023 |
| LRRC24 | 0.43 | 0.0001 | 1.89 | 0.0009 | 0.82 | 0.0212 | 1.42 | 0.0898 | 0.61 | 0.0041 |
| HNRPH1 | 0.42 | 0.0000 | 1.64 | 0.0077 | 0.69 | 0.0094 | 1.70 | 0.0057 | 0.71 | 0.0144 |
| ARMETL1 | 0.38 | 0.0000 | 2.58 | 0.0000 | 0.98 | 0.7666 | 2.70 | 0.0000 | 1.02 | 0.7109 |
| LOC100041504 | 0.37 | 0.0000 | 2.02 | 0.0001 | 0.75 | 0.0061 | 1.84 | 0.0040 | 0.68 | 0.0094 |
| MMP9 | 0.32 | 0.0000 | 2.40 | 0.0006 | 0.77 | 0.0340 | 1.37 | 0.1834 | 0.44 | 0.0009 |
| CBFB | 0.28 | 0.0000 | 2.66 | 0.0304 | 0.75 | 0.1852 | 1.94 | 0.0056 | 0.55 | 0.0004 |
| MDH2 | 0.24 | 0.0000 | 1.20 | 0.0473 | 0.29 | 0.0000 | 1.12 | 0.1037 | 0.27 | 0.0000 |
| APCDD1 | 0.20 | 0.0000 | 1.98 | 0.2157 | 0.39 | 0.0059 | 4.55 | 0.0001 | 0.90 | 0.2873 |
| LOC654842 | 0.19 | 0.0000 | 1.28 | 0.1712 | 0.24 | 0.0000 | 1.07 | 0.8807 | 0.20 | 0.0001 |
| F2RL3 | 0.15 | 0.0000 | 5.78 | 0.0001 | 0.86 | 0.1901 | 4.92 | 0.0004 | 0.73 | 0.0310 |
| EIF3H | 0.13 | 0.0000 | 1.99 | 0.2185 | 0.26 | 0.0001 | 1.86 | 0.1997 | 0.24 | 0.0000 |
| AVIL | 0.12 | 0.0000 | 4.22 | 0.0156 | 0.52 | 0.0081 | 1.88 | 0.2270 | 0.23 | 0.0001 |
| ACTC1 | 0.08 | 0.0000 | 1.42 | 0.0346 | 0.11 | 0.0000 | 6.07 | 0.0098 | 0.48 | 0.0087 |

What is claimed is:

1. A compound comprising a modified oligonucleotide consisting of 20 to 30 linked nucleosides, wherein the nucleobase sequence of the modified oligonucleotide is at least 90% complementary to at least 20 contiguous nucleobases of an equal length portion of nucleobases 2077-2099 of SEQ ID NO:1;

wherein the modified oligonucleotide comprises at least one modified sugar moiety and/or at least one modified internucleoside linkage.

2. A compound comprising a modified oligonucleotide consisting of 20 to 30 linked nucleosides, wherein the nucleobase sequence of the modified oligonucleotide is at least 90% identical to any of the nucleobase sequences recited in SEQ ID NOs: 590-594, and wherein the modified oligonucleotide comprises at least one modified sugar moiety and/or at least one modified internucleoside linkage.

3. The compound of claim 1, wherein the modified oligonucleotide is a single-stranded oligonucleotide.

4. The compound of claim 1, wherein the modified oligonucleotide is a double-stranded oligonucleotide.

5. The compound of claim 1, wherein the nucleobase sequence of the modified oligonucleotide is 95% or 100% complementary to at least 20 contiguous nucleobases of an equal length portion of nucleobases 2077-2099 of SEQ ID NO: 1.

6. The compound of claim 1, wherein at least one internucleoside linkage is a modified internucleoside linkage.

7. The compound of claim 1, wherein at least one internucleoside linkage is a phosphorothioate internucleoside linkage.

8. The compound of claim 1, wherein each internucleoside linkage is a phosphorothioate internucleoside linkage.

9. The compound of claim 1, wherein at least one nucleoside comprises a modified sugar.

10. The compound of claim 9, wherein the modified sugar is a bicyclic sugar.

11. The compound of claim 9, wherein the modified sugar comprises a 2'-O-methoxyethyl.

12. The compound of claim 1, wherein at least one nucleoside comprises a modified nucleobase.

13. The compound of claim 12, wherein the modified nucleobase is a 5-methylcytosine.

14. The compound of claim 1, wherein the modified oligonucleotide comprises:

a gap segment consisting of 6 to 14 linked deoxynucleosides;

a 5' wing segment consisting of 3 to 8 linked nucleosides;

a 3' wing segment consisting of 3 to 8 linked nucleosides;

wherein the gap segment is positioned between the 5' wing segment and the 3' wing segment;

and wherein each nucleoside of each wing segment comprises a modified sugar.

15. The compound of claim 1, wherein the modified oligonucleotide consists of 20 linked nucleosides and comprises:

a gap segment consisting of ten linked deoxynucleosides;

a 5' wing segment consisting of five linked nucleosides;

a 3' wing segment consisting of five linked nucleosides;

wherein the gap segment is positioned between the 5' wing segment and the 3' wing segment;

wherein each nucleoside of each wing segment comprises a 2'-O-methoxyethyl sugar;

and wherein each internucleoside linkage is a phosphorothioate linkage.

16. The compound of claim 1, wherein the modified oligonucleotide consists of 18 to 22 linked nucleosides.

17. The compound of claim 1, further comprising a conjugate group.

18. The isolated compound of claim 1, wherein the nucleobase sequence of the modified oligonucleotide is at least 90% complementary to at least 20 contiguous nucleobases of an equal length portion of nucleobases 2079-2099 of SEQ ID NO: 1.

19. The isolated compound of claim 1, wherein the nucleobase sequence of the modified oligonucleotide is at least 95% complementary to at least 20 contiguous nucleobases of an equal length portion of nucleobases 2079-2099 of SEQ ID NO: 1.

20. A composition comprising the compound of claim 1 and a pharmaceutically acceptable carrier or diluent.

21. A method of treating a DMPK related disease or a symptom thereof in an animal in need thereof, wherein the method comprises administering to said animal a therapeutically effective amount of the compound of claim 1.

22. The method of claim 21, wherein the DMPK related disease or a symptom thereof is:

(a) myotonia, or (b) spliceopathy.

23. The method of claim 21, wherein the DMPK related disease or a symptom thereof is type 1 myotonic dystrophy.

24. The method of claim 21, wherein the DMPK related disease or a symptom thereof is muscleblind-like protein (MBNL) dependent spliceopathy.

* * * * *